United States Patent [19]
Takatani et al.

[11] Patent Number: 5,998,433
[45] Date of Patent: *Dec. 7, 1999

[54] CONDENSED COMPOUNDS, THEIR PRODUCTION AND USE

[75] Inventors: Muneo Takatani, Kyoto; Yasuo Sugiyama, Hyogo; Ryuichi Tozawa, Ibaragi; Kazumasa Hamamura, Hyogo, all of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/549,779

[22] PCT Filed: Oct. 9, 1995

[86] PCT No.: PCT/JP95/02062

§ 371 Date: Nov. 14, 1995

§ 102(e) Date: Nov. 14, 1995

[87] PCT Pub. No.: WO96/11201

PCT Pub. Date: Apr. 18, 1996

[30] Foreign Application Priority Data

Oct. 11, 1994 [JP] Japan ................................... 6-245704
Aug. 18, 1995 [JP] Japan ................................... 7-210893

[51] Int. Cl.⁶ ....................... C07D 491/04; A61K 31/435

[52] U.S. Cl. ............................. 514/301; 514/302; 546/16; 546/114; 546/115; 540/593; 548/453

[58] Field of Search ...................................... 546/114, 115, 546/16; 540/593; 548/453; 514/301, 302

[56] References Cited

U.S. PATENT DOCUMENTS

| 4,210,649 | 7/1980 | Blanchard et al. | 424/256 |
| 4,335,128 | 6/1982 | Blanchard et al. | 424/256 |
| 5,334,596 | 8/1994 | Hartman et al. | 514/301 |
| 5,532,240 | 7/1996 | Nakao et al. | 514/254 |

FOREIGN PATENT DOCUMENTS

| 0123998 | 11/1984 | European Pat. Off. . |
| 0421861 | 4/1991 | European Pat. Off. . |
| 0472116 | 2/1992 | European Pat. Off. . |
| 0596125 | 5/1994 | European Pat. Off. . |

*Primary Examiner*—Bernard Dentz
*Attorney, Agent, or Firm*—Fitzpatrick, Cella, Harper & Scinto

[57] ABSTRACT

This invention provides new condensed furan compounds which exhibit excellent 2,3-oxidosqualene cyclase inhibition and high-density lipoprotein-cholesterol elevating activities.

This invention also provides a therapeutic and prophylactic agent for hyperlipidemia, hypercholesterolemia and atherosclerosis.

32 Claims, No Drawings

CONDENSED COMPOUNDS, THEIR PRODUCTION AND USE

This application is a 371 of PCT/JP95/02062 filed Oct. 9, 1995.

TECHNICAL FIELD

The present invention relates to new condensed furan compounds which exhibit excellent 2,3-oxidosqualene cyclase inhibiting and high-density lipoprotein-cholesterol elevating activities and a method of their production.

The compounds are useful as lipid-modifying agent and are of value in the prevention and the treatment of hyperlipidemia, hypercholesterolemia and atherosclerosis.

The present invention also relates to compositions containing the compounds, a cholesterogenesis inhibitor and an antifugal agent.

BACKGROUND ART

Many epidemiological studies have shown that hypercholesterolemia, hypertension and smoking comprise the three major risk factors for arteriosclerotic diseases, such as myocardial infarction, angina pectoris and cerebral infarction. Appropriate control of blood cholesterol level is therefore critical to the prevention or treatment of arteriosclerotic diseases, such as ischemic heart diseases. Among the drugs that decrease the blood cholesterol level are drugs that capture bile acid and inhibit its absorption, such as cholestyramine and colestipol (disclosed in U.S. Pat. No. 4,027,009, for instance) and drugs that inhibit acyl coenzyme A cholesterol acyl transferase (ACAT) and suppresses intestinal absorption of cholesterol, such as melinamide (disclosed in British Patent No. 1123004), as well as drugs that suppress cholesterol biosynthesis, which have drawn attention. Cholesterol biosynthesis suppressors in pharmaceutical use include lovastatin (disclosed in U.S. Pat. No. 4,231,938), simvastatin (disclosed in U.S. Pat. Nos. 4,231, 938 and 4,444,784) and pravastatin (disclosed in U.S. Pat. No. 4,346,227), all inhibitors of 3-hydroxy-3-methylglutaryl coenzyme A (HMG-CoA) reductase. When HMG-COA reductase is inhibited, however, not only cholesterogenesis, but also biosynthesis of other components essential to be alive, such as ubiquinone, dolichol and heme A, are inhibited, resulting in adverse effects of concern. Ubiquinone, dolichol, heme A etc. are known to be biosynthesized from farnesyl pyrophosphate in the cholesterol biosynthesis pathway; to prevent adverse effects due to their reduction, it is desirable that the enzymes after farnesyl pyrophosphate in the cholesterogenesis are inhibited. For example, 2,3-oxidosqualene cyclase (EC 5.4.99.7) is an enzyme that converts 2,3-oxidosqualene to lanosterol; 2,3-oxidosqualene cyclase inhibition results in a diminishment of cholesterol synthesis, owing to inhibited production of lanosterol, which is used for conversion to cholesterol, eventually leading to lower blood cholesterol levels. Also, the 2,3-oxidosqualene accumulation, as a result of 2,3-oxidosqualene cyclase inhibition, is metabolically converted to oxysterol via dioxide squalene, which is known as an HMG-COA reductase repressor [F. R. Taylor et al., Journal of Biological Chemistry, 1986, vol. 261 (32), pp. 15039–15044]. 2,3-Oxidosqualene cyclase inhibitors are therefore capable of inhibiting cholesterogenesis potently by the synergetic effect of HMG-COA reductase suppression at the transcription level, in addition to the inhibition of one enzyme after farnesyl pyrophosphate in the cholesterogenesis pathway. Already reported 2,3-oxidosqualene cyclase inhibitors include diphenyl derivatives (disclosed in European Patent No. 464465), aminoalkoxybenzene derivatives (disclosed in European Patent No. 410359), piperidine derivatives (described by D. S. Dodd et al. in the Journal of Organic Chemistry, 1992, vol. 57, pp. 2794–2803 and 7226–7234; Japanese Patent Unexamined Publication No. 234362/1992), decalin derivatives, azadecalin derivatives and indane derivatives [described in WO 80/08450; Journal of Biological Chemistry, 1981, vol. 254, pp. 11258–11263; N. Gerst et al., Biochemical Pharmacology, 1988, vol. 37, pp. 1955–1964; M. W. Wannamaker, Journal of Medicinal Chemistry, 1992, vol. 35, pp. 3581–3583; Japanese Patent Unexamined Publication Nos. 140112/1993 and 3144/1989], 2-aza-2,3-dihydrosqualene and 2,3-epiminosqualene [described by A. Duriatti et al. in Biochemical Pharmacology, 1985, vol. 34, pp. 2765–2777], squalenoid epoxide vinyl ether [described by M. Ceruti et al. in the Journal of the Chemical Society, Perkin Transaction 1, 1988, pp. 461–469], 29-methyliden-2,3-oxidosqualene [described in the Journal of American Chemical Society, 1991, vol. 113, pp. 9673–9674], azacycloalkane derivatives (disclosed in Japanese Patent Unexamined Publication No. 192256/1994) and arylcycloalkylamine derivatives (Japanese Patent Unexamined Publication No. 211763/1994). As concerns infectious diseases, the sterol biosynthesized by fungi is ergosterol, while that by mammals is cholesterol; however, since the process of biosynthesis to lanosterol is common between the two kinds of sterol, inhibition of the process at a point before lanosterol suppresses the synthesis of both. 2,3-Oxidosqualene cyclase inhibitors are therefore expected to exhibit antifungal action [J. L. Adams et al., Comprehensive Medicinal Chemistry, 1990, vol. 2, pp. 333–364].

Compounds that inhibit cholesterol biosynthesis are useful in the treatment of some syndromes, especially hypercholesterolemia and hyperlipidemia, which comprise risk factors for onset of atherosclerotic vascular lesions and diseases subsequent thereto, such as coronary artery disease (CHD), cerebral ischemia, intermittent claudication and necrosis. Major symptoms of atherosclerosis are intimal proliferation of macrophages and vascular smooth muscle cells, and cholesterol accumulation in such cells. It is a well-known that hypercholesterolemia, especially increased low-density lipoprotein (LDL)-cholesterol, is an important risk factor in the development of atherosclerosis. Since epidemiological studies have revealed that the incidence of coronary heart disease can be decreased by lowering blood cholesterol [see Lipidology 2(4), 234, 1991], blood lipid-lowering agents have been used to suppress atherosclerotic vascular lesions. Such use, however, is for prophylaxis, rather than treatment.

It is also known epidemiologically that high-density lipoprotein (HDL)-cholesterol lowers the incidence of heart disease. Regarding the mechanism of this action, HDL is known to reduce cholesterol from foam cells. However, there is no report regarding substances used to increase blood HDL or HDL-cholesterol.

Japanese Patent Unexamined Publication No. 41332/1979 describes as a sickle cell anemia or sicklemia remedy, possessing anti-inflammatory, vasodilating and platelet aggregation-inhibiting activities, a compound represented by the formula:

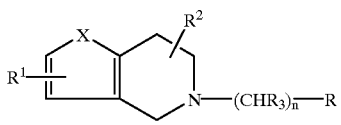

wherein x represents an atom of oxygen or sulfur; R represents a group selected from the group consisting of hydrogen atom; phenyl group; phenyl groups substituted by at least one substituent selected from the group consisting of halogen atoms, lower alkyl, lower alkoxy, nitro, amino, sulfonylamino, aryl, carboxy, alkoxycarbonyl, cyano, hydroxymethyl and methylenedioxy groups; styryl, naphthyl, thienyl and benzhydryl groups, each of which may be substituted by at least one substituent selected from the group consisting of halogen atoms, lower alkyl, lower alkoxy, aryl, nitro, amino, sulfonylamino, carboxy, alkoxycarbonyl, cyano, hydroxymethyl and methylenedioxy groups; benzoyl group; and benzoyl groups substituted by at least one substituent selected from the group consisting of halogen atoms, lower alkyl, lower alkoxy, nitro, amino and sulfonylamino groups; $R^1$ and $R^2$ independently represent at least one atom or group selected from the group consisting of hydrogen atom, halogen atoms, hydroxy, lower alkyl, lower alkoxy, nitro and amino groups; $R^3$ represents a group selected from the group consisting of hydrogen atom, halogen atoms, hydroxy, lower alkyl, lower alkoxy, nitro and amino groups; n represents an integer from 0 to 15; when n is greater than 1, the $R^3$ radicals in the respective $CHR^3$ groups may have different meanings. PCT International Patent Application WO93/13105 describes as an antipsychotic or antianxiety drug a compound represented by the formula:

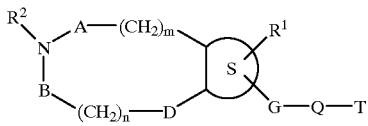

wherein ring S is a thiophene ring; $R^1$ represents a hydrogen atom, a halogen, an alkyl, or the like; $R^2$ represents a hydrogen atom, an alkyl, an acyl, or the like; G represents —CH$_2$—, —CH(OH)—, —CO—, or the like; Q represents an alkylene; T represents —NH$_2$, —NHRa (Ra represents an alkyl, a cycloalkyl, or the like), or —N(Rb)(Rc) (Rb and Rc independently represent an alkyl, or the like, or bind together to form a cyclic amino); D represents —CH$_2$— or —S—; A and B independently represent a carbonyl or thiocarbonyl, or none; m and n each represent an integer from 0 to 4, but m+n does not exceed 4, exemplified in Example 41 by a compound represented by the formula:

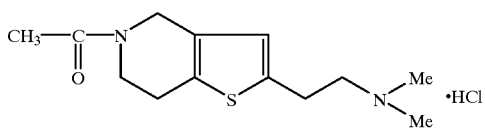

However, no compounds have been found that are fully satisfactory in 2,3-oxidosqualene cyclase-inhibiting and blood cholesterol-lowering activities; there is need for the development of such compounds.

DISCLOSURE OF INVENTION

Through extensive investigations, the present inventors synthesized, for the first time, a new compound represented by the formula:

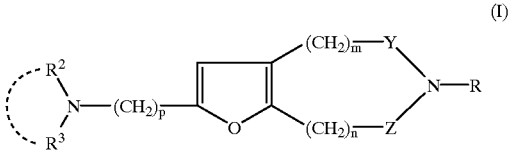

(I)

wherein R has the same definition as that given below, which is characterized by a chemical structure in which an acyl group or a hydrocarbon group is present as a substituent for the nitrogen atom of a condensed furan ring represented by the formula:

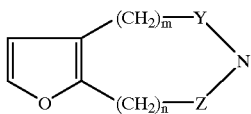

wherein m and n have the same definitions as those given above and an aminoalkyl group present as a substituent at the 2-position of the furan ring, and found that compound (I) and a compound resulting from replacement of the furan ring of compound (I) with a thiophene ring are useful as blood lipid-lowering agents, antifungal agents and the like, since they unexpectedly exhibit excellent 2,3-oxidosqualene cyclase-inhibiting action, cholesterogenesis-inhibiting action, blood high-density lipoprotein (HDL) elevating agent useful in the treatment or prevention of atherosclerosis-associated diseases, low-density lipoprotein receptor-increasing action, antifungal action and other actions attributable to the unique chemical structure described above, and are safe, with low toxicity. The inventors conducted further investigations based on this finding, and completed the present invention.

Accordingly, the present invention relates to:

(1) a compound represented by the formula:

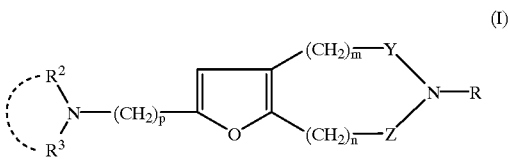

(I)

wherein R represents an acyl group or a hydrocarbon group that may be substituted; $R^2$ and $R^3$, independently, represent a hydrogen atom or a hydrocarbon group that may be substituted, or may form a ring with the adjacent nitrogen atom; Y and Z independently represent —CO— or a bond; p represents an integer of 1 to 5, m and n independently represent an integer of 0 to 5 with the proviso that both m and n are not identically 0, or a salt thereof, (2) A compound of term (1) above, wherein Y and Z are a bond, m and n independently represent an integer of 1 to 5, (3) a compound of term (1) above, wherein R is —A—$R^1$ in which $R^1$ represents a hydrocarbon group that may be substituted or a heterocyclic group that may be substituted; A represents a bond, —CO—, —SO$_2$—, —SO—, —COO— or —CON($R^4$)— ($R^4$ represents a hydrogen atom or a hydrocarbon group that may be substituted), (4) a compound of term (1) above, wherein the hydrocarbon group represented by R is an alkyl group, a cycloalkyl group, an alkenyl group, an aryl group or an aralkyl group, (5) a compound of term (1) above, wherein the substituent for said hydrocarbon group represented by R is (i) nitro group, (ii) hydroxyl group, (iii) cyano group, (iv) carbamoyl group, (v) a mono- or di-$C_{1-4}$ alkyl-carbamoyl group (vi) carboxyl group, (vii) a $C_{1-4}$ alkoxy-carbonyl group, (viii) sulfone group, (ix) a halogen atom, (x) a $C_{1-6}$ alkoxy group, (xi) phenoxy group, naphthoxy group or benzyloxy group, (xii) a halogenophenoxy group, (xiii) a $C_{1-4}$ alkylthio group, (xiv) mercapto group, (xv) phenylthio group, (xvi) pyridylthio group, (xvii) a $C_{1-4}$ alkylsulfinyl group or phenylsulfinyl group, (xviii) a $C_{1-4}$ alkylsulfonyl group or phenylsulfonyl group, (xix) amino group, (xx) a $C_{1-3}$ acylamino group, (xxi) a mono- or di-$C_{1-4}$ alkylamino group, (xxii) a 4- to 6-membered cyclic amino group, (xxiii) a $C_{1-6}$ acyl group, (xxiv) benzoyl group that may be substituted by halogen atoms, (xxv) a 5- to 10-membered heterocyclic group or (xxvi) a 5- to 10-membered heterocyclic ring-carbonyl group, (6) a compound of term (3) above, wherein the hydrocarbon group represented by $R^1$ and $R^4$ is an alkyl group, a cycloalkyl group, an alkenyl group, an aryl group or an aralkyl group, (7) a compound of term (3) above, wherein the substituent for said hydrocarbon group represented by $R^1$ and $R^4$ is (i) nitro group, (ii) hydroxyl group, (iii) cyano group, (iv) carbamoyl group, (v) a mono- or di-$C_{1-4}$ alkyl-carbamoyl group, (vi) carboxyl group, (vii) a $C_{1-4}$ alkoxy-carbonyl group, (viii) sulfone group, (ix) a halogen atom, (x) a $C_{1-6}$ alkoxy group, (xi) phenoxy group, naphthoxy group or benzyloxy group, (xii) a halogenophenoxy group, (xiii) a $C_{1-4}$ alkylthio group, (xiv) mercapto group, (xv) phenylthio group, (xvi) pyridylthio group, (xvii) a $C_{1-4}$ alkylsulfinyl group or phenylsulfinyl group, (xviii) a $C_{1-4}$ alkylsulfonyl group or phenylsulfonyl group, (xix) amino group, (xx) a $C_{1-3}$ acylamino group, (xxi) a mono- or di-$C_{1-4}$ alkylamino group, (xxii) a 4- to 6-membered cyclic amino group, (xxiii) a $C_{1-6}$ acyl group, (xxiv) benzoyl group that may be substituted by halogen atoms, (xxv) a 5- to 10-membered heterocyclic group or (xxvi) a 5- to 10-membered heterocyclic ring-carbonyl group, (8) a compound of term (3) above, wherein $R^1$ represents an aralkyl group or an aryl group, (9) a compound of term (3) above, wherein said heterocyclic group represented by $R^1$ is a 5- to 8-membered ring, or a condensed ring containing 1 to 4 hetero atoms selected from atoms of oxygen, sulfur, and nitrogen,

(10) a compound of term (3) above, wherein $R^1$ represents a $C_{7-20}$ aralkyl group that may be substituted by one to four substituent(s) selected from the group consisting of (i) nitro group, (ii) hydroxyl group, (iii) cyano group, (iv) carbamoyl group, (v) mono- or di-$C_{1-4}$ alkyl-carbamoyl groups, (vi) carboxyl group, (vii) $C_{1-4}$ alkoxy-carbonyl groups, (viii) sulfone group, (ix) halogen atoms, (x) $C_{1-6}$ alkoxy groups, (xi) phenoxy group, naphthoxy group or benzyloxy group, (xii) halogenophenoxy groups, (xiii) $C_{1-4}$ alkylthio groups (xiv) mercapto group, (xv) phenylthio group, (xvi) pyridylthio group, (xvii) $C_{1-4}$ alkylsulfinyl groups or phenylsulfinyl group, (xviii) $C_{1-4}$ alkylsulfonyl groups or phenylsulfonyl group, (xix) amino group, (xx) $C_{1-3}$ acylamino groups, (xxi) mono- or di-$C_{1-4}$ alkyl amino groups, (xxiii) $C_{1-6}$ acyl groups, (xxiv) benzoyl group that may be substituted by halogen atoms, (xxv) 5- to 10-membered heterocyclic groups and (xxvi) 5- to 10-membered heterocyclic ring-carbonyl groups,

(11) a compound of term (3) above, wherein $R^1$ represents a $C_{6-14}$ aryl group that may be substituted by an acyl group,

(12) a compound of term (3) above, wherein A is —CO—, —$SO_2$— or —COO—,

(13) a compound of term (3) above, wherein A is —CO— or —$SO_2$—, $R^1$ is a halogeno-$C_{7-20}$ aralkyl group,

(14) a compound of term (1) above, wherein $R^2$ and $R^3$ are independently a lower alkyl group,

(14) a compound of term (1) above, wherein $R^2$ and $R^3$ are independently a lower alkyl group,

(15) a compound of term (1) above, wherein m or n is 1,

(16) a compound of term (1) above, wherein both m and n are independently an integer of 1 to 3,

(17) a compound of term (1) above, wherein p is an integer of 1 to 3,

(18) a compound of term (1) above, wherein Y is —CO—,

(19) a compound of term (18) above, wherein m is 0, n is an integer of 1 to 3 and Z is a bond,

(20) a compound of term (19) above, wherein R is a $C_{7-20}$ aralkyl group or a $C_{6-14}$ aryl group,

(21) a compound of term (1) above, which is 1-(2-dimethylaminomethyl-6,7-dihydro-4H-furo[3,2-c]pyridin-5-yl)-6-phenylhexan-1-one, 1-(2-dimethylaminomethyl-5,7-dihydro-4H-furo[2,3-c]pyridin-6-yl)-6-phenylhexan-1-one, N,N-dimethyl-[6-(4-phenylbutoxycarbonyl)-4,5,6,7-tetrahydrofuro[2,3-c]pyridin-2-ylmethyl]amine, N,N-dimethyl-[5-(5-phenylpentylsulfonyl)-4,5,6,7-tetrahydrofuro[3,2-c]pyridin-2-ylmethyl]amine, N,N-dimethyl-[6-(4-benzoylbenzoyl)-4,5,6,7-tetrahydrofuro[2,3-c]pyridin-2-ylmethyl]amine, N,N-diethyl-[6-(4-benzoylbenzoyl)-4,5,6,7-tetrahydrofuro[2,3-c]pyridin-2-ylmethyl]amine, 1-(2-methylaminomethyl-5,7-dihydro-4H-furo[2,3-c]pyridin-6-yl)-6-phenylhexan-1-one, 1-(2-dimethylaminomethyl-4,5,6,8-tetrahydrofuro[2,3-c]azepin-7-yl)-6-phenylhexan-1-one, N,N-dimethyl-[6-(4-phenethylbenzoyl)-4,5,6,7-tetrahydrofuro[2,3-c]pyridin-2-ylmethyl]amine, N,N-dimethyl-[6-(4-benzyloxybenzoyl)-4,5,6,7-tetrahydrofuro[2,3-c]pyridin-2-ylmethyl]amine, 6-[4-(1-phenylethenyl)benzoyl]-2-(1-pyrrolidinylmethyl)-4,5,6,7-tetrahydrofuro[2,3-c]pyridine, N,N-dimethyl-[6-[4-(1-phenylcyclopropyl)benzoyl]-4,5,6,7-tetrahydrofuro[2,3-c]pyridin-2-ylmethyl]amine, N,N-dimethyl-[6-[4-(2-phenyl-1,3-dithiolane-2-yl)benzoyl]-4,5,6,7-tetrahydrofuro[2,3-c]pyridin-2-ylmethyl]amine, (Z)-5-(3-chlorostilbene-4'-sulfonyl)-2-(1-pyrrolidinylmethyl)-4,5,6,7-tetrahydrofuro[3,2-c]pyridine, 2-dimethylaminomethyl-5-(6-phenylhexyl)-6,7-dihydro-5H-furo[3,2-c]pyridin-4-one, or an acid addition salts thereof,

(22) a method of producing the compound of term (1) above, which comprises reacting a compound represented by the formula:

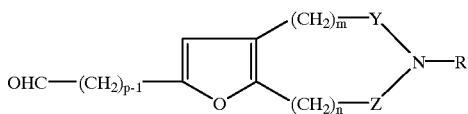

wherein the symbols have the same definitions as those given in term (1), or a salt thereof, with a compound represented by the formula:

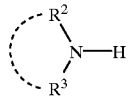

wherein the symbols have the same definitions as those given in term (1), or a salt thereof, followed by reduction, (23) a method of producing the compound of term (1) above, which comprises reacting a compound represented by the formula:

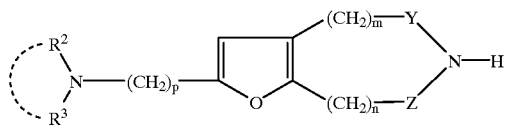

wherein the symbols have the same definitions as those given in term (1), or a salt thereof, with a compound represented by the formula:

$E^1$—R wherein $E^1$ represents a leaving group; R has the same definition as that given in term (1), or a salt thereof, (24) a composition comprising a compound represented by the formula:

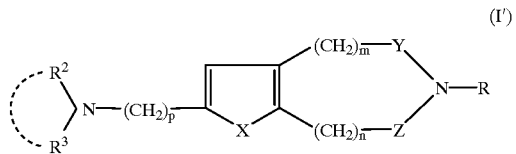

wherein X represents an oxygen atom or a sulfur atom; the other symbols have the same definitions as those given in term (1), or a salt thereof,
(25) a composition of (24), which is a 2,3-oxidosqualene cyclase inhibitor,
(26) a composition of (24), which is a cholesterogenesis inhibitor,
(27) a composition of (24), which is a low-density lipoprotein receptor-increasing agent,
(28) a composition of (24), which is a high-density lipoprotein-cholesterol elevating agent,
(29) a composition of (24), which is a lipid-modifying agent,
(30) a composition of (24), which is an antifungal agent,
(31) a method for preventing or treating hyperlipidemia in a mammal which comprises administering to said mammal a pharmaceutically effective amount of a compound of the formula (I') as defined in term (24) or a salt thereof, and
(32) use of a compound of the formula (I') as defined in term (24) or a salt thereof for the manufacture of a medicament for hyperlipidemia.

The term "acyl group" as used herein is defined as an acyl group obtained by removing the OH group from a carboxylic acid such as $R^1COOH$ or $R^1OCOOH$, a sulfonic acid such as $R^1SO_3H$, a sulfinic acid such as $R^1SO_2H$, a carbamic acid such as $R^1N(R^4)COOH$ ($R^1$ and $R^4$ have the same definitions as those given above), or the like. Specifically, useful acyl groups include $R^1CO$, $R^1OCO$, $R^1SO_2$, $R^1SO$ and $R^1N(R^4)CO$ ($R^1$ and $R^4$ have the same definitions as those given above).

The "hydrocarbon group" for the term "hydrocarbon group that may be substituted" as used herein is exemplified by alkyl groups, cycloalkyl groups, alkenyl groups, aryl groups and aralkyl groups. Here, alkyl groups include linear or branched $C_{1-20}$ alkyl groups, such as methyl, ethyl, propyl, isopropyl, butyl, isobutyl, sec-butyl, tert-butyl, pentyl, hexyl, heptyl, octyl, nonyl, decyl, undecyl, tridecyl, tetradecyl and pentadecyl, with preference given to linear or branched $C_{8-18}$ alkyl groups, such as octyl, nonyl, decyl, dodecyl and octadecyl. Useful cycloalkyl groups include $C_{3-8}$ cycloalkyl groups, such as cyclopropyl, cyclobutyl, cyclopentyl, cyclohexyl, cycloheptyl and cyclooctyl. Useful alkenyl groups include $C_{2-20}$ alkenyl groups, such as vinyl, allyl, isopropenyl, 3-butenyl, 3-octenyl and 9-octadecenyl, with preference given to linear or branched $C_{8-18}$ alkenyl groups, such as 3-octenyl, 9-octadecenyl and farnesyl. Useful aryl groups include $C_{6-14}$ aryl groups, such as phenyl, 1-naphthyl, 2-naphthyl, phenanthryl and anthryl, with preference given to phenyl, 1-naphthyl and 2-naphthyl. Useful aralkyl groups include $C_{7-20}$ aralkyl groups, such as benzyl, 2-phenylethyl, 3-phenylpropyl, 4-phenylbutyl, 5-phenylpentyl, 6-phenylhexyl, 8-phenyloctyl, 2-(1-naphthyl)ethyl and 2-(2-naphthyl)ethyl, with preference given to phenyl-$C_{4-10}$ alkyl groups, such as 4-phenylbutyl and 8-phenyloctyl, and naphthyl-$C_{2-10}$ alkyl groups, such as 2-(1-naphthyl)ethyl and 2-(2-naphthyl)ethyl.

The "substituent" for the "hydrocarbon group that may be substituted" is exemplified by (i) nitro group, (ii) hydroxyl group, (iii) cyano group, (iv) carbamoyl group, (v) mono- or di-$C_{1-4}$ alkyl-carbamoyl groups (e.g., N-methylcarbamoyl, N-ethylcarbamoyl, N,N-dimethylcarbamoyl, N,N-diethylcarbamoyl), (vi) carboxyl group, (vii) $C_{1-4}$ alkoxy-carbonyl groups (e.g., methoxycarbonyl, ethoxy-carbonyl, propoxycarbonyl, isopropoxycarbonyl), (viii) sulfone group, (ix) halogen atoms (e.g., fluorine, chlorine, bromine, iodine), (x) $C_{1-6}$ alkoxy groups (e.g., methoxy, ethoxy, propoxy, isopropoxy), (xi) phenoxy group, naphthoxy group, benzyloxy group, (xii) halogenophenoxy groups (e.g., o-, m- or p-chlorophenoxy, o-, m- or p-bromophenoxy), (xiii) $C_{1-4}$ alkylthio groups (e.g., methylthio, ethylthio, n-propylthio, isopropylthio, n-butylthio), (xiv) mercapto group, (xv) phenylthio group, (xvi) pyridylthio group, (xvii) $C_{1-4}$ alkylsulfinyl groups (e.g., methylsulfinyl, ethylsulfinyl), phenylsulfinyl group, (xviii) $C_{1-4}$ alkylsulfonyl groups (e.g., methylsulfonyl, ethylsulfonyl), phenylsulfonyl group, (xix) amino group, (xx) $C_{1-3}$ acylamino groups (e.g., acetylamino, propionylamino), (xxi) mono- or di-$C_{1-4}$ alkylamino groups (e.g., methylamino, ethylamino, dimethylamino, diethylamino), (xxii) 4- to 6-membered cyclic amino groups (e.g., 1-azetidinyl, 1-pyrrolidinyl, piperidino, morpholino, 1-piperazinyl), (xxiii) $C_{1-6}$ acyl groups (e.g., formyl, acetyl), (xxiv) benzoyl group that may be substituted by halogen (atoms) (e.g., benzoyl, o-, m- or p-chlorobenzoyl, o-, m- or p-bromobenzoyl), (xxv) 5- to 10-membered heterocyclic groups containing 1 to 4 hetero atoms selected from atoms of oxygen, sulfur and nitrogen (e.g, 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 1,2,3- or 1,2,4-triazolyl, 1H- or 2H-tetrazolyl, 2-, 3- or 4-pyridyl, 2-, 4- or 5-pyrimidyl, 3- or 4-pyridazinyl, quinolyl, isoquinolyl indolyl) and (xxvi) 5- to 10-membered heterocyclic ring-carbonyl groups containing 1 to 4 hetero atoms selected from atoms of oxygen, sulfur and nitrogen (e.g., 2- or 3-thienylcarbonyl, 2- or 3-furylcarbonyl, 3-, 4- or 5-pyrazolylcarbonyl, 2-, 4- or 5-thiazolylcarbonyl, 3-, 4- or 5-isothiazolylcarbonyl, 2-, 4- or 5-oxazolylcarbonyl, 1,2,3- or 1,2,4-triazolylcarbonyl, 1H- or 2H-tetrazolyl-carbonyl, 2-, 3- or 4-pyridylcarbonyl, 2-, 4- or 5-pyrimidylcarbonyl, 3- or 4-pyridazinylcarbonyl, quinolylcarbonyl, isoquinolylcarbonyl, indolylcarbonyl). When the "hydrocarbon group" is a cycloalkyl group, an aryl group or an aralkyl group, it may be substituted by, for example, $C_{1-10}$ alkyl groups (e.g., methyl, ethyl, propyl, isopropyl, decyl), $C_{2-10}$ alkenyl groups (e.g., vinyl, allyl, 2-butenyl, 3-butenyl), phenyl-$C_{2-4}$ alkenyl groups (e.g., phenylethenyl), mono- or di-$C_{1-6}$ alkenyl-carbamoyl groups (e.g., N-vinylcarbamoyl), $C_{6-14}$ aryl groups (e.g., phenyl, 1-naphthyl, 2-naphthyl), $C_{7-20}$ aralkyl groups [e.g., benzyl, 2-phenylethyl, 3-phenylpropyl, 4-phenylbutyl, 5-phenylpentyl, 6-phenylhexyl, 2-(1-naphthyl)ethyl, 2-(2-naphthyl)ethyl], styryl groups, oxo group, and the like. For the "hydrocarbon group," 1 to 4 substituents may be present at any possible positions.

The heterocyclic group for the term "heterocyclic group that may be substituted" as used herein is exemplified by 5- to 8-membered rings, or condensed rings thereof, containing 1 to 4 hetero atoms selected from atoms of oxygen, sulfur, nitrogen etc., in addition to carbon atoms, more specifically 5-membered ring groups containing 1 to 4 hetero atoms selected from atoms of oxygen, sulfur, nitrogen etc., in addition to carbon atoms, such as 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl and 1H- or 2H-tetrazolyl; 6-membered cyclic ring groups containing 1 to 4 hetero atoms selected from atoms of oxygen, sulfur, nitrogen etc., in addition to carbon atoms, such as N-oxide-2-, 3- or 4-pyridyl, 2-, 4- or 5-pyrimidinyl, N-oxide-2-, 4- or 5-pyrimidinyl, thiomorpholinyl, morpholinyl, oxoimidazinyl, dioxotriazinyl, pyrrolidinyl, piperidinyl, pyranyl, thiopyranyl, 1,4-oxazinyl, 1,4-thiazinyl, 1,3-thiazinyl, piperazinyl, triazinyl, oxotriazinyl, 3- or 4-pyridazinyl, pyrazinyl and N-oxide-3- or 4-pyridazinyl; and bicyclic or tricyclic condensed ring groups containing 1 to 4 hetero atoms selected from atoms of oxygen, sulfur, nitrogen etc., in addition to carbon atoms, such as benzofuryl, benzothiazolyl, benzoxazolyl, tetrazolo[1,5-b] pyridazinyl, triazolo[4,5-b]pyridazinyl, benzimidazolyl, quinolyl, isoquinolyl, cinnolinyl, phthalazinyl, quinazolinyl, quinoxalinyl, indolidinyl, quinolidinyl, 1,8-naphthylidinyl, purinyl, pteridinyl, dibenzofuranyl, carbazolyl, acridinyl, phenanthridinyl, chromanyl, benzoxazinyl, phenazinyl, phenothiazinyl and phenoxazinyl.

The "substituent" for the "heterocyclic group that may be substituted" is exemplified by the groups mentioned to exemplify the "substituent" for the "hydrocarbon group that may be substituted" described above, particularly substituents for the "hydrocarbon group" when it is a cycloalkyl group, an aryl group or an aralkyl group. One to 5, preferably 1 or 2 such substituents may be present at any possible positions on the heterocyclic ring.

The term "ring formed with the adjacent nitrogen atom" as used herein is exemplified by 4- to 6-membered cyclic amino groups (e.g., 1-pyrrolidinyl, piperidino, morpholino, 1-piperazinyl).

With respect to the above formula (I), when both Y and Z are a bond, R is preferably —A—$R^1$; preferable groups for A include —CO—, —SO$_2$— and —COO—, preferable groups for $R^1$ include $C_{7-20}$ aralkyl groups that may be substituted and $C_{6-14}$ aryl groups that may be substituted. Preferable groups for $R^2$ and $R^3$ include hydrogen atoms and lower alkyl groups that may be substituted. $R^4$ is preferably a hydrogen atom, a lower alkyl group that may be substituted, or the like. It is preferable that p, m and n be 1 to 3, and that X be O.

With respect to the above formula (I), when Y is —CO—, m is preferably 0, preferable group for R includes $C_{7-20}$ aralkyl groups that may be substituted. Preferable groups for $R^2$ and $R^3$ include a hydrogen atom or lower alkyl groups that may be substituted. p and n are preferably 1 to 3. x is preferably an oxygen atom.

The "$C_{7-20}$ aralkyl group" and "substituent" for the term "$C_{7-20}$ aralkyl group that may be substituted" as used herein are exemplified by the groups mentioned for the "hydrocarbon group that may be substituted" described above.

The "$C_{6-14}$ aryl group" and "substituent" for the term "$C_{6-14}$ aryl group that may be substituted" as used herein are exemplified by the groups mentioned for the "hydrocarbon group that may be substituted" described above.

The term "lower alkyl group" as used herein indicates a linear or branched alkyl group having 1 to 6 carbon atoms, such as methyl, ethyl, propyl, isopropyl, butyl, isobutyl, sec-butyl, tert-butyl, pentyl or hexyl.

The "lower alkyl group" for the "lower alkyl group that may be substituted" mentioned as a preferable group for $R^2$, $R^3$ and $R^4$ above is exemplified by the groups mentioned above; the "substituent" is exemplified by 1 to 4 substituents selected from halogens, lower alkoxy groups, hydroxy group, lower alkoxycarbonyl groups, carboxyl group, carbamoyl group, lower alkylcarbamoyl groups, pyridylthio group etc. Here, useful halogens include fluorine, chlorine, bromine and iodine. Useful lower alkoxy groups include linear or branched alkoxy groups having 1 to 6 carbon atoms, such as methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethyl-propoxy, 1-ethylpropoxy, hexyloxy, isohexyloxy, 1,1-dimethylbutoxy, 2,2-dimethylbutoxy, 3,3-dimethylbutoxy and 2-ethylbutoxy. Useful lower alkoxycarbonyl groups include alkoxycarbonyl groups having 1 to 6 carbon atoms in their alkoxy moiety, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyl-oxycarbonyl and tert-pentyloxycarbonyl. Useful lower alkylcarbamoyl groups include N-alkylcarbamoyl groups having 1 to 6 carbon atoms in their alkyl moiety, such as N-methylcarbamoyl, N-ethylcarbamoyl, N-propylcarbamoyl and N-butylcarbamoyl; N,N-dialkylcarbamoyl groups having 1 to 6 carbon atoms in their alkyl moiety, such as N,N-dimethylcarbamoyl, N,N-diethylcarbamoyl, N,N-dipropylcarbamoyl, N,N-dibutylcarbamoyl and N-ethyl-N-methylcarbamoyl; and 5- or 6-membered cyclic aminocarbonyl groups, such as 1-azetidinylcarbonyl, morpholinocarbonyl, 1-pyrrolidinylcarbonyl, 1-piperidinocarbonyl and 1-piperazinylcarbonyl.

The salt of compound (I) or (I') is exemplified by acid adduct salts. Acids used to form such salts include inorganic acids such as hydrochloric acid, hydrobromic acid, sulfuric acid and phosphoric acid, and organic acids such as acetic acid, oxalic acid, methanesulfonic acid, maleic acid, fumaric acid, citric acid, tartaric acid and lactic acid. Provided that compound (I) or (II) has an acidic group, such as —COOH, in a substituent thereof, it may form a salt with an inorganic base (e.g., an alkali metal or alkaline earth metal such as sodium, potassium, calcium or magnesium, or ammonia) or an organic base (e.g., a tri-$C_{1-3}$ alkylamine such as triethylamine). The salt is preferably a pharmaceutically acceptable salt.

When the above-described compounds have asymmetric carbons in their molecular structure, two kinds of stereoisomers, respectively of the R- and S-configurations, are present, both of which (and mixtures thereof) are included in the scope of the present invention.

Examples of the compound (I) of the present invention or salt thereof are given below.

1-(2-dimethylaminomethyl-6,7-dihydro-4H-furo[3,2-c]pyridin-5-yl)-6-phenylhexan-1-one,
1-(2-dimethylaminomethyl-5,7-dihydro-4H-furo[2,3-c]pyridin-6-yl)-6-phenylhexan-1-one,
N,N-dimethyl-[6-(4-phenylbutoxycarbonyl)-4,5,6,7-tetrahydrofuro[2,3-c]pyridin-2-ylmethyl]amine,
N,N-dimethyl-[5-(5-phenylpentylsulfonyl)-4,5,6,7-tetrahydrofuro[3,2-c]pyridin-2-ylmethyl]amine,
N,N-dimethyl-[6-(4-benzoylbenzoyl)-4,5,6,7-tetrahydrofuro[2,3-c]pyridin-2-ylmethyl]amine,
N,N-diethyl-[6-(4-benzoylbenzoyl)-4,5,6,7-tetrahydrofuro[2,3-c]pyridin-2-ylmethyl]amine,
1-(2-methylaminomethyl-5,7-dihydro-4H-furo[2,3-c]pyridin-6-yl)-6-phenylhexan-1-one,
1-(2-dimethylaminomethyl-4,5,6,8-tetrahydrofuro[2,3-c]azepin-7-yl)-6-phenylhexan-1-one,
N,N-dimethyl-[6-(4-phenethylbenzoyl)-4,5,6,7-tetrahydrofuro[2,3-c]pyridin-2-ylmethyl]amine,
N,N-dimethyl-[6-(4-benzyloxybenzoyl)-4,5,6,7-tetrahydrofuro[2,3-c]pyridin-2-ylmethyl]amine,
6-[4-(1-phenylethenyl)benzoyl]-2-(1-pyrrolidinylmethyl)-4,5,6,7-tetrahydrofuro[2,3-c]pyridine,
N,N-dimethyl-[6-[4-(1-phenylcyclopropyl)benzoyl]-4,5,6,7-tetrahydrofuro[2,3-c]pyridin-2-ylmethyl]amine,
N,N-dimethyl-[6-[4-(2-phenyl-1,3-dithiolane-2-yl)benzoyl]-4,5,6,7-tetrahydrofuro[2,3-c]pyridin-2-ylmethyl]amine,
(Z)-5-(3-chlorostilbene-4'-sulfonyl)-2-(1-pyrrolidinylmethyl)-4,5,6,7-tetrahydrofuro[3,2-c]pyridine,
2-dimethylaminomethyl-5-(6-phenylhexyl)-6,7-dihydro-5H-furo[3,2-c]pyridin-4-one, or an acid addition salts thereof.

The compound (I) of the present invention or salt thereof can, for example, be synthesized by the methods described below.

Method (A)

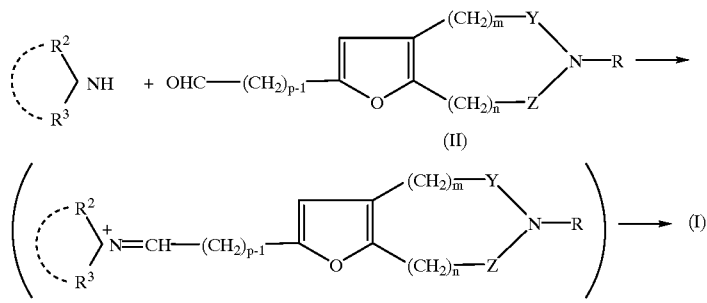

wherein the symbols have the same definitions as those given above.

Method (B)

Formula (I) wherein $R^2$ and $R^3$ independently represent a hydrocarbon group, with p=1.

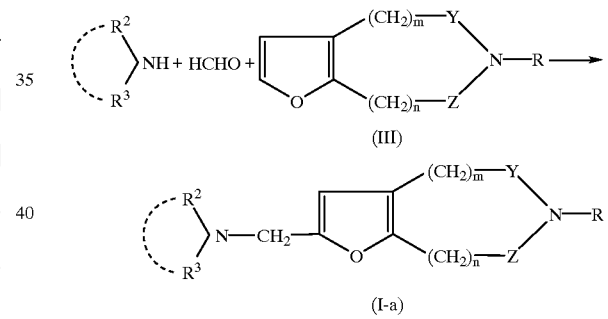

wherein the symbols have the same definitions as those given above.

Method (C)

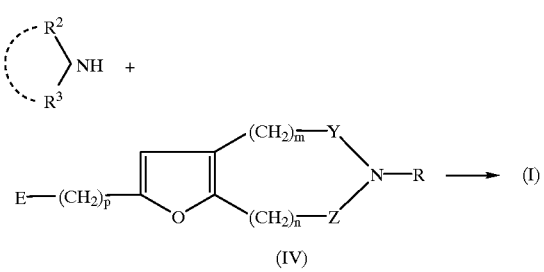

wherein E represents a halogen such as chlorine, bromine or iodine, or a leaving group such as a methanesulfonyloxy or p-toluenesulfonyloxy; the other symbols have the same definitions as those given above.

Method (D)

Formula (I) wherein $R^2$ and $R^3$, independently represent a hydrocarbon group.

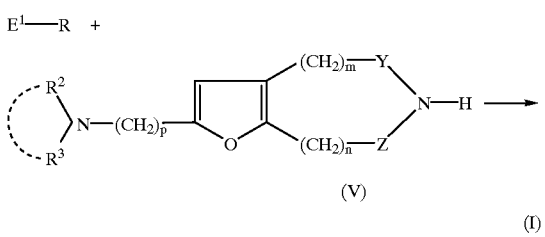

(I)

wherein $E^1$ represents a halogen such as chlorine, bromine or iodine, or a leaving group such as a methanesulfonyloxy, p-toluenesulfonyloxy or phenoxy group or —O—A—$R^1$ (A and $R^1$ have the same definitions as those given above); the other symbols have the same definitions as those given above.

In methods A through D described above, the starting compound capable of forming a salt may be used in a salt form. Such salts include, but are not limited to, the salts mentioned for compound (I) above. In the following description of the respective methods, all compounds include their salts.

In method A, compound (I) is obtained by what is called a reductive amination reaction, by which compound (II) is reacted with ammonia or a primary or secondary amine (NH($R_2$)($R_3$)) to yield an imine or iminium ion, which is then reduced to an amine. In this reaction, the amount of ammonia or amine used is 1 equivalent or more (preferably 1–10 equivalents), relative to compound (II). In this case, an acid (e.g., a mineral acid such as hydrochloric acid, phosphoric acid or sulfuric acid, or an organic acid such as toluenesulfonic acid, methanesulfonic acid or acetic acid) may be added at 0.1 to 2 equivalents. Useful methods of reduction include reduction with reducing agents, e.g., metal-hydrogen complex compounds such as sodium borohydride, sodium cyanoborohydride and lithium aluminum hydride, and diborane; catalytic reduction in the presence of catalysts such as palladium and Raney nickel; and electrolytic reduction with lead or platinum as the cathode. The amount of reducing agent used is 1 equivalent or more (preferably 1–10 equivalents). The solvent used can be chosen as appropriate, according to the method of reduction used. Useful solvents include alcohols (e.g., methanol, ethanol), ethers (e.g., tetrahydrofuran, dioxane, diethyl ether), halogenated hydrocarbons (e.g., methylene chloride, chloroform), aprotonic polar solvents (e.g., N,N-dimethylformamide, dimethyl sulfoxide). Reaction time is normally 0.5 to 72 hours, preferably 1 to 24 hours. Reaction temperature is –30 to 100° C. (preferably 0 to 60° C.).

Method B is a method by which compound (I) is obtained by Mannich reaction of compound (III), formaldehyde and a secondary (NH($R^2$)($R^3$)) amine to yield an aminomethyl derivative. In this reaction, the amount of secondary amine used is 1 equivalent or more (preferably 1–10 equivalents), and the amount of formaldehyde used is 1 equivalent or more (preferably 1–10 equivalents), relative to compound (III). The solvent used is exemplified by alcohols (e.g., methanol, ethanol), ethers (e.g., tetrahydrofuran, dioxane, diethyl ether), halogenated hydrocarbons (e.g., methylene chloride, chloroform) and lower fatty acids (e.g., acetic acid, propionic acid). Reaction time is normally 0.5 to 24 hours, preferably 1 to 6 hours. Reaction temperature is –30 to 150° C. (preferably 20 to 120° C.).

Method C is a method by which compound (I) is obtained by reaction of compound (IV) with an amine. In this reaction, the amount of amine used is 1 equivalent or more (preferably 1–10 equivalents), relative to compound (IV). In this reaction, 1–10 equivalents of a basic compound, such as sodium hydroxide, potassium hydroxide, sodium hydride, potassium carbonate, triethylamine, diisopropylethylamine, pyridine, 1,8-diazabicyclo[5.4.0]-7-undecene or 1,4-diazabicyclo[2.2.2]octane (DABCO) may be used. The reaction may also be carried out in the presence of 1 equivalent or more (preferably 1–10 equivalents) of sodium iodide as a reaction accelerator. The solvent used is exemplified by water, alcohols (e.g., methanol, ethanol), ethers (e.g., tetrahydrofuran, dioxane, diethyl ether), halogenated hydrocarbons (e.g., methylene chloride, chloroform), ketones (e.g., acetone, methyl ethyl ketone) and aprotonic polar solvents (e.g., N,N-dimethylformamide, dimethyl sulfoxide). Reaction time is normally 10 minutes to 24 hours, preferably 0.5 to 6 hours. Reaction temperature is –20 to 200° C.

Method D is a method by which compound (I) is obtained by reaction of compound (V) with $E^1$—R. This reaction is carried out under the same conditions as for the reaction of compound (IV) and an amine in method C.

Compound (II) can, for example, be synthesized by the methods described below.

(i)

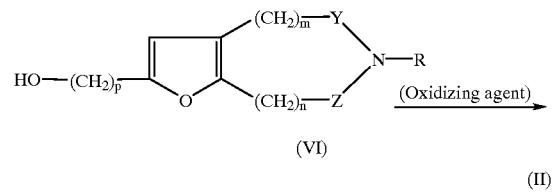

In the oxidation reaction of compound (VI), the oxidizing agent is used at 1 to 20 equivalents, relative to compound (VI). Such oxidizing agents include activated manganese dioxide, pyridinium chlorochromate (PCC), pyridinium dichromate (PDC), dimethyl sulfoxide-acid anhydrides (e.g., acetic anhydride, trifluoroacetic anhydride), dimethyl sulfoxide-thionyl chloride, dimethyl sulfoxide-sulfuryl chloride, dimethyl sulfoxide-oxalyl chloride, dimethyl sulfoxide-chlorine, and dimethyl sulfoxide-dicyclohexylcarbodiimide (DCC) in the presence of an acid (e.g., phosphoric acid, trifluoroacetic acid, dichloroacetic acid). The solvent used can be chosen as appropriate, according to the kind of oxidizing agent used. Useful solvents include ethers (e.g., tetrahydrofuran, dioxane, diethyl ether), halogenated hydrocarbons (e.g., methylene chloride, chloroform), ketones (e.g., acetone, methyl ethyl ketone) and aprotonic polar solvents (e.g., N,N-dimethylformamide, dimethyl sulfoxide). Reaction time is normally 0.5 to 48 hours, preferably 1 to 24 hours. Reaction temperature is chosen as appropriate over the range from –80 to 100° C., according to the type of oxidizing agent used.

(ii) p=1

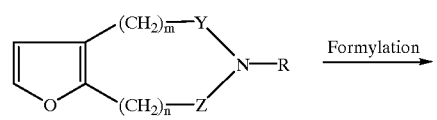

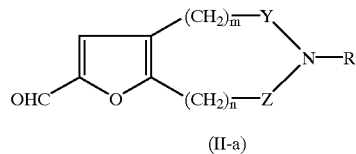

(II-a)

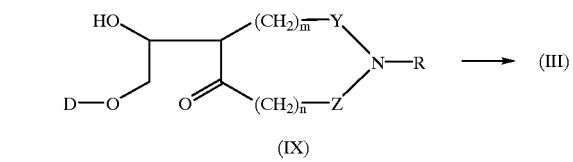

(IX)

In the formylation reaction of compound (III), 1 to 5 equivalents of a formylating agent is used, relative to equivalent of compound (III). Such formylating agents include N,N-dimethylformamide-phosphorus oxychloride (Vilsmier reagent). Useful solvent include ethers (e.g., tetrahydrofuran, dioxane, diethyl ether), halogenated hydrocarbons (e.g., methylene chloride, chloroform), hydrocarbons (e.g., hexane, pentane, benzene, toluene) and aprotonic polar solvents (e.g., N,N-dimethylformamide, dimethyl sulfoxide). Reaction time is normally 0.5 to 48 hours, preferably 1 to 24 hours. Reaction temperature is −20 to 100° C. (preferably 0 to 80° C.). The formylation reaction of compound (III) can also be carried out by reacting compound (III) with 1 to 3 equivalents of an organic lithium reagent, then reacting with 1–10 equivalents of a formamide (e.g., N,N-dimethylformamide, N-methylformanilide). Useful organic lithium reagents include n-butyl lithium and phenyl lithium. Solvents for this formylation include ethers (e.g., tetrahydrofuran, dioxane, diethyl ether) and hydrocarbons (e.g., hexane, pentane, benzene, toluene). Reaction time is normally 0.5 to 48 hours, preferably 1 to 24 hours. Reaction temperature is normally −100 to 50° C., (preferably −80 to 0° C.).

Compound (III) can, for example, be synthesized by the methods described below.

(i)

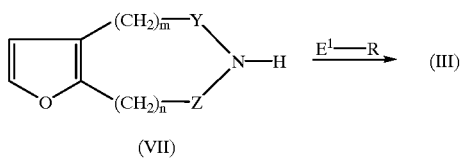

(VII)

Reaction of compound (VII) with $E^1$—R can be carried out under the same conditions as for the reaction of compound (IV) and an amine in method C.

(ii) n=1 and R is —A—$R^1$ (A=bond, C=O or C(=O)O)

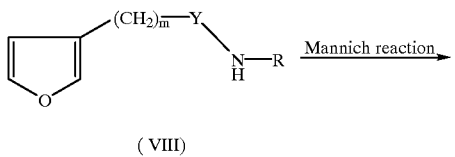

(VIII)

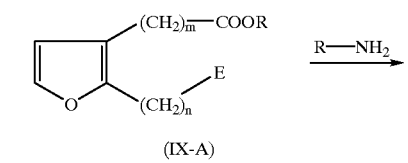

(III-a)

In the cyclization of compound (VIII) with a formaldehyde by the Mannich reaction, a formaldehyde is used in excess (preferably 2 to 20 equivalents), relative to compound (VIII). This reaction can be carried out under the same conditions as for the Mannich reaction of compound (III) and an amine in method B.

wherein D represents a hydroxyl group-protecting group, such as trityl, trimethylsilyl, t-butyldimethylsilyl, benzyloxymethyl or methoxymethyl.

The cyclization reaction of compound (IX) is carried out using an acid in an amount of 1 equivalent or more (preferably 2 to 20 equivalents), relative to compound (IX), after the hydroxyl group-protecting group is removed from compound (IX). Removal of the hydroxyl group-protecting group can be achieved under conditions of commonly known reactions. When the hydroxyl group-protecting group can be removed under acidic conditions, e.g., trityl, trimethylsilyl, t-butyldimethylsilyl, benzyloxymethyl or methoxymethyl, the cyclization reaction can be carried out simultaneously with protecting group removal. Such acids include mineral acids such as hydrochloric acid, phosphoric acid and sulfuric acid, and organic acids such as toluenesulfonic acid, methanesulfonic acid and acetic acid. The solvent used is exemplified by water, alcohols (e.g., methanol, ethanol) and ethers (e.g., tetrahydrofuran, dioxane). Reaction time is normally 0.5 to 48 hours, preferably 1 to 24 hours. Reaction temperature is −20 to 100° C. (preferably 0 to 80° C.).

(iv) Y is —CO—, Z is a bond

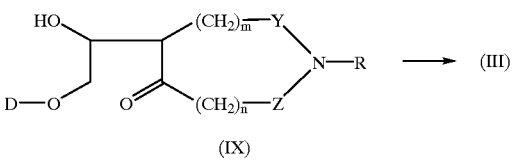

(IX-A)

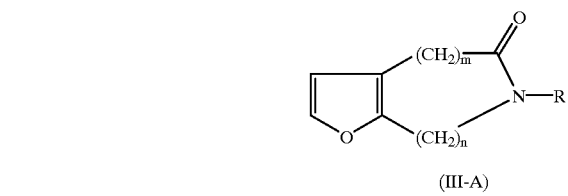

(III-A)

The reaction of compound (IX-A) with R—$NH_2$ can be carried out under the same conditions as for the reaction of compound (IV) with amine in Method C.

(v) Y is a bond, Z is —CO—

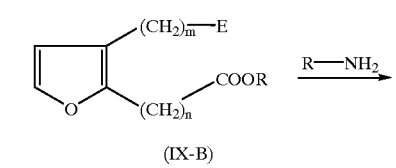

(IX-B)

-continued

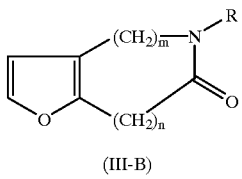

(III-B)

The reaction of compound (IX-B) with R—NH$_2$ can be carried out under the same conditions as for the reaction of compound (IV) with amine in Method C.

Compound (IV) can, for example, be synthesized by the method described below.

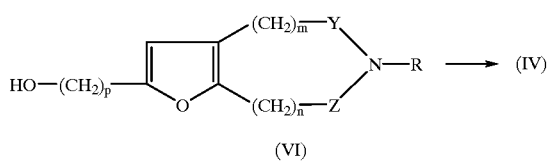

When E is a halogen, conversion of the hydroxyl group of compound (VI) to E is achieved by reacting 1 equivalent of compound (VI) with 1 to 5 equivalents of a halogenating agent, e.g., a phosphorus halide such as phosphorus trichloride, phosphorus oxychloride, phosphorus pentachloride or phosphorus tribromide, red phosphorus with halogen, or thionyl chloride. When E is a toluenesulfonyloxy group or a methanesulfonyloxy group, such conversion is achieved by reacting 1 equivalent of compound (VI) with 1 to 5 equivalents of toluenesulfonyl chloride or methanesulfonyl chloride. In this reaction, 1 to 10 equivalents of an inorganic base such as potassium carbonate or sodium hydrogen carbonate, or an organic base such as 4-N,N-dimethylaminopyridine, triethylamine, pyridine, dimethylaniline or 1,4-diazabicyclo[2.2.2]octane (DABCO) may be used. Useful solvents include halogenated hydrocarbons (e.g., methylene chloride, chloroform, dichloroethane), ethers (e.g., diethyl ether, tetrahydrofuran), esters (e.g., methyl acetate, ethyl acetate) and aprotonic polar solvents (e.g., N,N-dimethylformamide, dimethyl sulfoxide, acetonitrile). Reaction temperature is 0 to 100° C. (preferably 0 to 50° C.). Reaction time is normally 10 minutes to 100 hours, preferably 3 to 24 hours.

Compound (V) can, for example, be synthesized by the method described below.

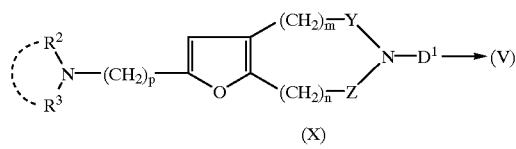

wherein D$^1$ represents a secondary amino group-protecting group, such as benzyloxycarbonyl, tert-butoxycarbonyl, trifluoroacetyl, trityl or benzyl; the other symbols have the same definitions as those given above.

Removal of the secondary amino group from compound (X) can be achieved under conditions of commonly known reactions. For example, a benzyloxycarbonyl group or a benzyl group, as a protecting group for the amino group, can be removed in the presence of a catalyst (e.g., palladium-carbon, platinum oxide) in a solvent (e.g., alcohol, acetic acid, water, tetrahydrofuran, mixture thereof) by catalytic reduction reaction (at room temperature to 100° C.). When the protecting group is a trityl group or a tert-butoxycarbonyl group, it can be removed at 0 to 150° C. in a solvent (e.g., water, alcohol, tetrahydrofuran, dioxane) in the presence of an acid (e.g., a mineral acid such as hydrochloric acid, phosphoric acid or sulfuric acid, or an organic acid such as toluenesulfonic acid, methanesulfonic acid or acetic acid). When the protective group is a tert-butoxycarbonyl group, it can also be removed by treatment with iodotrimethylsilane in a solvent such as chloroform. A trifluoroacetyl group as a protective group can easily be removed by treatment with an alkali (e.g., aqueous solution of sodium hydroxide or sodium hydrogen carbonate). Reaction time is normally 10 minutes to 48 hours, preferably 10 minutes to 24 hours.

Compound (VI) can, for example, be synthesized by the methods described below.

(i) p=1

In the reduction of compound (II), a reducing agent is used in an amount of 1 equivalent or more (preferably 1–10 equivalents), relative to compound (II). Reducing agents include metal-hydrogen complex compounds such as sodium borohydride, sodium cyanoborohydride and lithium aluminum hydride, and diborane. The solvent used can be chosen as appropriate, according to the type of reducing agent used. Useful solvents include alcohols (e.g., methanol, ethanol), ethers (e.g., tetrahydrofuran, dioxane, diethyl ether), halogenated hydrocarbons (e.g., methylene chloride, chloroform) and aprotonic polar solvents (e.g., N,N-dimethylformamide, dimethyl sulfoxide). Reaction time is normally 0.5 to 72 hours, preferably 1 to 24 hours. Reaction temperature is −30 to 100° C.

(ii) p≧2

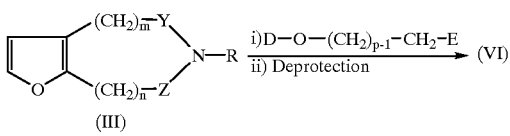

Reaction of compound (III) with D—O—(CH$_2$)$_{p-1}$—CH$_2$—E is carried out by reacting compound (III) with 1 to 3 equivalents of an organic lithium reagent, then reacting with 1 to 10 equivalents of D—O—(CH$_2$)$_{p-1}$—CH$_2$—E. Useful organic lithium reagents include n-butyl lithium and phenyl lithium. Solvents for this alkylation include ethers (e.g., tetrahydrofuran, dioxane, diethyl ether) and hydrocarbons (e.g., hexane, pentane, benzene, toluene). Reaction time is normally 0.5 to 48 hours, preferably 1 to 24 hours. Reaction temperature is normally −100 to 50° C., preferably −80 to 0° C. Removal of the hydroxyl group-protecting group can be achieved under conditions of commonly known reactions.

Compound (VII) can, for example, be synthesized by the methods described or cited in the Journal of Organic Chemistry, 1991, vol. 56, pp. 2936–2938, or the Journal of Heterocyclic Chemistry, 1990, vol. 27, pp. 1169–1171, or modifications thereof.

Compound (VIII) can, for example, be synthesized by the method described below.

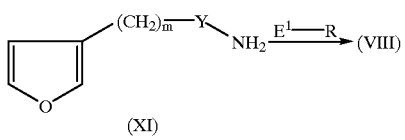

(XI)

Reaction of compound (XI) with E¹—R can be carried out under the same conditions as for the reaction of compound (V) with E¹—R in method D.

Compound (IX) can, for example, be synthesized by the method described below.

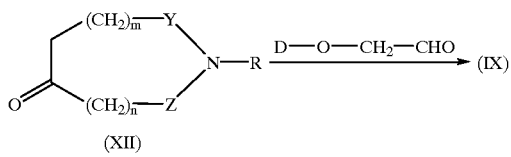

(XII)

Aldol reaction of compound (XII) with D—O—CH$_2$—CHO is carried out by reacting compound (III) with 1 to 3 equivalents of an organic lithium reagent to yield lithium enolate, followed by reaction with 1 to 3 equivalents of D—O—CH$_2$—CHO. Alternatively, this aldol reaction can be carried out by the method in which the lithium enolate is converted to the enolate of titanium, boron, tin, aluminum, magnesium, or the like, then the enolate is reacted with D—O—CH$_2$—CHO; or the method in which compound (XII) is converted to an enamine, which is then reacted with 1 to 3 equivalents of an organic lithium reagent, and further with 1 to 3 equivalents of D—O—CH$_2$—CHO [Journal of American Chemical Society, 1980, vol. 102, pp. 5866–5872]. Useful organic lithium regents include lithium diisopropylamide (LDA), n-butyl lithium and phenyl lithium. Solvents for the aldol reaction include ethers (e.g., tetrahydrofuran, dioxane, diethyl ether) and hydrocarbons (e.g., hexane, pentane, benzene, toluene). Reaction time is normally 0.5 to 48 hours, preferably 1 to 24 hours. Reaction temperature is normally –100 to 50° C., (preferably –80 to 0° C).

Compound (X) can be synthesized under the same conditions as for the reactions in methods A, B and C, when R is an amino group-protecting group (D¹) in compounds (II), (III) and (IV), respectively.

Compound (XI) can, for example, be synthesized by the methods described or cited in the Journal of Heterocyclic Chemistry, 1990, vol. 27, pp. 1169–1171, or modifications thereof.

Compound (XII) can, for example, be synthesized by the method described below.

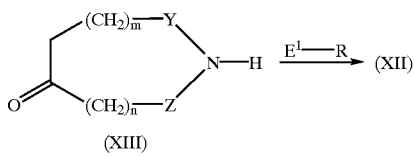

(XIII)

Reaction of compound (XIII) with E¹—R is carried out under the same conditions as for the reaction of compound (V) with E¹—R in method D.

Compound (XIII) can be synthesized by the methods described or cited in the Journal of American Chemical Society, 1931, vol. 53, pp. 2692–2696, or the Journal of Organic Chemistry, 1945, vol. 10, pp. 277–282, or modifications thereof.

Compound (IX-A) can fpr example, be synthesized by the method described below.

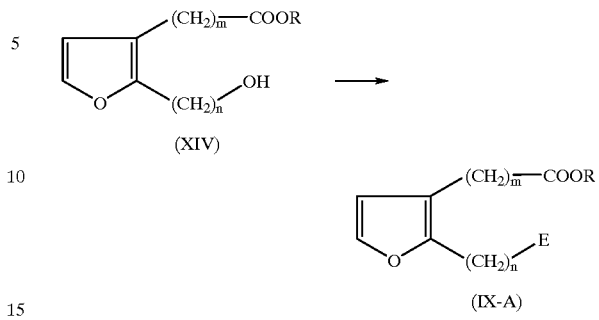

Conversion of compound (XIV) into compound (IX-A) is carried out under the same conditions as for the conversion of (VI) into compound (IV).

Compound (IX-B) can for example, be synthesized by the method described below.

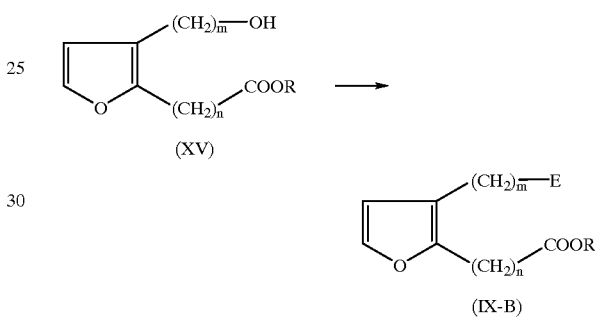

Conversion of compound (XV) into compound (IX-B) is carried out under the same conditions as for the conversion of compound (VI) into compound (IV).

Comopound (XIV) can for example, be synthesized by the method described below.

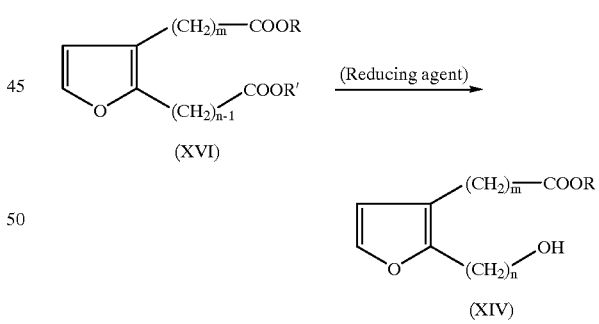

The reduction of compound (XVI) is carried out under the same conditions as for the reduction of compound (II) in the synthesis of (VI).

Compound (XV) can for example, be synthesized by the method described or cited in Tetrahedron letters, 1983, vol. 24, pp. 5835–5838.

Compound (XVI) can for example, be synthesized by the method described or cited in Chem. Pharm. Bull, 1994, vol. 42, pp. 2167–2169.

When the starting compound, used in each of the reactions for synthesizing the above-described desired compounds or starting compounds, has an amino group, carboxyl group or hydroxyl group as a substituent, these substituents may have a protective group in common use in peptide chemistry etc.; the desired compound can be obtained by removing as appropriate the protective group after completion of the reaction.

Amino group-protecting groups include $C_{1-6}$ alkylcarbonyls that may be substituted (e.g., formyl, methylcarbonyl, ethylcarbonyl), phenylcarbonyl, $C_{1-6}$ alkyloxycarbonyls (e.g., methoxycarbonyl, ethoxycarbonyl), phenyloxycarbonyls (e.g., benzoxycarbonyl), $C_{7-10}$ aralkyl-carbonyls (e.g., benzyloxycarbonyl), trityl and phthaloyl. Substituents for these groups include halogen atoms (e.g., fluorine, chlorine, bromine, iodine), $C_{1-6}$ alkyl-carbonyls (e.g., methylcarbonyl, ethylcarbonyl, butylcarbonyl) and nitro groups, the number of substituents being 1 to 3.

Carboxyl group-protecting groups include $C_{1-6}$ alkyls that may be substituted (e.g., methyl, ethyl, n-propyl, i-propyl, n-butyl, tert-butyl), phenyl, trityl and silyl. Substituents for these groups include halogen atoms (e.g., fluorine, chlorine, bromine, iodine), $C_{16}$ alkylcarbonyls (e.g., formyl, methylcarbonyl, ethylcarbonyl, butylcarbonyl) and nitro groups, the number of substituents being 1 to 3.

Hydroxyl group-protecting groups include $C_{1-6}$ alkyls that may be substituted (e.g., methyl, ethyl, n-propyl, i-propyl, n-butyl, tert-butyl), phenyl, $C_{7-10}$ aralkyls (e.g., benzyl), $C_{1-6}$ alkylcarbonyls (e.g., formyl, methylcarbonyl, ethylcarbonyl), phenyloxycarbonyls (e.g., benzoxycarbonyl), $C_{7-10}$ aralkyl-carbonyls (e.g., benzyloxycarbonyl), pyranyl, furanyl and silyl. Substituents for these groups include halogen atoms (e.g., fluorine, chlorine, bromine, iodine), $C_{1-6}$ alkyls, phenyl, $C_{7-10}$ aralkyls and nitro groups, the number of substituents being 1 to 4.

Protecting groups can be removed by commonly known methods or modifications thereof, including treatments with acids, bases, reducing agents, ultraviolet rays, hydrazine, phenylhydrazine, sodium N-methyldithiocarbamate, tetrabutylammonium fluoride, palladium acetate etc.

Compound (I) is fractionally purified from the reaction mixture by ordinary methods of fractional purification (e.g., extraction, concentration, filtration, recrystallization, column chromatography, thin-layer chromatography).

When compound (I) is obtained in free form, it can be converted into a salt by a known method or a modification thereof (e.g., neutralization). When compound (I) is obtained as a salt, it can be converted into a free form or another salt, by a known method or a modification thereof.

Compound (I') can, for example, be synthesized by methods similar to production methods (A) through (D) for compound (I), and can also be synthesized by the method described in PCT International Application 93/13105 or a modification thereof.

Compound (I') of the present invention and pharmaceutically acceptable salts thereof possess 2,3-oxidosqualene cyclase-inhibiting activity, cholesterogenesis-inhibiting activity, low-density lipoprotein (LDL) receptor-increasing activity, high density lipoprotein-cholesterol elevating activity and antifungal activity.

They are useful as lipid-modifying agent and particularly suited to the treatment and prevention of hyperlipidemic diseases, particularly hypercholesterolemia, hyperlipoproteinemia and hypertriglyceridemia, atherosclerotic vascular lesions caused thereby and diseases subsequent thereto, such as coronary heart disease (CHD), cerebral ischemia, intermittent claudication, necrosis, glomerulosclerosis and nephropathy, in mammals (e.g., mice, rats, rabbits, dogs, cats, bovines, swines, humans). In treating these diseases, the compound represented by general formula (I') or salt thereof may be used alone, or in combination with other cholesterol- or lipid-lowering drugs. Although these compounds may be administered non-orally, it is preferable that they may be administered as oral preparations; they may also be administered in the form of rectal preparations as suppositories. Concomitantly usable components include bile acid-binding resins (e.g., cholestyramine, colestipol), cholesterol absorption-suppressing compounds (e.g., sitosterol, neomycin) and cholesterogenesis-inhibiting compounds (e.g., HMG-COA reductase inhibitors such as lovastatin, simvastatin and pravastatin, squalene epoxidase inhibitors, squalene synthase inhibitors). Other concomitantly usable components include fibrates, such as clofibrate, bezafibrate and gemfibrozil, nicotinic acid and derivatives and analogs thereof, such as acipimox and probucol. Concomitant use of hypotensive agents, such as calcium antagonists, al receptor blockers, angiotensin-converting enzyme inhibitors and angiotensin receptor antagonists, is also possible.

The compound represented by general formula (I') or salt thereof is suited to the treatment of diseases associated with excess cell proliferation. Major examples of diseases associated with excess cell proliferation are tumors. Tumor growth is reportedly suppressed by serum cholesterol level reduction or cholesterol biosynthesis inhibition by HMG-CoA reductase inhibitors, in cell culture and in vivo (Lancet 339:1154–1156, 1992). Possessing cholesterogenesis-inhibiting activity, compound (I') of the present invention or salt thereof can therefore be used to treat tumors, either alone or in combination with known therapies. Other diseases to which compound (I') of the present invention or salt thereof is applicable include hyperplastic dermal diseases, such as psoriasis, basal cell carcinoma, squamous cell carcinoma, keratosis and cornifying diseases.

Hyperplastic vascular diseases, such as the vascular anastomosis and occlusion caused by surgical maneuvers such as PTCA (percutaneous transluminal coronary angioplasty) or bypass surgery, are based on smooth muscle cell proliferation; the compound of the present invention, judging from its cholesterogenesis inhibiting action, is also suited to the treatment and prevention of these diseases. In such cases, the compound may be used alone, or in combination with known active compounds, such as intravenous heparin, preferably by oral administration.

Among other potential uses of the compound of the present invention are the prevention and treatment of gallstones. When the biliary cholesterol level exceeds maximum solubility, cholesterol precipitates and forms biliary calculi. Lipid-lowering drugs, such as fibrates, increase neutral steroid secretion in bile, and enhances sensitivity to biliary calculus formation. In contrast, cholesterogenesis inhibitors, such as lovastatin and pravastatin, do not promote biliary calculus formation, but are capable of decreasing the biliary calculus formation index by decreasing the biliary cholesterol level (Gut 31:348–350, 1990). Also, lovastatin has been reported as effective in dissolving biliary calculi when combined with ursodeoxycholic acid (Gastroenterology 102, No. 4, Pt. 2, A319, 1992). The compound of the present invention is therefore suited to the prevention and treatment of gallstones, judging from its mode of action. In such case, the compound may be used alone, or in combination with known therapeutic drugs (e.g., ursodeoxycholic acid) or known therapies (e.g., percussion wave lithotripsy), preferably by oral administration.

The substance of the present invention is a blood HDL-cholesterol-elevating agent. Because increased blood HDL-cholesterol promotes cholesterol efflux from cells with excess cholesterol (Current Opinion in Lipidology 4:392–400), the substance of the present invention is suited to the treatment and prevention of atherosclerosis. In consideration of its biological nature, the substance of the present invention is particularly suited to the treatment and prevention of atherosclerotic vascular lesions and diseases subsequent thereto, such as coronary artery disease (CHD), cerebral ischemia, intermittent claudication and necrosis.

Another use of the present invention is based on the antioxidant action of HDL. Blood lipid peroxides are much more sensitive to HDL than to LDL; HDL also serves to prevent lipid peroxidation in the body, such as LDL oxidation (Current Opinion in Lipidology 4:392–400; Current Opinion in Lipidology 5:354–364). The substance of the present invention is a blood HDL-cholesterol-increasing agent. In consideration of its biological nature, the substance of the present invention is suited to the treatment and prevention of atherosclerotic vascular lesions; diseases subsequent thereto, such as coronary heart disease (CHD), cerebral ischemia, intermittent claudication and necrosis; and allergies, inflammation, brain dysfunction, liver dysfunction, ophthalmologic diseases etc.

Still another use of the present invention targets hypertension and diseases subsequent thereto. HDL is known to prevent the inhibition of EDRF biosynthesis and liberation by oxidized LDL, and increase the vasohypotonic factor prostacyclin in macrophages (Current Opinion in Lipidology 5:354–364). The substance of the present invention is a blood HDL-cholesterol-elevating agent. In consideration of its biological nature, the substance of the present invention is particularly suited to the treatment and prevention of hypertension and diseases subsequent thereto, such as coronary heart disease (CHD) and cerebral ischemia.

A potential use of the substance of the present invention is based on cytoprotective action against cytotoxic secretions such as gastric/pancreatic juice and bile. Cells between humor and tissue mainly express apoJ, and serve as a natural barrier against cytotoxic secretions such as gastric/pancreatic juice and bile, HDL being an apoJ (clusterin) carrier (Current Opinion in Lipidology 4:392–400). In consideration of its blood HDL-cholesterol-elevating action, the substance of the present invention is suited to the treatment and prevention of gastric ulcer, pancreatitis, hepatitis etc.

Another potential use of the present invention is based on cell growth activity. HDL, alone or together with growth factors, promotes the growth of such cells as vascular endothelial cells (EC) and corneal endothelium, HDL also promoting the growth of human lymphocytes (Current Opinion in Lipidology 3:222–226). The substance of the present invention is a blood HDL-cholesterol-elevating agent. In consideration of its cell growth activity, the substance of the present invention is particularly suited to the treatment and prevention of atherosclerotic vascular lesions and diseases subsequent thereto, such as coronary artery disease and corneal damage. It is also suited to the treatment and prevention of diseases due to decreased immunocompetence, such as infectious diseases and malignant tumors.

As regards yet another potential use of the present invention, HDL specifically acts on transplanted human placental tissue to cause lactogen secretion, and also promotes apoE secretion from macrophages (Current Opinion in Lipidology 3:222–226). In consideration of its secretion-promoting activity, the substance of the present invention is suited to the treatment and prevention of fetal dysgenesis etc.

The compound of the present invention is also suited to the treatment of infectious diseases caused by such pathogenic microorganisms as *Candida albicans* and *Aspergillus niger*. As stated above, the final product of sterol biosynthesis in fungi is not cholesterol, but ergosterol, and is essential to fungal cell membrane survival and function. Suppression of ergosterol biosynthesis therefore affects fungal cell growth, probably resulting in fungal cell collapse. In the treatment of mycosis, the compound represented by general formula (I') or salt thereof can be administered orally or locally. These can be used singly, or in combination with known antifungal compounds, especially those which act on them in other stages of sterol biosynthesis, including terbinafine and naftifine, both squalene epoxidase inhibitors, and azole-type lanosterol-14$\alpha$-demethylase inhibitors, such as ketoconazole and fluconazole.

The compound of the present invention is also applicable to poultry rearing. In hen egg laying, administration of lovastatin, an HMG-CoA reductase inhibitor, has been reported as decreasing egg cholesterol content (FASEB Journal 4, A 533, Abstracts 1543, 1990). The production of low-cholesterol eggs is important, because eating such eggs can reduce the cholesterol load on the body, without changes in dietary habit. With cholesterogenesis-inhibiting activity, the compound of the present invention can be used to rear poultry for low-cholesterol egg production, and is preferably administered to feed additives.

Although compound (I') or salt thereof may be used in the form of bulk powder as such, it is normally administered in a preparation prepared by a conventional method, using appropriate amounts of ordinary pharmaceutical additives, such as excipients (e.g., calcium carbonate, kaolin, sodium hydrogen carbonate, lactose, starch, crystalline cellulose, talc, granular sugar, porous substances), binders (e.g., dextrin, rubbers, alcoholated starch, gelatin, hydroxypropyl cellulose, hydroxypropylmethyl cellulose, pullulan), disintegrating agents (e.g., carboxymethyl cellulose calcium, croscarmellose sodium, crospovidone, low-substitutional hydroxypropyl cellulose, partially alpha-converted starch), lubricants (e.g., magnesium stearate, calcium stearate, talc, starch, sodium benzoate), coloring agents (e.g., tar pigments, caramel, iron sesquioxide, titanium oxide, riboflavins), correctives (e.g., sweeteners, flavors), stabilizers (e.g., sodium sulfite) and preservatives (e.g., parabens, sorbic acid). The therapeutic agents of the present invention, including such preparations, contain compound (I') or salt thereof in an amount effective for treating or preventing the target disease. The content of compound (I') or salt thereof in the preparation of the present invention is normally 0.1 to 100% by weight of the entire preparation. The preparation for the present invention may contain as active ingredients pharmaceutical components other than compound (I') or salt thereof. These components are not subject to limitation, as long as the object of the present invention is accomplished, and may be used in appropriate mixing ratios. Useful dosage forms include tablets (including sugar-coated tablets and film-coated tablets), pills, capsules, granules, fine subtilaes, powders, syrups, emulsions, suspensions, injectable preparations, inhalants and ointments. These preparations are prepared by conventional methods (e.g., methods described in the Pharmacopoeia of Japan).

Specifically, tablets can be produced by granulating a pharmaceutical, or in a uniform mixture with excipients, binders, disintegrating agents and other appropriate additives, by an appropriate method, then adding lubricants etc., and subjecting the mixture to compressive shaping, or by subjecting to direct compressive shaping a pharmaceutical as-is, or in a uniform mixture with excipients, binders, disintegrating agents and other appropriate additives, or subjecting to compressive shaping previously prepared granules as-is, or in a uniform mixture with appropriate additives. These tablets may incorporate coloring agents, correctives etc. as necessary. These tablets may also be coated with appropriate coating agents.

Injectable preparations can be produced by dissolving, suspending or emulsifying a given amount of a pharmaceutical in an aqueous solvent such as water for injection, physiological saline or Ringer's solution, or a non-aqueous solvent such as a vegetable oil, and diluting to a given amount, or transferring a given amount of a pharmaceutical into an ampule for injection and sealing the ampule.

Useful carriers for oral preparations include substances in common use in pharmaceutical production, such as starch, mannitol, crystalline cellulose and carboxymethyl cellulose. Useful carriers for injectable preparations include distilled water, physiological saline, glucose solutions and transfusions. Other additives in common use for pharmaceutical production can also be added, as appropriate.

With low toxicity, the compound represented by the formula (I') or salt thereof can be safely used. Depending on patient condition and body weight, type of compound, route of administration and other factors, the daily dose of the compound or salt thereof is about 1–500 mg, preferably about 10–200 mg for each adult (about 60 kg), when orally administered as a lipid-modifying agent or hypercholesteremia remedy; no toxicity is noted within this dose range.

When the compound represented by the formula (I') or salt thereof is administered to mammals (e.g., humans, rats) as a 2,3-oxide squalene cyclase inhibitor, its daily effective dose is about 1–500 mg, preferably about 10–200 mg for each adult (about 60 kg), for oral administration, and about 0.1–100 mg, preferably about 1–20 mg for non-oral administration (e.g., injectable preparations, suppositories).

The compound represented by general formula (I) exhibits a broad spectrum of antibacterial activity, as determined by the broth or agar dilution method. When the compound represented by general formula (I') or salt thereof is administered to mammals (e.g., humans, rats) to treat fungal diseases, its daily effective dose is about 0.1–100 mg, preferably about 1–50 mg for each adult (about 60 kg), for oral administration, and about 0.1–100 mg, preferably about 1–50 mg/kg for non-oral administration (e.g., injectable preparations, suppositories). When the compound represented by general formula (I') or salt thereof is administered to treat fungal infections, it is recommended that the compound or salt thereof be used at 2–5 mg/kg of unit dose for each adult.

For rearing poultry which produce low-cholesterol eggs, the compound represented by general formula (I') or salt thereof is administered to the animal as an appropriate food additive. The final concentration of compound (I') or salt thereof in the feed is normally 0.01–1%, preferably 0.05–0.5%. Compound (I') or salt thereof may, as necessary, contain corn, soybean flour, meat flour, feed fat and soybean oil, as a food for promoting hen egg laying, in addition to usually added vitamin-mineral mixtures, provided that it can be added as-is to the feed.

BEST MODE FOR CARRYING OUT THE INVENTION

The present invention is hereinafter described in more detail by means of the following reference examples, examples and test examples. These examples exemplify, but do not limit, the present invention, and may be varied, as long as they remain within the scope of the invention.

In the following reference examples and examples, the term "room temperature" is generally defined as 10 to 30° C. The solvent ratio for purification by silica gel column chromatography is by volume (vol./vol.). The following abbreviations are defined as follows:

s: Singlet
d: Doublet
t: Triplet
quint: Quintet
m: Multiplet
br: Broad
Hz: Hertz
$CDCl_3$: Heavy chloroform
$CD_3OD$ : Heavy methanol
$^1$H-NMR: Proton nuclear magnetic resonance

Reference Example 1

Synthesis of 4,5,6,7-tetrahydrofuro[2,3-c]pyridine hydrochloride a) Synthesis of 6-tert-butoxycarbonyl-4,5,6,7-tetrahydrofuro[2,3-c]pyridine Method A To a solution of 10.035 g (104.43 mmol) of 3-furaldehyde and 6.37 g (104 mmol) of nitromethane in 200 ml of ethanol, 11.0 ml of 10 N aqueous sodium hydroxide was added dropwise under ice-cooling, after which the reaction mixture was added dropwise to about 15% aqueous hydrochloric acid; the resulting precipitate was collected by filtration, washed with water and dried to yield 2-(3-furyl)-1-nitroethylene as a brown powder (yield 9.320 g). This crude product, without purification, was used for the next reaction.

To a suspension of 2.54 g (67.0 mmol) of lithium aluminum hydride in 200 ml of tetrahydrofuran, a solution of the above-described 2-(3-furyl)-1-nitroethylene in 100 ml of tetrahydrofuran was added dropwise at room temperature over 1 hour, followed by stirring for 0.5 hours. The reaction mixture was cooled in an ice water bath; ethyl acetate was added to decompose the excess lithium aluminum hydride; subsequently, water was carefully added until a precipitate formed. This precipitate was filtered using Celite and washed with ethyl acetate; the combined filtrate was evaporated under reduced pressure. The residue was dissolved in 200 ml of dichloromethane; a solution of 14.6 g (67.0 mmol) of di-tert-butyl dicarbonate in 50 ml of dichloromethane was added dropwise at room temperature, followed by stirring for 0.5 hours. The solvent was distilled off under reduced pressure; the resulting crude product was purified by silica gel column chromatography (hexane/ethyl acetate=15/1 to 6/1) to yield N-tert-butoxycarbonyl-2-(3-furyl)ethylamine.

Orange oil Yield 5.384 g (24%)

$^1$H-NMR (CDCl$_3$, 200 MHz) δ1.439 (9H, s), 2.611 (2H, t, J=6.8 Hz), 3.316 (2H, q, J=6.6 Hz), 4.570 (1H, br s), 6.289 (1H, s), 7.264 (1H, s), 7.374 (1H, t, J=1.7 Hz);

IR(neat) 3358, 2978, 1699, 1508, 1250, 1164, 1024, 781 cm$^{-1}$

A solution of 0.266 g (1.259 mmol) of N-tert-butoxycarbonyl-2-(3-furyl)ethylamine, 76 mg (2.5 mmol) of powdered paraformaldehyde and 12 mg (0.06 mmol) of p-toluenesulfonic acid monohydrate in 50 ml of toluene was refluxed under dehydrating conditions for 2 hours in a Dean-Stark trap. The reaction mixture was cooled to room temperature and diluted with ethyl acetate, after which it was washed with aqueous sodium hydrogen carbonate; the organic layer was dried over anhydrous magnesium sulfate; the solvent was distilled off under reduced pressure. The resulting crude product was purified by silica gel column chromatography (hexane/ethyl acetate=15/1 to 9/1) to yield the desired product.

White solid Yield 0.120 g (43%)

$^1$H-NMR (CDCl$_3$, 200 MHz) δ1.482 (9H, s), 2.517 (2H, br t, J=5.7 Hz), 3.630 (2H, t, J=5.7 Hz), 4.440 (2H, s), 6.246 (1H, d, J=1.6 Hz), 7.290 (1H, d, J=1.8 Hz);

IR (nujol) 1689, 1419, 1279, 1227, 1169, 1124, 764 cm$^{-1}$

Method B

To 20 ml of methyl methylsulfinylmethyl sulfide, 1.34 g (33.5 mmol) of powdered sodium hydroxide was added, followed by stirring at 80° C. for 30 minutes. This mixture was added to 9.627 g (100.2 mmol) of 3-furaldehyde, followed by stirring at 80° C. for 3 hours. After this was cooled to room temperature, water was added, followed by 3 extractions with dichloromethane. The combined organic layer was dried over anhydrous magnesium sulfate; the solvent was distilled off under reduced pressure. The resulting crude product was purified by silica gel column chromatography (hexane/ethyl acetate=3/1 to 1/2) to yield 2-(3-furyl)-1-(methylsulfinyl)-1-(methylthio)ethylene.

Black-brown oil Yield 14.146 g (70%)

$^1$H-NMR (CDCl$_3$, 200 MHz) δ2.348 (3H, s), 2.737 (3H, s), 7.127 (1H,d, J=1.6 Hz), 7.479 (1H, t, J=1.7 Hz), 7.532 (1H, s), 7.942 (1H, s);

IR (neat) 3124, 1414, 1169, 1059, 874, 797 cm$^{-1}$ 2-(3-Furyl)-1-(methylsulfinyl)-1-(methylthio)ethylene 13.109 g (64.800 mmol) was dissolved in 300 ml of about 10% hydrogen chloride in methanol. To this solution, 4.36 g (32.4 mmol) of anhydrous copper chloride (II) was added, followed by stirring at room temperature for 2.5 days. The solvent was distilled off under reduced pressure; water was added, followed by 3 extractions with dichloromethane. The resulting crude product was purified by silica gel column chromatography (hexane/ethyl acetate=15/1 to 9/1) to yield methyl 3-furylacetate.

Pale yellow oil Yield 10.825 g (99%)

$^1$H-NMR (CDCl$_3$, 200 MHz) δ3.476 (2H, s), 3.718 (3H, s), 6.387 (1H, t, J=1.1 Hz), 7.387 (2H, m);

IR (neat) 1741, 1437, 1277, 1246, 1167, 1022, 874, 787, 746 cm$^{-1}$

To a suspension of 3.64 g (95.9 mmol) of lithium aluminum hydride in 300 ml of tetrahydrofuran, a solution of 8.964 g (63.97 mmol) of methyl 3-furylacetate in 100 ml of tetrahydrofuran was added dropwise under ice-cooling, followed by stirring at room temperature for 3 hours. The reaction mixture was cooled in an ice water bath; ethyl acetate was added dropwise to decompose the excess lithium aluminum hydride; subsequently, water was carefully added. The resulting white precipitate was filtered using Celite and washed with ethyl acetate. The combined filtrate was evaporated under reduced pressure. The crude 2-(3-furyl)ethanol thus obtained was used for the next reaction without purification.

To a solution of the crude 2-(3-furyl)ethanol and 10.7 ml (76.8 mmol) of triethylamine in 300 ml of diethyl ether, a solution of 5.45 ml (70.4 mmol) of methanesulfonyl chloride in 50 ml of diethyl ether was added dropwise under ice-cooling, followed by stirring for 0.5 hours. The reaction mixture was poured into water and extracted with ethyl acetate 3 times. The combined organic layer was dried over anhydrous magnesium sulfate; the solvent was distilled off under reduced pressure. The resulting crude 2-(3-furyl)ethyl methanesulfonate was used for the next reaction without purification.

To a solution of the 2-(3-furyl)ethyl methanesulfonate in 500 ml of N,N-dimethylformamide, 14.2 g (76.8 mmol) of potassium phthalimide was added, followed by overnight stirring at 100° C. After cooling to room temperature, the reaction mixture was added to water while being stirred vigorously. The resulting precipitate was filtered, washed with water and dried to yield N-[2-(3-furyl)ethyl]phthalimide.

Pale brown solid Yield 9.033 g (59%)

$^1$H-NMR (CDCl$_3$, 200 MHz) δ2.845 (2H, t, J=7.5 Hz), 3.889 (2H, t, J=7.5 Hz), 6.348 (1H,d, J=1.8 Hz), 7.266 (1H, s), 7.347 (1H, t, J=1.6 Hz), 7.667–7.752 (2H, m), 7.796–7.884 (2H, m);

Anal. Calcd for C$_{14}$H$_{11}$NO$_3$: C, 69.70; H, 4.60; N, 5.81. Found: C, 69.49; H, 4.64; N, 5.99.

IR (nujol) 1707, 1400, 1088, 999, 870, 812, 714 cm$^{-1}$

A solution of 19.020 g (78.839 mmol) of N-[2-(3-furyl)ethyl]phthalimide and 5.74 ml (118 mmol) of hydrazine monohydrate in 200 ml of ethanol was refluxed for 1 hour. After cooling to room temperature, the reaction mixture was poured into aqueous sodium hydroxide and extracted with dichloromethane 3 times. The combined organic layer was dried over anhydrous magnesium sulfate; the solvent was distilled off under reduced pressure. The resulting crude 2-(3-furyl)ethylamine was dissolved in 150 ml of dichloromethane; a solution of 22.4 g (102 mmol) of di-tert-butyl dicarbonate in 50 ml of dichloromethane was added dropwise at room temperature, followed by stirring for 0.5 hours. The solvent was distilled off under reduced pressure; the resulting crude product was purified by silica gel column chromatography (hexane/ethyl acetate=15/1 to 6/1) to yield N-tert-butoxycarbonyl-2-(3-furyl)ethylamine as a mixture with di-tert-butyl dicarbonate.

Colorless oil Yield 17.141 g

A solution of the above 17.141 g of N-tert-butoxycarbonyl-2-(3-furyl)ethylamine, 4.74 g (158 mmol) of powdered paraformaldehyde and 0.75 g (3.9 mmol) of p-toluenesulfonic acid monohydrate in 200 ml of toluene was refluxed for 1 hour under dehydrating conditions in a Dean-Stark trap. The reaction mixture was cooled to room temperature and diluted with ethyl acetate, after which it was washed with an aqueous sodium hydrogen carbonate; the organic layer was dried over anhydrous magnesium sulfate; the solvent was distilled off under reduced pressure. The resulting crude product was purified by silica gel column chromatography (hexane/ethyl acetate=15/1 to 9/1) to yield the desired product.

White solid Yield 10.825 g (62%)

$^1$H-NMR (CDCl$_3$, 200 MHz) δ1.482 (9H, s), 2.517 (2H, br t, J=5.7 Hz), 3.630 (2H, t, J=5.7 Hz), 4.440 (2H, s), 6.246 (1H,d, J=1.6 Hz), 7.290 (1H,d, J=1.8 Hz);

IR (nujol) 1689, 1419, 1279, 1227, 1169, 1124, 764 cm$^{-1}$ b) Synthesis of 4,5,6,7-tetrahydrofuro[2,3-c]pyridine hydrochloride To a solution of 5.324 g (23.85 mmol) of 6-tert-butoxycarbonyl-4,5,6,7-tetrahydrofuro[2,3-c]pyridine in 100 ml of methanol, 5 ml of concentrated hydrochloric acid was added, followed by stirring at room temperature for 1 hour. The solvent was distilled off under reduced pressure to yield the desired product.

Black-brown crystal Yield 3.763 g (99%)

$^1$H-NMR (CD$_3$OD, 200 MHz) δ2.850 (2H, tt, J=1.7&6.1 Hz), 3.463 (2H, t, J=6.1 Hz), 4.271 (2H, s), 6.406 (1H,d, J=1.8 Hz), 7.489 (1H,d, J=1.8 Hz);

IR (nujol) 2758–2455, 1146, 1111, 1030, 895, 756 cm$^{-1}$;

Anal. Calcd for C$_7$H$_{10}$ClNO: C, 52.67; H, 6.31; N, 8.78. Found: C, 52.53; H, 6.21; N, 8.69.

Reference Example 2

Synthesis of 4,5,6,7-tetrahydrofuro[3,2-c]pyridine hydrochloride

Method A

To a solution of 5.075 g (23.90 mmol) of 3-tert-butyldimethylsiloxymethylfuran in 150 ml of diethyl ether, 16.4 ml (26.3 mmol) of 1.6 M n-butyl lithium in hexane was added dropwise at room temperature, followed by stirring for 1 hour. After this reaction mixture was cooled to −78° C., 1.4 g of oxirane (obtained by adding 19 g of potassium carbonate to a solution of 8.8 g of 2-bromoethanol in 50 ml of tetrahydrofuran, followed by heating at 50° C., the resulting oxirane gas being trapped using a dry ice-acetone bath) was added; subsequently, 2.94 ml (23.9 mmol) of a boron trifluoride diethyl etherate was added. This reaction mixture was allowed to warm from −78° C. to room temperature, and stirred overnight. After aqueous sodium hydrogen carbonate was added, the reaction mixture was stirred and extracted with diethyl ether 3 times. The combined organic layer was dried over anhydrous magnesium sulfate; the solvent was distilled off under reduced pressure. The resulting crude product was purified by silica gel flush chromatography (hexane/ethyl acetate=6/1) to yield 2-(3-tert-butyldimethylsiloxymethylfuran-2-yl)ethanol.

Yellow oil Yield 2.643 g (43%)

$^1$H-NMR (CDCl$_3$, 200 MHz) δ0.104 (6H, s), 0.909 (9H, s), 2.434 (1H, t, J=6.1 Hz), 2.912 (2H, t, J=5.9 Hz), 3.804 (2H, q, J=5.9 Hz), 4.524 (2H, s), 6.310 (1H,d, J=1.8 Hz), 7.277 (1H,d, J=1.8 Hz);

IR (neat) 3390, 2929, 2858, 1468, 1255, 1072, 839, 777, 733 cm$^{-1}$

To a solution of 1.595 g (6.220 mmol) of 2-(3-tert-butyldimethylsiloxymethylfuran-2-yl)ethanol in 50 ml of tetrahydrofuran, 6.22 ml (6.220 mmol) of a 1.0 M tetra-n-butylammonium fluoride in tetrahydrofuran was added at room temperature, followed by stirring at room temperature for 1 hour. After the solvent was distilled off from the reaction mixture under reduced pressure, the resulting residue was subjected to silica gel column chromatography (hexane/ethyl acetate=3/1 to ethyl acetate). The resulting 2-(3-hydroxymethylfuran-2-yl)ethanol was used for the next reaction without further purification.

Yellow oil Yield 0.590 g

To a solution of the crude 2-(3-hydroxymethylfuran-2-yl)ethanol and 1.74 ml (9.96 mmol) of N,N-diisopropylethylamine in 50 ml of dichloromethane, 0.71 ml (9.13 mmol) of methanesulfonyl chloride was added dropwise under ice-cooling, followed by stirring at room temperature for 2 hours. The reaction mixture was diluted with ethyl acetate and washed with water and then saturated sodium chloride. After which it was dried over anhydrous magnesium sulfate; the solvent was distilled off under reduced pressure. The resulting residue was dissolved in 50 ml of ethanol, 0.36 g (6.22 mmol) of allylamine and 2.38 ml (13.7 mmol) of N,N-diisopropylethylamine were added, followed by overnight stirring at 80° C. The solvent was distilled off under reduced pressure from the reaction mixture; the resulting crude product was purified by silica gel column chromatog-raphy (hexane/ethyl acetate=9/1 to 6/1) to yield 5-allyl-4,5,6,7-tetrahydrofuro[3,2-c]pyridine.

Orange oil Yield 0.239 g (24%)

$^1$H-NMR (CDCl$_3$, 200 MHz) δ2.559–2.848 (4H, m), 3.208 (2H, td, J=1.3&6.6 Hz), 3.418 (2H, t, J=1.6 Hz), 5.145–5.292 (2H, m), 5.945 (1H, tdd, J=6.6,10.2&17.2 Hz), 6.181 (1H, d, J=2.0 Hz), 7.258 (1H, d, J=2.0 Hz);

IR (neat) 2937, 2856, 2769, 1452, 1018, 787, 700 cm$^{-1}$

A solution of 2.408 g (14.75 mmol) of 5-allyl-4,5,6,7-tetrahydrofuro[3,2-c]pyridine, 0.55 g (0.59 mmol) of chlorotris(triphenylphosphine)rhodium (I) and 0.33 g (2.95 mmol) of 1,4-diazabicyclo[2,2,2]octane in 30 ml of 90% aqueous ethanol was refluxed for 2.5 hours. After cooling to room temperature, the reaction mixture was poured into aqueous sodium hydroxide and extracted with dichloromethane 3 times. The combined organic layer was dried over anhydrous magnesium sulfate; the solvent was distilled off under reduced pressure. The resulting residue (crude 4,5,6,7-tetrahydrofuro[3,2-c]pyridine) was dissolved in 20 ml of dichloromethane. To this solution, a solution of 3.22 g (14.8 mmol) of di-tert-butyl dicarbonate in 5 ml of dichloromethane was added dropwise at room temperature, followed by stirring for 0.5 hours. The solvent was distilled off under reduced pressure; the resulting crude product was purified by silica gel column chromatography (hexane/ethyl acetate=15/1) to yield 5-tert-butoxycarbonyl-4,5,6,7-tetrahydrofuro[3,2-c]pyridine.

Colorless oil Yield 2.296 g (70%)

$^1$H-NMR (CDCl$_3$, 200 MHz) δ1.480 (9H, s), 2.691 (2H, br t, J=5.5 Hz), 3.722 (2H, t, J=5.8 Hz), 4.337 (2H, br s), 6.233 (1H, d, J=1.8 Hz), 7.290 (1H, d, J=1.8 Hz);

IR (neat) 2976, 1695, 1416, 1272, 1252, 1227, 1171, 1140, 1111, 770, 731 cm$^{-1}$ To a solution of 5.123 g (22.95 mmol) of 5-tert-butoxycarbonyl-4,5,6,7-tetrahydrofuro[3,2-c]pyridine in 50 ml of methanol, 3 ml of concentrated hydrochloric acid was added, followed by stirring at room temperature for 2 hours. The solvent was distilled off under reduced pressure to yield the desired product.

Brown crystal Yield 3.334 g (91%)

$^1$H-NMR (CD$_3$OD, 200 MHz) δ3.002 (2H, t, J=6.2 Hz), 3.544 (2H, t, J=6.2 Hz), 4.171 (2H, s), 6.396 (1H, d, J=1.8 Hz), 7.466 (1H, d, J=2.2 Hz);

IR (nujol) 2794–2461, 1113, 1031, 766, 748 cm$^{-1}$;

Anal. Calcd for C$_7$H$_{10}$ClNO: C, 52.67; H, 6.31; N, 8.78. Found: C, 52.58; H, 6.32; N, 8.72.

Method B

A solution of 6.019 g (62.64 mmol) of 3-furaldehyde and 5.37 g (94.0 mmol) of allylamine in 100 ml of methanol was stirred at room temperature for 0.5 hours. To this reaction mixture, 4.74 g (125 mmol) of sodium borohydride was added portionwise under ice-cooling, followed by stirring at room temperature for 1 hour. The reaction mixture was poured into an aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=1/1 to ethyl acetate) to yield N-allyl-3-furylmethylamine.

Pale yellow oil Yield 6.597 g (77%)

$^1$H-NMR (CDCl$_3$, 200 MHz) a 1.553 (1H, br s), 3.282 (2H, td, J=1.4&6.1 Hz), 3.656 (2H, s), 5.081–5.248 (2H, m), 5.923 (1H, tdd, J=6.0,10.1&17.2 Hz), 6.394 (1H, d, J=1.0 Hz), 7.347–7.391 (2H, m);

IR (neat) 3745, 2818, 1502, 1454, 1157, 1022, 920, 874, 785 cm$^{-1}$

To a solution of 6.597 g (48.09 mmol) of N-allyl-3-furylmethylamine and 18.0 g (144 mmol) of 2-bromoethanol in 100 ml of N,N-dimethylformamide, 33.2 g of potassium carbonate was added, followed by overnight stirring at 90° C. The reaction mixture was poured into water and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=3/1 to 1/1) to yield 2-[allyl-(3-furylmethyl)amino]ethanol.

Orange oil Yield 9.258 g (quantitative)

$^1$H-NMR (CDCl$_3$, 200 MHz) δ1.994 (1H, br s), 2.645 (2H, t, J=5.4 Hz), 3.138 (2H, td, J=1.2&6.4 Hz), 3.542 (2H, s), 3.592 (2H, t, J=5.4 Hz), 4.525 (2H, s), 5.160–5.254 (2H, m), 5.855 (1H, tdd, J=6.5,9.7&17.5 Hz), 6.359 (1H, d, J=1.6 Hz), 7.330 (1H, s), 7.399 (1H, t, J=1.7 Hz);

IR (neat) 3423, 2929, 2821, 1807, 1159, 1074, 874, 781 cm$^{-1}$

To a solution of 9.255 g (51.07 mmol) of the above 2-[allyl-(3-furylmethyl)amino]ethanol, 10.7 ml (76.6 mmol) of triethylamine and 0.1 g of 4-dimethylaminopyridine in 150 ml of dichloromethane, 11.7 g (61.3 mmol) of p-toluenesulfonyl chloride was added at room temperature, followed by overnight stirring at room temperature. The reaction mixture was poured into water and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=15/1 to 9/1) to yield N-allyl-N-(3-furylmethyl)-2-chloroethylamine as a mixture with p-toluenesulfonyl chloride.

Yellow oil Yield 9.03 g

To a solution of 9.03 g of the above crude N-allyl-N-(3-furylmethyl)-2-chloroethylamine in 200 ml of tetrahydrofuran, 63.8 ml (102 mmol) of 1.6 M n-butyl lithium hexane was added under ice-cooling, followed by stirring at room temperature for 4 hours. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=9/1) to yield 5-allyl-4,5,6,7-tetrahydrofuro[3,2-c]pyridine.

Orange oil Yield 1.880 g (23%)

This compound was converted to the desired product 4,5,6,7-tetrahydrofuro[3,2-c]pyridine hydrochloride, in the same manner as in method A.

Method C

A solution of 5.082 g (53.00 mmol) of 3-furaldehyde and 8.50 g (79.3 mmol) of benzylamine in 50 ml of methanol was overnight stirred at room temperature. This reaction mixture was concentrated under reduced pressure to yield a Schiff base. The Schiff base was dissolved in 100 ml of ethanol; 4.00 g (106 mmol) of sodium borohydride was added portionwise under ice-cooling, followed by stirring at room temperature for 1 hour. The reaction mixture was poured into aqueous sodium chloride and extracted with ethyl acetate 3 times. The combined organic layer was dried over anhydrous magnesium sulfate; the solvent was distilled off under reduced pressure. The resulting crude product was purified by silica gel column chromatography (hexane/ethyl acetate=1/1 to ethyl acetate) to yield N-benzyl-3-furylmethylamine.

Yellow oil Yield 9.344 g (94%)

$^1$H-NMR (CDCl$_3$, 200 MHz) δ1.598 (1H, br s), 3.667 (2H, s), 3.816 (2H, s), 6.407 (1H, d, J=1.4 Hz), 7.229–7.428 (7H, m);

IR (neat) 3320, 2821, 1498, 1452, 1157, 1022, 784, 737, 700 cm$^{-1}$

To a solution of 0.641 g (3.423 mmol) of N-benzyl-3-furylmethylamine and 0.64 g (5.1 mmol) of 2-bromoethanol in 30 ml of N,N-dimethylformamide, 0.95 g of potassium carbonate was added, followed by stirring at 80° C. for 2 hours. 0.64 g (5.1 mmol) of 2-bromoethanol was further added, followed by overnight stirring at 80° C. The reaction mixture was poured into water and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=3/1) to yield 2-[benzyl-(3-furylmethyl)amino]ethanol.

Colorless oil Yield 0.405 g (51%)

$^1$H-NMR (CDCl$_3$, 200 MHz) δ2.335 (1H, br s), 2.674 (2H, t, J=5.3 Hz), 3.525 (2H, s), 3.594 (2H, t, J=5.8 Hz), 3.624 (2H, s), 6.589 (1H, d, J=1.0 Hz), 7.253–7.407 (7H, m);

IR (neat) 3425, 2825, 1498, 1452, 1052, 1022, 787, 737, 700 cm$^{-1}$

To a solution of 0.397 g (1.716 mmol) of 2-[benzyl-(3-furylmethyl)amino]ethanol, 0.36 ml (2.6 mmol) of triethylamine and 10 mg of 4-dimethylaminopyridine in 30 ml of dichloromethane, 0.39 g (2.1 mmol) of p-toluenesulfonyl chloride was added at room temperature, followed by stirring at room temperature for 6 hours. The reaction mixture was poured into water and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=15/1 to 9/1) to yield N-benzyl-N-(3-furylmethy)-2-chloroethylamine.

Colorless oil Yield 0.209 g (49%)

$^1$H-NMR (CDCl$_3$, 200 MHz) δ2.814 (2H, t, J=7.1 Hz), 3.483 (2H, t, J=7.3 Hz), 3.520 (2H, s), 3.634 (2H, s), 6.287 (1H, d, J=1.2 Hz), 7.226–7.372 (7H, m);

IR (neat) 2808, 1498, 1452, 1159, 1022, 787, 737, 700 cm$^{-1}$

To a solution of 0.209 g (0.837 mmol) of N-benzyl-N-(3-furylmethyl)-2-chloroethylamine in 50 ml of tetrahydrofuran, 1.05 ml (1.67 mmol) of 1.6 M n-butyl lithium in hexane was added under ice-cooling, followed by stirring at room temperature for 2 hours. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=9/1) to yield 5-benzyl-4,5,6,7-tetrahydrofuro[3,2-c]pyridine.

Yellow oil Yield 0.027 g (15%)

$^1$H-NMR (CDCl$_3$, 200 MHz) δ2.684–2.737 (2H, m), 2.798–2.855 (2H, m), 3.417 (1H, t, J=1.8 Hz), 3.715 (2H, s), 6.158 (1H, d, J=1.8 Hz), 7.234–7.413 (6H, m);

IR (neat) 2926, 2798, 1072, 730, 698 cm$^{-1}$

To a solution of 15.023 g (70.438 mmol) of 5-benzyl-4,5,6,7-tetrahydrofuro[3,2-c]pyridine in 100 ml of methanol, 2 ml of acetic acid was added, followed by hydrogenation over 5 g of 10% palladium-carbon (50% hydrated) at room temperature at atmospheric pressure for 8 hours. The mixture was filtered using Celite to remove the catalyst; the Celite was washed with methanol 3 times. The combined methanol solution was evaporated under reduced pressure. The resulting residue (crude 4,5,6,7-tetrahydrofuro[3,2-c]pyridine) was dissolved in 100 ml of dichloromethane. To this solution, a solution of 15.4 g (70.4 mmol) of di-tert-butyl dicarbonate in 50 ml of dichloromethane was added dropwise at room temperature, followed by stirring for 0.5 hours. The solvent was distilled off under reduced pressure; the resulting crude product was purified by silica gel column chromatography (hexane/ethyl acetate=15/1) to yield 5-tert-butoxycarbonyl-4,5,6,7-tetrahydrofuro[3,2-c]pyridine as a mixture with di-tert-butyl dicarbonate.

Colorless oil Yield 14.64 g

To a solution of the above 5-tert-butoxycarbonyl-4,5,6,7-tetrahydrofuro[3,2-c]pyridine (containing di-tert-butyl dicarbonate) in 100 ml of methanol, 5 ml of concentrated hydrochloric acid was added, followed by stirring at room temperature for 1 hour. The solvent was distilled off under reduced pressure to yield the desired product.

Pale yellow crystal Yield 9.074 g (81%)

$^1$H-NMR (CD$_3$OD, 200 MHz) δ3.002 (2H, t, J=6.2 Hz), 3.544 (2H, t, J=6.2 Hz), 4.171 (2H, s), 6.396 (1H, d, J=1.8 Hz), 7.466 (1H, d, J=2.2 Hz);

IR (nujol) 2794–2461, 1113, 1031, 766, 748 cm$^{-1}$;

Anal. Calcd for C$_7$H$_{10}$ClNO: C, 52.67; H, 6.31; N, 8.78. Found: C, 52.58; H, 6.32; N, 8.72.

Method D

A solution of 3.347 g (17.69 mmol) of 1-benzyl-4-piperidinone and 1.75 g (17.7 mmol) of cyclohexylamine in 150 ml of toluene was refluxed under dehydrating conditions for 2.5 hours in a Dean-Stark trap. After the reaction mixture was cooled to room temperature, the solvent was distilled off under reduced pressure to yield N-(1-benzyl-4-piperidylidene)cyclohexylamine. This product was used for the next reaction without purification.

Yellow oil Yield 4.81 g (100%)

The above N-(1-benzyl-4-piperidylidene)cyclohexylamine (4.81 g (17.69 mmol)) was dissolved in 150 ml of tetrahydrofuran. After this solution was cooled to −78° C., 13.3 ml (21.2 mmol) of 1.6 M n-butyl lithium in hexane was added dropwise. After the reaction mixture was stirred for 30 minutes under ice-cooling, a solution of 4.01 g (23.0 mmol) of tert-butyldimethylsiloxyacetaldehyde in 50 ml of tetrahydrofuran was added, followed by stirring for 1 hour under ice-cooling. To the reaction mixture, aqueous ammonium chloride was added, followed by stirring for 10 minutes and 3 extractions with ethyl acetate. The combined organic layer was dried over anhydrous magnesium sulfate; the solvent was distilled off under reduced pressure. The resulting residue was purified by silica gel column chromatography (hexane/ethyl acetate=3/1) to yield 1-benzyl-3-(2-tert-butyldimethylsiloxy-1-hydroxyethyl)-4-piperidinone.

Yellow oil Yield 4.060 g (63%)

$^1$H-NMR (CDCl$_3$, 200 MHz) δ0.014 (4H, s), 0.032 (2H, s), 0.860 (6H, s), 0.869 (3H, s), 1.627 (1H, br s), 2.506–3.034 (7H, m), 3.453–3.717 (4H, m), 3.921–4.049 (1H, m), 7.333 (5H, br s);

IR (neat) 3471, 2929, 1712, 1468, 1255, 1120, 837, 779, 739 cm$^{-1}$

After 3.055 g (8.403 mmol) of 1-benzyl-3-(2-tert-butyldimethylsiloxy-1-hydroxyethyl)-4-piperidinone was dissolved in 100 ml of methanol, 10 ml of concentrated hydrochloric acid was added, followed by stirring at room temperature for 10 minutes. The solvent was distilled off under reduced pressure with heating. The resulting residue was dissolved in water. After this solution was alkalified with aqueous sodium hydroxide, it was extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=9/1 to 6/1) to yield 5-benzyl-4,5,6,7-tetrahydrofuro[3,2-c]pyridine.

Pale yellow oil Yield 1.565 g (87%)

This compound was converted to the desired product 4,5,6,7-tetrahydrofuro[3,2-c]pyridine hydrochloride, in the same manner as in method A.

Reference Example 3

Synthesis of 7-tert-butoxycarbonyl-5,6,7,8-tetrahydro-4H-furo[2,3-c]azepine a) Synthesis of ethyl (E)-3-(3-furyl)acrylate To a solution of 17.7 g (78.8 mmol) of ethyl diethylphosphonoacetate in 150 ml of benzene, 2.89 g (72.2 mmol) of sodium hydride (60% in oil) was added under ice-cooling, followed by stirring for 30 minutes. To this solution, a solution of 6.308 g (65.65 mmol) of 3-furaldehyde in 50 ml of benzene was added dropwise, followed by stirring at room temperature for 30 minutes and refluxing for 30 minutes. After the reaction mixture was cooled to room temperature, ether was added; the mixture was then washed with water. The ether solution was dried over anhydrous magnesium sulfate; the solvent was distilled off under reduced pressure. The resulting crude product was purified by silica gel column chromatography (hexane to hexane/ethyl acetate=9/1) to yield the desired product.

White solid Yield 9.956 g (91%)

$^1$H-NMR (CDCl$_3$, 200 MHz) δ1.320 (3H, t, J=7.1 Hz), 4.240 (2H, q, J=7.1 Hz), 6.156 (1H, d, J=15.6 Hz), 6.585 (1H, d, J=2.0 Hz), 7.423 (1H, t, J=2.2 Hz), 7.571 (1H, d, J=15.8 Hz), 7.637 (1H, s);

IR (nujol) 1699, 1639, 1313, 1219, 1186, 1151 cm$^{-1}$ b) Synthesis of ethyl 3-(3-furyl)propionate To a solution of 8.186 g (49.26 mmol) of ethyl (E)-3-(3-furyl)acrylate, 24.7 g (493 mmol) of hydrazine monohydrate, 5 ml of acetic acid and 5 ml of saturated aqueous copper sulfide in 500 ml of ethanol, a solution of 52.7 g (246 mmol) of sodium periodate in 300 ml of water was added dropwise over a period of 1 hour, followed by stirring at room temperature for 1 day. The reaction mixture was extracted with ether 3 times. The combined organic layer was washed with dilute hydrochloric acid and then aqueous sodium hydrogen carbonate, and dried over anhydrous magnesium sulfate; the solvent was distilled off under reduced pressure. The resulting crude product was purified by silica gel column chromatography (hexane/ethyl acetate=15/1) to yield the desired product.

Pale yellow oil Yield 6.060 g (73%)

$^1$H-NMR (CDCl$_3$, 200 MHz) δ1.249 (3H, t, J=7.1 Hz), 2.509–2.590 (2H, m), 2.766 (2H, dd, J=6.9&7.7 Hz), 4.140 (2H, q, J=7.1 Hz), 6.274 (1H, s), 7.241 (1H, d, J=0.8 Hz), 7.343 (1H, t, J=1.7 Hz);

IR (neat) 2981, 1734, 1165, 1024, 789 cm$^{-1}$ c) Synthesis of N-allyl-3-(3-furyl)propylamine To a suspension of 1.21 g (31.8 mmol) of lithium aluminum hydride in 150 ml of ether, a solution of 3.561 g (21.17 mmol) of ethyl 3-(3-furyl)propionate in 50 ml of ether was added dropwise, followed by stirring at room temperature for 1 hour. To decompose the excess lithium aluminum hydride, ethyl acetate was added dropwise to the reaction mixture under ice-cooling; subsequently, water was added until a white precipitate formed. The white precipitate was filtered using Celite and washed with ethyl acetate 3 times. The combined filtrate was concentrated under reduced pressure. The resulting crude 3-(3-furyl)propanol was used for the next reaction without purification.

To a solution of 4.03 g (31.8 mmol) of oxalyl chloride in 100 ml of dichloromethane, 4.51 ml (63.5 mmol) of dimethyl sulfoxide was added dropwise at −78° C. After 5 minutes of stirring, a solution of the above crude 3-(3-furyl)propanol in 50 ml of dichloromethane was added dropwise, followed by stirring for 15 minutes. To this mixture, 17.7 ml (127 mmol) of triethylamine was added; the reaction mixture was warmed to room temperature with stirring. The reaction mixture was diluted with ether, washed with water, and the organic layer was dried over anhydrous magnesium sulfate; the solvent was distilled off under reduced pressure. The resulting crude 3-(3-furyl)propanal was used for the next reaction without purification.

To a solution of the above crude 3-(3-furyl)propanal, 7.94 ml (106 mmol) of allylamine and 2.54 ml (42.3 mmol) of acetic acid in 100 ml of methanol, 1.33 g (21.2 mmol) of sodium cyanoborohydride was added at room temperature, followed by stirring at room temperature for 1 day. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 1.803 g (52%)

$^1$H-NMR (CDCl$_3$, 200 MHz) δ1.689–1.837 (3H, m), 2.476 (2H, t, J=7.7 Hz), 2.654 (2H, t, J=7.2 Hz), 3.252 (2H, td, J=1.5&5.9 Hz), 5.059–5.222 (2H, m), 5.910 (1H, tdd, J=6.1,10.2&17.2 Hz), 6.270 (1H, s), 7.220 (1H, s), 7.349 (1H, t, J=1.6 Hz);

IR (neat) 2929, 2858, 1502, 1452, 1157, 1024, 920, 874, 779 cm$^{-1}$ d) Synthesis of 7-allyl-5,6,7,8-tetrahydro-4H-furo[2,3-c]azepine To a solution of 1.803 g (10.912 mmol) of N-allyl-3-(3-furyl)propylamine in 50 ml of acetic acid, 1.06 g (13.1 mmol) of 37% aqueous formaldehyde was added, followed by stirring at 100° C. for 1 hour. After the solvent was distilled off under reduced pressure, the residual solution was alkalified with aqueous sodium hydroxide, and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=6/1 to 3/1) to yield the desired product.

Pale yellow oil Yield 0.847 g (44%)

$^1$H-NMR (CDCl$_3$, 200 MHz) δ1.731–1.843 (2H, m), 2.526 (2H, t, J=5.8 Hz), 2.964–3.015 (2H, m), 3.123 (2H, d, J=6.6 Hz), 3.786 (2H, s), 5.105–5.211 (2H, m), 5.879 (1H, tdd, J=6.5,9.5&17.8 Hz), 6.174.(1H, d, J=1.8 Hz), 7.140 (1H, d, J=1.6 Hz);

IR (neat) 2927, 2845, 1439, 1136, 1111, 1080, 1049, 922, 727 cm$^{-1}$ e) Synthesis of 7-tert-butoxycarbonyl-5,6,7,8-tetrahydro-4H-furo[2,3-c]azepine A solution of 0.847 g (4.779 mmol) of 7-allyl-5,6,7,8-tetrahydro-4H-furo[2,3-c]azepine, 0.22 g (0.24 mmol) of chlorotris(triphenylphosphine)rhodium (I) and 0.11 g (0.96 mmol) of 1,4-diazabicyclo[2,2,2]octane in 50 ml of 90% aqueous ethanol was refluxed for 5 hours. After cooling to room temperature, the reaction mixture was poured into aqueous sodium hydroxide and extracted with dichloromethane 3 times. The combined organic layer was dried over anhydrous magnesium sulfate; the solvent was distilled off under reduced pressure. The resulting residue (crude 5,6,7,8-tetrahydro-4H-furo[2,3-c]azepine) was dissolved in 50 ml of dichloromethane. To this solution, a solution of 1.56 g (7.17 mmol) of di-tert-butyl dicarbonate in 20 ml of dichloromethane was added dropwise at room temperature, followed by overnight stirring. The solvent was distilled off under reduced pressure; the resulting crude product was purified by silica gel column chromatography (hexane/ethyl acetate=15/1) to yield the desired product.

Yellow oil Yield 0.383 g (34%)

$^1$H-NMR (CDCl$_3$, 200 MHz) δ1.438 (9H, br s), 1.888 (2H, br s), 2.559 (2H, t, J=6.2 Hz), 3.566 (2H, br s), 4.500 (1H, br s), 4.561 (1H, br s), 6.164 (1H, br s), 7.182 (1H, d, J=1.8 Hz);

IR (neat) 2976, 2931, 1697, 1458, 1411, 1365, 1248, 1167, 1115, 1088, 895, 770, 729 cm$^{-1}$ Reference Example 4

Synthesis of 6-tert-butoxycarbonyl-5,6,7,8-tetrahydro-4H-furo[2,3-d]azepine a) Synthesis of 2-[3-(2-hydroxyethyl)furan-2-yl]ethanol To a suspension of 3.08 g (81.1 mmol) of lithium aluminum hydride in 200 ml of diethyl ether, a solution of 7.579 g (54.08 mmol) of methyl 3-furylacetate in 50 ml of diethyl ether was added dropwise under ice-cooling, followed by stirring at room temperature for 0.5 hours. The reaction mixture was cooled in an ice water bath; ethyl acetate was added dropwise to decompose the excess lithium aluminum hydride; subsequently, water was carefully added until a precipitate formed. This white precipitate was filtered using Celite and washed with ethyl acetate. The combined filtrate was concentrated under reduced pressure. The resulting crude 2-(3-furyl)ethanol was used for the next reaction without purification.

To a solution of the above crude 2-(3-furyl)ethanol in 200 ml of diethyl ether, 74.4 ml (119 mmol) of 1.6 M n-butyl lithium in hexane was added dropwise under ice-cooling, followed by stirring at room temperature for 1 hour. This reaction mixture was cooled to −78° C.; oxirane (obtained by adding dropwise a solution of 20.3 g (162 mmol) of 2-bromoethanol in 50 ml of tetrahydrofuran to a solution of 6.49 g (162 mmol) of sodium hydride (60% dispersion in meneral oil) in 50 ml of tetrahydrofuran, at 50° C., and trapping the resulting oxirane gas with a dry ice-acetone bath) was added; and then, 6.65 ml (54.1 mmol) of a boron trifluoride diethyl etherate was added. This reaction mixture was allowed to warm to room temperature, and stirred overnight. After aqueous sodium hydrogen carbonate was added, the reaction mixture was stirred and extracted with diethyl ether 10 times. The combined organic layer was dried over anhydrous magnesium sulfate; the solvent was distilled off under reduced pressure. The resulting crude product was purified by silica gel flush column chromatography (hexane/ethyl acetate=6/1 to 3/1 to 1/1 to ethyl acetate) to yield the desired product.

Yellow oil Yield 2.666 g (32%)

$^1$H-NMR (CDCl$_3$, 200 MHz) δ1.641 (1H, br s), 2.623 (2H, t, J=5.6 Hz), 2.691 (1H, br s), 2.852 (2H, t, J=5.8 Hz), 3.759 (2H, t, J=5.8 Hz), 3.843 (2H, t, J=5.6 Hz), 6.236 (1H, d, J=2.0 Hz), 7.312 (1H, d, J=1.8 Hz);

IR (neat) 3363, 2935, 2879, 1101, 1049, 739 cm$^{-1}$ b) Synthesis of 6-benzyl-5,6,7,8-tetrahydro-4H-furo[2,3-d]azepine To a solution of 1.208 g (7.735 mmol) of 2-[3-(2-hydroxyethyl)furan-2-yl]ethanol and 4.04 ml (23.2 mmol) of N,N-diisopropylethylamine in 50 ml of dichloromethane, 1.32 ml (17.0 mmol) of methanesulfonyl chloride was added dropwise under ice-cooling, followed by stirring at room temperature for 1 hour. The reaction mixture was poured into water and extracted with diethyl ether 3 times. The combined organic layer was dried over anhydrous magnesium sulfate; the solvent was distilled off under reduced pressure. The resulting residue was dissolved in 100 ml of ethanol; 0.83 g (7.7 mmol) of benzylamine and 2.37 ml (17.0 mmol) of triethylamine were added, followed by stirring at 80° C. for 3 days. After the solvent was distilled off from the reaction mixture under reduced pressure, aqueous sodium hydroxide was added, followed by 3 extractions with ethyl acetate. The combined organic layer was dried over anhydrous magnesium sulfate; the solvent was distilled off under reduced pressure. The resulting crude product was purified by silica gel column chromatography (hexane/ethyl acetate= 9/1) to yield the desired product.

Yellow oil Yield 0.515 g (29%)

$^1$H-NMR (CDCl$_3$, 200 MHz) δ2.557 (2H, t, J=5.5 Hz), 2.878 (4H, s), 2.916 (2H, t, J=5.7 Hz), 3.788 (2H, s), 6.144 (1H, d, J=1.4 Hz), 7.162 (1H, d, J=1.6 Hz), 7.248–7.413 (5H, m);

IR (neat) 2920, 2818, 1454, 1367, 1155,.1128, 733, 698 cm$^{-1}$ c) Synthesis of 6-tert-butoxycarbonyl-5,6,7,8-tetrahydro-4H-furo[2,3-d]azepine A solution of 0.515 g (2.266 mmol) of 6-benzyl-5,6,7,8-tetrahydro-4H-furo[2,3-d]azepine in 30 ml of methanol was hydrogenated overnight at room temperature at atmospheric pressure over 0.5 g of 10% palladium-carbon (50% hydrated). After the catalyst was filtered off, the filtrate was concentrated under reduced pressure. The resulting residue (crude 5,6,7,8-tetrahydro-4H-furo[2,3-d]azepine) was dissolved in 20 ml of dichloromethane. To this solution, a solution of 0.49 g (2.3 mmol) of di-tert-butyl dicarbonate in 5 ml of dichloromethane was added dropwise at room temperature, followed by overnight stirring. The solvent was distilled off under reduced pressure; water was added, followed by 3 extractions with ethyl acetate. The combined organic layer was dried over anhydrous magnesium sulfate; the solvent was distilled off under reduced pressure. The resulting crude product was purified by silica gel column chromatography (hexane/ethyl acetate=15/1) to yield the desired product.

Colorless oil Yield 0.402 g (75%)

$^1$H-NMR (CDCl$_3$, 200 MHz) δ1.471 (9H, s), 2.625 (2H, br s), 2.914 (2H, br s), 3.519–3.603 (4H, m), 6.158 (1H, br s), 7.180 (1H, d, J=1.8 Hz);

IR (neat) 2976, 2933, 1693, 1464, 1414, 1271, 1230, 1169, 1113 cm$^{-1}$

EXAMPLE 1

Synthesis of N,N-dimethyl-[6-(6-phenylhexyl)-4,5,6,7-tetrahydrofuro[2,3-c]pyridin-2-ylmethyl]amine dihydrochloride a) Synthesis of 6-(6-phenylhexyl)-4,5,6,7-tetrahydrofuro[2,3-c]pyridine To a solution of 0.39 g (2.2 mmol) of 6-phenylhexan-1-ol and 0.38 ml (2.7 mmol) of triethylamine in 20 ml of ether, methanesulfonyl chloride was added dropwise under ice-cooling, followed by stirring for 10 minutes. The ether solution was washed with water and saturated aqueous sodium chloride, after which it was dried over anhydrous magnesium sulfate; the solvent was distilled off under reduced pressure. The residual oil (crude 6-phenylhexyl methanesulfonate) was dissolved in 30 ml of acetonitrile; 0.289 g (1.811 mmol) of 4,5,6,7-tetrahydrofuro[2,3-c] pyridine hydrochloride and 0.76 ml (5.4 mmol) of triethylamine were added, followed by refluxing for 3 hours. The solvent was distilled off from the reaction mixture under reduced pressure. The resulting crude product was purified by silica gel column chromatography (hexane/ethyl acetate= 6/1) to yield the desired product.

Yellow oil Yield 0.121 g (24%)

$^1$H-NMR (CDCl$_3$, 200 MHz) δ1.332–1.440 (4H, m), 1.498–1.670 (4H, m), 2.489–2.729 (8H, m), 3.497 (2H, s), 6,216 (1H, d, J=1.8 Hz), 7.129–7.314 (6H, m);

IR (neat) 2931, 2769, 1454, 1363, 1137, 1026, 912, 802, 746, 698 cm$^{-1}$ b) Synthesis of N,N-dimethyl-[6-(6-phenylhexyl)-4,5,6,7-tetrahydrofuro[2,3-c]pyridin-2-ylmethyl]amine To a solution of 0.120 g (0.423 mmol) of 6-(6-phenylhexyl)-4,5,6,7-tetrahydrofuro[2,3-c]pyridine in 10 ml of acetic acid, 0.046 g (0.51 mmol) of 50% aqueous dimethylamine and 0.041 g (0.51 mmol) of 37% aqueous formaldehyde were added, followed by stirring at 100° C. for 15 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.088 g (61%)

$^1$H-NMR (CDCl$_3$, 200 MHz) δ1.326–1.396 (4H, m), 1.520–1.665 (4H, m), 2.240 (6H, s), 2.476–2.713 (8H, m), 3.385 (2H, s), 3.482 (2H, s), 6.015 (1H, s), 7.131–7.319 (5H, m);

IR (neat) 2931, 2769, 1454, 1363, 1137, 1026, 912, 802, 746, 698 cm$^{-1}$ c) Synthesis of N,N-dimethyl-[6-(6-phenylhexyl)-4,5,6,7-tetrahydrofuro[2,3-c]pyridin-2-ylmethyl]amine dihydrochloride N,N-Dimethyl-[6-(6-phenylhexyl)-4,5,6,7-tetrahydrofuro [2,3-c]pyridin-2-ylmethyl]amine 0.088 g was dissolved in 2 ml of methanol; hydrogen chloride in methanol was added in excess, followed by stirring. This mixture was concentrated to yield the desired product.

Brown solid Yield 0.109 g $^1$H-NMR (CD$_3$OD, 200 MHz) δ1.381–1.496 (4H, m), 1.606–1.711 (2H, m), 1.746–1.898 (2H, m), 2.634 (2H, t, J=7.4 Hz), 2.782–3.006 (2H, m), 2.878 (6H, s), 3.266–3.444 (3H, m), 3.769 (1H, ddd, J=2.8,6.0&10.3 Hz), 4.285 (1H, d, J=15.4 Hz), 4.400 (2H, s), 4.579 (1H, d, J=15.0 Hz), 6.737 (1H, s), 7.100–7.283 (5H, m);

IR (nujol) 2463, 1240, 941, 731, 694 cm$^{-1}$;

Anal. Calcd for C$_{22}$H$_{34}$Cl$_2$N$_2$O.0.3H$_2$O: C, 63.09; H, 8.33; N, 6.69. Found: C, 63.24; H, 8.18; N, 6.58.

EXAMPLE 2

Synthesis of N,N-dimethyl-[5-(6-phenylhexyl)-4,5,6,7-tetrahydrofuro[3,2-c]pyridin-2-ylmethyl]amine dihydrochloride a) Synthesis of N-(3-furylmethyl)-6-phenylhexylamine A solution of 9.138 g (29.73 mmol) of N-(6-phenylhexyl) phthalimide and 2.16 ml (44.6 mmol) of hydrazine monohydrate in 100 ml of ethanol was refluxed for 1 hour. After cooling to room temperature, the reaction mixture was poured into aqueous sodium hydroxide and extracted with dichloromethane 3 times. The combined organic layer was dried over anhydrous magnesium sulfate; the solvent was distilled off under reduced pressure. The resulting crude 6-phenylhexylamine was dissolved in 100 ml of methanol; 2.86 g (29.7 mmol) of 3-furaldehyde was added, followed by stirring at room temperature for 0.5 hours, after which 2.25 g (59.5 mmol) of sodium borohydride was added under ice-cooling, followed by stirring at room temperature for 1 hour. The reaction mixture was poured into aqueous sodium hydroxide and extracted with dichloromethane 3 times. The combined organic layer was dried over anhydrous magnesium sulfate; the solvent was distilled off under reduced pressure. The crude product was purified by silica gel column chromatography (hexane/ethyl acetate=1/1 to ethyl acetate) to yield the desired product.

Yellow oil Yield 7.060 g (92%)

$^1$H-NMR (CDCl$_3$, 200 MHz) δ1.310–1.656 (8H, m), 2.601 (2H, t, J=7.7 Hz), 2.612 (2H, t, J=7.2 Hz), 3.630 (2H, s), 6.379 (1H, d, J=1.8 Hz), 7.127–7.380 (7H, m);

IR (neat) 2927, 2854, 1498, 1454, 1157, 1022, 874, 783, 746, 698 cm$^{-1}$ b) Synthesis of 2-[(3-furylmethyl)-(6-phenylhexyl) amino] ethanol To a solution of 2.538 g (9.861 mmol) of N-(3-furylmethyl)-6-phenylhexylamine and 7.39 g (59.2 mmol) of 2-bromoethanol in 50 ml of N,N-dimethylformamide, 13.6 g (98.6 mmol) of potassium carbonate was added, followed by overnight stirring at 90° C. After cooling to room temperature, the reaction mixture was poured into water and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=3/1 to 1/1) to yield the desired product.

Brown oil Yield 3.195 g (100%)

$^1$H-NMR (CDCl$_3$, 200 MHz) δ1.258–1.647 (8H, m), 2.200 (1H, br s), 2.453 (2H, t, J=7.3 Hz), 2.594 (2H, t, J=7.7 Hz), 2.605 (2H, t, J=5.3 Hz), 3.511 (2H, s), 3.559 (2H, t, J=5.3 Hz), 6.331 (1H, dd, J=0.7&1.9 Hz), 7.131–7.314 (6H, m), 7.385 (1H, t, J=1.7 Hz);

IR (neat) 3427, 2929, 1498, 1456, 1159, 1051, 1024, 874, 783, 742, 700 cm$^{-1}$ c) Synthesis of N-(2-chloroethyl)-N-(3-furylmethyl)-6-phenylhexylamine To a solution of 2.533 g (8.470 mmol) of 2-[(3-furylmethyl)-(6-phenylhexyl)amino]ethanol, 1.77 ml (12.7 mmol) of triethylamine and 30 mg of 4-dimethylaminopyridine in 50 ml of dichloromethane, 1.94 g (10.2 mmol) of p-toluenesulfonyl chloride was added at room temperature, followed by overnight stirring at room temperature. The solvent was distilled off under reduced pressure; the resulting crude product was purified by silica gel column chromatography (hexane/ethyl acetate=15/1 to 9/1) to yield the desired product.

Pale yellow oil Yield 1.535 g (57%)

$^1$H-NMR (CDCl$_3$, 200 MHz) δ1.281–1.333 (4H, m), 1.415–1.648 (4H, m), 2.470 (2H, t, J=7.2 Hz), 2.597 (2H, t, J=7.6 Hz), 2.767 (2H, t, J=7.3 Hz), 3.483 (2H, t, J=7.4 Hz), 3.514 (2H, s), 6.348 (1H, s), 7.128 (7H, m);

IR (neat) 2931, 1456, 1379, 1022, 784, 742, 700 cm$^{-1}$ d) Synthesis of 5-(6-phenylhexyl)-4,5,6,7-tetrahydrofuro[3,2-c]pyridine To a solution of 1.533 g (4.793 mmol) of N-(2-chloroethyl)-N-(3-furylmethyl)-6-phenylhexylamine in 100 ml of tetrahydrofuran, 8.99 ml (14.4 mmol) of 1.6 M n-butyl lithium in hexane was added under ice-cooling, followed by stirring at room temperature for 4 hours. This reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=9/1) to yield the desired product.

Yellow oil Yield 0.434 g (32%)

$^1$H-NMR (CDCl$_3$, 200 MHz) δ1.330–1.440 (4H, m), 1.502–1.671 (4H, m), 2.487–2.645 (4H, m), 2.683–2.830 (4H, m), 3.403 (2H, s), 6.178 (1H, d, J=1.8 Hz), 7.131–7.319 (6H, m);

IR (neat) 2929, 2854, 1456, 1086, 725, 698 cm$^{-1}$ e) Synthesis of N,N-dimethyl-[5-(6-phenylhexyl)-4,5,6,7-tetrahydrofuro[3,2-c]pyridin-2-ylmethyl]amine To a solution of 0.288 g (1.016 mmol) of 5-(6-phenylhexyl)-4,5,6,7-tetrahydrofuro[3,2-c]pyridine in 20 ml of acetic acid, 0.11 g (1.2 mmol) of 50% aqueous dimethylamine and 0.10 g (1.2 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=2/1) to yield the desired product.

Yellow oil Yield 0.199 g (58%)

$^1$H-NMR (CDCl$_3$, 200 MHz) δ1.324–1.359 (4H, m), 1.495–1.661 (4H, m), 2.246 (6H, s), 2.509 (2H, t, J=7.5 Hz), 2.605 (2H, t, J=7.5 Hz), 2.709–2.764 (4H, m), 3.357 (2H, s), 3.394 (2H, s), 5.979 (1H, s), 7.151–7.279 (5H, m);

IR (neat) 2931, 1456, 1099, 1026, 746, 698 cm$^{-1}$ f) Synthesis of N,N-dimethyl-[5-(6-phenylhexyl)-4,5,6,7-tetrahydrofuro[3,2-c]pyridin-2-ylmethyl]amine dihydrochloride N,N-Dimethyl-[5-(6-phenylhexyl)-4,5,6,7-tetrahydrofuro[3,2-c]pyridin-2-ylmethyl)amine 0.199 g was dissolved in 2 ml of methanol; hydrogen chloride in methanol was added in excess, followed by stirring. After this mixture was concentrated, diethyl ether was added; the resulting solid was filtered and washed with diethyl ether to yield the desired product.

Brown solid Yield 0.182 g $^1$H-NMR (CD$_3$OD, 200 MHz) δ1.409–1.498 (4H, m), 1.606–1.735 (2H, m), 1.762–1.877 (2H, m), 2.636 (2H, t, J=7.5 Hz), 2.878 (6H, s), 3.044–3.299 (4H, m), 3.420–3.566 (1H, m), 3.784–3.896 (1H, m), 4.126 (1H, br d, J=15.0 Hz), 4.394 (2H, s), 4.431 (1H, br d, J=14.6 Hz), 6.717 (1H, s), 7.134–7.250 (5H, m);

IR (neat) 2929, 2472, 1471, 1257, 941, 700 cm$^{-1}$;

Anal. Calcd for C$_{22}$H$_{34}$Cl$_2$N$_2$O.0.2H$_2$O: C, 63.36; H, 8.31; N, 6.72. Found: C, 63.35; H, 8.31; N, 6.54.

EXAMPLE 3

Synthesis of N,N-dimethyl-(6-benzyl-4,5,6,7-tetrahydrofuro[3,2-c]pyridin-2-ylmethyl)amine dihydrochloride a) Synthesis of N,N-dimethyl-(6-benzyl-4,5,6,7-tetrahydrofuro[3,2-c]pyridin-2-ylmethyl)amine To a solution of 1.030 g (4.829 mmol) of 6-benzyl-4,5,6,7-tetrahydrofuro[3,2-c]pyridine in 30 ml of acetic acid, 0.52 g (5.80 mmol) of 50% aqueous dimethylamine and 0.47 g (5.80 mmol) of 37% aqueous formaldehyde were added, followed by stirring at 100° C. for 15 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.945 g (72%)

$^1$H-NMR (CDCl$_3$, 200 MHz) δ2.242 (6H, s), 2.661–2.722 (2H, m), 2.769 (2H, m), 3.379 (4H, s), 3.700 (2H, s), 5.951 (1H, s), 7.261–7.404 (5H, m);

IR (neat) 2937, 2765, 1454, 1363, 1091, 1024, 744, 700 cm$^{-1}$ b) Synthesis of N,N-dimethyl-(6-benzyl-4,5,6,7-tetrahydrofuro[3,2-c]pyridin-2-ylmethyl)amine dihydrochloride N,N-Dimethyl-(6-benzyl-4,5,6,7-tetrahydrofuro[3,2-c]pyridin-2-ylmethyl)amine 0.336 g was dissolved in 3 ml of methanol; hydrogen chloride in methanol was added in excess, followed by stirring. After this mixture was concentrated, diethyl ether was added; the resulting solid was filtered and washed with diethyl ether to yield the desired product.

Pale yellow solid Yield 0.367 g $^1$H-NMR (CD$_3$OD, 200 MHz) δ2.867 (6H, s), 3.005–3.222 (2H, m), 3.487–3.627 (1H, m), 3.825–3.932 (1H, m), 4.210 (2H, s), 4.384 (2H, s), 4.480 (1H,d,J=14.6 Hz), 4.577 (1H,d, J=13.2 Hz), 6.678 (1H, s), 7.483–7.641 (5H, m);

IR (nujol) 2474, 1255, 1151, 756, 702 cm$^{-1}$;

Anal. Calcd for C$_{17}$H$_{24}$Cl$_2$N$_2$O.0.9H$_2$O: C, 56.80; H, 7.23; N, 7.79. Found: C, 57.09; H, 7.55; N, 7.74.

EXAMPLE 4

Synthesis of 1-(2-dimethylaminomethyl-5,7-dihydro-4H-furo[2,3-c]pyridin-6-yl)decan-1-one hydrochloride a) Synthesis of 1-(5,7-dihydro-4H-furo[2,3-c]pyridin-6-yl)decan-1-one To a solution of 0.160 g (1.000 mmol) of 4,5,6,7-tetrahydrofuro[2,3-c]pyridine hydrochloride, 0.19 g (1.1 mmol) of n-decanoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with saturated aqueous sodium chloride and dried over anhydrous sodium sulfate; the solvent was distilled off under reduced pressure. The resulting crude product was purified by silica gel chromatography (hexane/ethyl acetate=10/1) to yield the desired product.

White crystal Yield 0.233 g (84%)

$^1$H-NMR (CDCl$_3$, 200 MHz) δ0.876 (3H, t, J=6.5 Hz), 1.260 (12H, br s), 1.608–1.670 (2H, m), 2.384 (2H, q, J=7.7 Hz), 2.524–2.605 (2H, m), 3.650 (1.2H, t, J=5.6 Hz), 3.828 (0.8H, t, J=5.6 Hz), 4.478 (0.8H, s), 4.616 (1.2H, s), 6.240–6.269 (1H, m), 7.300 (1H, s);

IR (neat) 2923, 2852, 1653, 1433, 1207, 1101, 1034, 895, 725 cm$^{-1}$ b) Synthesis of 1-(2-dimethylaminomethyl-5,7-dihydro-4H-furo[2,3-c]pyridin-6-yl)decan-1-one To a solution of 0.230 g (0.829 mmol) of 1-(5,7-dihydro-4H-furo[2,3-c]pyridin-6-yl)decan-1-one in 20 ml of acetic acid, 0.090 ml (1.0 mmol) of 50% aqueous dimethylamine and 0.080 ml (1.0 mmol) of 37% aqueous formaldehyde were added, followed by stirring at 100° C. for 1.5 hours. After the solvent was distilled off under reduced pressure, the residual solution was alkalified with aqueous sodium hydroxide and extracted with dichloromethane 2 times. The combined organic layer was washed with water and dried over anhydrous sodium sulfate; the solvent was distilled off under reduced pressure. The resulting crude product was purified by silica gel column chromatography (ethyl acetate to ethyl acetate/methanol=9/1) to yield the desired product.

Yellow oil Yield 0.135 g (49%)

$^1$H-NMR (CDCl$_3$, 200 MHz) δ0.878 (3H, t, J=6.4 Hz), 1.266 (12H, br s), 1.629–1.658 (2H, m), 2.267 (6H, s), 2.312–2.435 (2H, m), 2.492–2.571 (2H, m), 3.411 (2H, s), 3.640 (1.1H, t, J=5.5 Hz), 3.818 (0.9H, t, J=5.6 Hz), 4.465 (0.9H, s), 4.607 (1.1H, s), 6.055–6.068 (1H, m);

IR (neat) 2924, 2852, 1659, 1441, 1209, 1045, 1024, 966, 906, 847 cm$^{-1}$ c) Synthesis of 1-(2-dimethylaminomethyl-5,7-dihydro-4H-furo[2,3-c]pyridin-6-yl)decan-1-one hydrochloride 1-(2-Dimethylaminomethyl-5,7-dihydro-4H-furo[2,3-c]pyridin-6-yl)decan-1-one 0.135 g was dissolved in 2 ml of methanol; hydrogen chloride in ethyl acetate was added in excess, followed by stirring. After this mixture was concentrated, the resulting solid was washed with diethyl ether to yield the desired product.

Pale brown powder Yield 0.133 g $^1$H-NMR (D$_2$O, 200 MHz) δ0.905 (3H, t, J=6.4 Hz), 1.300 (12H, br s), 1.612–1.663 (2H, m), 2.505–2.679 (4H, m), 2.910 (6H, s), 3.773–3.821 (2H, m), 4.390 (2H, s), 4.628 (1.3H, s), 4.694 (0.7H, s), 6.704–6.715 (1H, m);

IR (nujol) 2441, 1643, 1244, 946, 824, 721 cm$^{-1}$;

Anal. Calcd for C$_{20}$H$_{35}$ClN$_2$O$_2$.0.2H$_2$O: C, 64.13; H, 9.53; N, 7.48. Found: C, 64.07; H, 9.38; N, 7.40.

EXAMPLE 5

Synthesis of 1-(2-dimethylaminomethyl-5,7-dihydro-4H-furo[2,3-c]pyridin-6-yl)-6-phenylhexan-1-one hydrochloride a) Synthesis of 1-(5,7-dihydro-4H-furo[2,3-c]pyridin-6-yl)-6-phenylhexan-1-one To a solution of 0.270 g (1.692 mmol) of 4,5,6,7-tetrahydrofuro[2,3-c]pyridine hydrochloride, 0.36 g (1.9 mmol) of 6-phenylhexanoic acid and 0.94 ml (6.8 mmol) of triethylamine in 30 ml of dichloromethane, 0.39 ml (2.5 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel chromatography (hexane/ethyl acetate=6/1 to 3/1) to yield the desired product.

Pale yellow oil Yield 0.493 g (98%)

$^1$H-NMR (CDCl$_3$, 200 MHz) δ1.346–1.478 (2H, m), 1.626–1.782 (4H, m), 2.379 (2H, q, J=7.6 Hz), 2.485–2.659 (4H, m), 3.632 (1.2H, t, J=5.7 Hz), 3.824 (0.8H, t, J=5.7 Hz), 4.460 (0.8H, s), 4.624 (1.2H, s), 6.244 (0.6H,d, J=1.8 Hz), 6.264 (0.4H,d, J=1.8 Hz), 7.132–7.310 (6H, m);

IR (neat) 2929, 2854, 1653, 1433, 1207, 1105, 1034, 895, 744, 700 cm$^{-1}$ b) Synthesis of 1-(2-dimethylaminomethyl-5,7-dihydro-4H-furo[2,3-c]pyridin-6-yl)-6-phenylhexan-1-one To a solution of 0.493 g (1.658 mmol) of 1-(5,7-dihydro-4H-furo[2,3-c]pyridin-6-yl)-6-phenylhexan-1-one in 20 ml of acetic acid, 0.18 g (2.0 mmol) of 50% aqueous dimethylamine and 0.16 g (2.0 mmol) of 37% aqueous formaldehyde were added, followed by stirring at 100° C. for 15 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.417 g (71%)

$^1$H-NMR (CDCl$_3$, 200 MHz) δ1.352–1.473 (2H, m), 1.572–1.775 (4H, m), 2.259 (6H, s), 2.304–2.654 (6H, m), 3.405 (2H, s), 3.616 (1.2H, t, J=5.7 Hz), 3.810 (0.8H, t, J=5.6 Hz), 4.442 (0.8H, s), 4.598 (1.2H, s), 6.045 (0.6H, s), 6.059 (0.4H, s), 7.131–7.318 (5H, m);

IR (neat) 2935, 1653, 1450, 1432, 1209, 1043, 1024, 906, 747, 700 cm$^{-1}$ c) Synthesis of 1-(2-dimethylaminomethyl-5,7-dihydro-4H-furo[2,3-c]pyridin-6-yl)-6-phenylhexan-1-one hydrochloride 1-(2-Dimethylaminomethyl-5,7-dihydro-4H-furo[2,3-c]pyridin-6-yl)-6-phenylhexan-1-one 0.417 g was dissolved in 2 ml of methanol; hydrogen chloride in methanol was added in excess, followed by stirring. After this mixture was concentrated, diethyl ether was added; the resulting solid was filtered and washed with diethyl ether to yield the desired product.

Pale yellow powder Yield 0.398 g $^1$H-NMR (CD$_3$OD, 200 MHz) δ1.354–1.474 (2H, m), 1.573–1.744 (4H, m), 2.409–2.652 (6H, m), 2.861 (6H, s), 3.742 (1.5H, t, J=5.7 Hz), 3.815 (0.5H, t, J=5.9 Hz), 4.363 (2H, s), 4.601 (2H, s), 6.642 (1H, s), 7.090–7.281 (5H, m);

IR (nujol) 2465, 1626, 1244, 947, 698 cm$^{-1}$;

Anal. Calcd for C$_{22}$H$_{31}$ClN$_2$O$_2$.0.3H$_2$O: C, 66.67; H, 8.04; N, 7.07. Found: C, 66.70; H, 7.90; N, 7.05.

EXAMPLE 6

Synthesis of 1-(2-dimethylaminomethyl-6,7-dihydro-4H-furo[3,2-c]pyridin-5-yl)-6-phenylhexan-1-one hydrochloride a) Synthesis of 1-(6,7-dihydro-4H-furo[3,2-c]pyridin-5-yl)-6-phenylhexan-1-one To a solution of 0.250 g (1.566 mmol) of 4,5,6,7-tetrahydrofuro[3,2-c]pyridine hydrochloride, 0.33 g (1.7 mmol) of 6-phenylhexanoic acid and 0.87 ml (6.3 mmol) of triethylamine in 30 ml of dichloromethane, 0.36 ml (2.4 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel chromatography (hexane/ethyl acetate=6/1 to 3/1) to yield the desired product.

Pale yellow oil Yield 0.403 g (87%)

$^1$H-NMR (CDCl$_3$, 200 MHz) δ1.346–1.478 (2H, m), 1.579 (4H, m), 2.380 (2H, td, J=7.5&5.5 Hz), 2.619 (2H, t, J=7.5 Hz), 2.702–2.768 (2H, m), 3.709 (1H, t, J=5.7 Hz), 3.911 (1H, t, J=5.7 Hz), 4.356 (1H, s), 4.510 (1H, s), 6.233 (0.5H,d, J=1.8 Hz), 6.249 (0.5H,d, J=1.8 Hz), 7.145–7.310 (6H, m);

IR (neat) 2931, 2854, 1647, 1427, 1225, 1134, 1032, 735, 700 cm$^{-1}$ b) Synthesis of 1-(2-dimethylaminomethyl-6,7-dihydro-4H-furo[3,2-c]pyridin-5-yl)-6-phenylhexan-1-one To a solution of 0.403 g (1.355 mmol) of 1-(6,7-dihydro-4H-furo[3,2-c]pyridin-5-yl)-6-phenylhexan-1-one in 20 ml of acetic acid, 0.15 g (1.6 mmol) of 50% aqueous dimethylamine and 0.13 g (1.6 mmol) of 37% aqueous formaldehyde were added, followed by stirring at 100° C. for 15 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.294 g (61%)

$^1$H-NMR (CDCl$_3$, 200 MHz) δ1.337–1.471 (2H, m), 1.575–1.768 (4H, m), 2.257 (3.3H, s), 2.266 (2.7H, s), 2.380 (2H, td, J=7.6&5.1 Hz), 2.617 (2H, t, J=7.7 Hz), 2.671–2.760 (2H, m), 3.394 (1.1H, s), 3.403 (0.9H, s), 3.693 (1.1H, t, J=5.9 Hz), 3.896 (0.9H, t, J=5.6 Hz), 4.315 (0.9H, s), 4.471 (1.1H, s), 6.030 (0.45H, s), 6.046 (0.55H, s), 7.149–7.310 (5H, m);

IR (neat) 2931, 2854, 1653, 1450, 1429, 1224, 1122, 1041, 1024, 802, 748, 700 cm$^{-1}$ c) Synthesis of 1-(2-dimethylaminomethyl-6,7-dihydro-4H-furo[3,2-c]pyridin-5-yl)-6-phenylhexan-1-one hydrochloride 1-(2-Dimethylaminomethyl-6,7-dihydro-4H-furo[3,2-c]pyridin-5-yl)-6-phenylhexan-1-one 0.294 g was dissolved in 2 ml of methanol; hydrogen chloride in methanol was added in excess, followed by stirring. After this mixture was concentrated, diethyl ether was added; the resulting solid was filtered and washed with diethyl ether to yield the desired product.

Pale yellow powder Yield 0.324 g $^1$H-NMR (CD$_3$OD, 200 MHz) δ1.344–1.471 (2H, m), 1.573–1.698 (4H, m), 2.476 (2H, q, J=7.2 Hz), 2.612 (2H, t, J=7.5 Hz), 2.696–2.810 (2H, m), 2.857 (6H, s), 3.834 (1.2H, t, J=5.7 Hz), 3.911 (0.8H, t, J=5.3 Hz), 4.363 (2H, s), 4.488 (2H, s), 6.642 (0.6H, s), 6.662 (0.4H, s), 7.089–7.281 (5H, m);

IR (nujol) 2467, 1643, 1124, 950, 698 cm$^{-1}$;

Anal. Calcd for C$_{22}$H$_{31}$ClN$_2$O$_2$.0.7H$_2$O: C, 65.48; H, 8.09; N, 6.94. Found: C, 65.49; H, 7.84; N, 6.97.

EXAMPLE 7

Synthesis of 1-(2-dimethylaminomethyl-5,7-dihydro-4H-furo[2,3-c]pyridin-6-yl)-4-phenylbutan-1-one hydrochloride a) Synthesis of 1-(5,7-dihydro-4H-furo[2,3-c]pyridin-6-yl)-4-phenylbutan-1-one To a solution of 0.160 g (1.000 mmol) of 4,5,6,7-tetrahydrofuro[2,3-c]pyridine hydrochloride, 0.18 g (1.1 mmol) of 4-phenylbutyric acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel chromatography (hexane/ethyl acetate=10/1 to 5/1) to yield the desired product.

Yellow oil Yield 0.219 g (81%)

$^1$H-NMR (CDCl$_3$, 200 MHz) δ1.974–2.100 (2H, m), 2.392 (2H, q, J=7.9 Hz), 2.523 (2H, t, J=5.6 Hz), 2.695 (2H, dt, J=2.6&7.4 Hz), 3.571 (1.2H, t, J=5.7 Hz), 3.822 (0.8H, t, J=5.7 Hz), 4.398 (0.8H, s), 4.613 (1.2H, s), 6.229–6.261 (1H, m), 7.180–7.286 (6H, m);

IR (neat) 2920, 2850, 1645, 1435, 1205, 1103, 1032, 895, 746, 700 cm$^{-1}$ b) Synthesis of 1-(2-dimethylaminomethyl-5,7-dihydro-4H-furo[2,3-c]pyridin-6-yl)-4-phenylbutan-1-one To a solution of 0.210 g (0.780 mmol) of 1-(5,7-dihydro-4H-furo[2,3-c]pyridin-6-yl)-4-phenylbutan-1-one in 20 ml of acetic acid, 0.11 ml (1.2 mmol) of 50% aqueous dimethylamine and 0.095 ml (1.2 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 2 times. The combined organic layer was washed with water and dried over anhydrous sodium sulfate; the solvent was distilled off under reduced pressure. The resulting crude product was purified by silica gel column chromatography (ethyl acetate/methanol=9/1 to 5/1) to yield the desired product.

Yellow oil Yield 0.161 g (63%)

$^1$H-NMR (CDCl$_3$, 200 MHz) δ1.969–2.044 (2H, m), 2.256 (6H, s), 2.313–2.402 (2H, m), 2.439–2.514 (2H, m), 2.641–2.734 (2H, m), 3.393–3.405 (2H, m), 3.557 (1.1H, t, J=5.6 Hz), 3.807 (0.9H, t, J=5.6 Hz), 4.389 (0.9H, s), 4.597 (1.1 H, s), 6.037–6.052 (1H, m), 7.177–7.277 (5H, m);

IR (neat) 2933, 2854, 2775, 1651, 1444, 1211, 1026, 906, 848, 700 cm$^{-1}$ c) Synthesis of 1-(2-dimethylaminomethyl-5,7-dihydro-4H-furo[2,3-c]pyridin-6-yl)-4-phenylbutan-1-one hydrochloride 1-(2-Dimethylaminomethyl-5,7-dihydro-4H-furo[2,3-c]pyridin-6-yl)-4-phenylbutan-1-one 0.161 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

Pale brown powder Yield 0.153 g $^1$H-NMR (CD$_3$OD, 200 MHz) δ1.907–1.987 (2H, m), 2.414–2.716 (6H, m), 2.857 (6H, s), 3.685 (1.4H, t, J=5.7 Hz), 3.812 (0.6H, t, J=5.7 Hz), 4.367 (2H, s), 4.537 (0.6H, s), 4.598 (1.4H, s), 6.634 (1H, s), 7.153–7.263 (5H, m);

IR (nujol) 2463, 1626, 1246, 949, 698 cm$^{-1}$;

Anal. Calcd for C$_{20}$H$_{27}$ClN$_2$O$_2$.0.2H$_2$O: C, 65.54; H, 7.54; N, 7.64. Found: C, 65.63; H, 7.44; N, 7.63.

EXAMPLE 8

Synthesis of 1-(2-dimethylaminomethyl-6,7-dihydro-4H-furo[3,2-c]pyridin-5-yl)-4-phenylbutan-1-one hydrochloride a) Synthesis of 1-(6,7-dihydro-4H-furo[3,2-c]pyridin-5-yl)-4-phenylbutan-1-one To a solution of 0.160 g (1.000 mmol) of 4,5,6,7-tetrahydrofuro[3,2-c]pyridine hydrochloride, 0.18 g (1.1 mmol) of 4-phenylbutyric acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel chromatography (hexane/ethyl acetate=3/1) to yield the desired product.

Yellow oil Yield 0.165 g (61%)

$^1$H-NMR (CDCl$_3$, 200 MHz) δ1.954–2.084 (2H, m), 2.344–2.447 (2H, m), 2.649–2.736 (4H, m), 3.647 (1H, t, J=5.9 Hz), 3.909 (1H, t, J=5.9 Hz), 4.281 (1H, s), 4.510 (1H, s), 6.225 (1H, dd, J=1.4&8.8 Hz), 7.164–7.321 (6H, m);

IR (neat) 2931, 2854, 1651, 1435, 1225, 1099, 1032, 891, 746, 702 cm$^{-1}$ b) Synthesis of 1-(2-dimethylaminomethyl-6,7-dihydro-4H-furo[3,2-c]pyridin-5-yl)-4-phenylbutan-1-one To a solution of 0.160 g (0.594 mmol) of 1-(6,7-dihydro-4H-furo[3,2-c]pyridin-5-yl)-4-phenylbutan-1-one in 20 ml of acetic acid, 0.080 ml (0.88 mmol) of 50% aqueous dimethylamine and 0.072 ml (0.88 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 2 times. The combined organic layer was washed with water and dried over anhydrous sodium sulfate; the solvent was distilled off under reduced pressure. The resulting crude product was purified by silica gel column chromatography (ethyl acetate to ethyl acetate/methanol=4/1) to yield the desired product.

Yellow oil Yield 0.122 g (63%)

$^1$H-NMR (CDCl$_3$, 200 MHz) δ1.954–2.062 (2H, m), 2.265 (6H,d, J=1.8 Hz), 2.339–2.442 (2H, m), 2.650–2.735 (4H, m), 3.405 (2H, s), 3.636 (1H, t, J=5.6 Hz), 3.894 (1H, t, J=5.8 Hz), 4.244 (1H, s), 4.473 (1.1H, s), 6.032 (1H,d, J=8.0 Hz), 7.164–7.281 (5H, m);

IR (neat) 2937, 2777, 1651, 1454, 1227, 1027, 750, 702 cm$^{-1}$ c) Synthesis of 1-(2-dimethylaminomethyl-6,7-dihydro-4H-furo[3,2-c]pyridin-5-yl)-4-phenylbutan-1-one hydrochloride 1-(2-Dimethylaminomethyl-6,7-dihydro-4H-furo[3,2-c]pyridin-5-yl)-4-phenylbutan-1-one 0.122 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

Pale brown powder Yield 0.102 g $^1$H-NMR (CD$_3$OD, 200 MHz) δ1.908–1.983 (2H, m), 2.478 (2H, q, J=7.6 Hz), 2.644–2.787 (4H, m), 2.854 (6H, s), 3.769 (1H, t, J=5.7 Hz), 3.901 (1H, t, J=5.7 Hz), 4.357 (2H, s), 4.393 (1H, s), 4.483 (1H, s), 6.625 (1H, s), 7.150–7.262 (5H, m);

IR (nujol) 2467, 1651, 1254, 1207, 1126, 696 cm$^{-1}$;

Anal. Calcd for C$_{20}$H$_{27}$ClN$_2$O$_2$.0.4H$_2$O: C, 64.91; H, 7.57; N, 7.57. Found: C, 65.10; H, 7.31; N, 7.53.

EXAMPLE 9

Synthesis of 1-(2-dimethylaminomethyl-5,7-dihydro-4H-furo[2,3-c]pyridin-6-yl)-3-(3-phenethylphenyl)propan-1-one hydrochloride a) Synthesis of 1-(5,7-dihydro-4H-furo[2,3-c]pyridin-6-yl)-3-(3-phenethylphenyl)propan-1-one To a solution of 0.163 g (1.021 mmol) of 4,5,6,7-tetrahydrofuro[2,3-c]pyridine hydrochloride, 0.29 g (1.1 mmol) of 3-(3-phenethylphenyl)propionic acid and 0.57 ml (4.1 mmol) of triethylamine in 30 ml of dichloromethane, 0.23 ml (1.5 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel chromatography (hexane/ethyl acetate =6/1 to 3/1) to yield the desired product.

Pale yellow oil Yield 0.338 g (92%)

$^1$H-NMR (CDCl$_3$, 200 MHz) δ2.453–2.557 (2H, m), 2.581–2.709 (2H, m), 2.888 (4H, s), 2.929–3.008 (2H, m), 3.570 (1.2H, t, J=5.6 Hz), 3.832 (0.8H, t, J=5.6 Hz), 4.367 (1.2H, s), 4.632 (0.8H, s), 6.227 (1.2H,d, J=1.8 Hz), 6.251 (0.8H,d, J=1.8 Hz), 6.979–7.072 (3H, m), 7.138–7.325 (7H, m);

IR (neat) 2924, 2854, 1653, 1439, 1205, 1103, 1034, 895, 789, 735, 702 cm$^{-1}$ b) Synthesis of 1-(2-dimethylaminomethyl-5,7-dihydro-4H-furo[2,3-c]pyridin-6-yl)-3-(3-phenethylphenyl)propan-1-one To a solution of 0.338 g (0.940 mmol) of 1-(5,7-dihydro-4H-furo[2,3-c]pyridin-6-yl)-3-(3-phenethylphenyl) propan- 1-one in 20 ml of acetic acid, 0.10 g (1.1 mmol) of 50% aqueous dimethylamine and 0.09 g (1.1 mmol) of 37% aqueous formaldehyde were added, followed by stirring at 100° C. for 15 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale yellow oil Yield 0.237 g (61%)

$^1$H-NMR (CDCl$_3$, 200 MHz) δ2.250 (6H, s), 2.419–2.515 (2H, m), 2.578–2.697 (2H, m), 2.886 (4H, s), 2.865–2.998 (2H, m), 3.393 (2H, s), 3.555 (1.1H, t, J=5.6 Hz), 3.815 (0.9H, t, J=5.7 Hz), 4.362 (0.9H, s), 4.615 (1.1H, s), 6.027 (0.55H, s), 6.048 (0.45H, s), 6.999–7.064 (3H, m), 7.142–7.322 (6H, m);

IR (neat) 2935, 2856, 1653, 1448, 1209, 1024, 791, 750, 702 cm$^{-1}$ c) Synthesis of 1-(2-dimethylaminomethyl-5,7-dihydro-4H-furo[2,3-c]pyridin-6-yl)-3-(3-phenethylphenyl)propan-1-one hydrochloride 1-(2-Dimethylaminomethyl-5,7-dihydro-4H-furo[2,3-c]pyridin-6-yl)-3-(3-phenethylphenyl)propan-1-one 0.237 g was dissolved in 2 ml of methanol; hydrogen chloride in methanol was added in excess, followed by stirring. After this mixture was concentrated, diethyl ether was added; the resulting solid was filtered and washed with diethyl ether to yield the desired product.

Pale brown powder Yield 0.166 g $^1$H-NMR (CD$_3$OD, 200 MHz) δ2.389–2.962 (6H, m), 2.826 (4H, s), 2.839 (6H, s), 3.625 (1.4H, t, J=5.6 Hz), 3.792 (0.6H, t, J=5.3 Hz), 4.315 (1.4H, s), 4.334 (0.6H, s), 4.418 (0.6H, s), 4.596 (1.4H, s), 6.585 (1H, s), 6.993–7.054 (3H, m), 7.089–7.277 (6H, m);

IR (nujol) 2470, 1624, 1228, 700 cm$^{-1}$;

Anal. Calcd for C$_{27}$H$_{33}$ClN$_2$O$_2$·0.5H$_2$O: C, 70.19; H, 7.42; N, 6.06. Found: C, 70.36; H, 7.38; N, 6.17.

EXAMPLE 10

Synthesis of 1-(2-dimethylaminomethyl-6,7-dihydro-4H-furo[3,2-c]pyridin-5-yl)-3-(3-phenethylphenyl)propan-1-one hydrochloride a) Synthesis of 1-(6,7-dihydro-4H-furo[3,2-c]pyridin-5-yl)-3-(3-phenethylphenyl)propan-1-one To a solution of 0.163 g (1.021 mmol) of 4,5,6,7-tetrahydrofuro[3,2-c]pyridine hydrochloride, 0.29 g (1.1 mmol) of 3-(3-phenethylphenyl)propionic acid and 0.57 ml (4.1 mmol) of triethylamine in 30 ml of dichloromethane, 0.23 ml (1.5 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel chromatography (hexane/ethyl acetate= 6/1 to 3/1) to yield the desired product.

Pale yellow oil Yield 0.331 g (90%)

$^1$H-NMR (CDCl$_3$, 200 MHz) δ2.603–2.731 (4H, m), 2.881 (4H, s), 2.901–3.004 (2H, m), 3.634 (1.1H, t, J=5.6 Hz), 3.922 (0.9H, t, J=5.9 Hz), 4.284 (1.1H, s), 4.526 (0.9H, s), 6.180 (0.9H, d, J=1.8 Hz), 6.246 (1.1H, d, J=1.8 Hz), 7.001–7.100 (3H, m), 7.156–7.281 (7H, m);

IR (neat) 2926, 2854, 1651, 1430, 1223, 1134, 1032, 789, 702 cm$^{-1}$ b) Synthesis of 1-(2-dimethylaminomethyl-6,7-dihydro-4H-furo[3,2-c]pyridin-5-yl)-3-(3-phenethylphenyl)propan-1-one To a solution of 0.331 g (0.921 mmol) of 1-(6,7-dihydro-4H-furo[3,2-c]pyridin-5-yl)-3-(3-phenethylphenyl) propan-1-one in 20 ml of acetic acid, 0.10 g (1.1 mmol) of 50% aqueous dimethylamine and 0.09 g (1.1 mmol) of 37% aqueous formaldehyde were added, followed by stirring at 100° C. for 15 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale yellow oil Yield 0.293 g (76%)

$^1$H-NMR (CDCl$_3$, 200 MHz) δ2.247 (3H, s), 2.261 (3H, s), 2.597–2.698 (4H, m), 2.883 (4H, s), 2.921–2.999 (2H, m), 3.381 (1H, s), 3.397 (1H, s), 3.622 (1H, t, J=5.7 Hz), 3.908 (1H, t, J=5.7 Hz), 4.253 (1H, s), 4.488 (1H, s), 5.988 (0.5H, s), 6.044 (0.5H, s), 6.998–7.062 (3H, m), 7.141–7.321 (6H, m);

IR (neat) 2935, 2856, 1651, 1449, 1224, 1124, 1024, 793, 752, 702 cm$^{-1}$ c) Synthesis of 1-(2-dimethylaminomethyl-6,7-dihydro-4H-furo[3,2-c]pyridin-5-yl)-3-(3-phenethylphenyl)propan-1-one hydrochloride 1-(2-Dimethylaminomethyl-6,7-dihydro-4H-furo[3,2-c]pyridin-5-yl)-3-(3-phenethylphenyl)propan-1-one 0.293 g was dissolved in 2 ml of methanol; hydrogen chloride in methanol was added in excess, followed by stirring. This mixture was concentrated to yield the desired product.

Yellow viscous oil Yield 0.278 g $^1$H-NMR (CD$_3$OD, 200 MHz) δ2.583–2.911 (6H, m), 2.834 (4H, s), 2.845 (6H, s), 3.693 (1.2H, t, J=5.5 Hz), 3.889 (0.8H, t, J=5.1 Hz), 4.308 (0.8H, s), 4.336 (2H, s), 4.488 (1.2H, s), 6.574 (0.4H, s), 6.614 (0.6H, s), 6.995–7.050 (3H, m), 7.098–7.226 (6H, m);

IR (nujol) 2665, 1645, 1227, 1132, 702 cm$^{-1}$;

Anal. Calcd for C$_{27}$H$_{33}$ClN$_2$O$_2$·1.1H$_2$O: C, 68.58; H, 7.50; N, 5.92. Found: C, 68.58; H, 7.51; N, 5.99.

EXAMPLE 11

Synthesis of N,N-dimethyl-[6-(4-benzoylbenzoyl)-4,5,6,7-tetrahydrofuro[2,3-c]pyridin-2-ylmethyl]amine hydrochloride a) Synthesis of N,N-dimethyl-[6-(4-benzoylbenzoyl)-4,5,6,7-tetrahydrofuro[2,3-c]pyridin-2-ylmethyl]amine Method A To a solution of 3.546 g (22.22 mmol) of 4,5,6,7-tetrahydrofuro[2,3-c]pyridine hydrochloride, 5.53 g (24.4 mmol) of 4-benzoylbenzoic acid and 12.4 ml (88.9 mmol) of triethylamine in 50 ml of dichloromethane, 4.35 g (26.7 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting residue was subjected to silica gel column chromatography (hexane/ethyl acetate=3/1 to 2/1). The resulting crude 6-(4-benzoylbenzoyl)-4,5,6,7-tetrahydrofuro[2,3-c]pyridine was used for the next reaction without further purification.

Orange oil Yield 7.771 g

To solution of 7.771 g of crude 6-(4-benzoylbenzoyl)-4,5,6,7-tetrahydrofuro[2,3-c]pyridine in 50 ml of acetic acid, 2.40 g (26.7 mmol) of 50% aqueous dimethylamine and 2.16 g (26.7 mmol) of 37% aqueous formaldehyde were added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=9/1) to yield the desired product.

Orange oil Yield 7.322 g (85%)

Method B

To a solution of 0.308 g (1.099 mmol) of N,N-dimethyl-(6-tert-butoxycarbonyl-4,5,6,7-tetrahydrofuro[2,3-c]pyridin-2-ylmethyl)amine in 5 ml of methanol, 1 ml of concentrated hydrochloric acid was added, followed by stirring at room temperature for 1 hour. The solvent was distilled off under reduced pressure. The resulting crude N,N-dimethyl-(4,5,6,7-tetrahydrofuro[2,3-c]pyridin-2-ylmethyl)amine dihydrochloride was used for the next reaction without purification.

Black-brown solid Yield 0.253 g

To a solution of 0.253 g (1.000 mmol) of the above N,N-dimethyl-(4,5,6,7-tetrahydrofuro[2,3-c]pyridin-2-ylmethyl)amine dihydrochloride, 0.27 g (1.2 mmol) of 4-benzoylbenzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with saturated aqueous sodium chloride and dried over anhydrous sodium sulfate; the solvent was distilled off under reduced pressure. The resulting crude product was purified by silica gel chromatography (chloroform/methanol=25/1) to yield the desired product.

Yellow oil Yield 0.329 g (77%)

$^1$H-NMR (CDCl$_3$, 200 MHz) δ2.282 (6H, br s), 2.504–2.678 (2H, m), 3.370–3.449 (2H, m), 3.548–3.658 (1.2H, m), 3.999 (0.8H, br s), 4.451 (0.8H, br s), 4.781 (1.2H, br s), 6.096 (1H, s), 7.464–7.664 (5H, m), 7.797–7.878 (4H, m);

IR (neat) 2947, 1633, 1504, 1444, 1277, 1043, 939, 752, 702 cm$^{-1}$ b) Synthesis of N,N-dimethyl-[6-(4-benzoylbenzoyl)-4,5,6,7-tetrahydrofuro[2,3-c]pyridin-2-ylmethyl]amine hydrochloride N,N-Dimethyl-[6-(4-benzoylbenzoyl)-4,5,6,7-tetrahydrofuro[2,3-c]pyridin-2-ylmethyl]amine 0.329 g was dissolved in 2 ml of methanol; hydrogen chloride in ethyl acetate was added in excess, followed by stirring. After this mixture was concentrated, the resulting solid was recrystallized from methanol-diethyl ether to yield the desired product.

White crystal Yield 0.261 g $^1$H-NMR (CD$_3$OD, 200 MHz) δ2.642 (2H, br s), 2.887 (6H, br s), 3.670 (1.3H, br s), 4.027 (0.7H, br s), 4.330–4.404 (2H, m), 4.557 (0.7H, br s), 4.804 (1.3H, br s), 6.679 (1H, s), 7.512–7.727 (5H, m), 7.792–7.912 (4H, m);

IR (nujol) 2472, 1632, 1282, 1157, 1113, 945, 696 cm$^{-1}$;

Anal. Calcd for C$_{24}$H$_{25}$ClN$_2$O$_3$·0.5H$_2$O: C, 66.43; H, 6.04; N, 6.46. Found: C, 66.41; H, 6.24; N, 6.21.

EXAMPLE 12

Synthesis of N,N-dimethyl-[5-(4-benzoylbenzoyl)-4,5,6,7-tetrahydrofuro[3,2-c]pyridin-2-ylmethyl]amine hydrochloride a) Synthesis of 5-(4-benzoylbenzoyl)-4,5,6,7-tetrahydrofuro[3,2-c]pyridine To a solution of 0.160 g (1.000 mmol) of 4,5,6,7-tetrahydrofuro[3,2-c]pyridine hydrochloride, 0.27 g (1.2 mmol) of 4-benzoylbenzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. This solution was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=5/1 to 3/1); the resulting solid was washed with diethyl ether to yield the desired product.

White crystal Yield 0.233 g (70%)

$^1$H-NMR (CDCl$_3$, 200 MHz) δ2.723–2.871 (2H, m), 3.678 (1.1H, br s), 4.066–4.121 (0.9H, m), 4.343 (0.9H, s), 4.690 (1.1H, s), 6.124 (0.5H, s), 6.321 (0.5H, s), 7.259–7.341 (1H, m), 7.457–7.659 (5H, m), 7.791–7.877 (4H, m);

IR (KBr) 3052, 2836, 2364, 1651, 1435, 1282, 1095, 943, 723 cm$^{-1}$ b) Synthesis of N,N-dimethyl-[5-(4-benzoylbenzoyl)-4,5,6,7-tetrahydrofuro[3,2-c]pyridin-2-ylmethyl]amine To a solution of 0.230 g (0.694 mmol) of 5-(4-benzoylbenzoyl)-4,5,6,7-tetrahydrofuro[3,2-c]pyridine in 20 ml of acetic acid, 0.094 ml (1.04 mmol) of 50% aqueous dimethylamine and 0.085 ml (1.04 mmol) of 37% aqueous formaldehyde were added, followed by stirring at 100° C. for 1 hour. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1); the resulting solid was washed with hexane to yield the desired product.

White crystal Yield 0.180 g (42%)

$^1$H-NMR (CDCl$_3$, 200 MHz) δ2.273 (6H, br s), 2.719–2.859 (2H, m), 3.426 (2H, br s), 3.658 (1.1H, s), 4.079 (0.9H, br s), 4.304 (0.9H, s), 4.654 (1.1H, s), 5.921 (0.4H, s), 6.125 (0.6H, s), 7.458–7.667 (5H, m), 7.790–7.874 (4H, m);

IR (KBr) 2775, 2494, 1632, 1429, 1281, 1109, 954 cm$^{-1}$ c) Synthesis of N,N-dimethyl-[5-(4-benzoylbenzoyl)-4,5,6,7-tetrahydrofuro[3,2-c]pyridin-2-ylmethyl]amine hydrochloride N,N-Dimethyl-[5-(4-benzoylbenzoyl)-4,5,6,7-tetrahydrofuro[3,2-c]pyridin-2-ylmethyl]amine 0.180 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

White crystal Yield 0.137 g $^1$H-NMR (CD$_3$OD, 200 MHz) δ2.877 (8H, br s), 3.716–3.752 (1.1H, m), 4.086–4.150 (0.9H, m), 4.351–4.432 (2.9H, m), 4.689 (1.1H, s), 6.520 (0.4H, s), 6.712 (0.6H, s), 7.504–7.718 (5H, m), 7.785–7.902 (4H, m);

IR (nujol) 2468, 1633, 1281, 1111, 928, 860, 698 cm$^{-1}$;

Anal. Calcd for $C_{24}H_{25}ClN_2O_3 \cdot 0.5H_2O$: C, 66.43; H, 6.04; N, 6.46. Found: C, 66.37; H, 6.27; N, 6.29.

EXAMPLE 13

Synthesis of N,N-dimethyl-[6-(3-benzoylbenzoyl)-4,5,6,7-tetrahydrofuro[2,3-c]pyridin-2-ylmethyl]amine hydrochloride a) Synthesis of dimethyl-[6-(3-benzoylbenzoyl)-4,5,6,7-tetrahydrofuro[2,3-c]pyridin-2-ylmethyl]amine To a solution of 0.278 g (0.992 mmol) of N,N-dimethyl-(6-tert-butoxycarbonyl-4,5,6,7-tetrahydrofuro[2,3-c]pyridin-2-ylmethyl)amine in 5 ml of methanol, 1 ml of concentrated hydrochloric acid was added, followed by stirring at room temperature for 1 hour. The solvent was distilled off under reduced pressure. The resulting crude N,N-dimethyl-(4,5,6,7-tetrahydrofuro[2,3-c]pyridin-2-ylmethyl)amine dihydrochloride was used for the next reaction without purification.

Black-brown solid Yield 0.228 g

To a solution of 0.228 g (0.900 mmol) of the above N,N-dimethyl-(4,5,6,7-tetrahydrofuro[2,3-c]pyridin-2-ylmethyl)amine dihydrochloride, 0.26 g (1.1 mmol) of 3-benzoylbenzoic acid and 0.53 ml (3.8 mmol) of triethylamine in 30 ml of dichloromethane, 0.23 g (1.43 mmol) of diethyl cyanophosphonate was added dropwise under ice-cooling, followed by overnight stirring at room temperature. The reaction mixture was poured into water and extracted with dichloromethane 2 times. The combined organic layer was washed with saturated aqueous sodium chloride and dried over anhydrous sodium sulfate; the solvent was distilled off under reduced pressure. The resulting crude product was purified by silica gel chromatography (chloroform to chloroform/methanol=50/1) to yield the desired product.

Yellow oil Yield 0.255 g (66%)

$^1$H-NMR (CDCl$_3$, 200 MHz) δ2.267 (6H, br s), 2.513–2.654 (2H, m), 3.372–3.430 (2H, m), 3.587 (1.2H, br s), 3.974 (0.8H, br s), 4.456 (0.8H, br s), 4.746 (1.2H, br s), 6.079 (1H, s), 7.462–7.905 (9H, m);

IR (neat) 2939, 2779, 1633, 1441, 1286, 1045, 906, 717 cm$^{-1}$ b) Synthesis of N,N-dimethyl-[6-(3-benzoylbenzoyl)-4,5,6,7-tetrahydrofuro[2,3-c]pyridin-2-ylmethyl]amine hydrochloride N,N-Dimethyl-[6-(3-benzoylbenzoyl)-4,5,6,7-tetrahydrofuro[2,3-c]pyridin-2-ylmethyl]amine 0.255 g was dissolved in 2 ml of methanol; hydrogen chloride in ethyl acetate was added in excess, followed by stirring. After this mixture was concentrated, the resulting solid was recrystallized from methanol-ethyl acetate to yield the desired product.

Pale brown crystal Yield 0.183 g $^1$H-NMR (CD$_3$OD, 200 MHz) δ2.563–2.712 (2H, m), 2.870 (6H, br s), 3.639–3.686 (1.4H, m), 3.972–4.025 (0.6H, m), 4.381 (2H, s), 4.560–4.608 (0.6H, m), 4.771 (1.4H, s), 6.658 (1H, s), 7.504–7.935 (9H, m);

IR (nujol) 2478, 1655, 1373, 1252, 714 cm$^{-1}$;

Anal. Calcd for $C_{24}H_{25}ClN_2O_3$: C, 67.84; H, 5.93; N, 6.59.

Found: C, 67.83; H, 6.05; N, 6.37.

EXAMPLE 14

Synthesis of N,N-dimethyl-[5-(3-benzoylbenzoyl)-4,5,6,7-tetrahydrofuro[3,2-c]pyridin-2-ylmethyl]amine hydrochloride a) Synthesis of 5-(3-benzoylbenzoyl)-4,5,6,7-tetrahydrofuro[3,2-c]pyridine To a solution of 0.160 g (1.000 mmol) of 4,5,6,7-tetrahydrofuro[3,2-c]pyridine hydrochloride, 0.27 g (1.2 mmol) of 3-benzoylbenzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1) to yield the desired product.

Colorless oil Yield 0.210 g (63%)

$^1$H-NMR (CDCl$_3$, 200 MHz) δ2.708–2.856 (2H, m), 3.686 (1H, br s), 4.054 (1H, br s), 4.353 (1H, br s), 4.659 (1H, br s), 6.122 (0.5H, br s), 6.312 (0.5H, br s), 7.315 (1H, br s), 7.458–7.712 (5H, m), 7.789–7.915 (4H, m);

IR (neat) 1630, 1442, 1254, 1136, 1093, 717 cm$^{-1}$ b) Synthesis of N,N-dimethyl-[5-(3-benzoylbenzoyl)-4,5,6,7-tetrahydrofuro[3,2-c]pyridin-2-ylmethyl]amine To a solution of 0.200 g (0.604 mmol) of 5-(3-benzoylbenzoyl)-4,5,6,7-tetrahydrofuro[3,2-c]pyridine in 20 ml of acetic acid, 0.082 ml (0.91 mmol) of 50% aqueous dimethylamine and 0.073 ml (0.73 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1 to 25/1) to yield the desired product.

Yellow oil Yield 0.155 g (66%)

$^1$H-NMR (CDCl$_3$, 200 MHz) δ2.264 (6H, s), 2.697–2.829 (2H, m), 3.408 (2H, s), 3.628–3.693 (1.2H, m), 4.020–4.047 (0.8H, m), 4.305 (0.8H, br s), 4.621 (1.2H, br s), 5.909 (0.5H, br s), 6.107 (0.5H, br s), 7.449–7.708 (5H, m), 7.779–7.905 (4H, m);

IR (neat) 2935, 2777, 1613, 1416, 1260, 1144, 1113, 1043, 719 cm$^{-1}$ c) Synthesis of N,N-dimethyl-[5-(3-benzoylbenzoyl)-4,5,6,7-tetrahydrofuro[3,2-c]pyridin-2-ylmethyl]amine hydrochloride N,N-Dimethyl-[5-(3-benzoylbenzoyl)-4,5,6,7-tetrahydrofuro[3,2-c]pyridin-2-ylmethyl]amine 0.155 g was dissolved in 2 ml of methanol; hydrogen chloride in ethyl acetate was added in excess, followed by stirring. After this mixture was concentrated, the resulting foam was washed with diethyl ether to yield the desired product.

Pale yellow foam Yield 0.157 g $^1$H-NMR (CD$_3$OD, 200 MHz) δ2.861 (8H, br s), 3.739–3.808 (1H, m), 4.070–4.114 (1H, m), 4.323–4.479 (3H, m), 4.603–4.695 (1H, m), 6.536–6.708 (1H, m), 7.276–7.930 (9H, m);

IR (nujol) 1786, 1637, 1238, 1113, 758 cm$^{-1}$;

Anal. Calcd for $C_{24}H_{25}ClN_2O_3 \cdot 0.7H_2O$: C, 65.88; H, 6.08; N, 6.40. Found: C, 65.92; H, 6.28; N, 6.31.

EXAMPLE 15

Synthesis of N,N-dimethyl-[6-(2-benzoylbenzoyl)-4,5,6,7-tetrahydrofuro[2,3-c]pyridin-2-ylmethyl]amine hydrochloride a) Synthesis of N,N-dimethyl-[6-(2-benzoylbenzoyl)-4,5,6,7-tetrahydrofuro[2,3-c]pyridin-2-ylmethyl]amine To a solution of 0.278 g (0.992 mmol) of N,N-dimethyl-(6-tert-butoxycarbonyl-4,5,6,7-tetrahydrofuro[2,3-c]pyridin-2-ylmethyl)amine in 5 ml of methanol, 1 ml of concentrated hydrochloric acid was added, followed by stirring at room temperature for 1 hour. The solvent was distilled off under reduced pressure. The resulting crude N,N-dimethyl-(4,5,6,7-tetrahydrofuro[2,3-c]pyridin-2-ylmethyl)amine dihydrochloride was used for the next reaction without purification.

Black-brown solid Yield 0.228 g

To a solution of 0.228 g (0.900 mmol) of the above N,N-dimethyl-(4,5,6,7-tetrahydrofuro[2,3-c]pyridin-2-ylmethyl)amine dihydrochloride, 0.24 g (1.1 mmol) of 2-benzoylbenzoic acid and 0.50 ml (3.6 mmol) of triethylamine in 30 ml of dichloromethane, 0.22 g (1.35 mmol) of diethyl cyanophosphonate was added dropwise under ice-cooling, followed by overnight stirring at room temperature. The reaction mixture was poured into water and extracted with dichloromethane 2 times. The combined organic layer was washed with saturated aqueous sodium chloride and dried over anhydrous sodium sulfate; the solvent was distilled off under reduced pressure. The resulting crude product was purified by silica gel chromatography (chloroform to chloroform/methanol=25/1) to yield the desired product.

Yellow oil Yield 0.291 g (76%)
$^1$H-NMR (CDCl$_3$, 200 MHz) δ2.272 (6H, s), 2.426–2.508 (2H, m), 3.369 (0.8H, s), 3.431 (1.2H, s), 3.547 (1.2H, t, J=5.0 Hz), 3.791 (0.8H, t, J=5.3 Hz), 4.340 (0.8H, s), 4.561 (1.2H, s), 6.067 (1H, s), 7.357–7.603 (7H, m), 7.698–7.811 (2H, m);
IR (neat) 2948, 2857, 2766, 1633, 1429, 1279, 1045, 937, 752, 704 cm$^{-1}$ b) Synthesis of N,N-dimethyl-[6-(2-benzoylbenzoyl)-4,5,6,7-tetrahydrofuro[2,3-c]pyridin-2-ylmethyl]amine hydrochloride N,N-Dimethyl-[6-(2-benzoylbenzoyl)-4,5,6,7-tetrahydrofuro[2,3-c]pyridin-2-ylmethyl)amine 0.291 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

Brown powder Yield 0.178 g
$^1$H-NMR (CD$_3$OD, 200 MHz) δ2.463–2.606 (2H, m), 2.853–2.876 (6H, m), 3.584–3.611 (1H, m), 3.828–3.839 (1H, m), 4.327–4.377 (2H, m), 4.436 (0.8H, s), 4.644 (1.2H, s), 6.648 (1H, s), 7.410–7.828 (9H, m);
IR (nujol) 2468, 1626, 1277, 931, 706 cm$^{-1}$;
Anal. Calcd for C$_{24}$H$_{25}$ClN$_2$O$_3$·0.8H$_2$O: C, 65.61; H, 6.10; N, 6.38. Found: C, 65.58; H, 6.32; N, 6.15.

EXAMPLE 16

Synthesis of N,N-dimethyl-[5-(2-benzoylbenzoyl)-4,5,6,7-tetrahydrofuro[3,2-c]pyridin-2-ylmethyl]amine hydrochloride a) Synthesis of 5-(2-benzoylbenzoyl)-4,5,6,7-tetrahydrofuro[3,2-c]pyridine To a solution of 0.160 g (1.000 mmol) of 4,5,6,7-tetrahydrofuro[3,2-c]pyridine hydrochloride, 0.27 g (1.2 mmol) of 2-benzoylbenzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate= 5/1 to 3/1) to yield the desired product.

Colorless oil Yield 0.152 g (46%)
$^1$H-NMR (CDCl$_3$, 200 MHz) δ2.527–2.566 (1H, m), 2.694–2.724 (1H, m), 3.639 (1H, t, 5.5 Hz), 3.829 (1H, t, 5.4 Hz), 4.280 (1H, s), 4.498 (1H, s), 6.112 (0.5H, s), 6.262 (0.5H, s), 7.306–7.817 (10H, m);
IR (neat) 3104, 2844, 2364, 1622, 1441, 1279, 1092, 930, 787, 700 cm$^{-1}$ b) Synthesis of N,N-dimethyl-[5-(2-benzoylbenzoyl)-4,5,6,7-tetrahydrofuro[3,2-c]pyridin-2-ylmethyl]amine To a solution of 0.140 g (0.422 mmol) of 5-(2-benzoylbenzoyl)-4,5,6,7-tetrahydrofuro[3,2-c]pyridine in 20 ml of acetic acid, 0.060 ml (0.63 mmol) of 50% aqueous dimethylamine and 0.052 ml (0.63 mmol) of 37% aqueous formaldehyde were added, followed by stirring at 100° C. for 45 minutes. After the solvent was distilled off under reduced pressure, the residual solution was alkalified with aqueous sodium hydroxide and extracted with dichloromethane 3 times. The combined organic layer was washed with water and dried over anhydrous sodium sulfate; the solvent was distilled off under reduced pressure. The resulting crude product was purified by silica gel column chromatography (chloroform to chloroform/methanol=25/1) to yield the desired product.

Yellow oil Yield 0.155 g (95%)
$^1$H-NMR (CDCl$_3$, 200 MHz) δ2.271 (6H, s), 2.552–2.558 (0.9H, m), 2.674–2.730 (1.1H, m), 3.406 (2H, s), 3.621 (1.1H, t, J=5.8 Hz), 3.811 (0.9H, t, J=5.2 Hz), 4.223 (0.9H, s), 4.451 (1.1H, s), 5.910 (0.5H, s), 6.064 (0.5H, s), 7.334–7.601 (7H, m), 7.698 (0.9H, d, J=7.4 Hz), 7.796 (1.1H, d, J=7.4 Hz);
IR (neat) 2942, 2777, 1633, 1429, 1279, 1120, 1038, 931, 750 cm$^{-1}$ c) Synthesis of N,N-dimethyl-[5-(2-benzoylbenzoyl)-4,5,6,7-tetrahydrofuro[3,2-c]pyridin-2-ylmethyl]amine hydrochloride N,N-Dimethyl-[5-(2-benzoylbenzoyl)-4,5,6,7-tetrahydrofuro[3,2-c]pyridin-2-ylmethyl]amine 0.155 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

Pale yellow solid Yield 0.143 g
$^1$H-NMR (CD$_3$OD, 200 MHz) δ2.583–2.642 (1H, m), 2.776–2.873 (7H, m), 3.697 (1H, t, J=5.6 Hz), 3.867–3.953 (1H, m), 4.340–4.378 (3H, m), 4.527 (1H, s), 6.470 (0.5H, s), 6.666 (0.5H, s), 7.335–7.798 (9H, m);
IR (nujol) 1622, 1375, 1279, 930, 702 cm$^{-1}$;
Anal. Calcd for C$_{24}$H$_{25}$ClN$_2$O$_3$·0.8H$_2$O: C, 65.61; H, 6.10; N, 6.38. Found: C, 65.56; H, 6.28; N, 6.12.

EXAMPLE 17

Synthesis of 2-(4-benzyloxy-3-methoxyphenyl)-1-(2-dimethylaminomethyl-5,7-dihydro-4H-furo[2,3-c]pyridin-6-yl)ethan-1-one hydrochloride a) Synthesis of 2-(4-benzyloxy-3-methoxyphenyl)-1-(5,7-dihydro-4H-furo[2,3-c]pyridin-6-yl)ethan-1-one To a solution of 0.160 g (1.000 mmol) of 4,5,6,7-tetrahydrofuro[2,3-c]pyridine hydrochloride, 0.33 g (1.2 mmol) of 4-benzyloxy-3-methoxyphenylacetic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1 to 2/1) to yield the desired product.

Pale yellow oil Yield 0.293 g (78%)
$^1$H-NMR (CDCl$_3$, 200 MHz) δ2.328 (1.2H, t, J=5.6 Hz), 2.543 (0.8H, t, J=5.6 Hz), 3.626 (1.2H, t, J=5.7 Hz), 3.715–3.746 (2H, m), 3.829–3.875 (3.8H, m), 4.463 (0.8H, s), 4.641 (1.2H, s), 5.124–5.135 (2H, m), 6.226 (1H, dd, J=1.8&9.8 Hz), 6.684–6.850 (3H, m), 7.267–7.448 (6H, m);
IR (neat) 1647, 1514, 1454, 1263, 1032, 750 cm$^{-1}$ b) Synthesis of 2-(4-benzyloxy-3-methoxyphenyl)-1-(2-dimethylaminomethyl-5,7-dihydro-4H-furo[2,3-c]pyridin-6-yl)ethan-1-one To a solution of 0.290 g (0.768 mmol) of 2-(4-benzyloxy-3-methoxyphenyl)-1-(5,7-dihydro-4H-furo[2,3-c]pyridin-6-yl)ethan-1-one in 20 ml of acetic acid, 0.104 ml (1.15 mmol) of 50% aqueous dimethylamine and 0.094 ml (1.15 mmol) of 37% aqueous formaldehyde were added, followed by stirring at 100° C. for 40 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1 to 25/1) to yield the desired product.

Brown oil Yield 0.197 g (59%)
$^1$H-NMR (CDCl$_3$, 200 MHz) δ2.256 (7H, s), 2.508 (1H, t, J=5.2 Hz), 3.378–3.404 (2H, m), 3.587–3.648 (1H, m), 3.706–3.739 (2H, m), 3.801–3.888 (4H, m), 4.403 (0.8H, s), 4.626 (1.2H, s), 5.122–5.164 (2H, m), 6.014–6.053 (1H, m), 6.695–6.848 (3H, m), 7.289–7.449 (5H, m);
IR (neat) 2943, 2860, 2779, 1651, 1516, 1454, 1265, 1230, 1144, 1026, 744 cm$^{-1}$ c) Synthesis of 2-(4-benzyloxy-3-methoxyphenyl)-1-(2-dimethylaminomethyl-5,7-dihydro-4H-furo[2,3-c]pyridin-6-yl)ethan-1-one hydrochloride 2-(4-Benzyloxy-3-methoxy-phenyl)-1-(2-dimethylaminomethyl-5,7-dihydro-4H-furo[2,3-c]pyridin-6-yl)ethane-1-one 0.197 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

Pale brown powder Yield 0.166 g
$^1$H-NMR (CD$_3$OD, 200 MHz) δ2.317–2.394 (1.3H, m), 2.544–2.592 (0.7H, m), 2.788–2.845 (6H, m), 3.729–3.881 (7H, m), 4.304–4.341 (2H, m), 4.570–4.632 (2H, m), 5.054–5.085 (2H, m), 6.578–6.594 (1H, m), 6.708–6.942 (3H, m), 7.283–7.464 (5H, m);
IR (nujol) 1738, 1633, 1217, 1138, 1022, 748 cm$^{-1}$;
Anal. Calcd for C$_{26}$H$_{31}$ClN$_2$O$_4$·0.8H$_2$O: C, 64.33; H, 6.77; N, 5.77. Found: C, 64.25; H, 6.77; N, 5.57.

EXAMPLE 18

Synthesis of 2-(4-benzyloxy-3-methoxyphenyl)-1-(2-dimethylaminomethyl-6,7-dihydro-4H-furo[3,2-c]pyridin-5-yl)ethan-1-one hydrochloride a) Synthesis of 2-(4-benzyloxy-3-methoxyphenyl)-1-(6,7-dihydro-4H-furo[3,2-c]pyridin-5-yl)ethan-1-one To a solution of 0.160 g (1.000 mmol) of 4,5,6,7-tetrahydrofuro[3,2-c]pyridine hydrochloride, 0.33 g (1.2 mmol) of 4-benzyloxy-3-methoxyphenylacetic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1 to 2/1) to yield the desired product.

Pale yellow oil Yield 0.263 g (70%)
$^1$H-NMR (CDCl$_3$, 200 MHz) δ2.478 (1.1H, t, J=5.7 Hz), 2.725 (0.9H, t, J=5.8 Hz), 3.664–3.746 (3.1H, m), 3.811–3.847 (3H, m), 3.935 (0.9H, t, J=5.8 Hz), 4.357 (0.9H, t, J=1.6 Hz), 4.531 (1.1H, t, J=1.8 Hz), 5.119–5.132 (2H, m), 6.196 (1H, dd, J=1.9&16.9 Hz), 6.640–6.839 (3H, m), 7.259–7.438 (6H, m);
IR (neat) 2933, 1645, 1520, 1454, 1263, 1032, 731 cm$^{-1}$ b) Synthesis of 2-(4-benzyloxy-3-methoxyphenyl)-1-(2-dimethylaminomethyl-6,7-dihydro-4H-furo[3,2-c]pyridin-5-yl)ethan-1-one To a solution of 0.260 g (0.689 mmol) of 2-(4-benzyloxy-3-methoxyphenyl)-1-(6,7-dihydro-4H-furo[3,2-c]pyridin-5-yl)ethan-1-one in 20 ml of acetic acid, 0.093 ml (1.03 mmol) of 50% aqueous dimethylamine and 0.084 ml (1.03 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1 to 25/1) to yield the desired product.

Pale yellow oil Yield 0.180 g (60%)
$^1$H-NMR (CDCl$_3$, 200 MHz) δ2.259 (6H, s), 2.506 (1.2H, t, J=5.6 Hz), 2.719 (0.8H, t, J=5.6 Hz), 3.395 (2H, s), 3.648–3.743 (3.2H, m), 3.826–3.853 (3H, m), 4.942 (0.8H, t, J=5.7 Hz), 4.324 (0.8H, s), 4.501 (1.2H, s), 5.120–5.138 (2H, m), 5.977 (0.4H, s), 6.053 (0.6H, s), 6.688–6.846 (3H, m), 7.291–7.452 (5H, m);
IR (neat) 2939, 2860, 2775, 1651, 1520, 1454, 1263, 1227, 1142, 1026, 747 cm$^{-1}$ c) Synthesis of 2-(4-benzyloxy-3-methoxyphenyl)-1-(2-dimethylaminomethyl-6,7-dihydro-4H-furo[3,2-c]pyridin-5-yl)ethan-1-one hydrochloride 2-(4-Benzyloxy-3-methoxyphenyl)-1-(2-dimethylaminomethyl-6,7-dihydro-4H-furo[3,2-c]pyridin-5-yl)ethan-1-one 0.180 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

White powder Yield 0.130 g
$^1$H-NMR (CD$_3$OD, 200 MHz) δ2.505 (1H, t, J=5.5 Hz), 2.734 (1H, t, J=5.7 Hz), 2.804–2.834 (6H, m), 3.776–3.857 (6H, m), 3.928 (1H, t, J=5.8 Hz), 4.311–4.332 (2H, m), 4.463–4.512 (2H, m), 5.040–5.073 (2H, m), 6.518 (0.4H, s), 6.615 (0.6H, s), 6.712–6.945 (3H, m), 7.275–7.433 (5H, m);
IR (nujol) 2662, 1635, 1516, 1263, 1227, 1140, 1032, 744 cm$^{-1}$;
Anal. Calcd for C$_{26}$H$_{31}$ClN$_2$O$_4$·1.0H$_2$O: C, 63.86; H, 6.80; N, 5.73. Found: C, 64.13; H, 7.02; N, 5.55.

EXAMPLE 19

Synthesis of N,N-dimethyl-[6-(4-phenylbenzoyl)-4,5,6,7-tetrahydrofuro[2,3-c]pyridin-2-ylmethyl]amine hydrochloride a) Synthesis of 6-(4-phenylbenzoyl)-4,5,6,7-tetrahydrofuro[2,3-c]pyridine To a solution of 0.160 g (1.000 mmol) of 4,5,6,7-tetrahydrofuro[2,3-c]pyridine hydrochloride and 0.55 ml (4.0 mmol) of triethylamine in 30 ml of dichloromethane, 0.26 g (1.2 mmol) of 4-biphenylcarbonyl chloride was added under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate= 4/1) to yield the desired product.

White crystal Yield 0.253 g (83%)

$^1$H-NMR (CDCl$_3$, 200 MHz) δ2.627 (2H, br s), 3.636–4.000 (2H, m), 4.546–4.812 (2H, m), 6.292(1H,d, J=1.8 Hz), 7.331–7.679 (10H, m);

IR (neat) 1628, 1423, 1225, 1092, 750 cm$^{-1}$ b) Synthesis of N,N-dimethyl-[6-(4-phenylbenzoyl)-4,5,6,7-tetrahydrofuro[2,3-c]pyridin-2-ylmethyl]amine To a solution of 0.250 g (0.824 mmol) of 6-(4-phenylbenzoyl)-4,5,6,7-tetrahydrofuro[2,3-c]pyridine in 20 ml of acetic acid, 0.112 ml (1.24 mmol) of 50% aqueous dimethylamine and 0.101 ml (1.24 mmol) of 37% aqueous formaldehyde were added, followed by stirring at 100° C. for 60 minutes. Additionally, 0.075 ml (0.82 mmol) of 50% aqueous dimethylamine and 0.067 ml (0.82 mmol) of 37% aqueous formaldehyde were added, followed by stirring for 20 minutes. After the solvent was distilled off under reduced pressure, the residual solution was alkalified with 5% aqueous solution of sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol 50/1 to =25/1) to yield the desired product.

Brown oil Yield 0.182 g (61%)

$^1$H-NMR (CDCl$_3$, 200 MHz) δ2.267 (6H, s), 2.528–2.665 (2H, m), 3.423 (2H, br s), 3.600–3.949 (2H, m), 4.516–4.744 (2H, m), 6.089 (1H, s), 7.374–7.660 (9H, m);

IR (neat) 2818, 2773, 1632, 1429, 1257, 1043, 849, 749 cm$^{-1}$ c) Synthesis of N,N-dimethyl-[6-(4-phenylbenzoyl)-4,5,6,7-tetrahydrofuro[2,3-c]pyridin-2-ylmethyl]amine hydrochloride N,N-Dimethyl-[6-(4-phenylbenzoyl)-4,5,6,7-tetrahydrofuro[2,3-c]pyridin-2-ylmethyl]amine 0.180 g was dissolved in 2 ml of methanol; hydrogen chloride in ethyl acetate was added in excess, followed by stirring. After concentration, the crude product recrystallized from ethanol-diethyl ether to yield the desired product.

White crystal Yield 0.138 g $^1$H-NMR (CD$_3$OD, 200 MHz) δ2.267 (6H, s), 2.528–2.665 (2H, m), 3.423 (2H, br s), 3.600–3.949 (2H, m), 4.516–4.744 (2H, m), 6.089 (1H, s), 7.374–7.660 (9H, m);

IR (nujol) 2470, 1624, 1230, 951, 743 cm$^{-1}$;

Anal. Calcd for $C_{23}H_{25}ClN_2O_2 \cdot 0.1H_2O$: C, 69.29; H, 6.37; N, 7.03. Found: C, 69.18; H, 6.41; N, 6.97.

EXAMPLE 20

Synthesis of N,N-dimethyl-[5-(4-phenylbenzoyl)-4,5,6,7-tetrahydrofuro[3,2-c]pyridin-2-ylmethyl]amine hydrochloride a) Synthesis of 5-(4-phenylbenzoyl)-4,5,6,7-tetrahydrofuro[3,2-c]pyridine To a solution of 0.160 g (1.000 mmol) of 4,5,6,7-tetrahydrofuro[3,2-c]pyridine hydrochloride and 0.55 ml (4.0 mmol) of triethylamine in 30 ml of dichloromethane, 0.26 g (1.2 mmol) of 4-biphenylcarbonyl chloride was added under ice-cooling, followed by overnight stirring at room temperature. This solution was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate= 4/1) to yield the desired product.

White crystal Yield 0.126 g (42%)

$^1$H-NMR (CDCl$_3$, 200 MHz) δ2.815 (2H, br s), 3.708–4.106 (2H, m), 4.411–4.669 (2H, m), 6.100–6.330 (1H, m), 7.326–7.679 (10H, m);

IR (neat) 1630, 1427, 1219, 1092, 773 cm$^{-1}$ b) Synthesis of N,N-dimethyl-[5-(4-phenylbenzoyl)-4,5,6,7-tetrahydrofuro[3,2-c]pyridin-2-ylmethyl]amine To a solution of 0.120 g (0.396 mmol) of 5-(4-phenylbenzoyl)-4,5,6,7-tetrahydrofuro[3,2-c]pyridine in 20 ml of acetic acid, 0.054 ml (0.59 mmol) of 50% aqueous dimethylamine and 0.048 ml (0.59 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1 to 25/1) to yield the desired product.

White crystal Yield 0.140 g (100%)

$^1$H-NMR (CDCl$_3$, 200 MHz) δ2.269 (6H, s), 2.758–2.803 (2H, m), 3.410 (2H, s), 3.679–3.728 (1.2H, m), 4.016–4.091 (0.8H, m), 4.368–4.627 (2H, m), 5.934–6.141 (1H, m), 7.337–7.667 (9H, m);

IR (KBr) 2858, 2771, 1641, 1429, 1365, 1263, 1225, 1111, 1020, 849, 746 cm$^{-1}$ c) Synthesis of N,N-dimethyl-[5-(4-phenylbenzoyl)-4,5,6,7-tetrahydrofuro[3,2-c]pyridin-2-ylmethyl]amine hydrochloride N,N-Dimethyl-[5-(4-phenylbenzoyl)-4,5,6,7-tetrahydrofuro[3,2-c]pyridin-2-ylmethyl]amine 0.140 g was dissolved in 2 ml of methanol; hydrogen chloride in ethyl acetate was added in excess, followed by stirring. After this mixture was concentrated, the resulting crude product was recrystallized from diethyl ether-ethanol to yield the desired product.

White crystal Yield 0.120 g $^1$H-NMR (CD$_3$OD, 200 MHz) δ2.866 (8H, s), 3.780–3.823 (1H, m), 4.080–4.099 (1H, m), 4.369 (2H, s), 4.470–4.660 (2H, m), 6.509–6.707 (1H, m), 7.377–7.764 (9H, m);

IR (nujol) 2453, 1628, 1425, 1269, 1115, 746 cm$^{-1}$;

Anal. Calcd for $C_{23}H_{25}ClN_2O_2 \cdot 0.3H_2O$: C, 68.66; H, 6.41; N, 6.96. Found: C, 68.59; H, 6.33; N, 7.05.

EXAMPLE 21

Synthesis of N,N-dimethyl-[6-(4-heptylbenzoyl)-4,5,6,7-tetrahydrofuro[2,3-c]pyridin-2-ylmethyl]amine hydrochloride a) Synthesis of 6-(4-heptylbenzoyl)-4,5,6,7-tetrahydrofuro[2,3-c]pyridine To a solution of 0.160 g (1.000 mmol) of 4,5,6,7-tetrahydrofuro[2,3-c]pyridine hydrochloride, 0.264 g (1.2 mol) of 4-heptylbenzoic acid and 0.55 ml (4.0 mmol) of triethylamine in 30 ml of dichloromethane, 0.24 g (1.5 mmol) of diethyl cyanophosphonate was added under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1) to yield the desired product.

Pale yellow oil Yield 0.270 g (83%)

$^1$H-NMR (CDCl$_3$, 200 MHz) δ0.883 (3H, t, J=6.6 Hz), 1.207–1.442 (8H, m), 1.546–1.718 (2H, m), 2.594–2.671 (4H, m), 3.565–3.971 (2H, m), 4.484–4.775 (2H, m), 6.277 (1H, s), 7.221 (2H, d, J=8.2 Hz), 7.307 (1H, s), 7.364 (2H, d, J=8.2 Hz);

IR (neat) 2930, 2854, 1633, 1417, 1265, 1092, 895, 727 cm$^{-1}$ b) Synthesis of N,N-dimethyl-[6-(4-heptylbenzoyl)-4,5,6,7-tetrahydrofuro[2,3-c]pyridin-2-ylmethyl]amine To a solution of 0.260 g (0.799 mmol) of 6-(4-heptylbenzoyl)-4,5,6,7-tetrahydrofuro[2,3-c]pyridine in 20 ml of acetic acid, 0.108 ml (1.20 mmol) of 50% aqueous dimethylamine and 0.097 ml (1.20 mmol) of 37% aqueous formaldehyde were added, followed by stirring at 100° C. for 60 minutes. Additionally, 0.072 ml (0.799 mmol) of 50% aqueous dimethylamine and 0.064 ml (0.799 mmol) of 37% aqueous formaldehyde were added, followed by stirring for 30 minutes. After the solvent was distilled off under reduced pressure, the residual solution was alkalified with 5% aqueous solution of sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1 to 25/1) to yield the desired product.

Brown oil Yield 0.173 g (57%)

$^1$H-NMR (CDCl$_3$, 200 MHz) δ0.881 (3H, t, J=6.5 Hz), 1.295 (8H, br s), 1.546–1.691 (2H, m), 2.256 (6H, s), 2.495–2.665 (4H, m), 3.400 (2H, s), 3.551–3.935 (2H, m), 4.464–4.753 (2H, m), 6.070 (1H, s), 7.209 (2H, d, J=8.0 Hz), 7.350 (2H, d, J=8.0 Hz);

IR (neat) 2931, 2778, 1633, 1425, 1287, 1230, 1043, 906, 847 cm$^{-1}$ c) Synthesis of N,N-dimethyl-[6-(4-heptylbenzoyl)-4,5,6,7-tetrahydrofuro[2,3-c]pyridin-2-ylmethyl]amine hydrochloride N,N-Dimethyl-[6-(4-heptylbenzoyl)-4,5,6,7-tetrahydrofuro[2,3-c]pyridin-2-ylmethyl]amine 0.173 g was dissolved in 2 ml of methanol; hydrogen chloride in ethyl acetate was added in excess, followed by stirring. After this mixture was concentrated, the resulting solid was washed with diethyl ether to yield the desired product.

Brown solid Yield 0.171 g $^1$H-NMR (CD$_3$OD, 200 MHz) δ0.897 (3H, t, J=6.6 Hz), 1.299–1.332 (8H, m), 1.609–1.677 (2H, m), 2.637–2.712 (4H, m), 2.864 (6H, s), 3.651–3.994 (2H, m), 4.373 (2H, s), 4.554–4.738 (2H, m), 6.659 (1H, s), 7.305 (2H, d, J=8.4 Hz), 7.386 (2H, d, J=8.2 Hz);

IR (nujol) 2474, 1622, 1236, 1115, 974, 721 cm$^{-1}$;

Anal. Calcd for C$_{24}$H$_{35}$ClN$_2$O$_2$·0.3H$_2$O: C, 67.92; H, 8.45; N, 6.60. Found: C, 67.94; H, 8.58; N, 6.84.

EXAMPLE 22

Synthesis of N,N-dimethyl-[5-(4-heptylbenzoyl)-4,5,6,7-tetrahydrofuro[3,2-c]pyridin-2-ylmethyl]amine hydrochloride a) Synthesis of 5-(4-heptylbenzoyl)-4,5,6,7-tetrahydrofuro[3,2-c]pyridine To a solution of 0.160 g (1.000 mmol) of 4,5,6,7-tetrahydrofuro[3,2-c]pyridine hydrochloride, 0.264 g (1.2 mmol) of 4-heptylbenzoic acid and 0.55 ml (4.0 mmol) of triethylamine in 30 ml of dichloromethane, 0.24 g (1.5 mmol) of diethyl cyanophosphonate was added under ice-cooling, followed by overnight stirring at room temperature. This solution was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=7/1) to yield the desired product.

Colorless oil Yield 0.193 g (59%)

$^1$H-NMR (CDCl$_3$, 200 MHz) δ0.800–0.950 (3H, m), 1.222–1.312 (8H, m), 1.553–2.044 (2H, m), 2.632 (2H, t, J=7.7 Hz), 2.696–2.850 (2H, m), 3.636–4.138 (2H, m), 4.347–4.647 (2H, m), 6.120–6.283 (1H, m), 7.219 (2H, d, J=8.0 Hz), 7.305 (1H, s), 7.361 (2H, d, J=8.4 Hz);

IR (neat) 2927, 2854, 1633, 1425, 1282, 1092, 893, 727 cm$^{-1}$ b) Synthesis of N,N-dimethyl-[5-(4-heptylbenzoyl)-4,5,6,7-tetrahydrofuro[3,2-c]pyridin-2-ylmethyl]amine To a solution of 0.190 g (0.584 mmol) of 5-(4-heptylbenzoyl)-4,5,6,7-tetrahydrofuro[3,2-c]pyridine in 20 ml of acetic acid, 0.079 ml (0.88 mmol) of 50% aqueous dimethylamine and 0.071 ml (0.88 mmol) of 37% aqueous formaldehyde were added, followed by stirring at 100° C. for 50 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=25/1) to yield the desired product.

Colorless oil Yield 0.158 g (71%)

$^1$H-NMR (CDCl$_3$, 200 MHz) δ0.883 (3H, t, J=6.6 Hz), 1.296 (8H, br s), 1.582–1.647 (2H, m), 2.265 (6H, s), 2.633 (2H, t, J=7.7 Hz), 2.745–2.772 (2H, m), 3.405 (2H, s), 3.607–4.073 (2H, m), 4.307–4.585 (2H, m), 5.934–6.127 (1H, m), 7.223 (2H, d, J=7.8 Hz), 7.363 (2H, d, J=8.0 Hz);

IR (neat) 2926, 2854, 1636, 1425, 1361, 1228, 1111, 843, 795 cm$^{-1}$ c) Synthesis of N,N-dimethyl-[5-(4-heptylbenzoyl)-4,5,6,7-tetrahydrofuro[3,2-c]pyridin-2-ylmethyl]amine hydrochloride N,N-Dimethyl-[5-(4-heptylbenzoyl)-4,5,6,7-tetrahydrofuro[3,2-c]pyridin-2-ylmethyl]amine 0.158 g was dissolved in 2 ml of methanol; hydrogen chloride in ethyl acetate was added in excess, followed by stirring. After this mixture was concentrated, the resulting solid was washed with diethyl ether to yield the desired product.

Brown solid Yield 0.156 g $^1$H-NMR (CD$_3$OD, 200 MHz) δ0.863–0.927 (3H, m), 1.299–1.330 (8H, m), 1.606–1.676 (2H, m), 2.671 (2H, t, J=7.5 Hz), 2.857 (8H, s), 3.700–4.050 (2H, m), 4.358 (2H, s), 4.450–4.650 (2H, m), 6.450–6.700 (1H, m), 7.277–7.402 (4H, m);

IR (nujol) 2465, 1618, 1248, 1115, 980, 800 cm$^{-1}$;

Anal. Calcd for C$_{24}$H$_{35}$ClN$_2$O$_2$·0.2H$_2$O: C, 68.21; H, 8.44; N, 6.63. Found: C, 68.14; H, 8.45; N, 6.68.

EXAMPLE 23

Synthesis of N,N-dimethyl-[6-(anthraquinone-2-carbonyl)-4,5,6,7-tetrahydrofuro[2,3-c]pyridin-2-ylmethyl]amine hydrochloride a) Synthesis of 6-(anthraquinone-2-carbonyl)-4,5,6,7-tetrahydrofuro[2,3-c]pyridine To a solution of 0.160 g (1.000 mmol) of 4,5,6,7-tetrahydrofuro[2,3-c]pyridine hydrochloride, 0.302 g (1.2 mmol) of anthraquinone-2-carboxylic acid and 0.55 ml (4.0 mmol) of triethylamine in 30 ml of dichloromethane, 0.24 g (1.5 mmol) of diethyl cyanophosphonate was added under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1 to 2/1); the resulting solid was washed with ethyl acetate to yield the desired product.

Pale green crystal Yield 0.292 g (82%)
$^1$H-NMR (CDCl$_3$, 200 MHz) δ2.613–2.618 (2H, m), 3.580–3.603 (1.2H, m), 4.000–4.040 (0.8H, m), 4.458–4.462 (0.8H, m), 4.818 (1.2H, s), 6.295 (1H,d, J=1.8 Hz), 7.363 (1H, s), 7.817–7.908 (3H, m), 8.311–8.421 (4H, m);
IR (KBr) 1645, 1437, 1323, 1296, 710 cm$^{-1}$ b) Synthesis of N,N-dimethyl-[6-(anthraquinone-2-carbonyl)-4,5,6,7-tetrahydrofuro[2,3-c]pyridin-2-ylmethyl] amine To a solution of 0.280 g (0.784 mmol) of 6-(anthraquinone-2-carbonyl)-4,5,6,7-tetrahydrofuro[2,3-c]pyridine in 20 ml of acetic acid, 0.106 ml (1.18 mmol) of 50% aqueous dimethylamine and 0.096 ml (1.18 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1) to yield the desired product.

Yellow oil Yield 0.227 g (70%)
$^1$H-NMR (CDCl$_3$, 200 MHz) δ2.170–2.297 (6H, m), 2.573–2.687 (2H, m), 3.368–3.460 (2H, m), 3.548–3.616 (1.2H, m), 4.015–4.030 (0.8H, m), 4.449–4.464 (1.2H, m), 4.804 (1.2H, s), 6.107 (1H, s), 7.819–7.900 (3H, m), 8.314–8.418 (4H, m);
IR (neat) 1676, 1636, 1435, 1294, 1172, 1043, 931, 708 cm$^{-1}$ c) Synthesis of N,N-dimethyl-[6-(anthraquinone-2-carbonyl)-4,5,6,7-tetrahydrofuro[2,3-c]pyridin-2-ylmethyl] amine hydrochloride N,N-Dimethyl-[6-(anthraquinone-2-carbonyl)-4,5,6,7-tetrahydrofuro[2,3-c]pyridin-2-ylmethyl]amine 0.227 g was dissolved in 2 ml of methanol; hydrogen chloride in ethyl acetate was added in excess, followed by stirring. After this mixture was concentrated, the resulting solid was recrystallized from diethyl ether-ethanol to yield the desired product.

Pale yellow crystal Yield 0.185 g
$^1$H-NMR (CD$_3$OD, 200 MHz) δ2.141–2.826 (8H, m), 3.613–3.648 (1.3H, m), 4.000–4.273 (2.7H, m), 4.500 (0.7H, br s), 4.860 (1.3H, br s), 6.715 (1H, br s), 7.839–7.916 (3H, m), 8.315–8.444 (4H, m);
IR (nujol) 2470, 1680, 1620, 1321, 1298, 1242, 939, 716 cm$^{-1}$;
Anal. Calcd for C$_{25}$H$_{23}$ClN$_2$O$_4$·0.4H$_2$O: C, 65.54; H, 5.24; N, 6.11. Found: C, 65.46; H, 4.95; N, 6.22.

EXAMPLE 24

Synthesis of N,N-dimethyl-[5-(anthraquinone-2-carbonyl)-4,5,6,7-tetrahydrofuro[3,2-c]pyridin-2-ylmethyl]amine hydrochloride a) Synthesis of 5-(anthraquinone-2-carbonyl)-4,5,6,7-tetrahydrofuro[3,2-c]pyridine To a solution of 0.160 g (1.000 mmol) of 4,5,6,7-tetrahydrofuro[3,2-c]pyridine hydrochloride, 0.302 g (1.2 mmol) of anthraquinone-2-carboxylic acid and 0.55 ml (4.0 mmol) of triethylamine in 30 ml of dichloromethane, 0.24 g (1.5 mmol) of diethyl cyanophosphonate was added under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel chromatography (hexane/ethyl acetate=2/1); the resulting solid was washed with ethyl acetate to yield the desired product.

Yellow crystal Yield 0.229 g (64%)
$^1$H-NMR (CDCl$_3$, 200 MHz) δ2.791–2.888 (2H, m), 3.652–3.678 (1H, m), 4.123 (1H, s), 4.363 (1H, s), 4.714 (1H, s), 6.088 (0.5H, s), 6.332 (0.5H, s), 7.290 (0.5H, s), 7.350 (0.5H, s), 7.812–7.903 (3H, m), 8.304–8.412 (4H, m);
IR (KBr) 1676, 1632, 1439, 1323, 1296, 710 cm$^{-1}$ b) Synthesis of N,N-dimethyl-[5-(anthraquinone-2-carbonyl)-4,5,6,7-tetrahydrofuro[3,2-c]pyridin-2-ylmethyl] amine To a solution of 0.220 g (0.616 mmol) of 5-(anthraquinone-2-carbonyl)-4,5,6,7-tetrahydrofuro[3,2-c]pyridine in 20 ml of acetic acid, 0.083 ml (0.92 mmol) of 50% aqueous dimethylamine and 0.075 ml (0.75 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1) to yield the desired product.

Yellow oil Yield 0.197 g (77%)
$^1$H-NMR (CDCl$_3$, 200 MHz) δ2.286 (6H, br s), 2.776–2.876 (2H, m), 3.394–3.443 (2H, m), 3.623–3.659 (1H, m), 4.088–4.131 (1H, m), 4.315 (1H, s), 4.680 (1H, s), 5.891 (0.5H, s), 6.138 (0.5H, s), 7.817–7.899 (3H, m), 8.315–8.417 (4H, m);
IR (neat) 2937, 2773, 1674, 1633, 1435, 1275, 1115, 931, 710 cm$^{-1}$ c) Synthesis of N,N-dimethyl-[5-(anthraquinone-2-carbonyl)-4,5,6,7-tetrahydrofuro[3,2-c]pyridin-2-ylmethyl] amine hydrochloride N,N-Dimethyl-[5-(anthraquinone-2-carbonyl)-4,5,6,7-tetrahydrofuro[3,2-c]pyridin-2-ylmethyl]amine 0.197 g was dissolved in 2 ml of methanol; hydrogen chloride in ethyl acetate was added in excess, followed by stirring. After this mixture was concentrated, the resulting crystal was washed with diethyl ether to yield the desired product.

Yellow crystal Yield 0.185 g
$^1$H-NMR (CD$_3$OD, 200 MHz) δ2.811 (8H, br s), 3.701–3.716 (1H, m), 4.097–4.252 (3H, m), 4.378 (1H, br s), 4.713 (1H, br s), 6.502–6.522 (0.5H, m), 6.683–6.707 (0.5H, m), 7.815–7.916 (3H, m), 8.310–8.436 (4H, m);
IR (nujol) 2445, 1678, 1628, 1327, 1296, 1271, 1119, 931, 708 cm$^{-1}$;
Anal. Calcd for C$_{25}$H$_{23}$ClN$_2$O$_4$·0.5H$_2$O: C, 65.29; H, 5.26; N, 6.09. Found: C, 65.41; H, 5.29; N, 6.04.

EXAMPLE 25

Synthesis of N,N-dimethyl-[6-(9,10,10-trioxo-9,10-dihydro-10λ$^6$-thioxanthene-3-carbonyl)-4,5,6,7-tetrahydrofuro[2,3-c]pyridin-2-ylmethyl]amine hydrochloride a) Synthesis of 6-(9-10,10-trioxo-9,10-dihydro-10λ$^6$-thioxanthene-3-carbonyl)-4,5,6,7-tetrahydrofuro[2,3-c]pyridine To a solution of 0.160 g (1.000 mmol) of 4,5,6,7-tetrahydrofuro[2,3-c]pyridine hydrochloride, 0.346 g (1.2 mmol) of 9-oxo-9H-thioxanthene-3-carboxylic acid 10,10-dioxide and 0.55 ml (4.0 mmol) of triethylamine in 30 ml of dichloromethane, 0.24 g (1.5 mmol) of diethyl cyanophosphonate was added under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=2/1 to chloroform); the resulting solid was recrystallized from diethyl ether-chloroform to yield the desired product.

White crystal Yield 0.255 g (65%)

$^1$H-NMR (CDCl$_3$, 200 MHz) δ2.574–2.725 (2H, m), 3.573–3.635 (1.3H, m), 3.984–4.037 (0.7H, m), 4.434–4.451 (0.7H, m), 4.799–4.807 (1.3H, m), 6.295 (1H, d, J=1.8 Hz), 7.330–7.358 (1H, m), 7.780–7.952 (3H, m), 8.172–8.232 (2H, m), 8.338–8.433 (2H, m);

IR (KBr) 1678, 1626, 1441, 1311, 1155, 924, 770 cm$^{-1}$ b) Synthesis of N,N-dimethyl-[6-(9,10,10-trioxo-9,10-dihydro-10λ$^6$-thioxanthene-3-carbonyl)-4,5,6,7-tetrahydrofuro[2,3-c]pyridin-2-ylmethyl]amine To a solution of 0.240 g (0.610 mmol) of 6-(9,10,10-trioxo-9,10-dihydro-10λ$^6$-thioxanthene-3-carbonyl)-4,5,6,7-tetrahydrofuro[2,3-c]pyridine in 20 ml of acetic acid, 0.083 ml (0.92 mmol) of 50% aqueous dimethylamine and 0.075 ml (0.92 mmol) of 37% aqueous formaldehyde were added, followed by stirring at 100° C. for 60 minutes. Additionally, 0.083 ml (0.92 mmol) of 50% aqueous dimethylamine and 0.075 ml (0.92 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=25/1) to yield the desired product.

Yellow oil Yield 0.133 g (48%)

$^1$H-NMR (CDCl$_3$, 200 MHz) δ2.288 (6H, br s), 2.546–2.685 (2H, m), 3.367–3.453 (3.2H, m), 3.991–4.026 (0.8H, m), 4.442–4.471 (0.8H, m), 4.786 (1.2H, s), 6.107 (1H, s), 7.781–7.953 (3H, m), 8.173–8.228 (2H, m), 8.342–8.431 (2H, m);

IR (neat) 1674, 1651, 1435, 1311, 1128, 1043, 922, 762 cm$^{-1}$ c) Synthesis of N,N-dimethyl-[6-(9,10,10-trioxo-9,10-dihydro-10λ$^6$-thioxanthene-3-carbonyl)-4,5,6,7-tetrahydrofuro[2,3-c]pyridin-2-ylmethyl]amine hydrochloride N,N-Dimethyl-[6-(9,10,10-trioxo-9,10-dihydro-10λ$^6$-thioxanthene-3-carbonyl)-4,5,6,7-tetrahydrofuro[2,3-c]pyridin-2-ylmethyl]amine 0.133 g was dissolved in 2 ml of methanol; hydrogen chloride in ethyl acetate was added in excess, followed by stirring. After this mixture was concentrated, the resulting solid was washed with diethyl ether to yield the desired product.

Yellow crystal Yield 0.131 g $^1$H-NMR (CD$_3$OD, 200 MHz) δ2.605–2.748 (2H, m), 2.826–2.890 (6H, m), 3.590–3.691 (1.3H, m), 4.026–4.063 (0.7H, m), 4.310–4.403 (2H, m), 4.541–4.577 (0.7H, m), 4.761–4.823 (1.3H, m), 6.678 (1H, s), 7.884–8.052 (3H, m), 8.177–8.244 (2H, m), 8.404 (2H, dd, J=8.0&15.2 Hz);

IR (nujol) 1674, 1628, 1306, 1155, 922 cm$^{-1}$;

Anal. Calcd for C$_{24}$H$_{23}$ClN$_2$O$_5$S.1.5H$_2$O: C, 56.08; H, 5.10; N, 5.45. Found: C, 56.16; H, 5.06; N, 5.25.

EXAMPLE 26

Synthesis of N,N-dimethyl-[5-(9,10,10-trioxo-9,10-dihydro-10λ$^6$-thioxanthene-3-carbonyl)-4,5,6,7-tetrahydrofuro[3,2-c]pyridin-2-ylmethyl]amine hydrochloride a) Synthesis of 5-(9,10,10-trioxo-9,10-dihydro-10λ$^6$-thioxanthene-3-carbonyl)-4,5,6,7-tetrahydrofuro[3,2-c]pyridine To a solution of 0.160 g (1.000 mmol) of 4,5,6,7-tetrahydrofuro[3,2-c]pyridine hydrochloride, 0.346 g (1.2 mmol) of 9-oxo-9H-thioxanthene-3-carboxylic acid 10,10-dioxide and 0.55 ml (4.0 mmol) of triethylamine in 30 ml of dichloromethane, 0.24 g (1.5 mmol) of diethyl cyanophosphonate was added under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=1/1) to yield the desired product.

Pale yellow foam Yield 0.202 g (51%)

$^1$H-NMR (CDCl$_3$, 200 MHz) δ2.776–2.884 (2H, m), 3.647–3.696 (1H, m), 4.078–4.138 (1H, m), 4.356 (1H, s), 4.701 (1H, s), 6.120 (0.5H, s), 6.330 (0.5H, s), 7.291–7.349 (1H, m), 7.778–7.950 (3H, m), 8.172–8.228 (2H, m), 8.335–8.426 (2H, m);

IR (neat) 1711, 1676, 1645, 1441, 1309, 1228, 1128, 764 cm$^{-1}$ b) Synthesis of N,N-dimethyl-[5-(9,10,10-trioxo-9,10-dihydro-10λ$^6$-thioxanthene-3-carbonyl)-4,5,6,7-tetrahydrofuro[3,2-c]pyridin-2-ylmethyl]amine To a solution of 0.190 g (0.483 mmol) of 5-(9,10,10-trioxo-9,10-dihydro-10λ$^6$-thioxanthene-3-carbonyl)-4,5,6,7-tetrahydrofuro[3,2-c]pyridine in 20 ml of acetic acid, 0.065 ml (0.72 mmol) of 50% aqueous dimethylamine and 0.059 ml (0.72 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1 to 25/1) to yield the desired product.

Yellow oil Yield 0.088 g (40%)

$^1$H-NMR (CDCl$_3$, 200 MHz) δ2.275 (6H, s), 2.767–2.901 (2H, m), 3.403–3.442 (2H, m), 3.623–3.678 (1H, m), 4.064–4.106 (1H, m), 4.313 (1H, s), 4.665 (1H, s), 5.920 (0.5H, s), 6.136 (0.5H, s), 7.783–7.955 (3H, m), 8.176–8.231 (2H, m), 8.341–8.427 (2H, m);

IR (neat) 2941, 2777, 1676, 1637, 1437, 1309, 1228, 1157, 924, 752 cm$^{-1}$ c) Synthesis of N,N-dimethyl-[5-(9,10,10-trioxo-9,10-dihydro-10λ$^6$-thioxanthene-3-carbonyl)-4,5,6,7-tetrahydrofuro[3,2-c]pyridin-2-ylmethyl]amine hydrochloride N,N-Dimethyl-[5-(9,10,10-trioxo-9,10-dihydro-10λ$^6$-thioxanthene-3-carbonyl)-4,5,6,7-tetrahydrofuro[3,2-c]pyridin-2-ylmethyl]amine 0.088 g was dissolved in 2 ml of methanol; hydrogen chloride in ethyl acetate was added in excess, followed by stirring. After this mixture was concentrated, the resulting solid was washed with diethyl ether to yield the desired product.

Yellow crystal Yield 0.085 g $^1$H-NMR (CD$_3$OD, 200 MHz) δ2.876 (8H, br s), 3.688–3.763 (1H, m), 4.100–4.141 (1H, m), 4.337–4.390 (3H, m), 4.663–4.706 (1H, m), 6.509 (0.5H, s), 6.718 (0.5H, s), 7.874–8.048 (3H, m), 8.172–8.225 (2H, m), 8.337–8.454 (2H, m);

IR (nujol) 1674, 1622, 1304, 1153, 746 cm$^{-1}$;

Anal. Calcd for C$_{24}$H$_{23}$ClN$_2$O$_5$S.1.3H$_2$O: C, 56.48; H, 5.06; N, 5.49. Found: C, 56.51; H, 5.22; N, 5.30.

EXAMPLE 27

Synthesis of 1-(2-dimethylaminomethyl-5,7-dihydro-4H-furo[2,3-c]pyridin-6-yl)-6-(4-fluorophenyl)hexan-1-one hydrochloride a) Synthesis of 1-(5,7-dihydro-4H-furo[2,3-c]pyridin-6-yl)-6-(4-fluorophenyl)hexan-1-one To a solution of 0.160 g (1.000 mmol) of 4,5,6,7-tetrahydrofuro[2,3-c]pyridine hydrochloride, 0.25 g (1.2 mmol) of 6-(4-fluorophenyl)hexanoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1) to yield the desired product.

Colorless oil Yield 0.289 g (92%)

$^1$H-NMR (CDCl$_3$, 200 MHz) δ1.320–1.447 (2H, m), 1.546–1.773 (4H, m), 2.376 (2H, q, J=7.4 Hz), 2.491–2.621 (4H, m), 3.630 (1.2H, t, J=5.6 Hz), 3.822 (0.8H, t, J=5.6 Hz), 4.458 (0.8H, s), 4.610 (1.2H, s), 6.234–6.265 (1H, m), 6.896–6.998 (2H, m), 7.072–7.141 (2H, m), 7.297 (1H, s);

IR (neat) 2929, 2854, 1649, 1508, 1433, 1219, 1105, 895, 729 cm$^{-1}$ b) Synthesis of 1-(2-dimethylaminomethyl-5,7-dihydro-4H-furo[2,3-c]pyridin-6-yl)-6-(4-fluorophenyl)hexan-1-one To a solution of 0.280 g (0.888 mmol) of 1-(5,7-dihydro-4H-furo[2,3-c]pyridin-6-yl)-6-(4-fluorophenyl) hexan-1-one in 20 ml of acetic acid, 0.120 ml (1.33 mmol) of 50% aqueous dimethylamine and 0.108 ml (1.33 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1 to 25/1) to yield the desired product.

Brown oil Yield 0.098 g (30%)

$^1$H-NMR (CDCl$_3$, 200 MHz) δ1.362–1.408 (2H, m), 1.589–1.729 (4H, m), 2.257 (6H, s), 2.302–2.423 (2H, m), 2.454–2.619 (4H, m), 3.408 (2H, s), 3.615 (1.1H, t, J=5.6 Hz), 3.806 (0.9H, t, J=5.6 Hz), 4.439 (0.9H, s), 4.594 (1.1H, s), 6.052 (1H, d, J=3.0 Hz), 6.896–6.784 (2H, m), 7.106 (2H, dd, J=5.6&8.6 Hz);

IR (neat) 2931, 2854, 2771, 1651, 1508, 1435, 1219, 1045, 822 cm$^{-1}$ c) Synthesis of 1-(2-dimethylaminomethyl-5,7-dihydro-4H-furo[2,3-c]pyridin-6-yl)-6-(4-fluorophenyl)hexan-1-one hydrochloride 1-(2-Dimethylaminomethyl-5,7-dihydro-4H-furo[2,3-c]pyridin-6-yl)-6-(4-fluorophenyl)hexan-1-one 0.098 g was dissolved in 2 ml of methanol; hydrogen chloride in ethyl acetate was added in excess, followed by stirring. After this mixture was concentrated, the resulting solid was washed with diethyl ether to yield the desired product.

Brown solid Yield 0.063 g $^1$H-NMR (CD$_3$OD, 200 MHz) δ1.380–1.414 (2H, m), 1.589–1.701 (4H, m), 2.446–2.637 (6H, m), 2.862 (6H, s), 3.714–3.807 (2H, m), 4.370 (2H, s), 4.593 (2H, s), 6.641 (1H, s), 6.949 (2H, t, J=8.8 Hz), 7.161 (2H, dd, J=5.8&8.2 Hz);

IR (nujol) 2593, 2465, 1626, 1244, 976, 825 cm$^{-1}$;

Anal. Calcd for C$_{22}$H$_{30}$ClFN$_2$O$_2$.0.3H$_2$O: C, 63.77; H, 7.44; N, 6.76. Found: C, 63.60; H, 7.25; N, 6.73.

EXAMPLE 28

Synthesis of 1-(2-dimethylaminomethyl-6,7-dihydro-4H-furo[3,2-c]pyridin-5-yl)-6-(4-fluorophenyl)hexan-1-one hydrochloride a) Synthesis of 1-(6,7-dihydro-4H-furo[3,2-c]pyridin-5-yl)-6-(4-fluorophenyl)hexan-1-one To a solution of 0.160 g (1.000 mmol) of 4,5,6,7-tetrahydrofuro[3,2-c]pyridine hydrochloride, 0.25 g (1.2 mmol) of 6-(4-fluorophenyl)hexanoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1) to yield the desired product.

Colorless oil Yield 0.329 g (100%)

$^1$H-NMR (CDCl$_3$, 200 MHz) δ1.335–1.432 (2H, m), 1.559–1.736 (4H, m), 2.334–2.436 (2H, m), 2.550–2.621 (2H, m), 2.671–2.771 (2H, m), 3.713 (1H, t, J=5.9 Hz), 3.912 (1H, t, J=5.9 Hz), 4.358 (1H, s), 4.510 (1H, s), 6.228–6.255 (1H, m), 6.944 (2H, m), 7.290–7.303 (1H, m);

IR (neat) 2931, 2856, 1651, 1508, 1427, 1219, 1097, 835, 731 cm$^{-1}$ b) Synthesis of 1-(2-dimethylaminomethyl-6,7-dihydro-4H-furo[3,2-c]pyridin-5-yl)-6-(4-fluorophenyl)hexan-1-one To a solution of 0.315 g (1.000 mmol) of 1-(6,7-dihydro-4H-furo[3,2-c]pyridin-5-yl)-6-(4-fluorophenyl) hexan-1-one in 20 ml of acetic acid, 0.135 ml (1.50 mmol) of 50% aqueous dimethylamine and 0.122 ml (1.50 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1) to yield the desired product.

Colorless oil Yield 0.231 g (62%)

$^1$H-NMR (CDCl$_3$, 200 MHz) δ1.331–1.410 (2H, m), 1.588–1.694 (4H, m), 2.255 (6H, s), 2.327–2.429 (2H, m), 2.584 (2H, t, J=7.7 Hz), 2.689–2.734 (2H, m), 3.397 (2H, s), 3.698 (1.1H, t, J=5.8 Hz), 3.897 (0.9H, t, J=5.8 Hz), 4.319

(0.9H, s), 4.474 (1.1H, s), 6.044 (1H, d, J=3.4 Hz), 6.949 (2H, t, J=8.8 Hz), 7.081–7.151 (2H, m);

IR (neat) 2939, 2860, 2779, 1649, 1510, 1452, 1221, 1124, 1045, 845 cm$^{-1}$ c) Synthesis of 1-(2-dimethylaminomethyl-6,7-dihydro-4H-furo[3,2-c]pyridin-5-yl)-6-(4-fluorophenyl)hexan-1-one hydrochloride 1-(2-Dimethylaminomethyl-6,7-dihydro-4H-furo[3,2-c]pyridin-5-yl)-6-(4-fluorophenyl)hexan-1-one 0.231 g was dissolved in 2 ml of methanol; hydrogen chloride in ethyl acetate was added in excess, followed by stirring. This mixture was concentrated and washed with diethyl ether to yield the desired product.

White solid Yield 0.196 g $^1$H-NMR (CD$_3$OD, 200 MHz) δ1.360–1.413 (2H, m), 1.587–1.698 (4H, m), 2.466 (2H, q, J=7.7 Hz), 2.549–2.827 (4H, m), 2.857 (6H, s), 3.798–3.899 (2H, m), 4.362 (2H, s), 4.477 (2H, s), 6.639 (1H, d, J=3.6 Hz), 6.950 (2H, t, J=8.8 Hz), 7.119–7.199 (2H, m);

IR (nujol) 2669, 2474, 1645, 1510, 1219, 1126, 822 cm$^{-1}$;

Anal. Calcd for C$_{22}$H$_{30}$ClFN$_2$O$_2$.0.5H$_2$O: C, 63.22; H, 7.48; N, 6.70. Found: C, 63.36; H, 7.43; N, 6.69.

EXAMPLE 29

Synthesis of (E)-N,N-dimethyl-[6-(4-stilbenecarbonyl)-4,5,6,7-tetrahydrofuro[2,3-c]pyridin-2-ylmethyl]amine hydrochloride a) Synthesis of (E)-6-(4-stilbenecarbonyl)-4,5,6,7-tetrahydrofuro[2,3-c]pyridine To a solution of 0.160 g (1.000 mmol) of 4,5,6,7-tetrahydrofuro[2,3-c]pyridine hydrochloride, 0.269 g (1.2 mmol) of (E)-4-stilbenecarboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate/dichloromethane=4/1/1), after which it was recrystallized from hexane to yield the desired product.

White crystal Yield 0.212 g (64%)

$^1$H-NMR (CDCl$_3$, 200 MHz) δ2.616 (2H, br s), 3.572–3.960 (2H, m), 4.513–4.786 (2H, m), 6.288 (1H, s), 7.148 (2H, d, J=3.0 Hz), 7.259–7.591 (10H, m);

IR (KBr) 1624, 1439, 1271, 1092, 731 cm$^{-1}$ b) Synthesis of (E)-N,N-dimethyl-[6-(4-stilbenecarbonyl)-4,5,6,7-tetrahydrofuro[2,3-c]pyridin-2-ylmethyl]amine To a solution of 0.200 g (0.607 mmol) of (E)-6-(4-stilbenecarbonyl)-4,5,6,7-tetrahydrofuro[2,3-c]pyridine in 20 ml of acetic acid, 0.082 ml (0.91 mmol) of 50% aqueous dimethylamine and 0.074 ml (0.91 mmol) of 37% aqueous formaldehyde were added, followed by stirring at 100° C. for 90 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=25/1) to yield the desired product.

Yellow oil Yield 0.153 g (65%)

$^1$H-NMR (CDCl$_3$, 200 MHz) δ2.268 (6H, s), 2.585 (2H, br s), 3.418 (2H, s), 3.619–4.000 (2H, m), 4.500–4.731 (2H, m), 6.087 (1H, s), 7.143 (2H, d, J=2.6 Hz), 7.281–7.583 (10H, m);

IR (neat) 2943, 2777, 1630, 1427, 966, 752 cm$^{-1}$ c) Synthesis of (E)-N,N-dimethyl-[6-(4-stilbenecarbonyl)-4,5,6,7-tetrahydrofuro[2,3-c]pyridin-2-ylmethyl]amine hydrochloride (E)-N,N-Dimethyl-[6-(4-stilbenecarbonyl)-4,5,6,7-tetrahydrofuro[2,3-c]pyridin-2-ylmethyl]amine 0.153 g was dissolved in 2 ml of methanol; hydrogen chloride in ethyl acetate was added in excess, followed by stirring. This mixture was concentrated; the resulting solid was washed with diethyl ether to yield the desired product.

Brown solid Yield 0.114 g $^1$H-NMR (CD$_3$OD, 200 MHz) δ2.647 (2H, br s), 2.865 (6H, s), 3.684–4.000 (2H, m), 4.374 (2H, s), 4.706–4.750 (2H, m), 6.666 (1H, s), 7.250–7.706 (11H, m);

IR (nujol) 2467, 1622, 1255, 1223, 968, 766 cm$^{-1}$;

Anal. Calcd for C$_{25}$H$_{27}$ClN$_2$O$_2$.0.7H$_2$O: C, 68.94; H, 6.57; N, 6.43. Found: C, 68.93; H, 6.59; N, 6.33.

EXAMPLE 30

Synthesis of (E)-N,N-dimethyl-[5-(4-stilbenecarbonyl)-4,5,6,7-tetrahydrofuro[3,2-c]pyridin-2-ylmethyl]amine hydrochloride a) Synthesis of (E)-5-(4-stilbenecarbonyl)-4,5,6,7-tetrahydrofuro[3,2-c]pyridine To a solution of 0.160 g (1.000 mmol) of 4,5,6,7-tetrahydrofuro[3,2-c]pyridine hydrochloride, 0.269 g (1.2 mmol) of (E)-4-stilbenecarboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was recrystallized from hexane-methanol to yield the desired product.

White crystal Yield 0.298 g (90%)

$^1$H-NMR (CDCl$_3$, 200 MHz) δ2.806 (2H, br s), 3.682–4.066 (2H, m), 4.403–4.656 (2H, m), 6.100–6.300 (1H, m), 7.145 (2H, d, J=2.6 Hz), 7.257–7.587 (10H, m);

IR (KBr) 3097, 1622, 1443, 1267, 1093, 968, 827, 741 cm$^{-1}$ b) Synthesis of (E)-N,N-dimethyl-[5-(4-stilbenecarbonyl)-4,5,6,7-tetrahydrofuro[3,2-c]pyridin-2-ylmethyl]amine To a solution of 0.280 g (0.850 mmol) of (E)-5-(4-stilbenecarbonyl)-4,5,6,7-tetrahydrofuro[3,2-c]pyridine in 20 ml of acetic acid, 0.115 ml (1.28 mmol) of 50% aqueous dimethylamine and 0.103 ml (1.28 mmol) of 37% aqueous formaldehyde were added, followed by stirring at 100° C. for 60 minutes. After the solvent was distilled off under reduced pressure, the residual solution was alkalified with 5% aqueous solution of sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1 to 25/1). The resulting product was washed with diethyl ether to yield the desired product.

White crystal Yield 0.208 g (63%)

$^1$H-NMR (CDCl$_3$, 200 MHz) δ2.267 (6H, s), 2.785 (2H, br s), 3.408 (2H, s), 3.657–4.020 (2H, m), 4.364–4.639 (2H, m), 5.900–6.099 (1H, m), 7.141 (2H, d, J=2.6 Hz), 7.231–7.584 (9H, m);

IR (KBr) 2929, 2777, 1622, 1429, 1224, 1109, 970, 766 cm$^{-1}$ c) Synthesis of (E)-N,N-dimethyl-[5-(4-stilbenecarbonyl)-4,5,6,7-tetrahydrofuro[3,2-c]pyridin-2-ylmethyl]amine hydrochloride (E)-N,N-Dimethyl-[5-(4-stilbenecarbonyl)-4,5,6,7-tetrahydrofuro[3,2-c]pyridin-2-ylmethyl]amine 0.208 g was dissolved in 2 ml of methanol; hydrogen chloride in ethyl acetate was added in excess, followed by stirring. This mixture was concentrated; the resulting solid was washed with diethyl ether to yield the desired product.

Brown solid Yield 0.206 g $^1$H-NMR (CD$_3$OD, 200 MHz) δ2.862 (8H, s), 3.773–4.100 (2H, m), 4.362 (2H, s), 4.468–4.645 (2H, m), 6.500–6.700 (1H, m), 7.241–7.695 (1H, m);

IR (nujol) 2468, 2360, 1630, 1414, 1221, 1115, 831 cm$^{-1}$;

Anal. Calcd for C$_{25}$H$_{27}$ClN$_2$O$_2$.0.2H$_2$O: C, 70.39; H, 6.47; N, 6.57. Found: C, 70.52; H, 6.54; N, 6.48.

EXAMPLE 31

Synthesis of N,N-dimethyl-[6-[4-(4-chlorobenzoyl)benzoyl]-4,5,6,7-tetrahydrofuro[2,3-c]pyridin-2-ylmethyl]amine hydrochloride a) Synthesis of 6-[4-(4-chlorobenzoyl)benzoyl]-4,5,6,7-tetrahydrofuro[2,3-c]pyridine To a solution of 0.160 g (1.000 mmol) of 4,5,6,7-tetrahydrofuro[2,3-c]pyridine hydrochloride, 0.287 g (1.1 mmol) of 4-(4-chlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=4/1). The resulting product was recrystallized from hexane-methanol to yield the desired product.

White crystal Yield 0.297 g (81%)

$^1$H-NMR (CDCl$_3$, 200 MHz) δ2.560–2.700 (2H, m), 3.595 (1.3H, br s), 4.003 (0.7H, br s), 4.455 (0.7H, br s), 4.788 (1.3H, br s), 6.287 (1H, d, J=2.0 Hz), 7.299–7.346 (1H, m), 7.462–7.582 (4H, m), 7.746–7.850 (4H, m);

IR (KBr) 2939, 2852, 1655, 1433, 1282, 1090, 930, 735 cm$^{-1}$ b) Synthesis of N,N-dimethyl-[6-[4-(4-chlorobenzoyl)benzoyl]-4,5,6,7-tetrahydrofuro[2,3-c]pyridin-2-ylmethyl]amine To a solution of 0.280 g (0.765 mmol) of 6-[4-(4-chlorobenzoyl)benzoyl]-4,5,6,7-tetrahydrofuro[2,3-c]pyridine in 20 ml of acetic acid, 0.10 ml (1.2 mmol) of 50% aqueous dimethylamine and 0.09 ml (1.2 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1 to 100/3) to yield the desired product.

Brown oil Yield 0.235 g (73%)

$^1$H-NMR (CDCl$_3$, 200 MHz) δ2.282 (6H, s), 2.503–3.463 (2H, m), 3.579 (1.2H, br s), 4.000 (0.8H, br s), 4.448 (0.8H, br s), 4.768 (l.2H, br s), 6.102 (1H, s), 7.451–7.574 (4H, m), 7.736–7.843 (4H, m);

IR (neat) 2937, 2775, 1633, 1433, 1275, 930, 748 cm$^{-1}$ c) Synthesis of N,N-dimethyl-[6-[4-(4-chlorobenzoyl)benzoyl]-4,5,6,7-tetrahydrofuro[2,3-c]pyridin-2-ylmethyl]amine hydrochloride N,N-Dimethyl-[6-[4-(4-chlorobenzoyl)benzoyl]-4,5,6,7-tetrahydrofuro[2,3-c]pyridin-2-ylmethyl]amine 0.235 g was dissolved in methanol; hydrogen chloride in ethyl acetate was added in excess, followed by stirring. After this mixture was concentrated, the resulting solid was washed with diethyl ether to yield the desired product.

Brown solid Yield 0.232 g $^1$H-NMR (CD$_3$OD, 200 MHz) δ2.639 (2H, br s), 2.885 (6H, br s), 3.634–3.713 (1.3H, m), 3.997–4.044 (0.7H, m), 4.325–4.402 (2H, m), 4.535–4.587 (0.7H, m), 4.744–4.825 (1.3H, m), 6.682 (1H, s), 7.571 (2H, d, J=8.4 Hz), 7.626 (2H, d, J=8.4 Hz), 7.811 (2H, d, J=8.4 Hz), 7.877 (2H, d, J=8.4 Hz);

IR (nujol) 2457, 1628, 1300, 1236, 1092, 931, 733 cm$^{-1}$;

Anal. Calcd for C$_{24}$H$_{24}$Cl$_2$N$_2$O$_3$.0.7H$_2$O: C, 61.08; H, 5.42; N, 5.94. Found: C, 61.01; H, 5.37; N, 5.91.

EXAMPLE 32

Synthesis of N,N-dimethyl-[5-[4-(4-chlorobenzoyl)benzoyl]-4,5,6,7-tetrahydrofuro[3,2-c]pyridin-2-ylmethyl]amine hydrochloride a) Synthesis of 5-[4-(4-chlorobenzoyl)benzoyl]-4,5,6,7-tetrahydrofuro[3,2-c]pyridine To a solution of 0.160 g (1.000 mmol) of 4,5,6,7-tetrahydrofuro[3,2-c]pyridine hydrochloride, 0.287 g (1.1 mmol) of 4-(4-chlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate/dichloromethane=4/1/1), after which it was recrystallized from hexane-methanol to yield the desired product.

White crystal Yield 0.319 g (87%)

$^1$H-NMR (CDCl$_3$, 200 MHz) δ2.729–2.868 (2H, m), 3.675 (1H, br s), 4.102 (1H, br s), 4.349 (1H, s), 4.688 (1H, s), 6.125 (0.5H, s), 6.330 (0.5H, s), 7.315–7.340 (1H, m), 7.517 (4H, dd, J=8.4&11.0 Hz), 7.805 (4H, dd, J=8.3&12.1 Hz);

IR (KBr) 1653, 1431, 1282, 1092, 931, 735 cm$^{-1}$ b) Synthesis of N,N-dimethyl-[5-[4-(4-chlorobenzoyl)benzoyl]-4,5,6,7-tetrahydrofuro[3,2-c]pyridin-2-ylmethyl]amine To a solution of 0.300 g (0.820 mmol) of 5-[4-(4-chlorobenzoyl)benzoyl]-4,5,6,7-tetrahydrofuro[3,2-c]pyridine in 20 ml of acetic acid, 0.11 ml (1.23 mmol) of 50% aqueous dimethylamine and 0.10 ml (1.23 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1) to yield the desired product.

Brown oil Yield 0.319 g (92%)

$^1$H-NMR (CDCl$_3$, 200 MHz) δ2.275 (6H, s), 2.744–2.854 (2H, m), 3.425 (2H, br s), 3.643 (1.1H, br s), 4.073 (0.9H, br s), 4.298 (0.9H, br s), 4.646 (1.1H, br s), 5.920 (0.4H, br s), 6.126 (0.6H, br s), 7.447–7.573 (4H, m), 7.743–7.843 (4H, m);

IR (neat) 2941, 2775, 1633, 1433, 1277, 1113, 930, 748 cm$^{-1}$ c) Synthesis of N,N-dimethyl-[5-[4-(4-chlorobenzoyl) benzoyl]-4,5,6,7-tetrahydrofuro[3,2-c]pyridin-2-ylmethyl] amine hydrochloride N,N-Dimethyl-[5-[4-(4-chlorobenzoyl)benzoyl]-4,5,6,7-tetrahydrofuro[3,2-c]pyridin-2-ylmethyl]amine 0.319 g was dissolved in methanol; hydrogen chloride in ethyl acetate was added in excess, followed by stirring. After this mixture was concentrated, the resulting solid was washed with diethyl ether to yield the desired product.

Pale brown solid Yield 0.276 g $^1$H-NMR (CD$_3$OD, 200 MHz) δ2.873 (8H, br s), 3.721–3.743 (1.2H, m), 4.097–4.126 (0.8H, m), 4.367–4.424 (2.8H, m), 4.661–4.857 (1.2H, m), 6.514 (0.4H, s), 6.713 (0.6H, s), 7.544–7.639 (4H, m), 7.787–7.891 (4H, m);

IR (nujol) 2580, 1629, 1281, 1113, 930, 733 cm$^{-1}$;

Anal. Calcd for C$_{24}$H$_{24}$Cl$_2$N$_2$O$_3$·0.5H$_2$O: C, 61.54; H, 5.38; N, 5.98. Found: C, 61.49; H, 5.24; N, 5.78.

EXAMPLE 33

Synthesis of (Z)-N,N-dimethyl-[6-(4-stilbenecarbonyl)-4,5,6,7-tetrahydrofuro[2,3-c] pyridin-2-ylmethyl]amine hydrochloride a) Synthesis of (Z)-6-(4-stilbenecarbonyl)-4,5,6,7-tetrahydrofuro[2,3-c]pyridine To a solution of 0.160 g (1.000 mmol) of 4,5,6,7-tetrahydrofuro[2,3-c]pyridine hydrochloride, 0.269 g (1.2 mmol) of (Z)-4-stilbenecarboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=6/1) to yield the desired product.

Colorless oil Yield 0.256 g (78%)

$^1$H-NMR (CDCl$_3$, 200 MHz) δ2.586 (2H, br s), 3.584–4.000 (2H, m), 4.400–4.695 (2H, m), 6.264 (1H, d, J=1.8 Hz), 6,625 (2H, q, J=11.1 Hz), 7.193–7.346 (10H, m);

IR (neat) 3018, 2929, 2852, 1630, 1423, 1265, 1228, 1092, 895, 733 cm$^{-1}$ b) Synthesis of (Z)-N,N-dimethyl-[6-(4-stilbenecarbonyl)-4,5,6,7-tetrahydrofuro[2,3-c]pyridin-2-ylmethyl]amine To a solution of 0.250 g (0.759 mmol) of (Z)-6-(4-stilbenecarbonyl)-4,5,6,7-tetrahydrofuro[2,3-c]pyridine in 20 ml of acetic acid, 0.10 ml (1.1 mmol) of 50% aqueous dimethylamine and 0.09 ml (1.1 mmol) of 37% aqueous formaldehyde were added, followed by stirring at 100° C. for 45 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1) to yield the desired product.

Brown oil Yield 0.174 g (59%)

$^1$H-NMR (CDCl$_3$, 200 MHz) δ2.258 (6H, s), 2.550 (2H, br s), 3.401 (2H, s), 3.600–3.950 (2H, m), 4.450–4.699 (2H, m), 6.066 (1H, s), 6.623 (2H, q, J=11.2 Hz), 7.187–7.294 (9H, m);

IR (neat) 2935, 2775, 1633, 1427, 1228, 1043, 845 cm$^{-1}$ c) Synthesis of (Z)-N,N-dimethyl-[6-(4-stilbenecarbonyl)-4,5,6,7-tetrahydrofuro[2,3-c]pyridin-2-ylmethyl]amine hydrochloride (Z)-N,N-Dimethyl-[6-(4-stilbenecarbonyl)-4,5,6,7-tetrahydrofuro[2,3-c]pyridin-2-ylmethyl]amine 0.174 g was dissolved in 2 ml of methanol; hydrogen chloride in ethyl acetate was added in excess, followed by stirring. This mixture was concentrated; the resulting solid was washed with diethyl ether to yield the desired product.

Brown solid Yield 0.160 g $^1$H-NMR (CD$_3$OD, 200 MHz) δ2.615 (2H, br s), 2.861 (6H, s), 3.650–3.950 (2H, m), 4.368 (2H, s), 4.550–4.724 (2H, m), 6.611–6.777 (3H, m), 7.215 (5H, s), 7.325 (4H, s);

IR (nujol) 2665, 1626, 1259, 974, 783, 700 cm$^{-1}$;

Anal. Calcd for C$_{25}$H$_{27}$ClN$_2$O$_2$·0.5H$_2$O: C, 69.51; H, 6.53; N, 6.49. Found: C, 69.61; H, 6.40; N, 6.52.

EXAMPLE 34

Synthesis of (Z)-N,N-dimethyl-[5-(4-stilbenecarbonyl)-4,5,6,7-tetrahydrofuro[3,2-c] pyridin-2-ylmethyl]amine hydrochloride a) Synthesis of (Z)-5-(4-stilbenecarbonyl)-4,5,6,7-tetrahydrofuro[3,2-c]pyridine To a solution of 0.160 g (1.000 mmol) of 4,5,6,7-tetrahydrofuro[3,2-c]pyridine hydrochloride, 0.269 g (1.2 mmol) of (Z)-4-stilbenecarboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=6/1) to yield the desired product.

Colorless oil Yield 0.302 g (92%)

$^1$H-NMR (CDCl$_3$, 200 MHz) δ2.757 (2H, br s), 3.643–4.100 (2H, m), 4.345–4.621 (2H, m), 4.345–4.621 (2H, m), 6.000–6.300 (1H, m), 6.627 (2H, q, J=11.1 Hz), 7.211–7.305 (10H,

IR (neat) 3014, 2850, 1630, 1425, 1265, 1092, 891, 700 cm$^{-1}$ b) Synthesis of (Z)-N,N-dimethyl-[5-(4-stilbenecarbonyl)-4,5,6,7-tetrahydrofuro[3,2-c]pyridin-2-ylmethyl]amine To a solution of 0.295 g (0.895 mmol) of (Z)-5-(4-stilbenecarbonyl)-4,5,6,7-tetrahydrofuro[3,2-c]pyridine in 20 ml of acetic acid, 0.12 ml (1.3 mmol) of 50% aqueous dimethylamine and 0.11 ml (1.3 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1) to yield the desired product.

Yellow oil Yield 0.281 g (81%)

$^1$H-NMR (CDCl$_3$, 200 MHz) δ2.258 (6H, s), 2.750 (2H, br s), 3.395 (2H, s), 3.641–4.050 (2H, m), 4.300–4.561 (2H, m), 5.850–6.100 (1H, m), 6.621 (2H, q, J=11.1 Hz), 7.230–7.297 (9H, m);

IR (neat) 2939, 2775, 1633, 1427, 1282, 1113, 752 cm$^{-1}$ c) Synthesis of (Z)-N,N-dimethyl-[5-(4-stilbenecarbonyl)-4,5,6,7-tetrahydrofuro[3,2-c]pyridin-2-ylmethyl]amine hydrochloride (Z)-N,N-Dimethyl-[5-(4-stilbenecarbonyl)-4,5,6,7-tetrahydrofuro[3,2-c]pyridin-2-ylmethyl]amine 0.281 g was dissolved in 2 ml of methanol; hydrogen chloride in ethyl acetate was added in excess, followed by stirring. This mixture was concentrated; the resulting solid was washed with diethyl ether to yield the desired product.

White solid Yield 0.234 g $^1$H-NMR (CD$_3$OD, 200 MHz) δ2.818–2.857 (8H, m), 3.700–4.050 (2H, m), 4.354–4.600 (4H, m), 6.500–6.775 (3H, m), 7.216 (5H, s), 7.321 (4H, s);

IR (nujol) 2667, 1624, 1240, 1117, 841, 702 cm$^{-1}$;

Anal. Calcd for C$_{25}$H$_{27}$ClN$_2$O$_2$.0.6H$_2$O: C, 69.23; H, 6.55; N, 6.46. Found: C, 69.19; H, 6.43; N, 6.26.

EXAMPLE 35

Synthesis of 1-(2-diethylaminomethyl-5,7-dihydro-4H-furo[2,3-c]pyridin-6-yl)-6-phenylhexan-1-one hydrochloride a) Synthesis of 1-(2-diethylaminomethyl-5,7-dihydro-4H-furo[2,3-c]pyridin-6-yl)-6-phenylhexan-1-one To a solution of 0.322 g (1.083 mmol) of 1-(5,7-dihydro-4H-furo[2,3-c]pyridin-6-yl)-6-phenylhexan-1-one in 20 ml of acetic acid, 0.13 g (1.3 mmol) of diethylamine and 0.11 g (1.3 mmol) of 37% aqueous formaldehyde were added, followed by stirring at 100° C. for 1.5 hours. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.178 g (43%)

$^1$H-NMR (CDCl$_3$, 200 MHz) δ1.075 (6H, t, J=7.1 Hz), 1.335–1.466 (2H, m), 1.571–1.732 (4H, m), 2.307–2.652 (10H, m), 3.591–3.638 (3.2H, m), 3.803 (0.8H, t, J=5.6 Hz), 4.438 (0.8H, s), 4.590 (1.2H, s), 6.034 (1H, s), 7.127–7.306 (5H, m);

IR (neat) 2929, 1653, 1431, 1207, 1049, 746, 700 cm$^{-1}$ b) Synthesis of 1-(2-diethylaminomethyl-5,7-dihydro-4H-furo[2,3-c]pyridin-6-yl)-6-phenylhexan-1-one hydrochloride 1-(2-Diethylaminomethyl-5,7-dihydro-4H-furo[2,3-c]pyridin-6-yl)-6-phenylhexan-1-one 0.178 g was dissolved in 2 ml of methanol; hydrogen chloride in methanol was added in excess, followed by stirring. This mixture was concentrated to yield the desired product.

Dark brown oil Yield 0.200 g $^1$H-NMR (CD$_3$OD, 200 MHz) δ1.321–1.471 (2H, m), 1.374 (6H, t, J=7.3 Hz), 1.575–1.736 (4H, m), 2.447–2.654 (6H, m), 3.191 (4H, q, J=7.2 Hz), 3.705–3.817 (2H, m), 4.394 (2H, s), 4.603 (2H, s), 6.660 (1H, s), 7.090–7.283 (5H, m);

IR (neat) 2933, 2856, 2576, 1647, 1448, 1213, 1045, 748, 702 cm$^{-1}$;

Anal. Calcd for C$_{24}$H$_{35}$ClN$_2$O$_2$.1.5H$_2$O: C, 64.63; H, 8.59; N, 6.28. Found: C, 64.43; H, 8.16; N, 6.06.

EXAMPLE 36

Synthesis of 1-(2-diethylaminomethyl-6,7-dihydro-4H-furo[3,2-c]pyridin-5-yl)-6-phenylhexan-1-one hydrochloride a) Synthesis of 1-(2-diethylaminomethyl-6,7-dihydro-4H-furo[3,2-c]pyridin-5-yl)-6-phenylhexan-1-one To a solution of 0.347 g (1.167 mmol) of 1-(6,7-dihydro-4H-furo[3,2-c]pyridin-5-yl)-6-phenylhexan-1-one in 20 ml of acetic acid, 0.14 ml (1.4 mmol) of diethylamine and 0.11 g (1.4 mmol) of 37% aqueous formaldehyde were added, followed by stirring at 100° C. for 1.5 hours. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.209 g (47%)

$^1$H-NMR (CDCl$_3$, 200 MHz) δ1.071 (6H, t, J=7.2 Hz), 1.338–1.466 (2H, m), 1.573–1.696 (4H, m), 2.324–2.426 (2H, m), 2.487–2.751 (8H, m), 3.591 (1H, s), 3.602 (1H, s), 3.688 (1H, t, J=5.7 Hz), 3.890 (1H, t, J=5.8 Hz), 4.309 (1H, s), 4.466 (1H, s), 6.014 (0.5H, s), 6.031 (0.5H, s), 7.128–7.306 (5H, m);

IR (neat) 2929, 2854, 1653, 1424, 1224, 1205, 1124, 748, 700 cm$^{-1}$ b) Synthesis of 1-(2-diethylaminomethyl-6,7-dihydro-4H-furo[3,2-c]pyridin-5-yl)-6-phenylhexan-1-one hydrochloride 1-(2-Diethylaminomethyl-6,7-dihydro-4H-furo[3,2-c]pyridin-5-yl)-6-phenylhexan-1-one 0.209 g was dissolved in 2 ml of methanol; hydrogen chloride in methanol was added in excess, followed by stirring. After this mixture was concentrated, diethyl ether was added; the resulting solid was filtered and washed with diethyl ether to yield the desired product.

Yellow solid Yield 0.229 g $^1$H-NMR (CD$_3$OD, 200 MHz) δ1.302–1.449 (2H, m), 1.374 (6H, t, J=7.3 Hz), 1.564–1.700 (4H, m), 2.472 (2H, q, J=6.9 Hz), 2.566–2.649 (2H, m), 2.705–2.828 (2H, m), 3.186 (4H, q, J=7.2 Hz), 3.803–3.938 (2H, m), 4.389 (2H, s), 4.482 (2H, s), 6.655 (1H, s), 7.090–7.281 (5H, m);

IR (nujol) 2492, 1660, 1429, 1128, 750, 700 cm$^{-1}$;

Anal. Calcd for C$_{24}$H$_{35}$ClN$_2$O$_2$.1.0H$_2$O: C, 65.96; H, 8.53; N, 6.41. Found: C, 66.02; H, 8.34; N, 6.52.

EXAMPLE 37

Synthesis of 1-(2-ethylmethylaminomethyl-5,7-dihydro-4H-furo[2,3-c]pyridin-6-yl)-6-phenylhexan-1-one hydrochloride a) Synthesis of 1-(2-ethylmethylaminomethyl-5,7-dihydro-4H-furo[2,3-c]pyridin-6-yl)-6-phenylhexan-1-one To a solution of 0.400 g (1.345 mmol) of 1-(5,7-dihydro-4H-furo[2,3-c]pyridin-6-yl)-6-phenylhexan-1-one in 20 ml of acetic acid, 0.14 ml (1.6 mmol) of N-Ethylmethylamine and 0.13 9 (1.6 mmol) of 37% aqueous formaldehyde were added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.108 g (22%)

$^1$H-NMR (CDCl$_3$, 200 MHz) δ1.095 (3H, t, J=7.0 Hz), 1.352–1.465 (2H, m), 1.583–1.773 (4H, m), 2.236 (3H, s), 2.304–2.652 (8H, m), 3.480 (0.8H, s), 3.495 (1.2H, s), 3.608 (1.2H, t, J=5.5 Hz), 3.803 (0.8H, t, J=5.7 Hz), 4.438 (0.8H, s), 4.594 (1.2H, s), 6.041 (0.6H, s), 6.052 (0.4H, s), 7.125–7.305 (5H, m);

IR (neat) 2929, 1653, 1448, 1431, 1211, 1045, 746, 700 cm$^{-1}$ b) Synthesis of 1-(2-ethylmethylaminomethyl-5,7-dihydro-4H-furo[2,3-c]pyridin-6-yl)-6-phenylhexan-1-one hydrochloride 1-(2-Ethylmethylaminomethyl-5,7-dihydro-4H-furo[2,3-c]pyridin-6-yl)-6-phenylhexan-1-one 0.108 g was dissolved in 2 ml of methanol; hydrogen chloride in methanol was added in excess, followed by stirring. This mixture was concentrated to yield the desired product.

Dark brown oil Yield 0.115 g $^1$H-NMR (CD$_3$OD, 200 MHz) δ1.366 (3H, t, J=7.1 Hz), 1.330–1.462 (2H, m), 1.617–1.723 (4H, m), 2.410–2.641 (6H, m), 2.810 (3H, s), 3.031–3.268 (2H, m), 3.709–3.832 (2H, m), 4.340 (1H, d, J=14.4 Hz), 4.439 (1H, d, J=14.4 Hz), 4.597 (2H, s), 6.660 (1H, s), 7.075–7.270 (5H, m);

IR (neat) 2933, 2669, 1645, 1630, 1452, 1214, 748, 700 cm$^{-1}$;

Anal. Calcd for C$_{23}$H$_{33}$ClN$_2$O$_2$·3.0H$_2$O: C, 60.18; H, 8.56; N, 6.10. Found: C, 60.35; H, 8.16; N, 6.25.

EXAMPLE 38

Synthesis of 1-(2-methylaminomethyl-5,7-dihydro-4H-furo[2,3-c]pyridin-6-yl)-6-phenylhexan-1-one hydrochloride a) Synthesis of 1-(2-formyl-5,7-dihydro-4H-furo[2,3-c]pyridin-6-yl)-6-phenylhexan-1-one To 30 ml of N,N-dimethylformamide, 0.33 ml (3.6 mmol) of phosphorus oxychloride was added under ice-cooling, followed by stirring at room temperature for 0.5 hours. To this mixture, a solution of 1.064 g (3.578 mmol) of 1-(5,7-dihydro-4H-furo[2,3-c]pyridin-6-yl)-6-phenylhexan-1-one in 20 ml of N,N-dimethylformamide was added, followed by overnight stirring at room temperature. After water was added, the reaction mixture was extracted with ethyl acetate 3 times. The combined organic layer was dried over anhydrous magnesium sulfate; the solvent was distilled off under reduced pressure. The resulting crude product was purified by silica gel flush column chromatography (hexane/ethyl acetate=2/1 to 1/1) to yield the desired product.

Orange oil Yield 0.410 g (62%)

$^1$H-NMR (CDCl$_3$, 200 MHz) δ1.319–1.496 (2H, m), 1.586–1.780 (4H, m), 2.384 (2H, q, J=8.1 Hz), 2.616 (4H, t, J=7.3 Hz), 3.671 (1.3H, t, J=5.7 Hz), 3.850 (0.7H, t, J=5.7 Hz), 4.552 (0.7H, s), 4.707 (1.3H, s), 7.094–7.312 (6H, m), 9.550 (1H, s);

IR (neat) 2931, 1680, 1649, 1525, 1429, 1302, 1213, 1120, 914, 748, 702 cm$^{-1}$ b) Synthesis of 1-[2-(N-tert-butoxycarbonyl-N-methylaminomethyl)-5,7-dihydro-4H-furo[2,3-c]pyridin-6-yl]-6-phenylhexan-1-one 1-(2-Formyl-5,7-dihydro-4H-furo[2,3-c]pyridin-6-yl)-6-phenylhexan-1-one 0.273 g (0.839 mmol), 0.33 g (4.2 mmol) of 40% methylamine in methanol and 2 drops of acetic acid were dissolved in 50 ml of methanol, followed by stirring at room temperature for 0.5 hours. To this solution, 0.11 g (1.7 mmol) of sodium cyanoborohydride was added at room temperature, followed by stirring for 3 days. The reaction mixture was poured into aqueous sodium hydroxide and extracted with dichloromethane 3 times. The combined organic layer was dried over anhydrous magnesium sulfate; the solvent was distilled off under reduced pressure. The resulting residue was dissolved in 50 ml of dichloromethane; a solution of 0.27 g (1.3 mmol) of di-tert-butyl dicarbonate in 3 ml of dichloromethane was added. After the mixture was stirred at room temperature for 0.5 hours, the solvent was distilled off under reduced pressure. The resulting crude product was purified by silica gel column chromatography (hexane/ethyl acetate=3/1 to 2/1) to yield the desired product.

Yellow oil Yield 0.133 g (36%)

$^1$H-NMR (CDCl$_3$, 200 MHz) δ1.352–1.506 (2H, m), 1.473 (9H, s), 1.584–1.777 (4H, m), 2.371 (2H, q, J=7.5 Hz), 2.443–2.546 (2H, m), 2.619 (2H, t, J=7.5 Hz), 3.616 (1.2H, t, J=5.7 Hz), 3.806 (0.8H, t, J=5.5 Hz), 4.319 (2H, br s), 4.425 (0.8H, br s), 4.579 (1.2H, br s), 6.056 (1H, br s), 7.131–7.318 (5H, m);

IR (neat) 2929, 1697, 1653, 1450, 1392, 1367, 1215, 1171, 1147, 1047, 876, 748, 700 cm$^{-1}$ c) Synthesis of 1-(2-methylaminomethyl-5,7-dihydro-4H-furo[2,3-c]pyridin-6-yl)-6-phenylhexan-1-one hydrochloride 1-[2-(N-tert-Butoxycarbonyl-N-methylaminomethyl)-5,7-dihydro-4H-furo[2,3-c]pyridin-6-yl]-6-phenylhexan-1-one 0.191 g was dissolved in 2 ml of methanol; 0.5 ml of concentrated hydrochloric acid was added, followed by stirring for 30 minutes. This mixture was concentrated to yield the desired product.

Brown foam Yield 0.157 g (96%)

$^1$H-NMR (CD$_3$OD, 200 MHz) δ1.308–1.458 (2H, m), 1.561–1.725 (4H, m), 2.390–2.636 (6H, m), 2.687 (3H, s), 3.685–3.823 (2H, m), 4.224 (2H, s), 4.579 (2H, s), 6.561 (1H, s), 7.078–7.277 (5H, m);

IR (neat) 2931, 2856, 2783, 1647, 1450, 1216, 1045, 748, 700 cm$^{-1}$;

Anal. Calcd for C$_{21}$H$_{29}$ClN$_2$O$_2$·1.5H$_2$O: C, 62.44; H, 7.98; N, 6.93. Found: C, 62.07; H, 7.11; N, 7.49.

EXAMPLE 39

Synthesis of N,N-diethyl-[6-(4-benzoylbenzoyl)-4,5,6,7-tetrahydrofuro[2,3-c]pyridin-2-ylmethyl]amine hydrochloride a) Synthesis of 6-(4-benzoylbenzoyl)-4,5,6,7-tetrahydrofuro[2,3-c]pyridine To a solution of 0.264 g (1.654 mmol) of 4,5,6,7-tetrahydrofuro[2,3-c]pyridine hydrochloride, 0.41 g (1.8 mmol) of 4-benzoylbenzoic acid and 0.92 ml (6.6 mmol) of triethylamine in 30 ml of dichloromethane, 0.30 ml (2.0 mmol) of diethyl cyanophosphonate was added dropwise under ice-cooling, followed by overnight stirring at room temperature. This solution was poured into aqueous sodium hydroxide and extracted with dichloromethane 3 times. The combined organic layer was dried over anhydrous sodium sulfate; the solvent was distilled off under reduced pressure. The resulting crude product was purified by silica gel column chromatography (hexane/ethyl acetate=3/1 to 2/1) to yield the desired product.

Yellow oil Yield 0.527 g (96%)

$^1$H-NMR (CDCl$_3$, 200 MHz) δ2.578 (1.2H, br s), 2.677 (0.8H, br s), 3.597 (1.2H, br s), 4.011 (0.8H, br s), 4.463 (0.8H, br s), 4.788 (1.2H, br s), 6.288 (1H, d, J=2.0 Hz), 7.346 (1H, br s), 7.459–7.667 (5H, m), 7.793–7.882 (4H, m);

IR (neat) 1653, 1630, 1433, 1277, 752, 702 cm$^{-1}$ b) Synthesis of N,N-diethyl-[6-(4-benzoylbenzoyl)-4,5,6,7-tetrahydrofuro[2,3-c]pyridin-2-ylmethyl]amine To a solution of 0.527 g (1.590 mmol) of 6-(4-benzoylbenzoyl)-4,5,6,7-tetrahydrofuro[2,3-c]pyridine in 20 ml of acetic acid, 0.20 ml (1.9 mmol) of diethylamine and 0.15 g (1.9 mmol) of 37% aqueous formaldehyde were added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=9/1) to yield the desired product.

Orange oil Yield 0.423 g (64%)

$^1$H-NMR (CDCl$_3$, 200 MHz) δ1.094 (6H, br t, J=6.2 Hz), 2.570 (4H, br q, J=6.2 Hz), 3.570 (1.2H, br s), 3.655 (2H, br s), 3.995 (0.8H, br s), 4.455 (0.8H, br s), 4.772 (1.2H, br s), 6.087 (1H, s), 7.459–7.659 (5H, m), 7.794–7.877 (4H, m);

IR (neat) 2931, 1653, 1633, 1431, 1277, 754, 702 cm$^{-1}$ c) Synthesis of N,N-diethyl-[6-(4-benzoylbenzoyl)-4,5,6,7-tetrahydrofuro[2,3-c]pyridin-2-ylmethyl]amine hydrochloride N,N-Diethyl-[6-(4-benzoylbenzoyl)-4,5,6,7-tetrahydrofuro[2,3-c]pyridin-2-ylmethyl]amine 0.423 g was dissolved in 2 ml of methanol; hydrogen chloride in methanol was added in excess, followed by stirring. This mixture was concentrated to yield the desired product.

Brown foam Yield 0.401 g $^1$H-NMR (CD$_3$OD, 200 MHz) δ1.390 (6H, br t, J=6.8 Hz), 2.645 (2H, br s), 3.218 (4H, br q, J=6.5 Hz), 3.678 (1.2H, br s), 4.024 (0.8H, br s), 4.425 (2H, br s), 4.561 (0.8H, br s), 4.805 (1.2H, br s), 6.693 (1H, s), 7.506–7.713 (5H, m), 7.790–7.913 (4H, m);

IR (neat) 2924, 2854, 2642, 1650, 1628, 1448, 1277, 704 cm$^{-1}$;

Anal. Calcd for C$_{26}$H$_{29}$ClN$_2$O$_3$.1.8H$_2$O: C, 64.33; H, 6.77; N, 5.77. Found: C, 64.53; H, 7.14; N, 5.69.

EXAMPLE 40

Synthesis of 1-(2-diethylaminomethyl-5,7-dihydro-4H-furo[2,3-c pyridin-6-yl)-3-(3-phenethylphenyl) propan-1-one hydrochloride a) Synthesis of 1-(2-diethylaminomethyl-5,7-dihydro-4H-furo[2,3-c]pyridin-6-yl)-3-(3-phenethylphenyl)propan-1-one To a solution of 0.393 g (1.093 mmol) of 1-(5,7-dihydro-4H-furo[2,3-c]pyridin-6-yl)-3-(3-phenethylphenyl) propan-1-one in 20 ml of acetic acid, 0.14 ml (1.3 mmol) of diethylamine and 0.11 g (1.3 mmol) of 37% aqueous formaldehyde were added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=9/1) to yield the desired product.

Orange oil Yield 0.208 g (43%)

$^1$H-NMR (CDCl$_3$, 200 MHz) δ1.064 (6H, t, J=7.1 Hz), 2.414–2.696 (8H, m), 2.887 (4H, s), 2.863–3.000 (2H, m), 3.550 (1.1H, t, J=5.5 Hz), 3.592 (2H, s), 3.814 (0.9H, t, J=5.7 Hz), 4.361 (0.9H, s), 4.612 (1.1H, s), 6.012 (0.55H, s), 6.032 (0.45H, s), 6.999–7.063 (3H, m), 7.153–7.319 (6H, m);

IR (neat) 2968, 2929, 2852, 1653, 1448, 1205, 1061, 912, 789, 750, 702 cm$^{-1}$ b) Synthesis of 1-(2-diethylaminomethyl-5,7-dihydro-4H-furo[2,3-c]pyridin-6-yl)-3-(3-phenethylphenyl)propan-1-one hydrochloride 1-(2-Diethylaminomethyl-5,7-dihydro-4H-furo[2,3-c]pyridin-6-yl)-3-(3-phenethylphenyl)propan-1-one 0.208 g was dissolved in 2 ml of methanol; hydrogen chloride in methanol was added in excess, followed by stirring. This mixture was concentrated to yield the desired product.

Dark brown oil Yield 0.225 g $^1$H-NMR (CD$_3$OD, 200 MHz) δ1.337 (6H, t, J=7.3 Hz), 2.400–2.480 (2H, m), 2.698–2.918 (4H, m), 2.812 (4H, s), 3.140 (4H, q, J=7.1 Hz), 3.606 (1.4H, t, J=5.3 Hz), 3.771 (0.6H, t, J=5.3 Hz), 4.347 (2H, s), 4.425 (0.6H, br s), 4.588 (1.4H, br s), 6.640 (1H, s), 7.001–7.039 (3H, m), 7.090–7.261 (6H, m);

IR (neat) 2935, 2642, 1647, 1630, 1448, 1211, 702 cm$^{-1}$;

Anal. Calcd for C$_{29}$H$_{37}$ClN$_2$O$_2$.2.1H$_2$O: C, 67.13; H, 8.00; N, 5.40. Found: C, 66.90; H, 7.78; N, 5.30.

EXAMPLE 41

Synthesis of 1-(2-dimethylaminomethyl-5,7-dihydro-4H-furo[2,3-c]pyridin-6-yl)-2-(2-naphthoxy)ethan-1-one hydrochloride a) Synthesis of 1-(5,7-dihydro-4H-furo[2,3-c]pyridin-6-yl)-2-(2-naphthoxy)ethan-1-one To a solution of 0.160 g (1.000 mmol) of 4,5,6,7-tetrahydrofuro[2,3-c]pyridine hydrochloride, 0.24 g (1.2 mmol) of 2-naphthoxyacetic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1 to 1/1). The resulting product was purified by recrystallization from hexane/ethyl acetate (=1/1)-dichloromethane to yield the desired product.

White crystal Yield 0.238 g (78%)

$^1$H-NMR (CDCl$_3$, 200 MHz) δ2.550–2.650 (2H, m), 3.777–3.850 (2H, m), 4.650 (2H, s), 4.861–4.881 (2H, m), 6.223–6.250 (1H, m), 7.187–7.500 (5H, m), 7.722–7.786 (3H, m);

IR (KBr) 2925, 2850, 1650, 1479, 1207, 1111, 1066, 897, 852, 747 cm$^{-1}$ b) Synthesis of 1-(2-dimethylaminomethyl-5,7-dihydro-4H-furo[2,3-c]pyridin-6-yl)-2-(2-naphthoxy)ethan-1-one To a solution of 0.230 g (0.748 mmol) of 1-(5,7-dihydro-4H-furo[2,3-c]pyridin-6-yl)-2-(2-naphthoxy)ethan-1-one in 20 ml of acetic acid, 0.10 ml (1.1 mmol) of 50% aqueous dimethylamine and 0.092 ml (1.1 mmol) of 37% aqueous formaldehyde were added, followed by stirring at 100° C. for 45 minutes. After the solvent was distilled off under reduced pressure, the residual solution was alkalified with aqueous sodium hydroxide and extracted with dichloromethane 2 times. The combined organic layer was washed with water and dried over anhydrous sodium sulfate; the solvent was distilled off under reduced pressure. The resulting crude product was purified by silica gel column chromatography (ethyl acetate/methanol=9/1 to 6/1) to yield the desired product.

Yellow oil Yield 0.216 g (79%)

$^1$H-NMR (CDCl$_3$, 200 MHz) δ2.256–2.265 (6H, m), 2.500–2.588 (2H, m), 3.405 (2H, s), 3.791–3.831 (2H, m), 4.634 (2H, s), 4.852–4.875 (2H, m), 6.039–6.062 (1H, m), 7.181–7.451 (4H, m), 7.722–7.783 (3H, m);

IR (neat) 2939, 2856, 2775, 1660, 1456, 1213, 1045, 906, 841, 748 cm$^{-1}$ c) Synthesis of 1-(2-dimethylaminomethyl-5,7-dihydro-4H-furo[2,3-c]pyridin-6-yl)-2-(2-naphthoxy)ethan-1-one hydrochloride 1-(2-Dimethylaminomethyl-5,7-dihydro-4H-furo[2,3-c]pyridin-6-yl)-2-(2-naphthoxy)ethan-1-one 0.216 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

Pale brown powder Yield 0.203 g $^1$H-NMR (CD$_3$OD, 200 MHz) δ2.550–2.700 (2H, m), 2.846–2.854 (6H, m), 3.834–3.885 (2H, m), 4.352 (2H, s), 4.673 (1.4H, s), 4.746 (0.6H, s), 4.980 (0.6H, s), 5.017 (1.4H, s), 6.629 (1H, s), 7.200–7.433 (4H, m), 7.722–7.803 (3H, m);

IR (nujol) 2665, 1655, 1215, 1028, 839, 741 cm$^{-1}$;

Anal. Calcd for C$_{22}$H$_{25}$ClN$_2$O$_3$.0.5H$_2$O: C, 64.46; H, 6.39; N, 6.83. Found: C, 64.58; H, 6.38; N, 6.66.

EXAMPLE 42

Synthesis of 1-(2-dimethylaminomethyl-6,7-dihydro-4H-furo[3,2-c]pyridin-5-yl)-2-(2-naphthoxy)ethan-1-one hydrochloride a) Synthesis of 1-(6,7-dihydro-4H-furo[3,2-c]pyridin-5-yl)-2-(2-naphthoxy)ethan-1-one To a solution of 0.160 g (1.000 mmol) of 4,5,6,7-tetrahydrofuro[3,2-c]pyridine hydrochloride, 0.24 g (1.2 mmol) of 2-naphthoxyacetic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate= 3/1 to 1/1). The resulting product was washed with diethyl ether to yield the desired product.

White crystal Yield 0.209 g (68%)

$^1$H-NMR (CDCl$_3$, 200 MHz) δ2.700–2.803 (2H, m), 3.850–3.950 (2H, m), 4.550 (2H, s), 4.867–4.887 (2H, m), 6.254 (1H, s), 7.197–7.500 (5H, m), 7.734–7.798 (3H, m);

IR (KBr) 2900, 2850, 2350, 1662, 1475, 1209, 1182, 1066, 891, 852, 744 cm$^{-1}$ b) Synthesis of 1-(2-dimethylaminomethyl-6,7-dihydro-4H-furo[3,2-c]pyridin-5-yl)-2-(2-naphthoxy)ethan-1-one To a solution of 0.200 g (0.651 mmol) of 1-(6,7-dihydro-4H-furo[3,2-c]pyridin-5-yl)-2-(2-naphthoxy)ethan-1-one in 20 ml of acetic acid, 0.088 ml (0.98 mmol) of 50% aqueous dimethylamine and 0.079 ml (0.98 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 2 times. The combined organic layer was washed with water and dried over anhydrous sodium sulfate; the solvent was distilled off under reduced pressure. The resulting crude product was purified by silica gel column chromatography (ethyl acetate/methanol=9/1 to 6/1) to yield the desired product.

Yellow oil Yield 0.190 g (80%)

$^1$H-NMR (CDCl$_3$, 200 MHz) δ2.257–2.277 (6H, m), 2.700–2.797 (2H, m), 3.407–3.435 (2H, m), 3.850–3.950 (2H, m), 4.513 (2H, s), 4.865–4.882 (2H, m), 6.064 (1H, s), 7.195–7.500 (4H, m), 7.728–7.794 (3H, m);

IR (neat) 2939, 2811, 2775, 2359, 1651, 1601, 1464, 1215, 1120, 1043 cm$^{-1}$ c) Synthesis of 1-(2-dimethylaminomethyl-6,7-dihydro-4H-furo[3,2-c]pyridin-5-yl)-2-(2-naphthoxy)ethan-1-one hydrochloride 1-(2-Dimethylaminomethyl-6,7-dihydro-4H-furo[3,2-c]pyridin-5-yl)-2-(2-naphthoxy)ethan-1-one 0.190 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

White powder Yield 0.185 g $^1$H-NMR (CD$_3$OD, 200 MHz) δ2.750–2.800 (2H, m), 2.836–2.853 (6H, m), 3.913–4.000 (2H, m), 4.336–4.359 (2H, m), 4.551 (1.2H, s), 4.597 (0.8H, s), 4.971 (0.8H, s), 5.010 (1.2H, s), 6.626 (0.6H, s), 6.663 (0.4H, s), 7.200–7.450 (4H, m), 7.716–7.789 (3H, m);

IR (nujol) 2468, 1659, 1077, 1215, 839 cm$^{-1}$;

Anal. Calcd for C$_{22}$H$_{25}$ClN$_2$O$_3$.0.8H$_2$O: C, 63.62; H, 6.46; N, 6.75. Found: C, 63.63; H, 6.54; N, 6.83.

EXAMPLE 43

Synthesis of 1-(2-dimethylaminomethyl-5,7-dihydro-4H-furo[2,3-c]pyridin-6-yl)-5-phenylthiopentan-1-one hydrochloride a) Synthesis of 1-(5,7-dihydro-4H-furo[2,3-c]pyridin-6-yl)-5-phenylthiopentan-1-one To a solution of 0.160 g (1.000 mmol) of 4,5,6,7-tetrahydrofuro[2,3-c]pyridine hydrochloride, 0.25 g (1.2 mmol) of 5-phenylthiopentanoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1) to yield the desired product.

Colorless oil Yield 0.292 g (93%)

$^1$H-NMR (CDCl$_3$, 200 MHz) δ1.677–1.864 (4H, m), 2.342–2.591 (4H, m), 2.953 (2H, t, J=6.7 Hz), 3.626 (2H, t, J=6.7 Hz), 3.626 (1.2H, t, J=5.6 Hz), 3.815 (0.8H, t, J=5.6 Hz), 4.454 (0.8H, s), 4.603 (1.2H, s), 6.235–6.269 (1H, m), 7.160–7.349 (6H, m);

IR (neat) 2932, 2850, 1645, 1437, 1209, 1103, 1032, 895, 741 cm$^{-1}$ b) Synthesis of 1-(2-dimethylaminomethyl-5,7-dihydro-4H-furo[2,3-c]pyridin-6-yl)-5-phenylthiopentan-1-one To a solution of 0.285 g (0.903 mmol) of 1-(5,7-dihydro-4H-furo[2,3-c]pyridin-6-yl)-5-phenylthiopentan-1-one in 20 ml of acetic acid, 0.122 ml (1.35 mmol) of 50% aqueous dimethylamine and 0.110 ml (1.35 mmol) of 37% aqueous formaldehyde were added, followed by stirring at 100° C. for 45 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1) to yield the desired product.

Yellow oil Yield 0.247 g (73%)

$^1$H-NMR (CDCl$_3$, 200 MHz) δ1.692–1.838 (4H, m), 2.256 (6H, s), 2.328–2.555 (4H, m), 2.946 (2H, td, J=6.8&2.6 Hz), 3.404 (2H, s), 3.614 (1.2H, t, J=5.6 Hz), 3.802 (0.8H, t, J=5.6 Hz), 3.802 (0.8H, t, J=5.6 Hz), 4.437 (0.8H, s), 4.590 (1.2H, s), 6.051 (1H, s), 7.125–7.354 (5H, m);

IR (neat) 2943, 2779, 1651, 1438, 1213, 1026, 741 cm$^{-1}$ c) Synthesis of 1-(2-dimethylaminomethyl-5,7-dihydro-4H-furo[2,3-c]pyridin-6-yl)-5-phenylthiopentan-1-one hydrochloride 1-(2-Dimethylaminomethyl-5,7-dihydro-4H-furo[2,3-c]pyridin-6-yl)-5-phenylthiopentan-1-one 0.247 g was dissolved in 2 ml of methanol; hydrogen chloride in ethyl acetate was added in excess, followed by stirring. After this mixture was concentrated, the resulting product was recrystallized from diethyl ether-ethanol to yield the desired product.

Pale brown powder Yield 0.228 g
$^1$H-NMR (CD$_3$OD, 200 MHz) δ1.684–1.780 (4H, m), 2.474–2.545 (2H, m), 2.613 (2H, t, J=5.6 Hz), 2.857 (6H, s), 2.960 (2H, td, J=6.9&3.2 Hz), 3.711–3.804 (2H, m), 4.361 (2H, s), 4.590 (2H, s), 6.628 (1H, s), 7.145–7.348 (5H, m);
IR (nujol) 2441, 1624, 1244, 1217, 976, 947, 735 cm$^{-1}$;
Anal. Calcd for C$_{21}$H$_{29}$ClN$_2$O$_2$S.0.1H$_2$O: C, 61.40; H, 7.16; N, 6.82. Found: C, 61.31; H, 7.10; N, 6.82.

EXAMPLE 44

Synthesis of 1-(2-dimethylaminomethyl-6,7-dihydro-4H-furo[3,2-c]pyridin-5-yl)-5-phenylthiopentan-1-one hydrochloride a) Synthesis of 1-(6,7-dihydro-4H-furo(3,2-c]pyridin-5-yl)-5-phenylthiopentan-1-one To a solution of 0.160 g (1.000 mmol) of 4,5,6,7-tetrahydrofuro[3,2-c]pyridine hydrochloride, 0.25 g (1.2 mmol) of 5-phenylthiopentanoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1) to yield the desired product.

Colorless oil Yield 0.256 g (81%)
$^1$H-NMR (CDCl$_3$, 200 MHz) δ1.665–1.819 (4H, m), 2.355–2.455 (2H, m), 2.663–2.770 (2H, m), 2.908–2.987 (2H, m), 3.703 (1H, t, J=5.8 Hz), 3.901 (1H, t, J=5.8 Hz), 4.305 (1H, s), 4.498 (1H, s), 6.222–6.247 (1H, m), 7.154–7.337 (6H, m);
IR (neat) 2916, 2850, 1651, 1450, 1209, 1134, 1097, 1026, 891, 741 cm$^{-1}$ b) Synthesis of 1-(2-dimethylaminomethyl-6,7-dihydro-4H-furo[3,2-c]pyridin-5-yl)-5-phenylthiopentan-1-one To a solution of 0.250 g (0.793 mmol) of 1-(6,7-dihydro-4H-furo[3,2-c]pyridin-5-yl)-5-phenylthiopentan-1-one in 20 ml of acetic acid, 0.107 ml (1.19 mmol) of 50% aqueous dimethylamine and 0.097 ml (1.19 mmol) of 37% aqueous formaldehyde were added, followed by stirring at 100° C. for 45 minutes. After the solvent was distilled off under reduced pressure, the residual solution was alkalified with 5% aqueous sodium hydrogen carbonate, and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1) to yield the desired product.

Colorless oil Yield 0.224 g (76%)
$^1$H-NMR (CDCl$_3$, 200 MHz) δ1.679–1.778 (4H, m), 2.270 (6H, d, J=2.2 Hz), 2.401 (2H, q, J=6.4 Hz), 2.685–2.762 (2H, m), 2.951 (2H, t, J=7.0 Hz), 3.415 (2H, d, J=2.2 Hz), 3.689 (1H, t, J=5.8 Hz), 3.886 ((1H, t, J=5.8 Hz), 4.313 (1H, s), 4.463 (1H, s), 6.053 (1H, s), 7.154–7.337 (5H, m);

IR (neat) 2943, 2777, 1649, 1439, 1227, 1122, 1026, 741 cm$^{-1}$ c) Synthesis of 1-(2-dimethylaminomethyl-6,7-dihydro-4H-furo[3,2-c]pyridin-5-yl)-5-phenylthiopentan-1-one hydrochloride 1-(2-Dimethylaminomethyl-6,7-dihydro-4H-furo[3,2-c]pyridin-5-yl)-5-phenylthiopentan-1-one 0.224 g was dissolved in 2 ml of methanol; hydrogen chloride in ethyl acetate was added in excess, followed by stirring. After this mixture was concentrated, diethyl ether was added; the resulting solid was filtered and washed with diethyl ether to yield the desired product.

White solid Yield 0.198 g
$^1$H-NMR (CD$_3$OD, 200 MHz) δ1.642–1.779 (4H, m), 2.488 (2H, q, J=7.5 Hz), 2.682–2.803 (2H, m), 2.855 (6H, s), 2.912–2.978 (2H, m), 3.818 (1H, t, J=5.8 Hz), 3.892 (1H, t, J=5.8 Hz), 4.362 (2H, s), 4.472 (2H, s), 6.643 (1H, d, J=4.2 Hz), 7.144–7.346 (5H, m);
IR (nujol) 2657, 1660, 1248, 1132, 930, 741 cm$^{-1}$;
Anal. Calcd for C$_{21}$H$_{29}$ClN$_2$O$_2$S.0.3H$_2$O: C, 60.87; H, 7.20; N, 6.76. Found: C, 60.86; H, 7.19; N, 6.69.

EXAMPLE 45

Synthesis of 1-(2-dimethylaminomethyl-5,7-dihydro-4H-furo[2,3-c]pyridin-6-yl)-5-phenylsulfonylpentan-1-one hydrochloride a) Synthesis of 1-(5,7-dihydro-4H-furo[2,3-c]pyridin-6-yl)-5-phenylsulfonylpentan-1-one To a solution of 0.160 g (1.000 mmol) of 4,5,6,7-tetrahydrofuro[2,3-c]pyridine hydrochloride, 0.29 g (1.2 mmol) of 5-phenylsulfoylpentanoic acid and 0.55 ml (4.0 mmol) of triethylamine in 30 ml of dichloromethane, 0.24 g (1.5 mmol) of diethyl cyanophosphonate was added under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=1/1) to yield the desired product.

Colorless oil Yield 0.311 g (90%)
$^1$H-NMR (CDCl$_3$, 200 MHz) δ1.749–1.786 (4H, m), 2.334–2.599 (4H, m), 3.099–3.167 (2H, m), 3.625 (1.2H, t, J=5.6 Hz), 3.801 (0.8H, t, J=5.6 Hz), 4.442 (0.8H, s), 4.586 (1.2H, s), 6.261 (1H, s), 7.312 (1H, s), 7.534–7.706 (3H, m), 7.909 (2H, d, J=6.8 Hz);
IR (neat) 2924, 2854, 1645, 1462, 1298, 1147, 1032, 895, 731 cm$^{-1}$ b) Synthesis of 1-(2-dimethylaminomethyl-5,7-dihydro-4H-furo[2,3-c]pyridin-6-yl)-5-phenylsulfonylpentan-1-one To a solution of 0.300 g (0.863 mmol) of 1-(5,7-dihydro-4H-furo[2,3-c]pyridin-6-yl)-5-phenylsulfonylpentan-1-one in 20 ml of acetic acid, 0.117 ml (1.29 mmol) of 50% aqueous dimethylamine and 0.105 ml (1.29 mmol) of 37% aqueous formaldehyde were added, followed by stirring at 100° C. for 20 minutes. After the solvent was distilled off under reduced pressure, the residual solution was alkalified with 1N aqueous sodium hydroxide and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1) to yield the desired product.

Yellow oil Yield 0.268 g (77%)
$^1$H-NMR (CDCl$_3$, 200 MHz) δ1.738–1.810 (4H, m), 2.261 (6H, d, J=2.2 Hz), 2.308–2.559 (4H, m), 3.092–3.161

(2H, m), 3.403 (2H, s), 3.606 (1.1H, t, J=5.7 Hz), 3.782 (0.9H, t, J=5.6 Hz), 4.412 (0.9H, s), 4.565 (1.1H, s), 6.051 (1H, s), 7.526–7.661 (3H, m), 7.903 (2H, d, J=7.6 Hz);

IR (neat) 2941, 2858, 1775, 1651, 1447, 1304, 1147, 1022, 906, 750 cm$^{-1}$ c) Synthesis of 1-(2-dimethylaminomethyl-5,7-dihydro-4H-furo[2,3-c]pyridin-6-yl)-5-phenylsulfonylpentan-1-one hydrochloride 1-(2-Dimethylaminomethyl-5,7-dihydro-4H-furo[m2,3-c]pyridin-6-yl)-5-phenylsulfonylpentan-1-one 0.268 g was dissolved in 2 ml of methanol; hydrogen chloride in ethyl acetate was added in excess, followed by stirring. This mixture was concentrated to yield the desired product.

Pale brown oil Yield 0.248 g $^1$H-NMR (CD$_3$OD, 200 MHz) δ1.732 (4H, br s), 2.474–2.614 (4H, m), 2.860 (6H, s), 3.223–3.256 (2H, m), 3.730–3.800 (2H, m), 4.364 (2H, s), 4.579 (2H, s), 6.637 (1H, s), 7.627–7.729 (3H, m), 7.910 (2H, d, J=7.8 Hz);

IR (nujol) 2678, 1628, 1290, 1147, 974, 733 cm$^{-1}$;

Anal. Calcd for C$_{21}$H$_{29}$ClN$_2$O$_4$S.1.0H$_2$O: C, 54.95; H, 6.81; N, 6.10. Found: C, 55.16; H, 6.71; N, 5.81.

EXAMPLE 46

Synthesis of 1-(2-dimethylaminomethyl-6,7-dihydro-4H-furo[3,2-c]pyridin-5-yl)-5-phenylsulfonylpentan-1-one hydrochloride a) Synthesis of 1-(6,7-dihydro-4H-furo[3,2-c]pyridin-5-yl)-5-phenylsulfonylpentan-1-one To a solution of 0.160 g (1.000 mmol) of 4,5,6,7-tetrahydrofuro[3,2-c]pyridine hydrochloride, 0.29 g (1.2 mmol) of 5-phenylsulfoylpentanoic acid and 0.55 ml (4.0 mmol) of triethylamine in 30 ml of dichloromethane, 0.24 g (1.5 mmol) of diethyl cyanophosphonate was added under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate= 1/1) to yield the desired product.

Colorless oil Yield 0.240 g (69%)

$^1$H-NMR (CDCl$_3$, 200 MHz) δ1.745–1.783 (4H, m), 2.353–2.448 (2H, m), 2.653–2.776 (2H, m), 3.097–3.163 (2H, m), 3.701 (1H, t, J=5.8 Hz), 3.886 (1H, t, J=5.8 Hz), 4.345 (1H, s), 4.481 (1H, s), 6.245 (1H, d, J=1.8 Hz), 7.293–7.313 (1H, m), 7.523–7.704 (3H, m), 7.904 (2H, d, J=8.0 Hz);

IR (neat) 2924, 1645, 1446, 1296, 1147, 1036, 891, 731 cm$^{-1}$ b) Synthesis of 1-(2-dimethylaminomethyl-6,7-dihydro-4H-furo[3,2-c]pyridin-5-yl)-5-phenylsulfonylpentan-1-one To a solution of 0.230 g (0.662 mmol) of 1-(6,7-dihydro-4H-furo[3,2-c]pyridin-5-yl)-5-phenylsulfonylpentan-1-one in 20 ml of acetic acid, 0.090 ml (0.99 mmol) of 50% aqueous dimethylamine and 0.081 ml (0.99 mmol) of 37% aqueous formaldehyde were added, followed by stirring at 100° C. for 60 minutes. After the solvent was distilled off under reduced pressure, the residual solution was alkalified with 1N aqueous sodium hydroxide and extracted with dichloromethane 2 times. The combined organic layer was washed with water and dried over anhydrous sodium sulfate; the solvent was distilled off under reduced pressure. The resulting crude product was purified by silica gel column chromatography (chloroform to chloroform/methanol=50/1 to 25/1) to yield the desired product.

Yellow oil Yield 0.081 g (30%)

$^1$H-NMR (CDCl$_3$, 200 MHz) δ1.705–1.866 (4H, m), 2.266 (6H, d, J=2.2 Hz), 2.345–2.405 (2H, m), 2.641–2.762 (2H, m), 3.096–3.163 (2H, m), 3.411 (2H, d, J=2.2 Hz), 3.683 (1H, t, J=6.0 Hz), 3.868 (1H, t, J=5.8 Hz), 4.303 (1H, s), 4.444 (1H, s), 6.046 (1H, s), 7.523–7.664 (3H, m), 7.904 (2H, d, J=8.0 Hz);

IR (neat) 2941, 2777, 1651, 1446, 1304, 1147, 1088, 798, 733 cm$^{-1}$ c) Synthesis of 1-(2-dimethylaminomethyl-6,7-dihydro-4H-furo[3,2-c]pyridin-5-yl)-5-phenylsulfonylpentan-1-one hydrochloride 1-(2-Dimethylaminomethyl-6,7-dihydro-4H-furo[3,2-c]pyridin-5-yl)-5-phenylsulfonylpentan-1-one 0.081 g was dissolved in 2 ml of methanol; hydrogen chloride in ethyl acetate was added in excess, followed by stirring. This mixture was concentrated to yield the desired product.

Brown oil Yield 0.083 g $^1$H-NMR (CD$_3$OD, 200 MHz) δ1.711–1.731 (4H, m), 2.465–2.503 (2H, m), 2.710–2.804 (2H, m), 2.855 (6H, s), 3.205–3.256 (2H, m), 3.786–3.887 (2H, m), 4.357 (2H, s), 4.462 (2H, s), 6.623 (1H, s), 7.583–7.728 (3H, m), 7.885–7.926 (2H, m);

IR (nujol) 2677, 1633, 1290, 1147, 941, 731 cm$^{-1}$;

Anal. Calcd for C$_{21}$H$_{29}$ClN$_2$O$_4$S.1.8CH$_3$OH: C, 54.92; H, 7.32; N, 5.62. Found: C, 54.61; H, 7.00; N, 5.55.

EXAMPLE 47

Synthesis of N,N-dimethyl-[6-(4-phenylbutoxycarbonyl)-4,5,6,7-tetrahydrofuro[2,3-c]pyridin-2-ylmethyl]amine hydrochloride a) Synthesis of N,N-dimethyl-[6-(4-phenylbutoxycarbonyl)-4,5,6,7-tetrahydrofuro[2,3-c]pyridin-2-ylmethyl]amine A solution of 0.226 g (1.416 mmol) of 4,5,6,7-tetrahydrofuro[2,3-c]pyridine hydrochloride and 0.57 g (2.1 mmol) of phenyl 4-phenylbutyl carbonate in 10 ml of pyridine was stirred at 100° C. overnight. The reaction mixture was poured into aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (hexane/ethyl acetate=15/1 to 9/1) to yield 6-(4-phenylbutoxycarbonyl)-4,5,6,7-tetrahydrofuro[2,3-c]pyridine as a mixture with phenol.

Colorless oil Yield 0.085 g

To a solution of 0.085 g (about 0.284 mmol) of the above 6-(4-phenylbutoxycarbonyl)-4,5,6,7-tetrahydrofuro[2,3-c]pyridine in 20 ml of acetic acid, 0.15 g (1.7 mmol) of 50% aqueous dimethylamine and 0.14 g (1.7 mmol) of 37% aqueous formaldehyde were added, followed by stirring at 100° C. for 15 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale yellow oil Yield 0.068 g (13%)

$^1$H-NMR (CDCl$_3$, 200 MHz) δ1.663–1.729 (4H, m), 2.262 (6H, s), 2.460–2.515 (2H, m), 2.594–2.685 (2H, m), 3.403 (2H, s), 3.656 (2H, br s), 4.129 (2H, t, J=6.0 Hz), 4.464 (2H, br s), 6.046 (1H, s), 7.098–7.362 (5H, m);

IR (neat) 2937, 1701, 1425, 1217, 1097, 1024, 748, 698 cm$^{-1}$ b) Synthesis of N,N-dimethyl-[6-(4-phenylbutoxycarbonyl)-4,5,6,7-tetrahydrofuro[2,3-c]pyridin-2-ylmethyl]amine hydrochloride N,N-Dimethyl-[6-(4-phenylbutoxycarbonyl)-4,5,6,7-tetrahydrofuro[2,3-c]pyridin-2-ylmethyl]amine 0.068 g was dissolved in 2 ml of methanol; hydrogen chloride in methanol was added in excess, followed by stirring. After this reaction mixture was concentrated, diethyl ether was added; the resulting solid was filtered and washed with diethyl ether to yield the desired product.

Pale yellow powder Yield 0.064 g $^1$H-NMR (CD$_3$OD, 200 MHz) δ1.667–1.714 (4H, m), 2.525–2.850 (4H, m), 2.850 (6H, s), 3.692 (2H, t, J=5.7 Hz), 4.115–4.171 (2H, m), 4.348 (2H, s), 4.505 (2H, s), 6.613 (1H, s), 7.095–7.350 (5H, m);

IR (nujol) 2468, 1693, 1223, 1097, 943, 744, 698 cm$^{-1}$;

Anal. Calcd for C$_{21}$H$_{29}$ClN$_2$O$_3$.0.6H$_2$O: C, 62.47; H, 7.54; N, 6.94. Found: C, 62.17; H, 7.25; N, 7.07.

EXAMPLE 48

Synthesis of N,N-dimethyl-[5-(4-phenylbutoxycarbonyl)-4,5,6,7-tetrahydrofuro[3,2-c]pyridin-2-ylmethyl]amine hydrochloride a) Synthesis of N,N-dimethyl-[5-(4-phenylbutoxycarbonyl)-4,5,6,7-tetrahydrofuro[3,2-c]pyridin-2-ylmethyl]amine A solution of 0.220 g (1.378 mmol) of 4,5,6,7-tetrahydrofuro[3,2-c]pyridine hydrochloride and 0.56 g (2.1 mmol) of phenyl 4-phenylbutyl carbonate in 10 ml of pyridine was stirred at 100° C. overnight. The reaction mixture was poured into aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (hexane/ethyl acetate=15/1 to 9/1) to yield 5-(4-phenylbutoxycarbonyl)-4,5,6,7-tetrahydrofuro[3,2-c]pyridine as a mixture with phenol.

Colorless oil Yield 0.218 g

To a solution of 0.218 g (about 0.728 mmol) of the above 5-(4-phenylbutoxycarbonyl)-4,5,6,7-tetrahydrofuro[3,2-c]pyridine in 20 ml of acetic acid, 0.08 g (0.9 mmol) of 50% aqueous dimethylamine and 0.07 g (0.9 mmol) of 37% aqueous formaldehyde were added, followed by stirring at 100° C. for 15 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale yellow oil Yield 0.189 g (38%)

$^1$H-NMR (CDCl$_3$, 200 MHz) δ1.667–1.735 (4H, m), 2.257 (6H, s), 2.617–2.715 (4H, m), 3.394 (2H, s), 3.742 (2H, br s), 4.129 (2H, t, J=6.1 Hz), 4.341 (2H, br s), 6.026 (1H, s), 7.096–7.327 (5H, m);

IR (neat) 2939, 1701, 1425, 1221, 1130, 1024, 748, 700 cm$^{-1}$ b) Synthesis of N,N-dimethyl-[5-(4-phenylbutoxycarbonyl)-4,5,6,7-tetrahydrofuro[3,2-c]pyridin-2-ylmethyl]amine hydrochloride N,N-Dimethyl-[5-(4-phenylbutoxycarbonyl)-4,5,6,7-tetrahydrofuro[3,2-c]pyridin-2-ylmethyl]amine 0.189 g was dissolved in 2 ml of methanol; hydrogen chloride in methanol was added in excess, followed by stirring. After this reaction mixture was concentrated, diethyl ether was added; the resulting solid was filtered and washed with diethyl ether to yield the desired product.

Pale yellow powder Yield 0.167 g $^1$H-NMR (CD$_3$OD, 200 MHz) δ1.661–1.710 (4H, m), 2.615–2.758 (4H, m), 2.848 (6H, s), 3.784 (2H, t, J=5.8 Hz), 4.128 (2H, t, J=6.0 Hz), 4.344 (2H, s), 4.392 (2H, br s), 6.610 (1H, s), 7.103–7.284 (5H, m);

IR (nujol) 2478, 1695, 1267, 1215, 1146, 944, 752, 702 cm$^{-1}$

Anal. Calcd for C$_{21}$H$_{29}$ClN$_2$O$_3$.0.5H$_2$O: C, 62.75; H, 7.52; N, 6.97. Found: C, 62.72; H, 7.35; N, 7.08.

EXAMPLE 49

Synthesis of N,N-diethyl-[6-(4-phenylbutoxycarbonyl)-4,5,6,7-tetrahydrofuro[2,3-c]pyridin-2-ylmethyl]amine hydrochloride a) Synthesis of N,N-diethyl-[6-(4-phenylbutoxycarbonyl)-4,5,6,7-tetrahydrofuro[2,3-c]pyridin-2-ylmethyl]amine 4,5,6,7-Tetrahydrofuro[2,3-c]pyridine hydrochloride 0.280 g (1.754 mmol) was dissolved in water. The solution was alkalified with aqueous sodium hydroxide and extracted with dichloromethane 3 times. The combined organic layer was dried over anhydrous magnesium sulfate; the solvent was distilled off under reduced pressure. A solution of the resulting crude 4,5,6,7-tetrahydrofuro[2,3-c]pyridine and 0.71 g (2.6 mmol) of phenyl 4-phenylbutyl carbonate in 10 ml of pyridine was stirred at 100° C. overnight. The solvent was distilled off under reduced pressure; the resulting crude product was purified by silica gel column chromatography (hexane/ethyl acetate=15/1 to 9/1) to yield 6-(4-phenylbutoxycarbonyl)-4,5,6,7-tetrahydrofuro[2,3-c]pyridine as a mixture with phenol.

Colorless oil Yield 0.267 g

To a solution of 0.267 g of the above 6-(4-phenylbutoxycarbonyl)-4,5,6,7-tetrahydrofuro[2,3-c]pyridine in 20 ml of acetic acid, 0.22 ml (2.1 mmol) of diethylamine and 0.17 g (2.1 mmol) of 37% aqueous formaldehyde were added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=9/1) to yield the desired product.

Orange oil Yield 0.198 g (29%)

$^1$H-NMR (CDCl$_3$, 200 MHz) δ1.066 (6H, t, J=7.2 Hz), 1.665–1.713 (4H, m), 2.533 (4H, q, J=7.1 Hz), 2.480–2.685 (4H, m), 3.588 (2H, s), 3.652 (2H, br s), 4.130 (2H, t, J=6.1 Hz), 4.462 (2H, br s), 6.023 (1H, s), 7.100–7.393 (5H, m);

IR (neat) 2933, 1703, 1425, 1217, 1097, 748, 698 cm$^{-1}$ b) Synthesis of N,N-diethyl-[6-(4-phenylbutoxycarbonyl)-4,5,6,7-tetrahydrofuro[2,3-c]pyridin-2-ylmethyl]amine hydrochloride N,N-Diethyl-[6-(4-phenylbutoxycarbonyl)-4,5,6,7-tetrahydrofuro[2,3-c]pyridin-2-ylmethyl]amine 0.198 g was dissolved in 2 ml of methanol; hydrogen chloride in methanol was added in excess, followed by stirring. This reaction mixture was concentrated to yield the desired product.

Dark brown oil Yield 0.202 g $^1$H-NMR (CD$_3$OD, 200 MHz) δ1.354 (6H, t, J=7.3 Hz), 1.658–1.724 (4H, m), 2.515–2.572 (2H, m), 2.610–2.682 (2H, m), 3.186 (4H, q, J=7.2 Hz), 3.687 (2H, t, J=5.7 Hz), 4.140 (2H, t, J=6.3 Hz), 4.396 (2H, s), 4.504 (2H, s), 6.645 (1H, s), 7.096–7.286 (5H, m);

IR (nujol) 2926, 2856, 2494, 1705, 1423, 1217, 750, 700 cm$^{-1}$;

Anal. Calcd for C$_{23}$H$_{33}$ClN$_2$O$_3$.1.0H$_2$O: C, 62.93; H, 8.04; N, 6.38. Found: C, 63.02; H, 8.04; N, 6.61.

EXAMPLE 50

Synthesis of N-(4-phenylbutyl)-(2-dimethylaminomethyl-5,7-dihydro-4H-furo[2,3-c]pyridin-6-yl)carboxyamide hydrochloride a) Synthesis of N-(4-phenylbutyl)-(5,7-dihydro-4H-furo[2,3-c]pyridin-6-yl)carboxyamide To a solution of 0.38 g (2.1 mmol) of 5-phenylpentanoic acid in 10 ml of benzene, 0.46 ml (2.1 mmol) of diphenylphosphoryl azide (DPPA) and 0.32 ml (2.3 mmol) of triethylamine were added, followed by refluxing for 1.5 hours. This reaction mixture was added to a solution of 0.284 g (1.779 mmol) of 4,5,6,7-tetrahydrofuro[2,3-c]pyridine hydrochloride and 1 ml of pyridine in 5 ml of benzene, followed by overnight refluxing. After the reaction mixture was cooled to room temperature, dilute hydrochloric acid was added, followed by 3 extractions with ethyl acetate. The combined organic layer was dried over anhydrous magnesium sulfate; the solvent was distilled off under reduced pressure. The resulting crude product was purified by silica gel column chromatography (hexane/ethyl acetate= 3/1 to 1/1) to yield the desired product.

Colorless oil Yield 0.503 g (95%)

$^1$H-NMR (CDCl$_3$, 200 MHz) δ1.473–1.749 (4H, m), 2.531 (2H, tt, J=1.8&5.7 Hz), 2.638 (2H, t, J=7.3 Hz), 3.277 (2H, br t, J=5.9 Hz), 3.597 (2H, t, J=5.5 Hz), 4.369 (2H, s), 4.464 (1H, br s), 6.246 (1H, d, J=1.8 Hz), 7.131–7.323 (6H, m);

IR (neat) 3340, 2929, 1622, 1541, 1272, 1223, 744, 700 cm$^{-1}$ b) Synthesis of N-(4-phenylbutyl)-(2-dimethylaminomethyl-5,7-dihydro-4H-furo[2,3-c]pyridin-6-yl)carboxyamide To a solution of 0.503 g (1.686 mmol) of N-(4-phenylbutyl)-(5,7-dihydro-4H-furo[2,3-c]pyridin-6-yl)carboxyamide in 20 ml of acetic acid, 0.18 g (2.0 mmol) of 50% aqueous dimethylamine and 0.16 g (2.0 mmol) of 37% aqueous formaldehyde were added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.599 g (100%)

$^1$H-NMR (CDCl$_3$, 200 MHz) δ1.503–1.708 (4H, m), 2.255 (6H, s), 2.493 (2H, t, J=5.6 Hz), 2.635 (2H, t, J=7.2 Hz), 3.264 (2H, q, J=6.4 Hz), 3.392 (2H, s), 3.589 (2H, t, J=5.6 Hz), 4.340 (2H, s), 4.428 (1H, br t, J=5.1 Hz), 6.042 (1H, s), 7.147–7.310 (5H, m);

IR (neat) 3340, 2933, 1626, 1539, 1454, 1267, 1227, 1024, 746, 700 cm$^{-1}$ c) Synthesis of N-(4-phenylbutyl)-(2-dimethylaminomethyl-5,7-dihydro-4H-furo[2,3-c]pyridin-6-yl)carboxyamide hydrochloride N-(4-Phenylbutyl)-(2-dimethylaminomethyl-5,7-dihydro-4H-furo[2,3-c]pyridin-6-yl)carboxyamide 0.599 g was dissolved in 2 ml of methanol. To this solution, hydrogen chloride in methanol was added in excess, followed by stirring. This mixture was concentrated to yield the desired product.

Brown foam Yield 0.561 g $^1$H-NMR (CD$_3$OD, 200 MHz) δ1.491–1.687 (4H, m), 2.489–2.658 (4H, m), 2.850 (6H, s), 3.202 (2H, t, J=6.8 Hz), 3.623 (2H, t, J=5.7 Hz), 6.612 (1H, s), 7.089–7.279 (5H, m);

IR (neat) 3313, 2933, 2667, 1624, 1542 cm$^{-1}$;

Anal. Calcd for C$_{21}$H$_{30}$ClN$_3$O$_2$·1.7H$_2$O: C, 59.69; H, 7.97; N, 9.94. Found; C, 59.51; H, 7.71; N, 10.07.

EXAMPLE 51

Synthesis of N-(4-phenylbutyl)-(2-dimethylaminomethyl-6,7-dihydro-4H-furo[3,2-c]pyridin-5-yl)carboxyamide hydrochloride a) Synthesis of N-(4-phenylbutyl)-(6,7-dihydro-4H-furo[3,2-c]pyridin-5-yl)carboxyamide To a solution of 0.38 g (2.1 mmol) of 5-phenylpentanoic acid in 10 ml of benzene, 0.46 ml (2.1 mmol) of diphenylphosphoryl azide (DPPA) and 0.32 ml (2.3 mmol) of triethylamine were added, followed by refluxing for 1.5 hours. This reaction mixture was added to a solution of 0.285 g (1.786 mmol) of 4,5,6,7-tetrahydrofuro[3,2-c]pyridine hydrochloride and 1 ml of pyridine in 5 ml of benzene, followed by overnight refluxing. After the reaction mixture was cooled to room temperature, dilute hydrochloric acid was added, followed by 3 extractions with ethyl acetate. The combined organic layer was dried over anhydrous magnesium sulfate; the solvent was distilled off under reduced pressure. The resulting crude product was purified by silica gel column chromatography (hexane/ethyl acetate= 3/1 to 1/1) to yield the desired product.

Colorless oil Yield 0.529 g (99%)

$^1$H-NMR (CDCl$_3$, 200 MHz) δ1.471–1.749 (4H, m), 2.638 (2H, t, J=7.3 Hz), 2.705 (2H, t, J=5.6 Hz), 3.274 (2H, q, J=6.5 Hz), 3.716 (2H, t, J=5.7 Hz), 4.237 (2H, t, J=1.8 Hz), 4.475 (1H, br t, J=5.5 Hz), 6.220 (1H, d, J=1.8 Hz), 7.131–7.321 (6H, m);

IR (neat) 3309, 2927, 1618, 1539, 1263, 1097, 748, 702 cm$^{-1}$ b) Synthesis of N-(4-phenylbutyl)-(2-dimethylaminomethyl-6,7-dihydro-4H-furo[3,2-c]pyridin-5-yl)carboxyamide To a solution of 0.529 g (1.773 mmol) of N-(4-phenylbutyl)-(6,7-dihydro-4H-furo[3,2-c]pyridin-5-yl)carboxyamide in 20 ml of acetic acid, 0.19 g (2.1 mmol) of 50% aqueous dimethylamine and 0.17 g (2.1 mmol) of 37% aqueous formaldehyde were added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.376 g (60%)

$^1$H-NMR (CDCl$_3$, 200 MHz) δ1.502–1.711 (4H, m), 2.260 (6H, s), 2.599–2.724 (4H, m), 3.270 (2H, q, J=6.3 Hz), 3.396 (2H, s), 3.698 (2H, t, J=5.7 Hz), 4.207 (2H, s), 4.497 (1H, br t, J=5.6 Hz), 6.026 (1H, s), 7.155–7.327 (5H, m);

IR (neat) 3340, 2935, 2856, 1626, 1539, 1454, 1273, 1022, 748, 700 cm$^{-1}$ c) Synthesis of N-(4-phenylbutyl)-(2-dimethylaminomethyl-6,7-dihydro-4H-furo[3,2-c]pyridin-5-yl)carboxyamide hydrochloride N-(4-Phenylbutyl)-(2-dimethylaminomethyl-6,7-dihydro-4H-furo[3,2-c]pyridin-5-yl)carboxyamide 0.376 g was dissolved in 2 ml of methanol. To this solution, hydrogen chloride in methanol was added in excess, followed by stirring. This mixture was concentrated to yield the desired product.

Yellow foam Yield 0.390 g $^1$H-NMR (CD$_3$OD, 200 MHz) δ1.513–1.688 (4H, m), 2.624 (2H, t, J=7.1 Hz), 2.730 (2H, t, J=5.8 Hz), 2.850 (6H, s), 3.203 (2H, t, J=6.8 Hz), 3.730 (2H, t, J=5.8 Hz), 4.314 (2H, s), 4.345 (2H, s), 6.618 (1H, s), 7.120–7.276 (5H, m);

IR (neat) 3325, 2926, 2671, 1620, 1542 cm$^{-1}$;

Anal. Calcd for $C_{21}H_{30}ClN_3O_2 \cdot 2.5H_2O$: C, 57.72; H, 8.07; N, 9.62. Found: C, 57.85; H, 7.67; N, 9.63.

EXAMPLE 52

Synthesis of N,N-dimethyl-[6-(5-phenylpentylsulfonyl)-4,5,6,7-tetrahydrofuro[2,3-c]pyridin-2-ylmethyl]amine hydrochloride a) Synthesis of 6-(5-phenylpentylsulfonyl)-4,5,6,7-tetrahydrofuro[2,3-c]pyridine To a solution of 0.236 g (1.479 mmol) of 4,5,6,7-tetrahydrofuro[2,3-c]pyridine hydrochloride and 0.82 ml (5.9 mmol) of triethylamine in 30 ml of dichloromethane, a solution of 0.73 g of crude 5-phenylpentylsulfonyl chloride (obtained by adding dropwise a diethyl ether solution of 5-phenylpentylmagnesium bromide, prepared from 5.860 g (25.80 mmol) of 1-bromo-5-phenylpentane and 0.94 g (38.7 mmol) of magnesium in 150 ml of diethyl ether, to a solution of 5.15 ml (51.6 mmol) of sulfuryl chloride in 50 ml of diethyl ether under ice-cooling, followed by stirring under ice-cooling for 3 hours, filtering and washing with diethyl ether the resulting precipitate, and evaporating the combined filtrate under reduced pressure) in 10 ml of dichloromethane was added dropwise under ice-cooling, followed by stirring under ice-cooling for 1 hour. The reaction mixture was poured into aqueous sodium hydrogen carbonate and extracted with dichloromethane 3 times. The combined organic layer was dried over anhydrous magnesium sulfate; the solvent was distilled off under reduced pressure. The resulting crude product was purified by silica gel flush column chromatography (hexane/ethyl acetate=6/1) to yield the desired product.

Yellow oil Yield 0.181 g (37%)

$^1$H-NMR (CDCl$_3$, 200 MHz) δ1.355–1.495 (2H, m), 1.564 (2H, m), 1.742–1.896 (2H, m), 2.564–2.638 (4H, m), 2.889–2.967 (2H, m), 3.542 (2H, t, J=5.7 Hz), 4.365 (2H, s), 6.260 (1H, d, 1.8 Hz), 7.127–7.310 (6H, m);

IR (neat) 2933, 2856, 1335, 1151, 1005, 910, 737, 700 cm$^{-1}$ b) Synthesis of N,N-dimethyl-[6-(5-phenylpentylsulfonyl)-4,5,6,7-tetrahydrofuro[2,3-c]pyridin-2-ylmethyl]amine To a solution of 0.181 g (0.543 mmol) of 6-(5-phenylpentylsulfonyl)-4,5,6,7-tetrahydrofuro[2,3-c]pyridine in 20 ml of acetic acid, 59 mg (0.65 mmol) of 50% aqueous dimethylamine and 53 mg (0.65 mmol) of 37% aqueous formaldehyde were added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.137 g (65%)

$^1$H-NMR (CDCl$_3$, 200 MHz) δ1.375–1.490 (2H, m), 1.560–1.893 (4H, m), 2.260 (6H, s), 2.543–2.636 (4H, m), 2.879–2.959 (2H, m), 3.408 (2H, s), 3.530 (2H, t, J=5.6 Hz), 4.345 (2H, s), 6.070 (1H, s), 7.116–7.314 (5H, m);

IR (neat) 2935, 1456, 1338, 1147, 1011, 941, 750, 700 cm$^{-1}$ c) Synthesis of N,N-dimethyl-[6-(5-phenylpentylsulfonyl)-4,5,6,7-tetrahydrofuro[2,3-c]pyridin-2-ylmethyl]amine hydrochloride N,N-Dimethyl-[6-(5-phenylpentylsulfonyl)-4,5,6,7-tetrahydrofuro[2,3-c]pyridin-2-ylmethyl]amine 0.137 g was dissolved in 2 ml of methanol; hydrogen chloride in methanol was added in excess, followed by stirring. After this mixture was concentrated, diethyl ether was added; the resulting solid was filtered and washed with diethyl ether to yield the desired product.

Pale brown powder Yield 0.137 g $^1$H-NMR (CD$_3$OD, 200 MHz) δ1.414–1.528 (2H, m), 1.586–1.838 (4H, m), 2.578–2.653 (2H, m), 2.852 (6H, s), 3.035–3.113 (2H, m), 3.541 (2H, t, J=5.6 Hz), 4.351 (2H, s), 4.381 (2H, s), 6.636 (1H, s), 7.093–7.285 (5H, m);

IR (nujol) 2470, 1319, 1138, 1012, 976, 943, 746, 700 cm$^{-1}$;

Anal. Calcd for $C_{21}H_{31}ClN_2O_3S \cdot 0.4H_2O$: C, 58.09; H, 7.38; N, 6.45. Found: C, 58.31; H, 7.09; N, 6.66.

EXAMPLE 53

Synthesis of N,N-dimethyl-[5-(5-phenylpentylsulfonyl)-4,5,6,7-tetrahydrofuro[3,2-c]pyridin-2-ylmethyl]amine hydrochloride a) Synthesis of 5-(5-phenylpentylsulfonyl)-4,5,6,7-tetrahydrofuro[3,2-c]pyridine To a solution of 0.298 g (1.867 mmol) of 4,5,6,7-tetrahydrofuro[3,2-c]pyridine hydrochloride and 1.30 ml (9.34 mmol) of triethylamine in 30 ml of dichloromethane, a solution of 1.38 g of crude 5-phenylpentylsulfonyl chloride (obtained by adding dropwise a diethyl ether solution of 5-phenylpentylmagnesium bromide, prepared from 5.860 g (25.80 mmol) of 1-bromo-5-phenylpentane and 0.94 g (38.7 mmol) of magnesium in 150 ml of diethyl ether, to a solution of 5.15 ml (51.6 mmol) of sulfuryl chloride in 50 ml of diethyl ether under ice-cooling, followed by stirring under ice-cooling for 3 hours, filtering and washing with diethyl ether the resulting precipitate, and evaporating the combined filtrate under reduced pressure) in 10 ml of dichloromethane was added dropwise under ice-cooling, followed by stirring under ice-cooling for 1 hour. The reaction mixture was poured into aqueous sodium hydrogen carbonate and extracted with dichloromethane 3 times. The combined organic layer was dried over anhydrous magnesium sulfate; the solvent was distilled off under reduced pressure. The resulting crude product was purified by silica gel flush column chromatography (hexane/ethyl acetate=6/1) to yield the desired product.

Orange oil Yield 0.335 g (54%)

$^1$H-NMR (CDCl$_3$, 200 MHz) δ1.348–1.487 (2H, m), 1.559–1.705 (2H, m), 1.736–1.892 (2H, m), 2.599 (2H, t, J=7.3 Hz), 2.768 (2H, t, J=5.7 Hz), 2.874–2.953 (2H, m), 3.629 (2H, t, J=5.9 Hz), 4.270 (2H, t, J=1.8 Hz), 6.225 (1H, d, J=2.0 Hz), 7.127–7.362 (6H, m);

IR (neat) 2935, 2858, 1336, 1142, 1003, 893, 737, 702 cm$^{-1}$ b) Synthesis of N,N-dimethyl-[5-(5-phenylpentylsulfonyl)-4,5,6,7-tetrahydrofuro[3,2-c]pyridin-2-ylmethyl]amine To a solution of 0.329 g (0.967 mmol) of 5-(5-phenylpentylsulfonyl)-4,5,6,7-tetrahydrofuro[3,2-c]pyridine in 20 ml of acetic acid, 0.11 g (1.2 mmol) of 50% aqueous dimethylamine and 96 mg (1.2 mmol) of 37% aqueous formaldehyde were added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.244 g (65%)

$^1$H-NMR (CDCl$_3$, 200 MHz) δ1.376–1.491 (2H, m), 1.564–1.898 (4H, m), 2.258 (6H, s), 2.603 (2H, t, J=7.3 Hz), 2.769 (2H, t, J=5.9 Hz), 2.874–2.954 (2H, m), 3.396 (2H, s), 3.627 (2H, t, J=5.9 Hz), 4.240 (2H, s), 6.032 (1H, s), 7.129–7.321 (5H, m);

IR (neat) 2929, 2858, 1452, 1338, 1157, 1140, 748, 702 cm$^{-1}$ c) Synthesis of N,N-dimethyl-[5-(5-phenylpentylsulfonyl)-4,5,6,7-tetrahydrofuro[3,2-c]pyridin-2-ylmethyl]amine hydrochloride N,N-Dimethyl-[5-(5-phenylpentylsulfonyl)-4,5,6,7-tetrahydrofuro[3,2-c]pyridin-2-ylmethyl]amine 0.244 g was dissolved in 2 ml of methanol; hydrogen chloride in methanol was added in excess, followed by stirring. After this mixture was concentrated, diethyl ether was added; the resulting solid was filtered and washed with diethyl ether to yield the desired product.

Pale yellow powder Yield 0.216 g $^1$H-NMR (CD$_3$OD, 200 MHz) δ1.412–1.535 (2H, m), 1.581–1.872 (4H, m), 2.616 (2H, t, J=7.5 Hz), 2.808 (2H, t, J=5.8 Hz), 2.852 (6H, s), 3.026–3.103 (2H, m), 3.640 (2H, t, J=5.7 Hz), 4.268 (2H, t, J=1.6 Hz), 4.348 (2H, s), 6.620 (1H, s), 7.096–7.288 (5H, m);

IR (nujol) 2465, 1336, 1140, 1007, 953, 762 cm$^{-1}$;

Anal. Calcd for C$_{21}$H$_{31}$ClN$_2$O$_3$S.0.6H$_2$O: C, 57.61; H, 7.41; N, 6.40. Found: C, 57.89; H, 7.19; N, 6.60.

EXAMPLE 54

Synthesis of N,N-diethyl-[5-(5-phenylpentylsulfonyl)-4,5,6,7-tetrahydrofuro[3,2-c]pyridin-2-ylmethyl]amine hydrochloride a) Synthesis of N,N-diethyl-[5-(5-phenylpentylsulfonyl)-4,5,6,7-tetrahydrofuro[3,2-c]pyridin-2-ylmethyl]amine To a solution of 0.269 g (0.807 mmol) of 5-(5-phenylpentylsulfonyl)-4,5,6,7-tetrahydrofuro[3,2-c]pyridine in 20 ml of acetic acid, 0.10 ml (0.97 mmol) of diethylamine and 79 mg (0.97 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=9/1) to yield the desired product.

Yellow oil Yield 0.168 g Recovery 50%

$^1$H-NMR (CDCl$_3$, 200 MHz) δ1.057 (6H, t, J=7.1 Hz), 1.366–1.481 (2H, m), 1.553–1.701 (2H, m), 1.730–1.885 (2H, m), 2.526 (4H, q, J=7.1 Hz), 2.593 (2H, t, J=5.4 Hz), 2.751 (2H, t, J=5.7 Hz), 2.863–2.942 (2H, m), 3.577 (2H, s), 3.606 (2H, t, J=5.8 Hz), 4.225 (2H, s), 6.007 (1H, s), 7.117–7.305 (5H, m);

IR (neat) 2933, 2819, 1466, 1336, 1142, 1068, 1005, 750, 702 cm$^{-1}$ b) Synthesis of N,N-diethyl-[5-(5-phenylpentylsulfonyl)-4,5,6,7-tetrahydrofuro[3,2-c]pyridin-2-ylmethyl]amine hydrochloride N,N-Diethyl-[5-(5-phenylpentylsulfonyl)-4,5,6,7-tetrahydrofuro[3,2-c]pyridin-2-ylmethyl]amine 0.168 g was dissolved in 2 ml of methanol; hydrogen chloride in methanol was added in excess, followed by stirring. This mixture was concentrated to yield the desired product.

Yellow oil 0.183 g $^1$H-NMR (CD$_3$OD, 200 MHz) δ1.376 (6H, t, J=7.4 Hz), 1.424–1.519 (2H, m), 1.572–1.862 (4H, m), 2.604 (2H, t, J=7.3 Hz), 2.801 (2H, t, J=5.7 Hz), 3.014–3.092 (2H, m), 3.174 (4H, q, J=7.3 Hz), 3.631 (2H, t, J=5.7 Hz), 4.261 (2H, s), 4.377 (2H, s), 6.662 ((1H, s), 7.096–7.288 (5H, m);

IR (neat) 2937, 2858, 2638, 1458, 1333, 1140, 1070, 1005, 750, 702 cm$^{-1}$;

Anal. Calcd for C$_{23}$H$_{35}$ClN$_2$O$_3$S.1.5H$_2$O: C, 57.30; H, 7.95; N, 5.81. Found: C, 57.52; H, 7.74; N, 5.64.

EXAMPLE 55

Synthesis of N,N-dimethyl-[7-(6-phenylhexyl)-5,6,7,8-tetrahydro-4H-furo[2,3-c]azepin-2-ylmethyl] amine dihydrochloride a) Synthesis of 7-(6-phenylhexyl)-5,6,7,8-tetrahydro-4H-furo[2,3-c]azepine To a suspension of 1.05 g (27.6 mmol) of lithium aluminum hydride in 100 ml of ether, a solution of 3.090 g (18.37 mmol) of ethyl 3-(3-furyl)propionate in 20 ml of ether was added dropwise under ice-cooling, followed by stirring at room temperature for 1 hour. To decompose the excess lithium aluminum hydride, ethyl acetate was added dropwise to the reaction mixture under ice-cooling; subsequently, water was added until a white precipitate formed. The white precipitate was filtered using Celite and washed with ethyl acetate 3 times. The combined filtrate was evaporated under reduced pressure. The obtained crude 3-(3-furyl)propanol was used for the next reaction without purification.

To a solution of 3.31 g (26.1 mmol) of oxalyl chloride in 100 ml of dichloromethane, 3.71 ml (52.2 mmol) of dimethyl sulfoxide was added dropwise at −78° C. After 5 minutes of stirring, a solution of the above crude 3-(3-furyl)propanol in 50 ml of dichloromethane was added dropwise, followed by stirring for 15 minutes. To this mixture, 14.6 ml (104 mmol) of triethylamine was added; the mixture was allowed to warm to room temperature with stirring. The reaction mixture was diluted with ether and washed with water, after which the organic layer was dried over anhydrous magnesium sulfate; the solvent was distilled off under reduced pressure. The resulting crude 3-(3-furyl)propanal was used for the next reaction without purification.

To a solution of the above crude 3-(3-furyl)propanal, 6-phenylhexylamine (obtained by refluxing a solution of 10.71 g (34.84 mmol) of N-(6-phenylhexyl)phthalimide and 2.54 ml (52.3 mmol) of hydrazine monohydrate in 100 ml of ethanol for 1 hour, followed by the addition of aqueous sodium hydroxide and 3 extractions with dichloromethane, drying the combined organic layer, over anhydrous magnesium sulfate, and distilling off the solvent under reduced pressure) and 1.05 ml (17.4 mmol) of acetic acid in 100 ml of methanol, 1.09 g (17.4 mmol) of sodium cyanoborohydride was added at room temperature, followed by stirring at room temperature for 1 day. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was subjected to silica gel column chromatography (ethyl acetate to ethyl acetate/methanol=9/1). The resulting crude N-[3-(3-furyl)propyl]-6-phenylhexylamine was used for the next reaction without further purification.

To a solution of the above crude N-[3-(3-furyl)propyl]-6-phenylhexylamine in 100 ml of dichloromethane, 2.49 g (11.4 mmol) of di-tert-butyl dicarbonate was added, followed by stirring at room temperature for 2 hours. The solvent was distilled off under reduced pressure. The resulting crude product was purified by silica gel column chromatography (hexane/ethyl acetate=9/1) to yield N-(tert-butoxycarbonyl)-N-[3-(3-furyl)propyl]-6-phenylhexylamine as a mixture with di-tert-butyl dicarbonate.

Colorless oil Yield 3.382 g

The above crude N-(tert-butoxycarbonyl)-N-[3-(3-furyl)propyl]-6-phenylhexylamine 3.382 g was dissolved in 50 ml of methanol; 6 ml of concentrated hydrochloric acid was added, followed by overnight stirring at room temperature. After the solvent was distilled off under reduced pressure, the reaction mixture was alkalified with aqueous sodium hydroxide, the solution was extracted with dichloromethane 3 times. The combined organic layer was dried over anhydrous magnesium sulfate; the solvent was distilled off under reduced pressure. The resulting crude N-[3-(3-furyl)propyl]-6-phenylhexylamine was used for the next reaction without purification.

To a solution of the above crude N-[3-(3-furyl)propyl]-6-phenylhexylamine in 100 ml of acetic acid, 0.74 g (9.1 mmol) of 37% aqueous formaldehyde was added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=9/1 to 3/1) to yield the desired product.

Colorless oil Yield 1.109 g (20%)

$^1$H-NMR (CDCl$_3$, 200 MHz) δ1.258–1.814 (10H, m), 2.402–2.631 (6H, m), 2.976–3.029 (2H, m), 3.808 (2H, s), 6.171 (1H, d, J=1.6 Hz), 7.135–7.310 (6H, m);

IR (neat) 2929, 1498, 1452, 1078, 727, 700 cm$^{-1}$ b) Synthesis of N,N-dimethyl-[7-(6-phenylhexyl)-5,6,7,8-tetrahydro-4H-furo[2,3-c]azepin-2-ylmethyl]amine To a solution of 0.945 g (3.18 mmol) of 7-(6-phenylhexyl)-5,6,7,8-tetrahydro-4H-furo[2,3-c]azepine in 20 ml of acetic acid, 0.34 g (3.8 mmol) of 50% aqueous dimethylamine and 0.31 g (3.8 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Brown oil Yield 0.739 g (66%)

$^1$H-NMR (CDCl$_3$, 200 MHz) δ1.289–1.775 (10H, m), 2.233 (6H, s), 2.399–2.506 (4H, m), 2.594 (2H, t, J=7.7 Hz), 2.951–3.002 (2H, m), 3.346 (2H, s), 3.793 (2H, s), 5.980 (1H, s), 7.151–7.283 (5H, m);

IR (neat) 2929, 1452, 1360, 1103, 1026, 747, 698 cm$^{-1}$ c) Synthesis of N,N-dimethyl-[7-(6-phenylhexyl)-5,6,7,8-tetrahydro-4H-furo[2,3-c]azepin-2-ylmethyl]amine dihydro-chloride N,N-Dimethyl-[7-(6-phenylhexyl)-5,6,7,8-tetrahydro-4H-furo[2,3-c]azepin-2-ylmethyl]amine 0.739 g was dissolved in 2 ml of methanol; hydrogen chloride in methanol was added in excess, followed by stirring. This mixture was concentrated to yield the desired product.

Brown oil Yield 0.780 g $^1$H-NMR (CD$_3$OD, 200 MHz) δ1.379–1.451 (4H, m), 1.621–1.698 (2H, m), 1.749–1.841 (2H, m), 2.106–2.185 (2H, m), 2.625 (2H, t, J=7.5 Hz), 2.742 (2H, t, J=5.6 Hz), 2.872 (6H, s), 3.141–3.224 (2H, m), 3.451–3.574 (1H, m), 3.693–3.813 (1H, m), 4.348 (2H, s), 4.560 (2H, d, J=3.2 Hz), 6.680 (1H, s), 7.134–7.285 (5H, m);

IR (neat) 2935, 2592, 1470, 982, 944, 702 cm$^{-1}$;

Anal. Calcd for C$_{23}$H$_{36}$Cl$_2$N$_2$O.1.5H$_2$O: C, 60.78; H, 8.65; N, 6.16. Found: C, 60.66; H, 8.64; N, 5.97.

EXAMPLE 56

Synthesis of 1-(2-dimethylaminomethyl-4,5,6,8-tetrahydrofuro[2,3-c]azepin-7-yl)-6-phenylhexan-1-one hydrochloride a) Synthesis of 1-(4,5,6,8-tetrahydrofuro[2,3-c]azepin-7-yl)-6-phenylhexan-1-one To a solution of 0.189 g (0.796 mmol) of 7-tert-butoxycarbonyl-5,6,7,8-tetrahydro-4H-furo[2,3-c]azepine in 5 ml of methanol, 1 ml of concentrated hydrochloric acid was added, followed by stirring at room temperature for 1 hour, after which the solvent was distilled off under reduced pressure. The resulting crude 5,6,7,8-tetrahydro-4H-furo[2,3-c]azepine hydrochloride was used for the next reaction without purification.

Black-brown solid Yield 0.130 g

To a solution of 0.130 g of the above crude 5,6,7,8-tetrahydro-4H-furo[2,3-c]azepine hydrochloride, 0.18 g (0.96 mmol) of 6-phenylhexanoic acid and 0.44 ml (3.2 mmol) of triethylamine in 30 ml of dichloromethane, 0.15 ml (0.96 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=3/1 to 2/1) to yield the desired product.

Pale yellow oil Yield 0.216 g (87%)

$^1$H-NMR (CDCl$_3$, 200 MHz) δ1.286–1.447 (2H, m), 1.528–1.764 (4H, m), 1.832–1.967 (2H, m), 2.330 (2H, t, J=7.5 Hz), 2.517–2.643 (4H, m), 3.597–3.651 (0.8H, m), 3.685–3.740 (1.2H, m), 4.508 (1.2H, s), 4.717 (0.8H, s), 6.135 (0.4H, d, J=1.4 Hz), 6.175 (0.6H, d, J=1.4 Hz), 7.131–7.299 (6H, m);

IR (neat) 2931, 2854, 1647, 1458, 1423, 1232, 1178, 1088, 748, 700 cm$^{-1}$ b) Synthesis of 1-(2-dimethylaminomethyl-4,5,6,8-tetrahydrofuro[2,3-c]azepin-7-yl)-6-phenylhexan-1-one To a solution of 0.216 g (0.694 mmol) of 1-(4,5,6,8-tetrahydrofuro[2,3-c]azepin-7-yl)-6-phenylhexan-1-one in 20 ml of acetic acid, 75 mg (0.83 mmol) of 50% aqueous dimethylamine and 68 mg (0.83 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale yellow oil Yield 0.192 g (76%)

$^1$H-NMR (CDCl$_3$, 200 MHz) δ1.290–1.451 (2H, m), 1.528–1.769 (4H, m), 1.828–1.967 (2H, m), 2.231 (4.2H, s), 2.242 (1.8H, s), 2.332 (2H, t, J=7.5 Hz), 2.482–2.647 (4H, m), 3.345 (2H, s), 3.577–3.632 (0.6H, m), 3.673–3.727 (1.4H, m), 4.511 (1.4H, s), 4.720 (0.6H, s), 5.953 (0.3H, s), 5.986 (0.7H, s), 7.136–7.303 (5H, m);

IR (neat) 2931, 2818, 1647, 1456, 1423, 1365, 1286, 1236, 1176, 1026, 746, 700 cm$^{-1}$ c) Synthesis of 1-(2-dimethylaminomethyl-4,5,6,8-tetrahydrofuro[2,3-c]azepin-7-yl)-6-phenylhexan-1-one hydrochloride 1-(2-Dimethylaminomethyl-4,5,6,8-tetrahydrofuro[2,3-c]pyridin-7-yl)-6-phenylhexan-1-one 0.192 g was dissolved in 2 ml of methanol; hydrogen chloride in methanol was added in excess, followed by stirring. This mixture was concentrated to yield the desired product.

Pale yellow oil Yield 0.213 g $^1$H-NMR (CD$_3$OD, 200 MHz) δ1.255–1.431 (2H, m), 1.491–1.700 (4H, m), 1.797–1.980 (2H, m), 2.411 (2H, t, J=7.3 Hz), 2.520–2.650 (4H, m), 2.819 (1.8H, s), 2.839 (4.2H, s), 3.709–3.792 (2H, m), 4.310 (2H, s), 4.675 (0.6H, s), 4.691 (1.4H, s), 6.559 (0.7H, s), 6.581 (0.3H, s), 7.078–7.277 (5H, m);

IR (neat) 2931, 2684, 1637, 1470, 1427, 1248, 1180, 1117, 984, 943, 748, 700 cm$^{-1}$;

Anal. Calcd for C$_{23}$H$_{33}$ClN$_2$O$_2$·1.5H$_2$O: C, 63.95; H, 8.40; N, 6.48. Found: C, 63.78; H, 8.46; N, 6.42.

EXAMPLE 57

Synthesis of N,N-dimethyl-[7-(4-benzoylbenzoyl)-5,6,7,8-tetrahydro-4H-furo[2,3-c]azepin-2-ylmethyl]amine hydrochloride a) Synthesis of 7-(4-benzoylbenzoyl)-5,6,7,8-tetrahydro-4H-furo[2,3-c]azepine To a solution of 0.185 g (0.780 mmol) of 7-tert-butoxycarbonyl-5,6,7,8-tetrahydro-4H-furo[2,3-c]azepine in 5 ml of methanol, 1 ml of concentrated hydrochloric acid was added, followed by stirring at room temperature for 1 hour, after which the solvent was distilled off under reduced pressure. The resulting crude 5,6,7,8-tetrahydro-4H-furo[2,3-c]azepine hydrochloride was used for the next reaction without purification.

Black-brown solid Yield 0.128 g

To a solution of 0.128 g of the above crude 5,6,7,8-tetrahydro-4H-furo[2,3-c]azepine hydrochloride, 0.21 g (0.94 mmol) of 4-benzoylbenzoic acid and 0.43 ml (3.1 mmol) of triethylamine in 30 ml of dichloromethane, 0.14 ml (0.94 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=3/1 to 1/1) to yield the desired product.

Pale yellow oil Yield 0.237 g (88%)

$^1$H-NMR (CDCl$_3$, 200 MHz) δ1.844 (0.5H, m), 2.037–2.143 (1.5H, m), 2.566–2.705 (2H, m), 3.618 (0.5H, br t, J=4.2 Hz), 3.925 (1.5H, br t, J=5.3 Hz), 4.491 (1.5H, s), 4.885 (0.5H, s), 6.220 (1H, s), 7.175–7.651 (6H, m), 7.777–7.840 (4H, m);

IR (neat) 2935, 1637, 1427, 1277, 754, 702 cm$^{-1}$ b) Synthesis of N,N-dimethyl-[7-(4-benzoylbenzoyl)-5,6,7,8-tetrahydro-4H-furo[2,3-c]azepin-2-ylmethyl]amine To a solution of 0.237 g (0.686 mmol) of 7-(4-benzoylbenzoyl)-5,6,7,8-tetrahydro-4H-furo[2,3-c]azepine in 20 ml of acetic acid, 74 mg (0.82 mmol) of 50% aqueous dimethylamine and 67 mg (0.82 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.166 g (60%)

$^1$H-NMR (CDCl$_3$, 200 MHz) δ1.828–1.885 (0.5H, m), 2.040–2.117 (1.5H, m), 2.227 (4.5H, s), 2.277 (1.5H, s), 2.568–2.672 (2H, m), 3.346 (1.5H, s), 3.396 (0.5H, s), 3.597 (0.5H, br t, J=5.3 Hz), 3.911 (1.5H, br t, J=5.3 Hz), 4.511 (1.5H, s), 4.891 (0.5H, s), 6.043 (1H, s), 7.378–7.660 (5H, m), 7.792–7.834 (4H, m);

IR (neat) 2937, 1637, 1454, 1427, 1277, 754, 704 cm$^{-1}$ c) Synthesis of N,N-dimethyl-[7-(4-benzoylbenzoyl)-5,6,7,8-tetrahydro-4H-furo[2,3-c]azepin-2-ylmethyl]amine hydrochloride N,N-Dimethyl-[7-(4-benzoylbenzoyl)-5,6,7,8-tetrahydro-4H-furo[2,3-c]azepin-2-ylmethyl]amine 0.166 g was dissolved in 2 ml of methanol; hydrogen chloride in methanol was added in excess, followed by stirring. This mixture was concentrated to yield the desired product.

Yellow foam Yield 0.174 g $^1$H-NMR (CD$_3$OD, 200 MHz) δ1.866 (1H, m), 1.062 (1H, m), 2.585–2.751 (2H, m), 2.810 (3H, s), 2.889 (3H, s), 3.718 (1H, br t, J=5.3 Hz), 3.951 (1H, br t, J=5.4 Hz), 4.301 (1H, s), 4.369 (1H, s), 4.585 (1H, s), 4.885 (1H, s), 6.616 (0.5H, s), 6.629 (0.5H, s), 7.257–7.704 (5H, m), 7.759–7.860 (4H, m);

IR (neat) 2941, 2679, 1630, 1468, 1429, 1277, 1115, 937, 704 cm$^{-1}$;

Anal. Calcd for C$_{25}$H$_{27}$ClN$_2$O$_3$·1.5H$_2$O: C, 64.44; H, 6.49; N, 6.01. Found: C, 64.45; H, 6.43; N, 5.95.

EXAMPLE 58

Synthesis of 1-(2-dimethylaminomethyl-4,5,7,8-tetrahydrofuro[2,3-d]azepin-6-yl)-6-phenylhexan-1-one hydrochloride a) Synthesis of 1-(4,5,7,8-tetrahydrofuro[2,3-d]azepin-6-yl)-6-phenylhexan-1-one To a solution of 0.207 g (0.872 mmol) of 6-tert-butoxycarbonyl-5,6,7,8-tetrahydro-4H-furo[2,3-d]azepine in 5 ml of methanol, 1 ml of concentrated hydrochloric acid was added, followed by stirring at room temperature for 1 hour, after which the solvent was distilled off under reduced pressure. The resulting crude 5,6,7,8-tetrahydro-4H-furo[2,3-d]azepine hydrochloride was used for the next reaction without purification.

Brown solid Yield 0.138 g

To a solution of 0.138 g of the above crude 5,6,7,8-tetrahydro-4H-furo[2,3-d]azepine hydrochloride, 0.20 g (1.05 mmol) of 6-phenylhexanoic acid and 0.49 ml (3.5 mmol) of triethylamine in 30 ml of dichloromethane, 0.16 ml (1.05 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=3/1 to 2/1) to yield the desired product.

Pale yellow oil Yield 0.230 g (85%)

$^1$H-NMR (CDCl$_3$, 200 MHz) δ1.321–1.456 (2H, m), 1.574–1.781 (4H, m), 2.343 (2H, t, J=7.5 Hz), 2.610 (4H, t, J=7.5 Hz), 2.874–2.947 (2H, m), 3.625 (2H, t, J=5.4 Hz), 3.717 (2H, t, J=5.5 Hz), 6.146 (0.5H, d, J=2.2 Hz), 6.156 (0.5H, d, J=1.8 Hz), 7.116–7.310 (6H, m);

IR (neat) 2929, 1643, 1450, 1423, 1030, 744, 700 cm$^{-1}$ b) Synthesis of 1-(2-dimethylaminomethyl-4,5,7,8-tetrahydrofuro[2,3-d]azepin-6-yl)-6-phenylhexan-1-one To a solution of 0.230 g (0.739 mmol) of 1-(4,5,7,8-tetrahydrofuro[2,3-d]azepin-6-yl)-6-phenylhexan-1-one in 20 ml of acetic acid, 80 mg (0.89 mmol) of 50% aqueous dimethylamine and 72 mg (0.89 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale yellow oil Yield 0.202 g (75%)

$^1$H-NMR (CDCl$_3$, 200 MHz) δ1.337–1.458 (2H, m), 1.575–1.780 (4H, m), 2.247 (6H, s), 2.343 (2H, t, J=7.5 Hz), 2.612 (4H, t, J=7.5 Hz), 2.922 (2H, t, J=5.1 Hz), 3.345 (2H, s), 3.623 (2H, t, J=5.7 Hz), 3.709 (2H, t, J=5.7 Hz), 5.964 (1H, s), 7.116–7.303 (5H, m);

IR (neat) 2931, 1643, 1452, 1423, 1371, 1201, 1180, 1024, 748, 700 cm$^{-1}$ c) Synthesis of 1-(2-dimethylaminomethyl-4,5,7,8-tetrahydrofuro[2,3-d]azepin-6-yl)-6-phenylhexan-1-one hydrochloride 1-(2-Dimethylaminomethyl-4,5,7,8-tetrahydrofuro[2,3-d] pyridin-6-yl)-6-phenylhexan-1-one 0.202 g was dissolved in 2 ml of methanol; hydrogen chloride in methanol was added in excess, followed by stirring. This mixture was concentrated to yield the desired product.

Pale yellow oil Yield 0.224 g $^1$H-NMR (CD$_3$OD, 200 MHz) δ1.315–1.463 (2H, m), 1.570–1.746 (4H, m), 2.443–2.531 (2H, m), 2.605 (2H, t, J=7.5 Hz), 2.654–2.748 (2H, m), 2.848 (6H, s), 2.911–3.031 (2H, m), 3.724–3.823 (4H, m), 4.321 (2H, s), 6.567 (0.5H, s), 6.581 (0.5H, s), 7.076–7.275 (5H, m);

IR (neat) 2933, 2696, 1630, 1471, 1433, 1375, 927, 702 cm$^{-1}$;

Anal. Calcd for $C_{23}H_{33}ClN_2O_2 \cdot 1.7H_2O$: C, 63.42; H, 8.42; N, 6.43. Found: C, 63.37; H, 8.49; N, 6.41.

EXAMPLE 59

Synthesis of N,N-dimethyl-[6-(4-benzoylbenzoyl)-5, 6,7,8-tetrahydro-4H-furo[2,3-d]azepin-2-ylmethyl] amine hydrochloride a) Synthesis of 6-(4-benzoylbenzoyl)-5,6,7,8-tetrahydro-4H-furo[2,3-d]azepine To a solution of 0.191 g (0.805 mmol) of 6-tert-butoxycarbonyl-5,6,7,8-tetrahydro-4H-furo[2,3-d]azepine in 5 ml of methanol, 1 ml of concentrated hydrochloric acid was added, followed by stirring at room temperature for 1 hour, after which the solvent was distilled off under reduced pressure. The resulting crude 5,6,7,8-tetrahydro-4H-furo[2, 3-d]azepine hydrochloride was used for the next reaction without purification.

Brown solid Yield 0.128 g

To a solution of 0.128 g of the above crude 5,6,7,8-tetrahydro-4H-furo[2,3-d]azepine hydrochloride, 0.22 g (0.97 mmol) of 4-benzoylbenzoic acid and 0.45 ml (3.2 mmol) of triethylamine in 30 ml of dichloromethane, 0.15 ml (0.97 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=3/1 to 1/1) to yield the desired product.

Colorless oil Yield 0.179 g (64%)

$^1$H-NMR (CDCl$_3$, 200 MHz) δ2.509 (1H, t, J=5.3 Hz), 2.764–2.841 (2H, m), 3.103 (1H, t, J=5.3 Hz), 3.574 (2H, t, J=5.3 Hz), 3.931 (2H, t, J=5.5 Hz), 6.147 (0.5H, s), 6.231 (0.5H, s), 7.211 (1H, d, J=1.8 Hz), 7.457–7.662 (5H, m), 7.792–7.878 (4H, m);

IR (neat) 2935, 1659, 1630, 1427, 1275, 924, 752, 702 cm$^{-1}$ b) Synthesis of N,N-dimethyl-[6-(4-benzoylbenzoyl)-5,6,7, 8-tetrahydro-4H-furo[2,3-d]azepin-2-ylmethyl]amine To a solution of 0.179 g (0.518 mmol) of 6-(4-benzoylbenzoyl)-5,6,7,8-tetrahydro-4H-furo[2,3-d]azepine in 20 ml of acetic acid, 56 mg (0.62 mmol) of 50% aqueous dimethylamine and 50 mg (0.62 mmol) of 37% aqueous formaldehyde were added, followed by stirring at 100° C. for 30 minutes. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.156 g (75%)

$^1$H-NMR (CDCl$_3$, 200 MHz) δ2.262 (6H, s), 2.471 (1H, t, J=5.3 Hz), 2.784 (2H, t, J=5.2 Hz), 3.103 (1H, t, J=5.3 Hz), 3.359 (2H, s), 3.557 (2H, t, J=5.5 Hz), 3.918 (2H, t, J=5.5 Hz), 5.955 (0.5H, s), 6.034 (0.5H, s), 7.457–7.656 (5H, m), 7.790–7.873 (4H, m);

IR (neat) 2939, 1659, 1630, 1466, 1429, 1275, 924, 752, 704 cm$^{-1}$ c) Synthesis of N,N-dimethyl-[6-(4-benzoylbenzoyl)-5,6,7, 8-tetrahydro-4H-furo[2,3-d]azepin-2-ylmethyl]amine hydrochloride N,N-Dimethyl-[6-(4-benzoylbenzoyl)-5,6,7,8-tetrahydro-4H-furo[2,3-d]azepin-2-ylmethyl]amine 0.156 g was dissolved in 2 ml of methanol; hydrogen chloride in methanol was added in excess, followed by stirring. This mixture was concentrated to yield the desired product.

Pale yellow foam Yield 0.165 g $^1$H-NMR (CD$_3$OD, 200 MHz) δ2.562 (1H, t, J=5.3 Hz), 2.793 (2H, m), 2.861 (6H, s), 3.108 (1H, t, J=5.3 Hz), 3.588–3.658 (2H, m), 3.901–3.971 (2H, m), 4.330 (2H, s), 6.546 (0.5H, s), 6.614 (0.5H, s), 7.250–7.380 (1H, m), 7.459–7.702 (5H, m), 7.761–7.878 (3H, m);

IR (neat) 2951, 2681, 1653, 1628, 1471, 1433, 1277, 1176, 926, 704 cm$^{-1}$;

Anal. Calcd for $C_{25}H_{27}ClN_2O_3 \cdot 1.5H_2O$: C, 64.44; H, 6.49; N, 6.01. Found: C, 64.54; H, 6.81; N, 5.97.

EXAMPLE 60

Synthesis of N,N-dimethyl-(6-trifluoroacetyl-4,5,6, 7-tetrahydrofuro[2,3-c]pyridin-2-ylmethyl)amine a) Synthesis of 6-trifluoroacetyl-4,5,6,7-tetrahydrofuro[2,3-c]pyridine To a solution of 1.020 g (6.391 mmol) of 4,5,6,7-tetrahydrofuro[2,3-c]pyridine hydrochloride and 1.55 ml (19.2 mmol) of pyridine in 50 ml of dichloromethane, a solution of trifluoroacetic anhydride in 30 ml of dichloromethane was added dropwise under ice-cooling, followed by stirring at room temperature for 30 minutes. The reaction mixture was evaporated under reduced pressure, the resulting residue was diluted with ethyl acetate and washed with dilute hydrochloric acid, after which it was dried over anhydrous magnesium sulfate; the solvent was distilled off under reduced pressure. The resulting crude product was purified by silica gel column chromatography (hexane/ethyl acetate=15/1 to 9/1) to yield the desired product.

Colorless oil Yield 1.223 g (87%)

$^1$H-NMR (CDCl$_3$, 200 MHz) δ2.601–2.700 (2H, m), 3.806 (1.4H, t, J=6.0 Hz), 3.916 (0.6H, t, J=5.6 Hz), 4.640 (0.6H, s), 4.695 (1.4H, s), 6.274–6.294 (1H, m), 7.335 (1H, d, J=2.0 Hz);

IR (neat) 1695, 1458, 1205, 1174, 1144, 1099, 897, 755, 737 cm$^{-1}$ b) Synthesis of N,N-dimethyl-(6-trifluoroacetyl-4,5,6,7-tetrahydrofuro[2,3-c]pyridin-2-ylmethyl)amine To a solution of 0.722 g (3.294 mmol) of 6-trifluoroacetyl-4,5,6,7-tetrahydrofuro[2,3-c]pyridine in 50 ml of acetic acid, 0.36 g (4.0 mmol) of 50% aqueous dimethylamine and 0.32 g (4.0 mmol) of 37% aqueous formaldehyde were added, followed by stirring at 100° C. for 1.5 hours. After the solvent was distilled off under reduced pressure, the residue was diluted with water, gently poured into ice-cooled aqueous sodium hydrogen carbonate, and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.629 g (69%)

$^1$H-NMR (CDCl$_3$, 200 MHz) δ2.268 (6H, s), 2.573–2.661 (2H, m), 3.418 (2H, s), 3.790 (1.4H, t, J=6.1 Hz), 3.900 (0.6H, t, J=5.9 Hz), 4.621 (0.6H, s), 4.674 (1.4H, s), 6.081 (1H, s);

IR (neat) 2943, 2777, 1695, 1456, 1205, 1174, 1144, 1045, 905, 754 cm$^{-1}$

EXAMPLE 61

Synthesis of N,N-dimethyl-(6-tert-butoxycarbonyl-4,5,6,7-tetrahydrofuro[2,3-c]pyridin-2-ylmethyl)amine To a solution of 0.485 g (1.756 mmol) of N,N-dimethyl-(6-trifluoroacetyl-4,5,6,7-tetrahydrofuro[2,3-c]pyridin-2-ylmethyl)amine in 10 ml of methanol, 0.49 g (3.5 mmol) of potassium carbonate was added, followed by stirring at room temperature for 1 hour. After the reaction mixture was filtered to remove insoluble substances, the solvent was distilled off under reduced pressure. The resulting residue was dissolved in 30 ml of dichloromethane; 0.38 g (1.8 mmol) of di-tert-butyl dicarbonate was added at room temperature, followed by stirring at room temperature for 0.5 hours. The solvent of the reaction mixture was distilled off under reduced pressure; the resulting crude product was purified by silica gel column chromatography (ethyl acetate to ethyl acetate/methanol=4/1) to yield the desired product.

Yellow oil Yield 0.308 g (63%)

$^1$H-NMR (CDCl$_3$, 200 MHz) δ1.477 (9H, s), 2.265 (6H, s), 3.402 (2H, s), 3.620 (2H, t, J=5.5 Hz), 4.428 (2H, s), 6.051 (1H, s);

IR (neat) 2974, 2933, 2771, 1699, 1456, 1412, 1365, 1225, 1169, 1093, 908, 768 cm$^{-1}$

EXAMPLE 62

Synthesis of 1-(2-dimethylaminomethyl-5,7-dihydro-4H-thieno[2,3-c]pyridin-6-yl)-6-phenylhexan-1-one hydrochloride a) Synthesis of 2-(3-thienyl)-1-(methylsulfinyl)-1-(methylthio)ethylene To 20 ml of methyl methylsulfinylmethyl sulfide, 1.27 g (31.8 mmol) of powdered sodium hydroxide was added, followed by stirring at 80° C. for 30 minutes. This mixture was added to 10.695 g (95.363 mmol) of 3-thiophenecarboxyaldehyde, followed by stirring at 80° C. for 3 hours. After the reaction mixture was cooled to room temperature, water was added, followed by 3 extractions with dichloromethane. The combined organic layer was dried over anhydrous magnesium sulfate; the solvent was distilled off under reduced pressure. The resulting crude product was purified by silica gel column chromatography (hexane/ethyl acetate=3/1 to 1/1) to yield the desired product.

Dark brown oil Yield 18.244 g (88%)

$^1$H-NMR (CDCl$_3$, 200 MHz) δ2.352 (3H, s), 2.753 (3H, s), 7.375 (1H, dd, J=3.0&5.2 Hz), 7.667 (1H, s), 7.787 (1H, dd, J=1.2&0.0 Hz), 7.937 (1H, dd, J=0.7&2.9 Hz);

IR (neat) 3088, 1595, 1414, 1283, 1061, 957, 784 cm$^{-1}$ b) Synthesis of methyl 3-thienylacetate 2-(3-Thienyl)-1-(methylsulfinyl)-1-(methylthio)ethylene 18.244 g (83.550 mmol) was dissolved in 100 ml of about 10% hydrogen chloride in methanol. To this solution, 5.62 g (41.8 mmol) of anhydrous copper chloride (II) was added, followed by stirring at room temperature for 10 hours. The solvent was distilled off under reduced pressure; water was added, followed by 3 extractions with dichloromethane. The combined organic layer was dried over anhydrous magnesium sulfate; the solvent was distilled off under reduced pressure. The resulting residue was purified by silica gel column chromatography (hexane/ethyl acetate=15/1 to 9/1) to yield the desired product.

Yellow oil Yield 12.111 g (93%)

$^1$H-NMR (CDCl$_3$, 200 MHz) δ3.667 (2H, s), 3.709 (3H, s), 7.041 (1H, dd, J=1.2&4.8 Hz), 7.151 (1H, d, J=2.2 Hz), 7.291 (1H, dd, J=2.9&5.1 Hz);

IR (neat) 1740, 1265, 1151, 1012, 164 cm$^{-1}$ c) Synthesis of N-[2-(3-thienyl)ethyl]phthalimide To a suspension of 3.27 g (86.2 mmol) of lithium aluminum hydride in 200 ml of tetrahydrofuran, a solution of 8.979 g (57.48 mmol) of methyl 3-thienylacetate in 50 ml of tetrahydrofuran was added dropwise under ice-cooling, followed by stirring at room temperature for 3 hours. The reaction mixture was cooled in an ice water bath; ethyl acetate was added dropwise to decompose the excess lithium aluminum hydride; subsequently, water was carefully added. The resulting white precipitate was filtered using Celite and washed with ethyl acetate. The combined filtrate was evaporated under reduced pressure. The resulting crude 2-(3-thienyl)ethanol thus obtained was used for the next reaction without purification.

To a solution of the above crude 2-(3-thienyl)ethanol and 9.61 ml (69.0 mmol) of triethylamine in 150 ml of diethyl ether, a solution of 4.89 ml (63.2 mmol) of methanesulfonyl chloride in 30 ml of diethyl ether was added dropwise under ice-cooling, followed by stirring for 0.5 hours. The reaction mixture was poured into water and extracted with ethyl acetate 3 times. The combined organic layer was dried over anhydrous magnesium sulfate; the solvent was distilled off under reduced pressure. The resulting crude 2-(3-thienyl)ethyl methanesulfonate was used for the next reaction without purification.

To a solution of the above crude 2-(3-thienyl)ethyl methanesulfonate in 400 ml of N,N-dimethylformamide, 12.8 g (69.0 mmol) of potassium phthalimide was added, followed by overnight stirring at 100° C. After cooling to room temperature, the reaction mixture was added to water with vigorous stirring. The resulting precipitate was filtered, washed with water and dried to yield the desired product.

White solid Yield 11.175 g (76%)

$^1$H-NMR (CDCl$_3$, 200 MHz) δ3.039 (2H, t, J=7.5 Hz), 3.941 (2H, t, J=7.6 Hz), 6.998–7.047 (2H, m), 7.263 (1H, dd, J=3.0&4.8 Hz), 7.671–7.754 (2H, m), 7.796–7.877 (2H, m);

IR (nujol) 1711, 1086, 997, 872, 785, 716 cm$^{-1}$;

Anal. Calcd for $C_{14}H_{11}NO_2S$: C, 65.35; H, 4.31; N, 5.44. Found: C, 65.43; H, 4.38; N, 5.71.

d) Synthesis of N-tert-butoxycarbonyl-2-(3-thienyl)ethylamine

A solution of 2.086 g (8.107 mmol) of N-[2-(3-thienyl)ethyl]phthalimide and 0.59 ml (12.2 mmol) of hydrazine monohydrate in 200 ml of ethanol was refluxed for 1 hour. After cooling to room temperature, the reaction mixture was poured into aqueous sodium hydroxide and extracted with dichloromethane 3 times. The combined organic layer was dried over anhydrous magnesium sulfate; the solvent was distilled off under reduced pressure. The resulting crude 2-(3-thienyl)ethylamine was dissolved in 50 ml of dichloromethane; a solution of 2.30 g (10.5 mmol) of di-tert-butyl dicarbonate in 10 ml of dichloromethane was added dropwise at room temperature, followed by stirring for 0.5 hours. The solvent was distilled off under reduced pressure, the resulting crude product was purified by silica gel column chromatography (hexane/ethyl acetate=15/1 to 6/1) to yield the desired product.

Colorless oil Yield 1.763 g (96%)

$^1$H-NMR (CDCl$_3$, 200 MHz) δ1.440 (9H, s), 2.827 (2H, t, J=7.0 Hz), 3.382 (2H, q, 6.5 Hz), 4.567 (1H, br s), 6.956 (1H, dd, J=1.2&5.0 Hz), 7.003–7.011 (1H, m), 7.284 (1H, dd, J=2.8&4.8 Hz);

IR (neat) 3350, 2976, 1693, 1514, 1250, 1171, 777 cm$^{-1}$ e) Synthesis of 6-tert-butoxycarbonyl-4,5,6,7-tetrahydrothieno[2,3-c]pyridine A solution of 1.753 g (7.711 mmol) of N-tert-butoxycarbonyl-2-(3-thienyl)ethylamine, 0.46 g (15.4 mmol) of powdered paraformaldehyde and 73 mg (0.39 mmol) of p-toluenesulfonic acid monohydrate in 150 ml of toluene was refluxed under dehydrating conditions for 0.5 hours in a Dean-Stark trap. The reaction mixture was cooled to room temperature and diluted with ethyl acetate, after which it was washed with aqueous sodium hydrogen carbonate; the organic layer was dried over anhydrous magnesium sulfate; the solvent was distilled off under reduced pressure. The resulting crude product was purified by silica gel column chromatography (hexane/ethyl acetate=15/1 to 9/1) to yield the desired product.

White solid Yield 1.650 g (89%)

$^1$H-NMR (CDCl$_3$, 200 MHz) δ1.483 (9H, s), 2.705 (2H, br t, J=5.8 Hz), 3.675 (2H, t, J=5.8 Hz), 4.624 (2H, br s), 6.785 (1H, d, J=5.0 Hz), 7.132 (1H, d, J=5.2 Hz);

IR (neat) 2976, 1697, 1414, 1240, 1169, 881, 704 cm$^{-1}$;

Anal. Calcd for $C_{12}H_{17}NO_2S$: C, 60.22; H, 7.16; N, 5.85. Found: C, 60.07; H, 7.03; N, 5.89.

f) Synthesis of 4,5,6,7-tetrahydrothieno[2,3-c]pyridine hydrochloride

To a solution of 1.427 g (5.962 mmol) of 6-tert-butoxycarbonyl-4,5,6,7-tetrahydrothieno[2,3-c]pyridine in 5 ml of methanol, 3 ml of concentrated hydrochloric acid was added, followed by stirring at room temperature for 1 hour. The solvent was distilled off under reduced pressure to yield the desired product.

White crystal Yield 1.025 g (98%)

$^1$H-NMR (CD$_3$OD, 200 MHz) δ3.022 (2H, tt, J=1.6&6.2 Hz), 3.507 (2H, t, J=6.3 Hz), 4.430 (2H, s), 6.915 (1H, d, J=5.0 Hz), 7.386 (1H, d, J=5.2 Hz);

IR (nujol) 2777–2416, 1157, 1090, 1036, 702 cm$^{-1}$;

Anal. Calcd for $C_7H_{10}ClNS$: C, 47.86; H, 5.74; N, 7.97. Found: C, 47.82; H, 5.63; N, 8.02.

g) Synthesis of 1-(5,7-dihydro-4H-thieno[2,3-c]pyridin-6-yl)-6-phenylhexan-1-one To a solution of 0.272 g (1.548 mmol) of 4,5,6,7-tetrahydrothieno[2,3-c]pyridine hydrochloride, 0.33 g (1.7 mmol) of 6-phenylhexanoic acid and 0.86 ml (6.2 mmol) of triethylamine in 30 ml of dichloromethane, 0.28 ml (1.9 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate= 6/1 to 3/1) to yield the desired product.

Colorless oil Yield 0.503 g (100%)

$^1$H-NMR (CDCl$_3$, 200 MHz) δ1.340–1.478 (2H, m), 1.577–1.789 (4H, m), 2.340–2.450 (2H, m), 2.573–2.786 (4H, m), 3.690 (1.2H, t, J=5.7 Hz), 3.868 (0.8H, t, J=5.8 Hz), 4.654 (0.8H, s), 4.800 (1.2H, s), 6.775–6.821 (1H, m), 7.134–7.314 (6H, m);

IR (neat) 2929, 1645, 1427, 1227, 702 cm$^{-1}$ h) Synthesis of 1-(2-dimethylaminomethyl-5,7-dihydro-4H-thieno[2,3-c]pyridin-6-yl)-6-phenylhexan-1-one To a solution of 0.503 g (1.548 mmol) of 1-(5,7-dihydro-4H-thieno[2,3-c]pyridin-6-yl)-6-phenylhexan-1-one in 20 ml of acetic acid, 0.17 g (1.9 mmol) of 50% aqueous dimethylamine and 0.15 g (1.9 mmol) of 37% aqueous formaldehyde were added, followed by stirring at 100° C. for 3 hours. Additionally, 0.5 g (5.5 mmol) of 50% aqueous dimethylamine and 0.5 g (6.2 mmol) of 37% aqueous formaldehyde were added, followed by stirring at 100° C. for 6 hours. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale yellow oil Yield 0.070 g (12%)

$^1$H-NMR (CDCl$_3$, 200 MHz) δ1.354–1.471 (2H, m), 1.586–1.757 (4H, m), 2.266 (6H, s), 2.321–2.434 (2H, m), 2.568–2.740 (4H, m), 3.553 (2H, s), 3.667 (1.2H, t, J=5.7 Hz), 3.845 (0.8H, t, J=5.9 Hz), 4.588 (0.8H, s), 4.737 (1.2H, s), 6.583 (1H, s), 7.131–7.308 (5H, m);

IR (neat) 2933, 1647, 1450, 1431, 1221, 1024, 746, 700 cm$^{-1}$ i) Synthesis of 1-(2-dimethylaminomethyl-5,7-dihydro-4H-thieno[2,3-c]pyridin-6-yl)-6-phenylhexan-1-one hydrochloride 1-(2-Dimethylaminomethyl-5,7-dihydro-4H-thieno[2,3-c]pyridin-6-yl)-6-phenylhexan-1-one 70 mg was dissolved in 2 ml of methanol; hydrogen chloride in methanol was added in excess, followed by stirring. After this mixture was concentrated, diethyl ether was added; the resulting solid was filtered and washed with diethyl ether to yield the desired product.

Pale yellow powder Yield 76 mg $^1$H-NMR (CD$_3$OD, 200 MHz) δ1.328–1.473 (2H, m), 1.559–1.704 (4H, m), 2.411–2.817 (6H, m), 2.861 (6H, s), 3.755–3.872 (2H, m), 4.479 (2H, s), 4.761 (2H, s), 7.074 (1H, s), 7.094–7.276 (5H, m);

IR (nujol) 2461, 1641, 1232, 1188, 743, 706 cm$^{-1}$;

Anal. Calcd for $C_{22}H_{31}ClN_2OS\cdot 0.6H_2O$: C, 63.24; H, 7.77; N, 6.70. Found: C, 63.06; H, 7.65; N, 6.78.

EXAMPLE 63

Synthesis of 6-(4-chlorophenyl)-1-(2-dimethylaminomethyl-5,7-dihydro-4H-furo[2,3-c]pyridin-6-yl)hexan-1-one hydrochloride a) Synthesis of 6-(4-chlorophenyl)-1-(2-dimethylaminomethyl-5,7-dihydro-4H-furo[2,3-c]pyridin-6-yl)hexan-1-one To a solution of 0.319 g (2.000 mmol) of 4,5,6,7-tetrahydrofuro[2,3-c]pyridine hydrochloride, 0.498 g (2.2 mmol) of 6-(4-chlorophenyl)hexanoic acid and 1.1 ml (8.0 mmol) of triethylamine in 30 ml of dichloromethane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 90 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.528 g (68%)

$^1$H-NMR (CDCl$_3$, 200 MHz) δ: 1.327–1.421(2H,m), 1.588–1.726(2H,m), 2.261(6H,s), 2.303–2.384(2H,m), 2.424–2.618(2H,m), 3.406(2H,d,J=2.0 Hz), 3.618(1.1H,t,J=5.6 Hz), 3.811(0.9H,t,J=5.6 Hz), 4.444(0.9H,s), 4.602(1.1H,s), 6.061(1H,d,J=3.2 Hz), 7.094(2H,d,J=8.4 Hz), 7.253(2H,d,J=8.4 Hz)

IR (neat): 2935, 2856, 2777, 1651, 1435, 1209, 1015, 802 cm$^{-1}$ b) Synthesis of 6-(4-chlorophenyl)-1-(2-dimethylaminomethyl-5,7-dihydro-4H-furo[2,3-c]pyridin-6-yl)hexan-1-one hydrochloride 6-(4-Chlorophenyl)-1-(2-dimethylaminomethyl-5,7-dihydro-4H-furo[2,3-c]pyridin-6-yl)hexan-1-one 0.528 g was dissolved in 2 ml of methanol; hydrogen chloride in ethyl acetate was added in excess, followed by stirring. This solution was concentrated and washed with diethyl ether to yield the desired product.

Brown powder Yield 0.500 g $^1$H-NMR (CD$_3$OD, 200 MHz) δ: 1.375–1.408(2H,m), 1.624–1.644(4H,m), 2.400–2.521(2H,m), 2.605(4H,t,J=7.4 Hz), 2.861(6H,s), 3.714–3.835(2H,m), 4.372(2H,s), 4.595 (2H,s), 6.643(1H,s), 7.133–7.263(4H,m)

IR (nujol): 2441, 1643, 1215, 947, 723 cm$^{-1}$;

Anal. Calcd for C$_{22}$H$_{30}$Cl$_2$N$_2$O$_2$.0.3H$_2$O: C, 61.34; H, 7.16; N, 6.50. Found: C, 61.29; H, 7.09; N, 6.44.

EXAMPLE 64

Synthesis of 1-[2-(2-oxazolin-2-yl)-5,7-dihydro-4H-furo[2,3-c]pyridin-6-yl]-6-phenylhexan-1-one hydrochloride a) Synthesis of N-benzyl-2-(3-furyl)ethylamine A solution of 8.029 g (33.281 mmol) of N-[2-(3-furyl)ethyl]phthalimide and 2.42 ml (49.9 mmol) of hydrazine monohydrate in 100 ml of ethanol was refluxed for 1 hour. After cooling to room temperature, the reaction mixture was poured into aqueous sodium hydroxide and extracted with dichloromethane 3 times. The combined organic layer was dried over anhydrous magnesium sulfate; the solvent was distilled off under reduced pressure. The resulting crude 2-(3-furyl)ethylamine was used for the next reaction without purification.

A solution of the above crude 2-(3-furyl)ethylamine and 4.24 g (39.9 mmol) of benzaldehyde in 50 ml of methanol was stirred at room temperature for 0.5 hours. The reaction mixture was cooled with ice-water; 1.89 g (49.9 mmol) of sodium borohydride was added portionwise followed by stirring at room temperature for 1 hour. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=1/1 to ethyl acetate) to yield the desired product.

Yellow oil Yield 5.619 g (84%)

$^1$H-NMR (CDCl$_3$, 200 MHz) δ: 1.557(1H,br s), 2.641 (2H,t,J=6.8 Hz), 2.834(2H,t,J=7.2 Hz), 3.801(2H,s), 6.270–6.279(1H,m), 7.206–7.334(6H,m), 7.354(1H,t,J=1.6 Hz)

IR (neat): 2920, 2819, 1497, 1454, 1024, 874, 779, 735, 698 cm$^{-1}$ b) Synthesis of 6-benzyl-4,5,6,7-tetrahydrofuro[2,3-c]pyridine To a solution of 5.603 g (27.838 mmol) of N-benzyl-2-(3-furyl)ethylamine in 50 ml of acetic acid, 2.71 g (33.4 mmol) of 37% aqueous formaldehyde was added, followed by stirring at 100° C. for 1 hour. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate=9/1) to yield the desired product.

Yellow oil Yield 4.314 g (73%)

$^1$H-NMR (CDCl$_3$, 200 MHz) δ: 2.535(2H,t,J=5.5 Hz), 2.741(2H,t,J=5.7 Hz), 3.517(2H,s), 3.721(2H,s), 6.229(1H, d,J=1.8 Hz), 7.242–7.395(6H,m)

IR (neat): 2920, 2798, 1500, 1454, 1153, 1068, 733, 700 cm$^{-1}$ c) Synthesis of methyl 6-benzyl-4,5,6,7-tetrahydrofuro[2,3-c]pyridine-2-carboxylate To a solution of 0.683 g (3.202 mmol) of 6-benzyl-4,5,6,7-tetrahydrofuro[2,3-c]pyridine in 30 ml of tetrahydrofuran, 4.0 ml (6.4 mmol) of 1.6 M n-butyl lithium in hexane was added under ice-cooling, followed by stirring for 0.5 hours. After the reaction mixture was cooled to −78° C., crushed dry ice was added; while the mixture was stirred vigorously, the mixture was allowed to warm to room temperature. After the solvent was distilled off under reduced pressure, the residue was dissolved in 50 ml of about 10% hydrogen chloride in methanol, followed by overnight stirring at room temperature. After the solvent was distilled off under reduced pressure, aqueous sodium hydrogen carbonate was added, followed by 3 extractions with dichloromethane. The combined organic layer was dried over anhydrous magnesium sulfate; the solvent was distilled off under reduced pressure. The resulting crude product was purified by silica gel column chromatography (hexane/ethyl acetate=6/1 to 3/1) to yield the desired product.

Orange oil Yield 0.290 g (33%)

$^1$H-NMR (CDCl$_3$, 200 MHz) δ: 2.559(2H,t,J=5.5 Hz), 2.757(2H,t,J=5.7 Hz), 3.564(2H,s), 3.718(2H,s), 3.859(3H, s), 7.028(1H,s), 7.261–7.371(5H,m)

IR (neat): 1726, 1539, 1315, 1178, 1092, 758, 700 cm$^{-1}$ d) Synthesis of methyl 4,5,6,7-tetrahydrofuro[2,3-c]pyridine-2-carboxylate A solution of 0.285 g (1.050 mmol) of methyl 6-benzyl-4,5,6,7-tetrahydrofuro[2,3-c]pyridine-2-carboxylate in 30 ml of methanol was hydrogenated at room temperature at atmospheric pressure over 0.2 g of 10% palladium-carbon (50% wet) overnight. After the catalyst was filtered off, the filtrate was evaporated under reduced pressure to yield the desired product.

Yellow oil Yield 0.195 g (100%)

$^1$H-NMR (CDCl$_3$, 200 MHz) δ: 2.561(2H,br s), 3.083 (2H,br s), 3.150(1H,br s), 3.878(3H,s), 3.940(2H,br s), 7.035 (1H,s)

IR (neat): 1714, 1516, 1439, 1323, 1174 cm$^{-1}$ e) Synthesis of methyl 6-(6-phenylhexanoyl)-4,5,6,7-tetrahydrofuro[2,3-c]pyridine-2-carboxylate To a solution of 95 mg (0.52 mmol) of methyl 4,5,6,7-tetrahydrofuro[2,3-c]pyridine-2-carboxylate, 0.12 g (0.63 mmol) of 6-phenylhexanoic acid and 0.15 ml (1.0 mmol) of triethylamine in 30 ml of dichloromethane, 0.10 ml (0.63 mmol) of diethyl cyanophosphonate was added dropwise under ice-cooling, followed by overnight stirring at room temperature. The reaction mixture was poured into aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (hexane/ethyl acetate= 3/1 to 2/1) to yield the desired product.

Pale yellow oil Yield 0.147 g (79%)

$^1$H-NMR (CDCl$_3$, 200 MHz) δ: 1.330–1.467(2H,m), 1.571–1.737(4H,m), 2.309–2.434(2H,m), 2.528–2.655(4H, m), 3.647(1.2H,t,J=5.6 Hz), 3.833(0.8H,t,J=5.7 Hz), 3.882 (3H,s), 4.522(0.8H,s), 4.681(1.2H,s), 7.042(1H,s), 7.129–7.316(5H,m)

IR (neat): 2931, 1724, 1651, 1539, 1435, 1311, 1209, 758, 700 cm$^{-1}$ f) Synthesis of 6-(6-phenylhexanoyl)-4,5,6,7-tetrahydrofuro[2,3-c]pyridine-2-carboxylic acid To a solution of 0.147 g (0.414 mmol) of methyl 6-(6-phenylhexanoyl)-4,5,6,7-tetrahydrofuro[2,3-c]pyridine-2-carboxylate in 10 ml of tetrahydrofuran, 1 ml of 1 N aqueous sodium hydroxide was added, followed by stirring at room temperature for 1 day. The reaction mixture was acidified with 10 ml of 1 N hydrochloric acid and extracted with diethyl ether 3 times. The combined organic layer was dried over anhydrous magnesium sulfate; the solvent was distilled off under reduced pressure to yield the desired product.

Pale yellow solid Yield 0.142 g (100%)

$^1$H-NMR (CDCl$_3$, 200 MHz) δ: 1.319–1.471(2H,m), 1.583–1.786(4H,m), 2.328–2.471(2H,m), 2.614(4H,t,J=7.2 Hz), 3.665(1.2H,t,J=5.5 Hz), 3.859(0.8H,t,J=5.5 Hz), 4.546 (0.8H,s), 4.709(1.2H,s), 7.142–7.303(6H,m), 9.116(1H,br s)

IR (neat): 2931, 1714, 1605, 1529, 1448, 1211, 1182, 912, 748, 700 cm$^{-1}$

Anal. Calcd for C$_{20}$H$_{23}$NO$_4$.0.2H$_2$O: C, 69,63; H, 6,84; N, 4.06. Found: C, 69,69; H, 6.96; N, 3.94 g) Synthesis of 1-[2-(2-oxazolin-2-yl)-5,7-dihydro-4H-furo[2,3-c]pyridin-6-yl]-6-phenylhexan-1-one To a solution of 0.884 g (2.590 mmol) of 6-(6-phenylhexanoyl)-4,5,6,7-tetrahydrofuro[2,3-c]pyridine-2-carboxylic acid, 0.16 g (2.59 mmol) of 2-aminoethanol, 1.08 ml (7.77 mmol) of triethylamine and 2.50 ml (25.9 mmol) of carbon tetrachloride in 50 ml of acetonitrile, 2.04 g (7.77 mmol) of triphenylphosphine was added under ice-cooling, followed by stirring at room temperature for 4 hours. The reaction mixture was poured into water and extracted with ethyl acetate 3 times. The combined organic layer was dried over anhydrous magnesium sulfate; the solvent was distilled off under reduced pressure. The resulting crude product was purified by silica gel flush column chromatography (ethyl acetate to ethyl acetate/methanol=20/1) to yield the desired product.

Colorless oil Yield 0.148 g (16%)

$^1$H-NMR (CDCl$_3$, 200 MHz) δ: 1.326–1.465(2H,m), 1.583–1.773(4H,m), 2.301–2.429(2H,m), 2.515–2.650(4H, m), 3.634(1.2H,t,J=5.5 Hz), 3.825(0.8H,t,J=5.7 Hz), 4.030 (2H,t,J=9.2 Hz), 4.385(2H,t,J=9.5 Hz), 4.510(0.8H,s), 4.667 (1.2H,s), 6.794(1H,s), 7.122–7.301(5H,m)

IR (neat): 2931, 2854, 1651, 1429, 1362, 1213, 1080, 702 cm$^{-1}$ h) Synthesis of 1-[2-(2-oxazolin-2-yl)-5,7-dihydro-4H-furo[2,3-c]pyridin-6-yl]-6-phenylhexan-1-one hydrochloride To a solution of 0.148 g of 1-[2-(2-oxazolin-2-yl)-5,7-dihydro-4H-furo[2,3-c]pyridin-6-yl]-6-phenylhexan-1-one in 10 ml of diethyl ether, 0.5 ml of about 10% hydrogen chloride in methanol was added, followed by stirring for 10 minutes, after which the solvent was distilled off under reduced pressure. The resulting crude product was crystallized from diethyl ether to yield the desired product.

White solid Yield 0.140 g $^1$H-NMR (CDCl$_3$, 200 MHz) δ: 1.336–1.451(2H,m), 1.555–1.734(4H,m), 2.394–2.635(6H,m), 3.620–3.828(6H, m), 4.611(2H,s), 7.005(1H,s), 7.075–7.259(5H,m)

IR (nujol): 3294, 1637, 1556, 1230, 916, 743 cm$^{-1}$

Anal. Calcd for C$_{22}$H$_{27}$ClN$_2$O$_3$.0.3H$_2$O: C, 64.71; H, 6.81; N, 6.86. Found: C, 64.79; H, 6.58; N, 6.88

EXAMPLE 65

Synthesis of N-methyl-[6-(4-benzoylbenzoyl)-4,5,6,7-tetrahydrofuro[2,3-c]pyridin-2-ylmethyl)amine hydrochloride a) Synthesis of 6-(4-benzoylbenzoyl)-4,5,6,7-tetrahydrofuro[2,3-c]pyridine-2-carbaldehyde To 30 ml of N,N-dimethylformamide, 0.20 ml (2.3 mmol) of oxalyl chloride was added at −78° C., followed by stirring at room temperature for 15 minutes. To this mixture, a solution of 0.684 g (2.064 mmol) of 6-(4-benzoylbenzoyl)-4,5,6,7-tetrahydrofuro[2,3-c]pyridine in 10 ml of N,N-dimethylformamide was added, followed by overnight stirring at room temperature. After water was added, the reaction mixture was extracted with ethyl acetate 3 times. The combined organic layer was dried over anhydrous magnesium sulfate; the solvent was distilled off under reduced pressure. The resulting crude product was purified by silica gel flush column chromatography (hexane/ethyl acetate=1/1 to 1/3) to yield the desired product.

Orange oil Yield 0.476 g (64%)

$^1$H-NMR (CDCl$_3$, 200 MHz) δ: 2.693(2H,br s), 3.676 (1.2H,br s), 4.019(0.8H,br s), 4.608(0.8H,br s), 4.867(1.2H, br s), 7.153(1H,s), 7.464–7.667(5H,m), 7.786–7.889(4H,m), 9.567(1H,s)

IR (neat): 1676, 1643, 1525, 1427, 1306, 1275, 1255, 914, 729, 704 cm$^{-1}$ b) Synthesis of N-tert-butoxycarbonyl-N-methyl-[6-(4-benzoylbenzoyl)-4,5,6,7-tetrahydrofuro[2,3-c]pyridin-2-ylmethyl]amine A solution of 0.512 g (1.425 mmol) of 6-(4-benzoylbenzoyl)-4,5,6,7-tetrahydrofuro[2,3-c]pyridine-2-carbaldehyde, 0.55 g (7.1 mmol) of 40% methylamine in methanol and 5 drops of acetic acid were dissolved in 30 ml of methanol, followed by stirring at room temperature for 0.5 hours. To this solution, 0.18 g (2.9 mmol) of sodium cyanoborohydride was added at room temperature, followed by stirring for 4.5 days. The reaction mixture was poured into aqueous sodium hydroxide and extracted with dichloromethane 3 times. The combined organic layer was dried over anhydrous magnesium sulfate; the solvent was distilled off under reduced pressure. The resulting residue was dissolved in 20 ml of dichloromethane; a solution of 0.47 g (2.1 mmol) of di-tert-butyl dicarbonate in 5 ml of dichloromethane was added. After stirring at room temperature for 1 hour, the solvent was distilled off under reduced pressure. The resulting crude product was purified by silica gel flush column chromatography (hexane/ethyl acetate=3/1 to 2/1) to yield the desired product.

Yellow foam Yield 97 mg (14%)

$^1$H-NMR (CDCl$_3$, 200 MHz) δ: 1.471(9H,br s), 2.546–2.682(4H,m), 2.823–2.883(3H,m), 3.594(1.2H,br s), 3.993(0.8H,br s), 4.343(2H,br s), 4.442(0.8H,br s), 4.761 (1.2H,br s), 6.083–6.212(1H,m), 7.462–7.671(5H,m), 7.796–7.884(4H,m)

IR (nujol): 1691, 1630, 1309, 1273, 1147, 1041, 700 cm$^{-1}$ c) Synthesis of N-methyl-[6-(4-benzoylbenzoyl)-4,5,6,7-tetrahydrofuro[2,3-c]pyridin-2-ylmethyl]amine hydrochloride N-tert-Butoxycarbonyl-N-methyl-[6-(4-benzoylbenzoyl)-4,5,6,7-tetrahydrofuro[2,3-c]pyridin-2-ylmethyl]amine 0.127 g (0.268 mmol) was dissolved in 5 ml of methanol; 1 ml of concentrated hydrochloric acid was added, followed by stirring for 30 minutes. This solution was concentrated to yield the desired product.

Brown foam Yield 0.110 g (100%)

$^1$H-NMR (CD$_3$OD, 200 MHz) δ: 2.557–2.709(5H,m), 3.650(1.4H,br s), 3.996(0.6H,br s), 4.271(2H,br s), 4.552 (0.6H,br s), 4.784(1.4H,br s), 6.601(1H,s), 7.451–7.731(5H,m), 7.775–7.892(4H,m)

IR (neat): 2962, 2765, 1651, 1626, 1441, 1277, 704 cm$^{-1}$

HRMS m/z Calcd for C$_{23}$H$_{22}$N$_2$O$_3$ 374.1632, Found: 374.1632

EXAMPLE 66

Synthesis of N-(2-methoxyethyl)-N-methyl-[6-(4-benzoylbenzoyl)-4,5,6,7-tetrahydrofuro[2,3-c]pyridin-2-ylmethyl]amine hydrochloride a) Synthesis of N-(2-methoxyethyl)-N-methyl-[6-(4-benzoylbenzoyl)-4,5,6,7-tetrahydrofuro[2,3-c]pyridin-2-ylmethyl]amine To a solution of 0.341 g (1.029 mmol) of 6-(4-benzoylbenzoyl)-4,5,6,7-tetrahydrofuro[2,3-c]pyridine in 10 ml of acetic acid, 0.18 g (1.2 mmol) of N-methyl-2-methoxyethylammonium acetate and 0.10 g (1.2 mmol) of 37% aqueous formaldehyde were added, followed by stirring at 100° C. for 1 hour. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.322 g (72%)

$^1$H-NMR (CDCl$_3$, 200 MHz) δ: 2.324(3H,br s), 2.524–2.627(4H,m), 3.359(3H,s), 3.493–3.608(5.4H,m), 3.993(0.6H,br s), 4.446(0.6H,br s), 4.770(1.4H,br s), 6.089 (1H,s), 7.462–7.664(5H,m), 7.796–7.876(4H,m)

IR (neat): 2927, 2850, 1655, 1635, 1433, 1277, 1117, 1045, 933, 704 cm$^{-1}$ b) Synthesis of N-(2-methoxyethyl)-N-methyl-[6-(4-benzoylbenzoyl)-4,5,6,7-tetrahydrofuro[2,3-c]pyridin-2-ylmethyl]amine hydrochloride N-(2-Methoxyethyl)-N-methyl-[6-(4-benzoylbenzoyl)-4,5,6,7-tetrahydrofuro[2,3-c]pyridin-2-ylmethyl]amine 0.322 g was dissolved in 2 ml of methanol; hydrogen chloride in methanol was added in excess, followed by stirring. The resulting mixture was then concentrated to yield the desired product.

Brown foam Yield 0.346 g $^1$H-NMR (CD$_3$OD, 200 MHz) δ: 2.625(2H,br s), 2.903 (3H,br s), 3.418(5H,br s), 3.649–3.760(3.4H,m), 4.010 (0.6H,br s), 4.488(2H,br s), 4.577(0.6H,br s), 4.794(1.4H,br s), 6.724(1H,s), 7.493–7.710(5H,m), 7.757–7.873(4H,m)

IR (neat): 2937, 2834, 1651, 1628, 1441, 1277, 1117, 704 cm$^{-1}$

Anal. Calcd for C$_{26}$H$_{29}$ClN$_2$O$_4$·2.0H$_2$O: C, 61.84; H, 6.59; N, 5.55. Found: C, 61.93; H, 6.44; N, 5.64

EXAMPLE 67

Synthesis of 6-(4-benzoylbenzoyl)-2-(1-pyrrolidinylmethyl)-4,5,6,7-tetrahydrofuro[2,3-c]pyridine hydrochloride a) Synthesis of 6-(4-benzoylbenzoyl)-2-(1-pyrrolidinylmethyl)-4,5,6,7-tetrahydrofuro[2,3-c]pyridine To a solution of 0.229 g (0.691 mmol) of 6-(4-benzoylbenzoyl)-4,5,6,7-tetrahydrofuro[2,3-c]pyridine in 10 ml of acetic acid, 0.09 ml (1.0 mmol) of pyrrolidine and 84 mg (1.0 mmol) of 37% aqueous formaldehyde were added, followed by stirring at 100° C. for 0.5 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.225 g (79%)

$^1$H-NMR (CDCl$_3$, 200 MHz) δ: 1.797(4H,br s), 2.552 (6H,br s), 3.610(3.2H,br s), 3.991(0.8H,br s), 4.462(0.8H,br s), 4.772(1.2H,br s), 6.089(1H,s), 7.453–7.658(5H,m), 7.788–7.783(4H,m)

IR (neat): 2964, 2791, 1651, 1632, 1429, 1277, 702 cm$^{-1}$ b) Synthesis of 6-(4-benzoylbenzoyl)-2-(1-pyrrolidinylmethyl)-4,5,6,7-tetrahydrofuro[2,3-c]pyridine hydrochloride 6-(4-Benzoylbenzoyl)-2-(1-pyrrolidinylmethyl)-4,5,6,7-tetrahydrofuro[2,3-c]pyridine 0.225 g was dissolved in 2 ml of methanol; hydrogen chloride in methanol was added in excess, followed by stirring. The resulting mixture was then concentrated to yield the desired product.

Pale brown foam Yield 0.246 g $^1$H-NMR (CD$_3$OD, 200 MHz) δ: 2.050–2.150(4H,m), 2.614(2H,br s), 3.220(2H,br s), 3.537–3.641(3.2H,m), 4.004 (0.8H,br s), 4.473(2H,br s), 4.563(0.8H,br s), 4.784(1.2H,br s), 6.655(1H,s), 7.385–7.702(5H,m), 7.765–7.878(4H,m)

IR (neat): 2949, 2594, 1651, 1628, 1441, 1277, 926, 704 cm$^{-1}$

Anal. Calcd for C$_{26}$H$_{27}$ClN$_2$O$_3$·1.0H$_2$O: C, 66.59; H, 6.23; N, 5.97. Found: C, 66.44; H, 6.50; N, 6.00

EXAMPLE 68

Synthesis of 6-(4-benzoylbenzoyl)-2-piperidinomethyl-4,5,6,7-tetrahydrofuro[2,3-c]pyridine hydrochloride a) Synthesis of 6-(4-benzoylbenzoyl)-2-piperidinomethyl-4,5,6,7-tetrahydrofuro[2,3-c]pyridine To a solution of 0.260 g (0.785 mmol) of 6-(4-benzoylbenzoyl)-4,5,6,7-tetrahydrofuro[2,3-c]pyridine in 10 ml of acetic acid, 0.12 ml (1.2 mmol) of piperidine and 96 mg (1.2 mmol) of 37% aqueous formaldehyde were added, followed by stirring at 100° C. for 1 hour. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.297 g (88%)

$^1$H-NMR (CDCl$_3$, 200 MHz) δ: 2.418–1.595(6H,m), 2.401–2.687(6H,m), 3.369–3.581(3.2H,m), 3.984(0.8H,br s), 4.453(0.8H,br s), 4.770(1.2H,br s), 6.076(1H,s), 7.453–7.660(5H,m), 7.787–7.869(4H,m)

IR (neat): 2933, 1653, 1633, 1431, 1277, 1111, 702 cm$^{-1}$ b) Synthesis of 6-(4-benzoylbenzoyl)-2-piperidinomethyl-4,5,6,7-tetrahydrofuro[2,3-c]pyridine hydrochloride 6-(4-Benzoylbenzoyl)-2-piperidinomethyl-4,5,6,7-tetrahydrofuro[2,3-c]pyridine 0.297 g was dissolved in 2 ml of methanol; hydrogen chloride in methanol was added in excess, followed by stirring. This was concentrated to yield the desired product.

Pale brown foam Yield 0.321 g $^1$H-NMR (CD$_3$OD, 200 MHz) δ: 1.500–2.007(6H,m), 2.625(2H,br s), 2.931–3.050(2H,m), 3.456–3.643(3.2H,m), 4.000(0.8H,br s), 4.387(2H,br s), 4.577(0.8H,br s), 4.786 (1.2H,br s), 6.697(1H,s), 7.244–7.697(5H,m), 7.754–7.867 (4H,m)

IR (neat): 2945, 2542, 1651, 1626, 1433, 1275, 933, 704 cm$^{-1}$

Anal. Calcd for C$_{27}$H$_{29}$ClN$_2$O$_3$·1.5H$_2$O: C, 65.91; H, 6.56; N, 5.69. Found: C, 65.68; H, 6.86; N, 5.97

EXAMPLE 69

Synthesis of N-(2-hydroxyethyl)-6-(4-benzoylbenzoyl)-4,5,6,7-tetrahydrofuro[2,3-c] pyridine-2-carboxamide a) Synthesis of methyl 6-(4-benzoylbenzoyl)-4,5,6,7-tetrahydrofuro[2,3-c]pyridine-2-carboxylate To a solution of 72 mg (0.40 mmol) of methyl 4,5,6,7-tetrahydrofuro[2,3-c]pyridin-2-carboxylate, 0.11 g (0.48 mmol) of 4-benzoylbenzoic acid and 0.11 ml (0.79 mmol) of triethylamine in 30 ml of dichloromethane, 0.07 ml (0.48 mmol) of diethyl cyanophosphonate was added dropwise at room temperature, followed by overnight stirring. After the reaction mixture was evaporated under reduced pressure, the resulting crude product was purified by silica gel column chromatography (hexane/ethyl acetate=3/1 to 1/1) to yield the desired product.

Colorless oil Yield 126 mg (82%)

$^1$H-NMR (CDCl$_3$, 200 MHz) δ: 2.643(2H,br s), 3.641 (1.4H,br s), 3.889(3H,s), 4.018(0.6H,br s), 4.565(0.6H,br s), 4.847(1.4H,br s), 7.079(1H,s), 7.469–7.668(5H,m), 7.796–7.889(4H,m)

IR (neat): 3007, 2949, 1726, 1645, 1539, 1433, 1313, 1275, 1203, 1149, 912, 758, 704 cm$^{-1}$ b) Synthesis of 6-(4-benzoylbenzoyl)-4,5,6,7-tetrahydrofuro[2,3-c]pyridine-2-carboxylic acid To a solution of 126 mg (0.324 mmol) of methyl 6-(4-benzoylbenzoyl)-4,5,6,7-tetrahydrofuro[2,3-c]pyridine-2-carboxylate in 10 ml of tetrahydrofuran, 1 ml of 2 N aqueous sodium hydroxide was added, followed by stirring at room temperature for 1 day. The reaction mixture was acidified with 10 ml of 1 N hydrochloric acid and extracted with diethyl ether 3 times. The combined organic layer was dried over anhydrous magnesium sulfate; the solvent was distilled off under reduced pressure. The resulting crude product was purified by silica gel column chromatography (ethyl acetate/methanol=4/1 to chloroform/methanol=1/1) to yield the desired product.

White solid Yield 90 mg (74%)

$^1$H-NMR (CDCl$_3$-CD$_3$OD 200 MHz) δ: 2.601(2H,br s), 3.317–3.682(1.2H,m), 4.004(0.8H,br s), 4.555(0.8H,br s), 4.799(1.2H,br s), 6.902(1H,s), 7.499–7.895(9H,m)

IR (nujol): 1643, 1620, 1597, 1537, 1414, 1275, 702 cm$^{-1}$ c) Synthesis of N-(2-hydroxyethyl)-6-(4-benzoylbenzoyl)-4,5,6,7-tetrahydrofuro[2,3-c]pyridine-2-carboxamide To a solution of 0.545 g (1.452 mmol) of 6-(4-benzoylbenzoyl)-4,5,6,7-tetrahydrofuro[2,3-c]pyridine-2-carboxylic acid, 98 mg (1.6 mmol) of 2-aminoethanol, 0.61 ml (4.4 mmol) of triethylamine and 1.40 ml (14.5 mmol) of carbon tetrachloride in 20 ml of acetonitrile, 1.14 g (4.36 mmol) of triphenylphosphine was added under ice-cooling, followed by stirring at room temperature for 4 hours. The reaction mixture was poured into aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=9/1); the resulting solid was washed with diethyl ether to yield the desired product.

White solid Yield 0.056 g (9%)

$^1$H-NMR (CDCl$_3$, 200 MHz) δ: 2.610(3H,br s), 3.596 (3.2H,br s), 3.786(2H,br s), 4.002(0.8H,br s), 4.490(0.8H,br s), 4.766(1.2H,br s), 6.780(1H,br s), 6.999(1H,s), 7.470–7.675(5H,m), 7.787–7.885(4H,m)

IR (nujol): 3307, 1657, 1570, 1313, 1286, 902, 704 cm$^{-1}$

Anal. Calcd for C$_{24}$H$_{22}$N$_2$O$_5$: C, 68.89; H, 5.30; N, 6.69. Found: C, 68.50; H, 5.19; N, 6.78

EXAMPLE 70

Synthesis of N,N-dimethyl-[6-[4-(4-methoxybenzoyl)benzoyl]-4,5,6,7-tetrahydrofuro[2,3-c]pyridin-2-ylmethyl]amine hydrochloride a) Synthesis of 6-[4-(4-methoxybenzoyl)benzoyl]-4,5,6,7-tetrahydrofuro[2,3-c]pyridine To a solution of 0.160 g (1.000 mmol) of 4,5,6,7-tetrahydrofuro[2,3-c]pyridine hydrochloride, 0.308 g (1.2 mmol) of 4-(4-methoxybenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times, The combined organic layer was washed with water and dried over anhydrous sodium sulfate; the solvent was distilled off under reduced pressure. The resulting crude product was purified by silica gel column chromatography (hexane/ethyl acetate/dichloromethane=3/1/1). The resulting purified product was washed with diethyl ether to yield the desired product.

White crystal Yield 0.297 g (82%)

$^1$H-NMR (CDCl$_3$, 200 MHz) δ: 2.610(2H,br s), 3.600–4.900(2H,m), 3.905(3H,s), 4.500–4.731(2H,m), 6.280(1H,d,J=1.8 Hz), 6.959–7.032(2H,m), 7.258–7.314 (3H,m), 7.493–7.561(2H,m), 8.122–8.195(2H,m)

IR (KBr): 2945, 2962, 1730, 1628, 1417, 1255, 1215, 1161, 1070, 893, 764 cm$^{-1}$ b) Synthesis of N,N-dimethyl-[6-[4-(4-methoxybenzoyl) benzoyl]-4,5,6,7-tetrahydrofuro[2,3-c]pyridin-2-ylmethyl] amine To a solution of 0.280 g (0.775 mmol) of 6-[4-(4-methoxybenzoyl)benzoyl]-4,5,6,7-tetrahydrofuro[2,3-c] pyridine in 10 ml of acetic acid, 0.105 ml (1.16 mmol) of 50% aqueous dimethylamine and 0.094 ml (1.16 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1) to yield the desired product.

Brown oil Yield 0.200 g (62%)

$^1$H-NMR (CDCl$_3$, 200 MHz) δ: 2.282(6H,s), 2.273(6H,s), 2.581(2H,br s), 3.425(2H,s), 3.600–3.900(2H,m), 3.909(3H, s), 4.500–4.718(2H,m), 6.092(1H,s), 7.002(2H,d,J=9.0 Hz), 7.282(2H,d,J=8.8 Hz), 7.527(2H,d,J=8.8 Hz), 8.166(2H,d, J=9.0 Hz)

IR (neat): 2939, 2777, 1732, 1605, 1425, 1257, 1165, 1066, 762 cm$^{-1}$ c) Synthesis of N,N-dimethyl-[6-[4-(4-methoxybenzoyl) benzoyl]-4,5,6,7-tetrahydrofuro[2,3-c]pyridin-2-ylmethyl] amine hydrochloride N,N-Dimethyl-[6-[4-(4-methoxybenzoyl)benzoyl]-4,5,6, 7-tetrahydrofuro[2,3-c]pyridin-2-ylmethyl]amine 0.200 g was dissolved in 2 ml of methanol; hydrogen chloride in ethyl acetate was added in excess, followed by stirring. This was concentrated; the resulting solid was washed with diethyl ether to yield the desired product.

Pale brown solid Yield 0.213 g $^1$H-NMR (CD$_3$OD, 200 MHz) δ: 2.654(2H,br s), 2.868 (6H,s), 3.699–4.000(2H,m), 3.908(3H,s), 4.379(2H,s), 4.600–4.762(2H,m), 6.670(1H,s), 7.081(2H,d,J=8.8 Hz), 7.356(2H,d,J=8.8 Hz), 7.573(2H,d,J=8.4 Hz), 8.143(2H,d, J=8.8 Hz)

IR (nujol): 2677, 1722, 1628, 1261, 1167, 1072, 756 cm$^{-1}$

Anal. Calcd for C$_{25}$H$_{27}$ClN$_2$O$_4$.2.0H$_2$O: C, 61.16; H, 6.36; N, 5.71. Found: C, 60.93; H, 6.00; N, 5.68

EXAMPLE 71

Synthesis of N,N-dimethyl-[5-[4-(4-methoxybenzoyl)benzoyl]-4,5,6,7-tetrahydrofuro[3, 2-c]pyridin-2-ylmethyl]amine hydrochloride a) Synthesis of 5-[4-(4-methoxybenzoyl)benzoyl]-4,5,6,7-tetrahydrofuro[3,2-c]pyridine To a solution of 0.160 g (1.000 mmol) of 4,5,6,7-tetrahydrofuro[3,2-c]pyridine hydrochloride, 0.308 g (1.2 mmol) of 4-(4-methoxybenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous magnesium sulfate; the solvent was distilled off under reduced pressure. The resulting crude product was purified by silica gel column chromatography (hexane/ethyl acetate=2/1) to yield the desired product.

Colorless oil Yield 0.360 g (100%)

$^1$H-NMR (CDCl$_3$, 200 MHz) δ: 2.807(2H,br s), 3.712–4.105(2H,m), 3.908(3H,s), 4.441–4.613(2H,m), 6.100–6.300(1H,m), 6.966–7.039(2H,m), 7.249–7.316(3H, m), 7.495–7.563(2H,m), 8.129–8.202(2H,m)

IR (neat): 3000, 2987, 2842, 1730, 1605, 1510, 1259, 1203, 1165, 1066, 760, cm$^{-1}$ b) Synthesis of N,N-dimethyl-[5-[4-(4-methoxybenzoyl) benzoyl]-4,5,6,7-tetrahydrofuro[3,2-c]pyridin-2-ylmethyl] amine To a solution of 0.350 g (0.968 mmol) of 5-[4-(4-methoxybenzoyl)benzoyl]-4,5,6,7-tetrahydrofuro[3,2-c] pyridine in 10 ml of acetic acid, 0.131 ml (1.45 mmol) of 50% aqueous dimethylamine and 0.118 ml (1.45 mmol) of 37% aqueous formaldehyde were added, followed by stirring at 100° C. for 90 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1 to 25/1). This was washed with diethyl ether to yield the desired product.

White crystal Yield 0.252 g (62%)

$^1$H-NMR (CDCl$_3$, 200 MHz) δ: 2.267(6H,s), 2.788(2H,br s), 3.408(2H,s), 3.644–4.003(2H,m), 3.906(3H,s), 4.370–4.582(2H,m), 5.900–6.100(1H,m), 6.997(2H,d,J=9.0 Hz), 7.275(2H,d,J=8.4 Hz), 7.520(2H,d,J=8.6 Hz), 8.159 (2H,d,J=9.0 Hz)

IR (KBr): 2931, 2777, 1726, 1624, 1427, 1265, 1203, 1165, 1068, 761 cm$^{-1}$ c) Synthesis of N,N-dimethyl-[5-[4-(4-methoxybenzoyl) benzoyl]-4,5,6,7-tetrahydrofuro[3,2-c]pyridin-2-ylmethyl] amine hydrochloride N,N-Dimethyl-(5-[4-(4-methoxybenzoyl)benzoyl]-4,5,6, 7-tetrahydrofuro[3,2-c]pyridin-2-ylmethyl]amine 0.252 g was dissolved in 2 ml of methanol; hydrogen chloride in ethyl acetate was added in excess, followed by stirring. This mixture was then concentrated; the resulting solid was washed with diethyl ether to yield the desired product.

White crystal Yield 0.262 g $^1$H-NMR (CD$_3$OD, 200 MHz) δ: 2.867(8H,br s), 3.750–4.100(2H,m), 3.910(3H,s), 4.370(2H,s), 4.450–4.650 (2H,m), 6.500–6.700(1H,m), 7.022(2H,d,J=9.0 Hz), 7.351 (2H,d,J=8.6 Hz), 7.571(2H,d,J=8.8 Hz), 8.135(2H,d,J=9.0 Hz)

IR (nujol): 2468, 1736, 1624, 1255, 1168, 1066, 1020, 760 cm$^{-1}$

Anal. Calcd for C$_{25}$H$_{27}$ClN$_2$O$_4$.1.3H$_2$O: C, 62.77; H, 6.24; N, 5.86. Found: C, 62.58; H, 5.84; N, 5.83

EXAMPLE 72

Synthesis of N,N-dimethyl-[6-[4-(2-methoxybenzoyl)benzoyl]-4,5,6,7-tetrahydrofuro[2, 3-c]pyridin-2-ylmethyl]amine hydrochloride a) Synthesis of 6-[4-(2-methoxybenzoyl)benzoyl]-4,5,6,7-tetrahydrofuro[2,3-c]pyridine To a solution of 0.160 g (1.000 mmol) of 4,5,6,7-tetrahydrofuro[2,3-c]pyridine hydrochloride, 0.308 g (1.2 mmol) of 4-(2-methoxybenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1) to yield the desired product.

Colorless oil Yield 0.333 g (92%)

$^1$H-NMR (CDCl$_3$, 200 MHz) δ: 2.614(2H,br s), 3.600–3.800(2H,m), 4.500–4,728(2H,m), 6.285(1H,d,J=1.8 Hz), 7.032–7.107(2H,m), 7.266–7.326(2H,m), 7.506–7.620 (3H,m), 8.036(1H,dd,J=7.8&1.9 Hz)

IR (neat): 2933, 2845, 1745, 1628, 1433, 1236, 1200, 1036, 891, 758 cm$^{-1}$ b) Synthesis of N,N-dimethyl-[6-[4-(2-methoxybenzoyl)benzoyl]-4,5,6,7-tetrahydrofuro[2,3-c]pyridin-2-ylmethyl]amine To a solution of 0.320 g (0.885 mmol) of 6-[4-(2-methoxybenzoyl)benzoyl]-4,5,6,7-tetrahydrofuro[2,3-c]pyridine in 10 ml of acetic acid, 0.120 ml (1.33 mmol) of 50% aqueous dimethylamine and 0.108 ml (1.33 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1) to yield the desired product.

Brown oil Yield 0.215 g (58%)

$^1$H-NMR (CDCl$_3$, 200 MHz) δ: 2.277(6H,s), 2.576(2H,br s), 3.431(2H,s), 3.600–3.800(2H,m), 3.953(3H,s), 4.400–4.800(2H,m), 6.095(1H,s), 7.029–7.100(2H,m), 7.266–7.330(2H,m), 7.485–7.616(3H,m), 8.033(1H,dd,J=7.8&1.8 Hz)

IR (neat): 1745, 1633, 1435, 1236, 1198, 1039 cm$^{-1}$ c) Synthesis of N,N-dimethyl-[6-[4-(2-methoxybenzoyl)benzoyl]-4,5,6,7-tetrahydrofuro[2,3-c]pyridin-2-ylmethyl]amine hydrochloride N,N-Dimethyl-[6-[4-(2-methoxybenzoyl)benzoyl]-4,5,6,7-tetrahydrofuro[2,3-c]pyridin-2-ylmethyl]amine 0.215 g was dissolved in 2 ml of methanol; hydrogen chloride in ethyl acetate was added in excess, followed by stirring. This mixture was then concentrated; the resulting solid was washed with diethyl ether to yield the desired product.

Pale brown solid Yield 0.156 g $^1$H-NMR (CD$_3$OD, 200 MHz) δ: 2.661(2H,br s), 2.873(6H,s), 3.600–3.900(2H,m), 3.940(3H,s), 4.384(2H,s), 4.600–4.800(2H,m), 6.676(1H,s), 7.100(1H,td,J=7.6&1.0 Hz), 7.211(1H,d,J=7.8 Hz), 7.363(2H,d,J=8.8 Hz), 7.550–7.683(3H,m), 7.999(1H,dd,J=1.9&7.7 Hz)

IR (nujol): 2675, 1741, 1628, 1238, 1200, 1038, 758 cm$^{-1}$

Anal. Calcd for C$_{25}$H$_{27}$ClN$_2$O$_4$.2.0H$_2$O: C, 61.16; H, 6.36; N, 5.71. Found: C, 61.05; H, 6.41; N, 5.51

EXAMPLE 73

Synthesis of N,N-dimethyl-[5-[4-(2-methoxybenzoyl)benzoyl]-4,5,6,7-tetrahydrofuro[3,2-c]pyridin-2-ylmethyl]amine hydrochloride a) Synthesis of 5-[4-(2-methoxybenzoyl)benzoyl]-4,5,6,7-tetrahydrofuro[3,2-c]pyridine To a solution of 0.160 g (1.000 mmol) of 4,5,6,7-tetrahydrofuro[3,2-c]pyridine hydrochloride, 0.308 g (1.2 mmol) of 4-(2-methoxybenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1) to yield the desired product.

Colorless oil Yield 0.240 g (67%)

$^1$H-NMR (CDCl$_3$, 200 MHz) δ: 2.798(2H,br s), 3.700–4.200(2H,m), 3.952(3H,s), 4.400–4.700(2H,m), 6.150–6.300(1H,m), 7.024–7.101(2H,m), 7.264–7.310(2H,m), 7.487–7.617(3H,m), 8.030(1H,dd,J=7.8&1.7 Hz)

IR (neat): 2918, 2845, 1745, 1628, 1433, 1238, 1200, 1036, 756 cm$^{-1}$ b) Synthesis of N,N-dimethyl-[5-[4-(2-methoxybenzoyl)benzoyl]-4,5,6,7-tetrahydrofuro[3,2-c]pyridin-2-ylmethyl]amine To a solution of 0.230 g (0.636 mmol) of 5-[4-(2-methoxybenzoyl)benzoyl]-4,5,6,7-tetrahydrofuro[3,2-c]pyridine in 10 ml of acetic acid, 0.086 ml (0.95 mmol) of 50% aqueous dimethylamine and 0.077 ml (0.95 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1) to yield the desired product.

Brown oil Yield 0.187 g (71%)

$^1$H-NMR (CDCl$_3$, 200 MHz) δ: 2.270(6H,s), 2.780(2H,br s), 3.412(2H,s), 3.600–4.050(2H,m), 3.953(3H,s), 4.350–4.594(2H,m), 5.900–6.100(1H,m), 7.032–7.102(2H,m), 7.293(2H,d,J=9.8 Hz), 7.486–7.619(3H,m), 8.034(1H,dd,J=8.0&1.9 Hz)

IR (neat): 2939, 2775, 1747, 1633, 1435, 1286, 1200, 1165, 1036, 756 cm$^{-1}$ c) Synthesis of N,N-dimethyl-[5-[4-(2-methoxybenzoyl)benzoyl]-4,5,6,7-tetrahydrofuro(3,2-c]pyridin-2-ylmethyl]amine hydrochloride N,N-Dimethyl-[5-[4-(2-methoxybenzoyl)benzoyl]-4,5,6,7-tetrahydrofuro[3,2-c]pyridin-2-ylmethyl]amine 0.187 g was dissolved in 2 ml of methanol; hydrogen chloride in ethyl acetate was added in excess, followed by stirring. This mixture was then concentrated to yield the desired product.

Pale yellow foam Yield 0.206 g $^1$H-NMR (CD$_3$OD, 200 MHz) δ: 2.860(8H,d,J=1.8 Hz), 3.800–4.200(2H,m), 3.933(3H,s), 4.353(2H,s), 4.450–4.647(2H,s), 6.500–6.700(1H,m), 6.835–7.222(2H,m), 7.346(2H,d,J=8.8 Hz), 7.535–7.673(3H,m), 7.987(1H,dd,J=1.8&7.8 Hz)

IR (nujol): 2671, 1743, 1606, 1242, 1200, 1038, 760 cm$^{-1}$

Anal. Calcd for C$_{25}$H$_{27}$ClN$_2$O$_4$.2.0H$_2$O: C, 61.16; H, 6.36; N, 5.71. Found: C, 60.89; H, 6.52; N, 5.54

EXAMPLE 74

Synthesis of N,N-dimethyl-[6-[4-(2-methylbenzoyl)benzoyl]-4,5,6,7-tetrahydrofuro[2,3-c]pyridin-2-ylmethyl]amine hydrochloride a) Synthesis of 6-[4-(2-methylbenzoyl)benzoyl]-4,5,6,7-tetrahydrofuro[2,3-c]pyridine To a solution of 0.160 g (1.000 mmol) of 4,5,6,7-tetrahydrofuro[2,3-c]pyridine hydrochloride, 0.288 g (1.2 mmol) of 4-(2-methylbenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. The reaction mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate=3/1) to yield the desired product.

Colorless oil Yield 0.257 g (75%)

$^1$H-NMR (CDCl$_3$, 200 MHz) δ: 2.357(3H,s), 2.529–2.683(2H,m), 3.572(1.2H,br s), 4.000(0.8H,br s), 4.432(0.8H,br s), 4.770(1.2H,br s), 6.277(1H,d,J=2.0 Hz), 7.258–7.538 (6H,m), 7.856(2H,d,J=8.2 Hz)

IR (neat): 2926, 2854, 1713, 1630, 1481, 1265, 1092, 930, 735 cm$^{-1}$ b) Synthesis of N,N-dimethyl-[6-[4-(2-methylbenzoyl) benzoyl]-4,5,6,7-tetrahydrofuro[2,3-c]pyridin-2-ylmethyl] amine To a solution of 0.250 g (0.724 mmol) of 6-[4-(2-methylbenzoyl)benzoyl]-4,5,6,7-tetrahydrofuro[2,3-c] pyridine in 10 ml of acetic acid, 0.098 ml (1.09 mmol) of 50% aqueous dimethylamine and 0.088 ml (1.09 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous magnesium sulfate; the solvent was distilled off under reduced pressure. The resulting crude product was purified by silica gel column chromatography (ethyl acetate/methanol=5/1) to yield the desired product.

Yellow oil Yield 0.192 g (66%)

$^1$H-NMR (CDCl$_3$, 200 MHz) δ: 2.273(6H,s), 2.357(3H,s), 2.506–2.700(2H,m), 3.351–3.441(2H,m), 3.556(1.2H,br s), 3.970(0.8H,br s), 4.400(0.8H,br s), 4.755(1.2H,br s), 6.084 (1H,s), 7.260–7.529(6H,m), 7.850(2H,d,J=8.0 Hz)

IR (neat): 2933, 2773, 1632, 1431, 1265, 1041, 928, 735 cm$^{-1}$ c) Synthesis of N,N-dimethyl-[6-[4-(2-methylbenzoyl) benzoyl]-4,5,6,7-tetrahydrofuro[2,3-c]pyridin-2-ylmethyl] amine hydrochloride N,N-Dimethyl-[6-[4-(2-methylbenzoyl)benzoyl]-4,5,6,7-tetrahydrofuro[2,3-c]pyridin-2-ylmethyl]amine 0.192 g was dissolved in 2 ml of methanol; hydrogen chloride in ethyl acetate was added in excess, followed by stirring. This was concentrated; the resulting solid was washed with diethyl ether to yield the desired product.

Brown powder Yield 0.195 g $^1$H-NMR (CD$_3$OD, 200 MHz) δ: 2.317(3H,s), 2.619–2.645(2H,m), 2.879(6H,br s), 3.600–3.700(1.4H,m), 3.950–4.050(0.6H,m), 4.350–4.450(2H,m), 4.788(1.4H,br s), 6.667(1H,s), 7.310–7.468(4H,m), 7.594(2H,d,J=8.0 Hz), 7.871(2H,d,J=8.0 Hz)

IR (nujol): 2661, 1622, 1265, 1163, 930, 735 cm$^{-1}$

Anal. Calcd for C$_{25}$H$_{27}$ClN$_2$O$_3$.1.0H$_2$O: C, 65.71; H, 6.40; N, 6.13 Found: C, 65.59; H, 6.54; N, 5.99

EXAMPLE 75

Synthesis of N,N-dimethyl-[6-[4-(4-fluorobenzoyl) benzoyl]-4,5,6,7-tetrahydrofuro[2,3-c]pyridin-2-ylmethyl]amine hydrochloride a) Synthesis of N,N-dimethyl-[6-(4-(4-fluorobenzoyl) benzoyl]-4,5,6,7-tetrahydrofuro[2,3-c]pyridin-2-ylmethyl] amine To a solution of 0.160 g (1.000 mmol) of 4,5,6,7-tetrahydrofuro[2,3-c]pyridine hydrochloride, 0.269 g (1.1 mmol) of 4-(4-fluorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous solution of sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.114 g (28%)

$^1$H-NMR (CDCl$_3$, 200 MHz) δ: 2.284(6H,br s), 2.517–2.663(2H,m), 3.372–3.458(2H,m), 3.581(1.2H,br s), 4.000(0.8H,br s), 4.446(0.8H,br s), 4.777(1.2H,br s), 6.100 (1H,s), 7.189(2H,t,J=8.7 Hz), 7.557(2H,d,J=7.8 Hz), 7.805–7.902(4H,m)

IR (neat): 2939, 2856, 2775, 1652, 1633, 1433, 1275, 1230, 930, 735 cm$^{-1}$ b) Synthesis of N,N-dimethyl-[6-[4-(4-fluorobenzoyl) benzoyl]-4,5,6,7-tetrahydrofuro[2,3-c]pyridin-2-ylmethyl] amine hydrochloride N,N-Dimethyl-[6-[4-(4-fluorobenzoyl)benzoyl]-4,5,6,7-tetrahydrofuro[2,3-c]pyridin-2-ylmethyl]amine 0.114 g was dissolved in 2 ml of methanol; hydrogen chloride in ethyl acetate was added in excess, followed by stirring. This was concentrated; the resulting solid was washed with diethyl ether to yield the desired product.

Brown solid Yield 0.101 g $^1$H-NMR (CD$_3$OD, 200 MHz) δ: 2.624–2.661(2H,m), 2.886(6H,s), 3.635–3.671(1.2H,m), 4.000–4.050(0.8H,m), 4.370–4.401(2H,m), 4.500–4.600(0.8H,m), 4.750–4.804 (1.2H,m), 6.678(1H,s), 7.295(2H,t,J=8.8 Hz), 7.631(2H,d, J=8.6 Hz), 7.859–7.943(4H,m)

IR (nujol): 2472, 1649, 1234, 1112, 933, 860, 739 cm$^{-1}$

Anal. Calcd for C$_{24}$H$_{24}$ClFN$_2$O$_3$.1.0H$_2$O: C, 62,54; H, 5.69; N, 6.08. Found: C, 62.61; H, 5.42; N, 6.00

EXAMPLE 76

Synthesis of N,N-dimethyl-[5-[4-(4-fluorobenzoyl) benzoyl]-4,5,6,7-tetrahydrofuro[3,2-c]pyridin-2-ylmethyl]amine hydrochloride a) Synthesis of N,N-dimethyl-[5-[4-(4-fluorobenzoyl) benzoyl]-4,5,6,7-tetrahydrofuro[3,2-c]pyridin-2-ylmethyl] amine To a solution of 0.160 g (1.000 mmol) of 4,5,6,7-tetrahydrofuro[3,2-c]pyridine hydrochloride, 0.269 g (1.1 mmol) of 4-(4-fluorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1). The resulting purified product was recrystallized from ethyl acetate-hexane to yield the desired product.

Pale yellow crystal Yield 0.116 g (28%)

$^1$H-NMR (CDCl$_3$, 200 MHz) δ: 2.272(6H,br s), 2.726–2.867(2H,m), 3.422(2H,s), 3.655(1H,br s), 4.080(1H, br s), 4.303(1H,br s), 4.655(1H,br s), 5.921(0.5H,br s), 6.124(0.5H,br s), 7.141–7.267(2H,m), 7.556(2H,d,J=8.2 Hz), 7.806–7.897(4H,m)

IR (KBr): 2938, 2860, 2783, 1649, 1599, 1431, 1279, 1240, 1111, 851, 739 cm$^{-1}$ b) Synthesis of N,N-dimethyl-[5-[4-(4-fluorobenzoyl)benzoyl]-4,5,6,7-tetrahydrofuro[3,2-c]pyridin-2-ylmethyl]amine hydrochloride N,N-Dimethyl-[5-[4-(4-fluorobenzoyl)benzoyl]-4,5,6,7-tetrahydrofuro[3,2-c]pyridin-2-ylmethyl]amine 0.116 g was dissolved in 2 ml of methanol; hydrogen chloride in ethyl acetate was added in excess, followed by stirring. This mixture was then concentrated; the resulting solid was washed with diethyl ether to yield the desired product.

Brown solid Yield 0.125 g $^1$H-NMR (CD$_3$OD, 200 MHz) δ: 2.871(8H,br s), 3.712–3.783(1H,m), 4.078–4.139(1H,m), 4.324–4.454(3H, m), 4.652–4.718(1H,m), 6.514(0.5H,br s), 6.710(0.5H,br s), 7.289(2H,t,J=8.8 Hz), 7.619(2H,d,J=8.0 Hz), 7.848–7.936 (4H,m)

IR (nujol): 2661, 1625, 1302, 1236, 1111, 931, 858, 739 cm$^{-1}$

Anal. Calcd for C$_{24}$H$_{24}$ClFN$_2$O$_3$.1.0H$_2$O: C, 62.54; H, 5.69; N, 6.08. Found: C, 62.37; H, 5.86; N, 6.05

EXAMPLE 77

Synthesis of N,N-diethyl-[6-[4-(4-chlorobenzoyl)benzoyl]-4,5,6,7-tetrahydrofuro[2,3-c]pyridin-2-ylmethyl]amine hydrochloride a) Synthesis of N,N-diethyl-[6-[4-(4-chlorobenzoyl)benzoyl]-4,5,6,7-tetrahydrofuro[2,3-c]pyridin-2-ylmethyl]amine To a solution of 1.647 g (4.502 mmol) of 6-[4-(4-chlorobenzoyl)benzoyl]-4,5,6,7-tetrahydrofuro[2,3-c]pyridine in 30 ml of acetic acid, 0.56 ml (5.40 mmol) of diethylamine and 0.44 g (5.40 mmol) of 37% aqueous formaldehyde were added, followed by stirring at 100° C. for 2 hours. After the solvent was distilled off under reduced pressure, the residual solution was alkalified with aqueous sodium hydroxide and extracted with dichloromethane 3 times. The combined organic layer was dried over anhydrous magnesium sulfate; the solvent was distilled off under reduced pressure. The resulting crude product was purified by silica gel column chromatography (ethyl acetate to ethyl acetate/methanol=9/1) to yield the desired product.

Orange oil Yield 1.047 g (52%)

$^1$H-NMR (CDCl$_3$, 200 MHz) δ: 1.083(6H,t,J=6.6 Hz), 2.535–2.672(6H,m), 3.546–3.629(3.2H,m), 4.002(0.8H,br s), 4.442(0.8H,br s), 4.770(1.2H,br s), 6.070(1H,s), 7.487 (2H,d,J=8.4 Hz), 7.558(2H,d,J=8.2 Hz), 7.773(2H,d,J=8.4 Hz), 7.825(2H,d,J=8.0 Hz)

IR (neat): 2969, 1659, 1633, 1431, 1277, 1090, 908, 743 cm$^{-1}$ b) Synthesis of N,N-diethyl-[6-[4-(4-chlorobenzoyl)benzoyl]-4,5,6,7-tetrahydrofuro[2,3-c]pyridin-2-ylmethyl]amine hydrochloride N,N-Diethyl-[6-[4-(4-chlorobenzoyl)benzoyl]-4,5,6,7-tetrahydrofuro[2,3-c]pyridin-2-ylmethyl]amine 1.047 g was dissolved in 2 ml of methanol; hydrogen chloride in methanol was added in excess, followed by stirring. This was concentrated to yield the desired product.

Brown foam Yield 1.092 g $^1$H-NMR (CD$_3$OD, 200 MHz) δ: 1.376(6H,br s), 2.627 (2H,br s), 3.204(4H,br s), 3.654(1.4H,br s), 3.988(0.6H,br s), 4.440(2H,br s), 4.554(0.6H,br s), 4.735(1.4H,br s), 6.673 (0.3H,s), 6.702(0.7H,s), 7.294–7.646(6H,m), 7.792–7.898 (2H,m)

IR (neat): 2944, 2646, 1651, 1628, 1434, 1277, 1113, 930, 741 cm$^{-1}$

Anal. Calcd for C$_{26}$H$_{28}$Cl$_2$N$_2$O$_3$.1.1H$_2$O: C, 61.57; H, 6.00; N, 5.22. Found: C, 61.95; H, 6.39; N, 5.58

EXAMPLE 78

Synthesis of N,N-dimethyl-[6-[4-(3-chlorobenzoyl)benzoyl]-4,5,6,7-tetrahydrofuro[2,3-c]pyridin-2-ylmethyl]amine hydrochloride a) Synthesis of 6-[4-(3-chlorobenzoyl)benzoyl]-4,5,6,7-tetrahydrofuro[2,3-c]pyridine To a solution of 0.114 g (0.720 mmol) of 4,5,6,7-tetrahydrofuro[2,3-c]pyridine hydrochloride, 0.188 g (0.7 mmol) of 4-(3-chlorobenzoyl)benzoic acid and 0.40 ml (2.9 mmol) of triethylamine in 30 ml of dichloromethane, 0.18 g (1.1 mmol) of diethyl cyanophosphonate was added dropwise under ice-cooling, followed by overnight stirring at room temperature. This mixture was poured into water and extracted with dichloromethane 2 times. The combined organic layer was washed with water and dried over anhydrous sodium sulfate; the solvent was distilled off under reduced pressure. The resulting crude product was purified by silica gel column chromatography (hexane/ethyl acetate/dichloromethane=4/1/1). The resulting purified product was washed with hexane to yield the desired product.

White crystal Yield 0.247 g (94%)

$^1$H-NMR (CDCl$_3$, 200 MHz) δ: 2.558–2.700(2H,m), 3.597(1.2H,br s), 3.950–4.050(0.8H,m), 4.791(1.2H,br s), 6.290(1H,d,J=1.8 Hz), 7.263–7.349(1H,m), 7.407–7.485 (1H,m), 7.551–7.703(4H,m), 7.787–7.872(3H,m)

IR (KBr): 2855, 1651, 1441, 1263, 1092, 958, 735 cm$^{-1}$ b) Synthesis of N,N-dimethyl-[6-[4-(3-chlorobenzoyl)benzoyl]-4,5,6,7-tetrahydrofuro[2,3-c]pyridin-2-ylmethyl]amine To a solution of 0.240 g (0.656 mmol) of 6-[4-(3-chlorobenzoyl)benzoyl]-4,5,6,7-tetrahydrofuro[2,3-c]pyridine in 10 ml of acetic acid, 0.089 ml (0.984 mmol) of 50% aqueous dimethylamine and 0.080 ml (0.984 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1) to yield the desired product.

Brown oil Yield 0.177 g (59%)

$^1$H-NMR (CDCl$_3$, 200 MHz) δ: 2.277(6H,s), 2.519–2.669 (2H,m), 3.345–3.438(2H,m), 3.559–3.627(1.2H,m), 3.986–4.010(0.8H,m), 4.446–4.460(1.2H,m), 6.090(1H,s), 7.411–7.699(5H,m), 7.827–7.867(3H,m)

IR (neat): 2939, 2775, 1632, 1431, 1267, 945, 750 cm$^{-1}$ c) Synthesis of N,N-dimethyl-[6-[4-(3-chlorobenzoyl)benzoyl]-4,5,6,7-tetrahydrofuro[2,3-c]pyridin-2-ylmethyl]dimethylamine hydrochloride N,N-Dimethyl-[6-[4-(3-chlorobenzoyl)benzoyl]-4,5,6,7-tetrahydrofuro[2,3-c]pyridin-2-ylmethyl]amine 0.184 g was dissolved in 2 ml of methanol; hydrogen chloride in ethyl acetate was added in excess, followed by stirring. This was concentrated; the resulting solid was washed with diethyl ether to yield the desired product.

Brown solid Yield 0.177 g $^1$H-NMR (CD$_3$OD, 200 MHz) δ: 2.649(2H,br s), 2.888(6H,s), 3.675(1.4H,br s), 4.348–4.403(2H,m), 4.570(0.6H,br s), 4.806(1.4H,s), 6.681(1H,s), 7.509–7.796(6H,m), 7.899(2H,d,J=8.2 Hz)

IR (nujol): 2470, 1628, 1282, 1161, 945, 725 cm$^{-1}$

Anal. Calcd for C$_{24}$H$_{24}$Cl$_2$N$_2$O$_3$.0.7H$_2$O: C, 61.08; H, 5.42; N, 5.94. Found: C, 61.07; H, 5.22; N, 5.81

EXAMPLE 79

Synthesis of N,N-dimethyl-[5-[4-(3-chlorobenzoyl)benzoyl]-4,5,6,7-tetrahydrofuro[3,2-c]pyridin-2-ylmethyl]amine hydrochloride a) Synthesis of 5-[4-(3-chlorobenzoyl)benzoyl]-4,5,6,7-tetrahydrofuro[3,2-c]pyridine To a solution of 0.114 g (0.720 mmol) of 4,5,6,7-tetrahydrofuro[3,2-c]pyridine hydrochloride, 0.175 g (0.67 mmol) of 4-(3-chlorobenzoyl)benzoic acid and 0.4 ml (2.9 mmol) of triethylamine in 30 ml of dichloromethane, 0.18 g (1.1 mmol) of diethyl cyanophosphonate was added dropwise under ice-cooling, followed by overnight stirring at room temperature. This mixture was poured into water and extracted with dichloromethane 2 times. The combined organic layer was washed with water and dried over anhydrous sodium sulfate; the solvent was distilled off under reduced pressure. The-resulting crude product was purified by silica gel column chromatography (hexane/ethyl acetate/dichloromethane=3/1/1). The resulting purified product was recrystallized from methanol-hexane to yield the desired product.

White crystal Yield 0.200 g (76%)

$^1$H-NMR (CDCl$_3$, 200 MHz) δ: 2.736–2.859(2H,m), 3.676(1.1H,br s), 4.104(0.9H,br s), 4.348(0.9H,br s), 4.694(1.1H,br s), 6.129(0.5H,br s), 6.327(0.5H,br s), 7.337(1H,br s), 7.411–7.489(1H,m), 7.550–7.708(4H,m), 7.791–7.872(3H,m)

IR (KBr): 1647, 1443, 1275, 1093, 854, 743 cm$^{-1}$ b) Synthesis of N,N-dimethyl-[5-[4-(3-chlorobenzoyl)benzoyl]-4,5,6,7-tetrahydrofuro[3,2-c]pyridin-2-ylmethyl]amine To a solution of 0.190 g (0.519 mmol) of 5-[4-(3-chlorobenzoyl)benzoyl]-4,5,6,7-tetrahydrofuro[3,2-c]pyridine in 10 ml of acetic acid, 0.070 ml (0.78 mmol) of 50% aqueous dimethylamine and 0.063 ml (0.78 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (chloroform/methanol=50/1) to yield the desired product.

Brown oil Yield 0.160 g (73%)

$^1$H-NMR (CDCl$_3$, 200 MHz) δ: 2.272(6H,s), 2.728–2.847(2H,m), 3.416(2H,s), 3.663(1.1H,br s), 4.073(0.9H,br s), 4.306(0.9H,br s), 4.654(1.1H,br s), 5.920(0.5H,br s), 6.126(0.5H,br s), 7.449(1H,t,J=7.8 Hz), 7.547–7.707(4H,m), 7.791–7.870(3H,m)

IR (neat): 2939, 2814, 2765, 1626, 1439, 1281, 1111, 860, 723 cm$^{-1}$ c) Synthesis of N,N-dimethyl-[5-[4-(3-chlorobenzoyl)benzoyl]-4,5,6,7-tetrahydrofuro[3,2-c]pyridin-2-ylmethyl]amine hydrochloride N,N-Dimethyl-[5-[4-(3-chlorobenzoyl)benzoyl]-4,5,6,7-tetrahydrofuro[3,2-c]pyridin-2-ylmethyl]amine 0.160 g was dissolved in 2 ml of methanol; hydrogen chloride in ethyl acetate was added in excess, followed by stirring. This was concentrated; the resulting solid was washed with diethyl ether to yield the desired product.

Pale brown solid Yield 0.132 g $^1$H-NMR (CD$_3$OD, 200 MHz) δ: 2.874(8H,s), 3.724–3.776(1.1H,m), 4.119(0.9H,br s), 4.375–4.430(2.9H,m), 4.685(1.1H,br s), 6.520(0.5H,br s), 6.721(0.5H,br s), 7.508–7.795(6H,m), 7.894(2H,d,J=8.0 Hz)

IR (nujol): 2470, 1628, 1281, 1111, 943, 723 cm$^{-1}$

Anal. Calcd for C$_{24}$H$_{24}$Cl$_2$N$_2$O$_3$.1.0H$_2$O: C, 60.38; H, 5.49; N, 5.87. Found: C, 60.47; H, 5.31; N, 5.83

EXAMPLE 80

Synthesis of N,N-dimethyl-[6-[4-(2,4-dichlorobenzoyl)benzoyl]-4,5,6,7-tetrahydrofuro[2,3-c]pyridin-2-ylmethyl]amine hydrochloride a) Synthesis of N,N-dimethyl-6-[4-(2,4-dichlorobenzoyl)benzoyl]-4,5,6,7-tetrahydrofuro[2,3-c]pyridin-2-ylmethyl]amine To a solution of 0.160 g (1.000 mmol) of 4,5,6,7-tetrahydrofuro[2,3-c]pyridine hydrochloride, 0.325 g (1.1 mmol) of 4-(2,4-dichlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.135 g (30%)

$^1$H-NMR (CDCl$_3$, 200 MHz) δ: 2.257–2.332(6H,m), 2.497–2.671(2H,m), 3.374–3.596(3.2H,m), 3.975–4.006(0.8H,m), 4.394–4.423(0.8H,m), 4.764(1.2H,br s), 6.099(1H,s), 7.266–7.579(5H,m), 7.753–7.874(2H,m)

IR(neat): 2939, 2856, 2775, 1674, 1633, 1433, 1282, 1244, 931, 860 cm$^{-1}$ b) Synthesis of N,N-dimethyl-[6-[4-(2,4-dichlorobenzoyl)benzoyl]-4,5,6,7-tetrahydrofuro[2,3-c]pyridin-2-ylmethyl]amine hydrochloride N,N-Dimethyl-[6-[4-(2,4-dichlorobenzoyl)benzoyl]-4,5,6,7-tetrahydrofuro[2,3-c]pyridin-2-ylmethyl]amine 0.135 g was dissolved in 2 ml of methanol; hydrogen chloride in ethyl acetate was added in excess, followed by stirring. This was concentrated; the resulting solid was washed with diethyl ether to yield the desired product.

Brown solid Yield 0.135 g $^1$H-NMR (CD$_3$OD, 200 MHz) δ: 2.610–2.653(2H,m), 2.882(6H,br s), 3.616–3.643(1H,m), 3.981–4.026(1H,m), 4.384–4.497(4H,m), 6.668(1H,s), 7.453–7.663(5H,m), 7.799–7.917(2H,m)

IR (nujol): 2563, 1626, 1282, 1246, 1151, 931 cm$^{-1}$

Anal. Calcd for C$_{24}$H$_{23}$Cl$_3$N$_2$O$_3$.0.5H$_2$O: C, 57.33; H, 4.81; N, 5.57. Found: C, 57.46; H, 5.08; N, 5.39

EXAMPLE 81

Synthesis of N,N-dimethyl-[5-[4-(2,4-dichlorobenzoyl)benzoyl]-4,5,6,7-tetrahydrofuro[3,2-c]pyridin-2-ylmethyl]amine hydrochloride a) Synthesis of N,N-dimethyl-[5-[4-(2,4-dichlorobenzoyl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.325 g (1.1 mmol) of 4-(2,4-dichlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off under reduced pressure, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.252 g (51%)
$^1$H-NMR (CDCl$_3$, 200 MHz) δ: 2.280–2.372(6H,m), 2.721–2.846(2H,m), 3.437(2H,s), 3.595–3.647(1.2H,m), 4.044–4.095(0.8H,m), 4.271(0.8H,br s), 4.642(1.2H,br s), 5.927(0.5H,br s), 6.130(0.5H,br s), 7.323–7.582(5H,m), 7.752–7.878(2H,m)
IR(neat): 2939, 2858, 2773, 1633, 1585, 1431, 1281, 1111, 930, 750 cm$^{-1}$ b) Synthesis of N,N-dimethyl-[5-[4-(2,4-dichlorobenzoyl)benzoyl]-4,5,6,7-tetrahydrofuro[3,2-c]pyridin-2-ylmethyl]amine hydrochloride N,N-Dimethyl-[5-[4-(2,4-dichlorobenzoyl)benzoyl]-4,5,6,7-tetrahydrofuro[3,2-c]pyridin-2-ylmethyl]amine 0.252 g was dissolved in 2 ml of methanol; hydrogen chloride in ethyl acetate was added in excess, followed by stirring. This was concentrated; the resulting solid was washed with diethyl ether to yield the desired product.

Yellow powder Yield 0.244 g
$^1$H-NMR (CD$_3$OD, 200 MHz) δ: 2.863(8H,br s), 3.649–3.735(1H,m), 4.063–4.127(1H,m), 4.348–4.429(2H,m), 4.642–4.684(1H,m), 6.499(0.5H,br s), 6.708(0.5H,br s), 7.442–7.656(5H,m), 7.792–7.898(2H,m)
IR (nujol): 2669, 1626, 1282, 1243, 1115, 930, 723 cm$^{-1}$
Anal. Calcd for C$_{24}$H$_{23}$Cl$_3$N$_2$O$_3$.0.5H$_2$O: C, 57.33; H, 4.81; N, 5.57. Found: C, 57.14; H, 4.83; N, 5.29

EXAMPLE 82

Synthesis of N,N-dimethyl-[6-[4-(3,4-dichlorobenzoyl)benzoyl]-4,5,6,7-tetrahydrofuro[2,3-c]pyridin-2-ylmethyl]amine hydrochloride a) Synthesis of N,N-dimethyl-[6-[4-(3,4-dichlorobenzoyl)benzoyl]-4,5,6,7-tetrahydrofuro[2,3-c]pyridin-2-ylmethyl]amine To a solution of 0.160 g (1.000 mmol) of 4,5,6,7-tetrahydrofuro[2,3-c]pyridine hydrochloride, 0.325 g (1.1 mmol) of 4-(3,4-dichlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous solution of formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1). The resulting purified product was washed with diethyl ether to yield the desired product.

Orange crystal Yield 0.153 g (34%)
$^1$H-NMR (CDCl$_3$, 200 MHz) δ: 2.288(6H,br s), 2.515–2.676(2H,m), 3.368–3.455(2H,m), 3.594(1.2H,br s), 3.999(0.8H,br s), 4.447(0.8H,br s), 4.779(1.2H,br s), 6.099 (1H,s), 7.554–7.678(4H,m), 7.828(2H,d,J=8.2 Hz), 7.917 (1H,d,J=1.8 Hz)
IR (KBr): 2947, 2816, 2767, 1662, 1630, 1437, 1282, 1030, 901, 731 cm$^{-1}$ b) Synthesis of N,N-dimethyl-[6-[4-(3,4-dichlorobenzoyl)benzoyl]-4,5,6,7-tetrahydrofuro[2,3-c]pyridin-2-ylmethyl]amine hydrochloride N,N-Dimethyl-[6-[4-(3,4-dichlorobenzoyl)benzoyl]-4,5,6,7-tetrahydrofuro[2,3-c]pyridin-2-ylmethyl]amine 0.153 g was dissolved in 2 ml of methanol; hydrogen chloride in ethyl acetate was added in excess, followed by stirring. This mixture was then concentrated, and recrystallized from methanol-diethyl ether to yield the desired product.

Brown solid Yield 0.132 g
$^1$H-NMR (CD$_3$OD, 200 MHz) δ: 2.604–2.694(2H,m), 2.890(6H,s), 3.658–3.712(1.2H,m), 4.000–4.050(0.8H,m), 4.335–4.406(2H,m), 4.547–4.571(0.8H,m), 4.753–4.804 (1.2H,m), 6.684(1H,s), 7.642(2H,d,J=8.6 Hz), 7.728(2H,d, J=1.2 Hz), 7.898(2H,d,J=8.4 Hz), 7.953(1H,t,J=1.2 Hz)
IR (nujol): 2663, 1630, 1288, 1236, 1163, 972, 729 cm$^{-1}$
Anal. Calcd for C$_{24}$H$_{23}$Cl$_3$N$_2$O$_3$.0.6H$_2$O: C, 57.12; H, 4.83; N, 5.55. Found: C, 57.02; H, 4.74; N, 5.54.

EXAMPLE 83

Synthesis of N,N-dimethyl-[5-[4-(3,4-dichlorobenzoyl)benzoyl]-4,5,6,7-tetrahydrofuro[3,2-c]pyridin-2-ylmethyl]amine hydrochloride a) Synthesis of N,N-dimethyl-[5-[4-(3,4-dichlorobenzoyl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.325 g (1.1 mmol) of 4-(3,4-dichlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1). The resulting purified product was washed with diethyl ether to yield the desired product.

Pale brown solid Yield 0.139 g (31%)

$^1$H-NMR (CDCl$_3$, 200 MHz) δ: 2.273(6H,s), 2.720–2.877 (2H,m), 3.423(2H,s), 3.648(1.1H,br s), 4.008(0.9H,br s), 4.307(0.9H,br s), 4.652(1.1H,br s), 5.925(0.4H,br,s), 6.129 (0.6H,br s), 7.554–7.680(4H,m), 7.830(2H,d,J=8.0 Hz), 7.911(1H,d,J=1.8 Hz)

IR (KBr): 2941, 2816, 2764, 1651, 1624, 1443, 1282, 1028, 731 cm$^{-1}$ b) Synthesis of N,N-dimethyl-[5-[4-(3,4-dichlorobenzoyl)benzoyl]-4,5,6,7-tetrahydrofuro[3,2-c]pyridin-2-ylmethyl]amine hydrochloride N,N-Dimethyl-[5-[4-(3,4-dichlorobenzoyl)benzoyl]-4,5,6,7-tetrahydrofuro[3,2-c]pyridin-2-ylmethyl]amine 0.139 g was dissolved in 2 ml of methanol; hydrogen chloride in ethyl acetate was added in excess, followed by stirring. This was concentrated, and recrystallized from methanol-diethyl ether to yield the desired product.

White solid Yield 0.150 g $^1$H-NMR (CD$_3$OD, 200 MHz) δ: 2.870(8H,br s), 3.715–3.770(1.2H,m), 4.096–4.123(0.8H,m), 4.347–4.422 (2.8H,m), 4.685(1.2H,s), 6.512(0.4H,br s), 6.711(0.6H,br s), 7.631(2H,d,J=8.0 Hz), 7.719(2H,d,J=1.0 Hz), 7.887(2H,d, J=8.0 Hz), 7.943(1H,d,J=1.2 Hz)

IR (nujol): 2461, 1632, 1282, 1246, 1115, 945, 729 cm$^{-1}$

Anal. Calcd for C$_{24}$H$_{23}$Cl$_3$N$_2$O$_3$.0.5H$_2$O: C, 57.33; H, 4.81; N, 5.57. Found: C, 57.22; H, 4.51; N, 5.44.

EXAMPLE 84

Synthesis of N,N-dimethyl-[6-[4-(3,5-dichlorobenzoyl)benzoyl]-4,5,6,7-tetrahydrofuro[2,3-c]pyridin-2-ylmethyl]amine hydrochloride a) Synthesis of N,N-dimethyl-[6-[4-(3,5-dichlorobenzoyl)benzoyl]-4,5,6,7-tetrahydrofuro[2,3-c]pyridin-2-ylmethyl]amine To a solution of 0.160 g (1.000 mmol) of 4,5,6,7-tetrahydrofuro[2,3-c]pyridine hydrochloride, 0.325 g (1.1 mmol) of 4-(3,5-dichlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.140 g (31%)

$^1$H-NMR (CDCl$_3$, 200 MHz) δ: 2.270–2.304(6H,m), 2.521–2.662(2H,m), 3.379–3.489(2H,m), 3.555–3.646 (1.2H,m), 3.992–4.012(0.8H,m), 4.177–4.452(0.8H,m), 4.780(1.2H,br s), 6.116(1H,s), 7.561–7.670(5H,m), 7.839 (2H,d,J=8.0 Hz)

IR (neat): 2937, 2856, 2775, 1736, 1633, 1564, 1431, 1271, 1045, 858, 733 cm$^{-1}$ b) Synthesis of N,N-dimethyl-[6-[4-(3,5-dichlorobenzoyl)benzoyl]-4,5,6,7-tetrahydrofuro[2,3-c]pyridin-2-ylmethyl]amine hydrochloride N,N-Dimethyl-[6-[4-(3,5-dichlorobenzoyl)benzoyl]-4,5,6,7-tetrahydrofuro[2,3-c]pyridin-2-ylmethyl]amine 0.140 g was dissolved in 2 ml of methanol; hydrogen chloride in ethyl acetate was added in excess, followed by stirring. This mixture was then concentrated and washed with diethyl ether to yield the desired product.

Brown solid Yield 0.134 g $^1$H-NMR (CD$_3$OD, 200 MHz) δ: 2.618–2.700(2H,m), 2.835–2.881(6H,m), 3.616–3.689(1.4H,m), 4.000–4.021 (0.7H,m), 4.328–4.398(2H,m), 4.550–4.600(0.7H,m), 4.795–4.817(1.4H,m), 6.671(1H,s), 7.624–7.781(5H,m), 7.900(2H,d,J=8.0 Hz)

IR (nujol): 2467, 1630, 1562, 1273, 1165, 974, 787 cm$^{-1}$

Anal. Calcd for C$_{24}$H$_{23}$Cl$_3$N$_2$O$_3$.1.0H$_2$O: C, 56.32; H, 4.92; N, 5.47. Found: C, 56.52; H, 4.89; N, 5.19.

EXAMPLE 85

Synthesis of N,N-dimethyl-[5-[4-(3,5-dichlorobenzoyl)benzoyl]-4,5,6,7-tetrahydrofuro[3,2-c]pyridin-2-ylmethyl]amine hydrochloride a) Synthesis of N,N-dimethyl-[5-[4-(3,5-dichlorobenzoyl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.325 g (1.1 mmol) of 4-(3,5-dichlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.200 g (44%)

$^1$H-NMR (CDCl$_3$, 200 MHz) δ: 2.279(6H,s), 2.735–2.865 (2H,m), 3.437(2H,br s), 3.660–3.697(1.2H,m), 4.080–4.091 (0.8H,m), 4.311(0.8H,br s), 4.657(1.2H,br s), 5.950(0.4H,br s), 6.137(0.6H,br s), 7.562–7.666(5H,m), 7.838(2H,d,J=8.2 Hz)

IR (neat): 2935, 2854, 2769, 1633, 1562, 1427, 1269, 1113, 972, 748 cm$^{-1}$ b) Synthesis of N,N-dimethyl-[5-[4-(3,5-dichlorobenzoyl)benzoyl]-4,5,6,7-tetrahydrofuro[3,2-c]pyridin-2-ylmethyl]amine hydrochloride N,N-Dimethyl-[5-[4-(3,5-dichlorobenzoyl)benzoyl]-4,5,6,7-tetrahydrofuro[3,2-c]pyridin-2-ylmethyl]amine 0.200 g was dissolved in 2 ml of methanol; hydrogen chloride in ethyl acetate was added in excess, followed by stirring. This was concentrated and washed with diethyl ether to yield the desired product.

Pale yellow solid Yield 0.197 g
$^1$H-NMR (CD$_3$OD, 200 MHz) δ: 2.870(8H,br s), 3.702–3.775(1.1H,m), 4.076–4.143(0.9H,m), 4.347–4.467 (2.9H,m), 4.640–4.684(1.1H,m), 6.515–6.534(0.5H,m), 6.715(0.5H,br s), 7.618–7.768(5H,m), 7.893(2H,d,J=7.8 Hz)
IR (nujol): 2472, 1630, 1269, 1115, 974, 785 cm$^{-1}$
Anal. Calcd for C$_{24}$H$_{23}$Cl$_3$N$_2$O$_3$.1.5H$_2$O: C, 55.35; H, 5.03; N, 5.38. Found: C, 55.58; H, 4.98; N, 5.28

EXAMPLE 86

Synthesis of N,N-dimethyl-[6-[4-(2,3-dichlorobenzoyl)benzoyl]-4,5,6,7-tetrahydrofuro[2,3-c]pyridin-2-ylmethyl]amine hydrochloride a) Synthesis of N,N-dimethyl-6-[4-(2,3-dichlorobenzoyl)benzoyl]-4,5,6,7-tetrahydrofuro[2,3-c]pyridin-2-ylmethyl] amine To a solution of 0.160 g (1.000 mmol) of 4,5,6,7-tetrahydrofuro[2,3-c]pyridine hydrochloride, 0.325 g (1.1 mmol) of 4-(2,3-dichlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.203 g (45%) $^1$H-NMR (CDCl$_3$, 200 MHz) δ: 2.280(6H,br s), 2.485–2.664(2H,m), 3.355–3.445 (2H,m), 3.522–3.549(1.2H,m), 3.968–3.995(0.8H,m), 4.385–4.400(1.2H,m), 4.733–4.760(1.2H,m), 6.090(1H,s), 7.254–7.398(2H,m), 7.533(2H,d,J=8.2 Hz), 7.630(1H,dd,J=1.8&7.8 Hz), 7.866(2H,d,J=8.2 Hz)

IR (neat): 2937, 2856, 2775, 1736, 1632, 1433, 1282, 1045, 955, 738 cm$^{-1}$ b) Synthesis of N,N-dimethyl-[6-[4-(2,3-dichlorobenzoyl)benzoyl]-4,5,6,7-tetrahydrofuro[2,3-c]pyridin-2-ylmethyl] amine hydrochloride N,N-Dimethyl-[6-[4-(2,3-dichlorobenzoyl)benzoyl]-4,5,6,7-tetrahydrofuro[2,3-c]pyridin-2-ylmethyl]amine 0.203 g was dissolved in 2 ml of methanol; hydrogen chloride in ethyl acetate was added in excess, followed by stirring. This was concentrated and washed with diethyl ether to yield the desired product.

Brown solid Yield 0.192 g
$^1$H-NMR (CD$_3$OD, 200 MHz) δ: 2.615–2.652(2H,m), 2.882(6H,br s), 3.587–3.660(1.2H,m), 3.961–4.074(0.8H,m), 4.369–4.417(2H,m), 4.450–4.500(0.8H,m), 4.774–4.786(1.2H,m), 6.665(1H,s), 7.376–7.637(4H,m), 7.757(1H,dd,J=1.7&7.6 Hz), 7.895(2H,d,J=8.4 Hz)
IR (nujol): 2669, 1630, 1435, 1282, 1157, 951, 729 cm$^{-1}$
Anal. Calcd for C$_{24}$H$_{23}$Cl$_3$N$_2$O$_3$.1.0H$_2$O: C, 56.32; H, 4.92; N, 5.47. Found: C, 56.18; H, 4.94; N, 5.35.

EXAMPLE 87

Synthesis of N,N-dimethyl-[5-[4-(2,3-dichlorobenzoyl)benzoyl]-4,5,6,7-tetrahydrofuro[3,2-c]pyridin-2-ylmethyl]amine hydrochloride a) Synthesis of N,N-dimethyl-[5-[4-(2,3-dichlorobenzoyl)benzoyl]-4,5,6,7-tetrahydrofuro[3,2-c]pyridin-2-ylmethyl] amine To a solution of 0.160 g (1.000 mmol) of 4,5,6,7-tetrahydrofuro[3,2-c]pyridine hydrochloride, 0.325 g (1.1 mmol) of 4-(2,3-dichlorobenzoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.256 g (56%)
$^1$H-NMR (CDCl$_3$, 200 MHz) δ: 2.276(6H,s), 2.696–2.883 (2H,m), 3.412–3.434(2H,m), 3.595–3.659(1.2H,m), 4.039–4.177(0.8H,m), 4.251–4.299(0.8H,m), 4.612–4.668 (1.2H,m), 5.922–5.931(0.4H,m), 6.111–6.128(0.6H,m), 7.248–7.395(2H,m), 7.534(2H,d,J=8.4 Hz), 7.625(1H,dd,J=1.8&7.8 Hz), 7.845(2H,d,J=8.2 Hz)

IR (neat): 2939, 2858, 2775, 1678, 1633, 1433, 1282, 1113, 955, 737 cm$^{-1}$ b) Synthesis of N,N-dimethyl-[5-[4-(2,3-dichlorobenzoyl)benzoyl]-4,5,6,7-tetrahydrofuro[3,2-c]pyridin-2-ylmethyl] amine hydrochloride N,N-Dimethyl-[5-[4-(2,3-dichlorobenzoyl)benzoyl]-4,5,6,7-tetrahydrofuro[3,2-c]pyridin-2-ylmethyl]amine 0.256 g was dissolved in 2 ml of methanol; hydrogen chloride in ethyl acetate was added in excess, followed by stirring. This mixture was then concentrated and washed with diethyl ether to yield the desired product.

Pale yellow solid Yield 0.226 g
$^1$H-NMR (CD$_3$OD, 200 MHz) δ: 2.796–2.689(8H,m), 3.622–3.713(1.1H,m), 4.080–4.115(0.9H,m), 4.324–4.382 (2.9H,m), 4.661(1.1H,br s), 6.496–6.526(0.4H,m), 6.666–6.707(0.6H,m), 7.368–7.528(2H,m), 7.608(2H,d,J=8.4 Hz), 7.752(1H,dd,J=2.0&8.0 Hz), 7.886(2H,d,J=8.2 Hz)
IR (nujol): 2669, 1628, 1434, 1282, 1115, 953, 725 cm$^{-1}$
Anal. Calcd for C$_{24}$H$_{23}$Cl$_3$N$_2$O$_3$.1.0H$_2$O: C, 56.32; H. 4.92; N, 5.47. Found: C, 56.60; H, 5.26; N, 5.22

EXAMPLE 88

Synthesis of N,N-dimethyl-[6-[4-(2-thenoyl)benzoyl]-4,5,6,7-tetrahydrofuro[2,3-c]pyridin-2-ylmethyl]amine hydrochloride a) Synthesis of 6-[4-(2-thenoyl)benzoyl]-4,5,6,7-tetrahydrofuro[2,3-c]pyridine To a solution of 0.173 g (1.084 mmol) of 4,5,6,7-tetrahydrofuro[2,3-c]pyridine hydrochloride, 0.38 g (1.6 mmol) of 4-(2-thenoyl)benzoic acid and 0.60 ml (4.3 mmol) of triethylamine in 30 ml of dichloromethane, 0.25 ml (1.6 mmol) of diethyl cyanophosphonate was added dropwise at room temperature, followed by overnight stirring. This mixture was poured into aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (hexane/ethyl acetate=3/1 to 2/1) to yield the desired product.

Yellow solid Yield 0.311 g (85%)

$^1$H-NMR (CDCl$_3$, 200 MHz) δ: 2.577–2.696(2H,m), 3.607(1.2H,br s), 4.006(0.8H,br s), 4.466(0.8H,br s), 4.793 (1.2H,br s), 6.294(1H,d,J=1.4 Hz), 7.194(1H,dd,J=3.8&5.0 Hz), 7.352(1H,br s), 7.576(2H,d,J=8.0 Hz), 7.634(1H,dd,J= 0.9&3.5 Hz), 7.772(1H,dd,J=1.1&4.7 Hz), 7.924(2H,d,J= 8.0 Hz)

IR (nujol): 1622, 1437, 1410, 1284, 1230, 1090, 837, 710 cm$^{-1}$ b) Synthesis of N,N-dimethyl-[6-[4-(2-thenoyl)benzoyl]-4,5,6,7-tetrahydrofuro[2,3-c]pyridin-2-ylmethyl]amine To a solution of 0.251 g (0.744 mmol) of 6-[4-(2-thenoyl) benzoyl]-4,5,6,7-tetrahydrofuro[2,3-c]pyridine in 10 ml of acetic acid, 0.10 g (1.1 mmol) of 50% aqueous dimethylamine and 0.09 g (1.1 mmol) of 37% aqueous formaldehyde were added, followed by stirring at 100° C. for 0.5 hours. After the solvent was distilled off under reduced pressure, the residual solution was alkalified with an aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow solid Yield 0.239 g (81%)

$^1$H-NMR (CDCl$_3$, 200 MHz) δ: 2.279(6H,br s), 2.517–2.676(2H,m), 3.372–3.444(2H,m), 3.585(1.2H,br s), 4.000(0.8H,br s), 4.460(0.8H,br s), 4.777(1.2H,br s), 6.096 (1H,s), 7.194(1H,dd,J=3.8&5.0 Hz), 7.570(2H,d,J=8.6 Hz), 7.656(1H,dd,J=1.2&3.8 Hz), 7.769(1H,dd,J=1.1&5.1 Hz), 7.919(2H,d,J=8.2 Hz)

IR (nujol): 1622, 1414, 1292, 748, 723 cm$^{-1}$ c) Synthesis of N,N-dimethyl-[6-[4-(2-thenoyl)benzoyl]-4,5,6,7-tetrahydrofuro[2,3-c]pyridin-2-ylmethyl]amine hydrochloride N,N-Dimethyl-[6-[4-(2-thenoyl)benzoyl]-4,5,6,7-tetrahydrofuro[2,3-c]pyridin-2-ylmethyl]amine 0.197 g was dissolved in 2 ml of methanol; hydrogen chloride in methanol was added in excess, followed by stirring. This mixture was then concentrated to yield the desired product.

Yellow foam Yield 0.215 g $^1$H-NMR (CD$_3$OD, 200 MHz) δ: 2.632(2H,br s), 2.898 (6H,br s), 3.652(1.4H,br s), 4.010(0.6H,br s), 4.361(0.6H,br s), 4.425(1.4H,br s), 4.570(0.6H,br s), 4.792(1.4H,br s), 6.695(1H,s), 7.258(1H,dd,J=3.8&5.0 Hz), 7.635(2H,d,J=8.2 Hz), 7.737(1H,dd,J=1.0&3.8 Hz), 7.939(2H,d,J=8.4 Hz), 7.976(1H,dd,J=1.0&5.0 Hz)

IR (nujol): 2667, 1626, 1410, 1292, 725 cm$^{-1}$

Anal. Calcd for C$_{22}$H$_{23}$ClN$_2$O$_3$·1.5H$_2$O: C, 57.70; H, 5.72; N, 6.12. Found: C, 57.75; H, 5.99; N, 6.08.

EXAMPLE 89

Synthesis of N,N-dimethyl-[5-[4-(2-thenoyl) benzoyl]-4,5,6,7-tetrahydrofuro[3,2-c]pyridin-2-ylmethyl]amine hydrochloride a) Synthesis of N,N-dimethyl-[5-[4-(2-thenoyl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.279 g (1.2 mmol) of 4-(2-thenoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1). The resulting purified product was recrystallized from ethyl acetate-hexane to yield the desired product.

Pale yellow solid Yield 0.184 g (47%)

$^1$H-NMR (CDCl$_3$, 200 MHz) δ: 2.273(6H,m), 2.716–2.883(2H,m), 3.379–3.421(2H,m), 3.638–3.698 (1.1H,m), 4.063–4.176(0.9H,m), 4.294–4.325(0.9H,m), 4.625–4.650(1.1H,m), 5.913–5.931(0.5H,m), 6.106–6.123 (0.5H,m), 7.189(1H,dd,J=3.8&4.9 Hz), 7.565(2H,d,J=8.4 Hz), 7.650(1H,dd,J=1.2&4.9 Hz), 7.916(2H,d,J=8.0 Hz)

IR (KBr): 2931, 2860, 2779, 1628, 1414, 1302, 1225, 1111, 1018, 839, 727 cm$^{-1}$ b) Synthesis of N,N-dimethyl-[5-[4-(2-thenoyl)benzoyl]-4,5,6,7-tetrahydrofuro[3,2-c]pyridin-2-ylmethyl]amine hydrochloride N,N-Dimethyl-[5-[4-(2-thenoyl)benzoyl]-4,5,6,7-tetrahydrofuro[3,2-c]pyridin-2-ylmethyl]amine 0.184 g was dissolved in 2 ml of methanol; hydrogen chloride in ethyl acetate was added in excess, followed by stirring. This mixture was then concentrated, and recrystallized from methanol-diethyl ether to yield the desired product.

Pale yellow solid Yield 0.186 g $^1$H-NMR (CD$_3$OD, 200 MHz) δ: 2.874(8H,br s), 3.718–3.766(1.1H,m), 4.083–4.143(0.9H,m), 4.350–4.433 (2.9H,m), 4.684(1.1H,br s), 6.523(0.5H,br s), 6.719(0.5H,br s), 7.265(1H,dd,J=3.8&4.9 Hz), 7.635(2H,d,J=8.2 Hz), 7.751(1H,d,J=3.0 Hz), 7.935–7.995(3H,m)

IR (nujol): 2461, 1626, 1460, 1377, 1282, 1113, 717 cm$^{-1}$

Anal. Calcd for C$_{22}$H$_{23}$ClN$_2$O$_3$·0.7H$_2$O: C, 59.57; H, 5.54; N, 6.32. Found: C, 59.53; H, 5.32; N, 6.12.

EXAMPLE 90

Synthesis of N,N-dimethyl-[6-[4-(2-furoyl) benzoyl]-4,5,6,7-tetrahydrofuro[2,3-c]pyridin-2-ylmethyl]amine hydrochloride a) Synthesis of 6-[4-(2-furoyl)benzoyl]-4,5,6,7-tetrahydrofuro[2,3-c]pyridine To a solution of 0.165 g (1.034 mmol) of 4,5,6,7-tetrahydrofuro[2,3-c]pyridine hydrochloride, 0.25 g (1.1 mmol) of 4-(2-furoyl)benzoic acid and 0.58 ml (4.1 mmol) of triethylamine in 30 ml of dichloromethane, 0.19 ml (1.2 mmol) of diethyl cyanophosphonate was added dropwise at room temperature, followed by overnight stirring. This mixture was poured into aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (hexane/ethyl acetate=3/1 to 2/1) to yield the desired product.

Yellow oil Yield 0.325 g (98%)

$^1$H-NMR (CDCl$_3$, 200 MHz) δ: 2.563–2.688(2H,m), 3.595(1.2H,br s), 4.000(0.8H,br s), 4.457(0.8H,br s), 4.788

(1.2H,br s), 6.294(1H,d,J=1.8 Hz), 6.634(1H,dd,J=1.8&3.8 Hz), 7.279(1H,d,J=3.8 Hz), 7.350(1H,br s), 7.575(2H,d,J= 8.0 Hz), 7.743(1H,d,J=1.8 Hz), 8.046(2H,d,J=8.0 Hz)

IR (neat): 3126, 2927, 2854, 1645, 1462, 1433, 1311, 1288, 1236, 1038, 872, 735 cm$^{-1}$ b) Synthesis of N,N-dimethyl-[6-[4-(2-furoyl)benzoyl]-4,5,6,7-tetrahydrofuro[2,3-c]pyridin-2-ylmethyl]amine To a solution of 0.323 g (1.005 mmol) of 6-[4-(2-furoyl)benzoyl]-4,5,6,7-tetrahydrofuro[2,3-c]pyridine in 10 ml of acetic acid, 0.14 g (1.5 mmol) of 50% aqueous dimethylamine and 0.12 g (1.5 mmol) of 37% aqueous formaldehyde were added, followed by stirring at 100° C. for 0.5 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.290 g (76%)

$^1$H-NMR (CDCl$_3$, 200 MHz) δ: 2.279(6H,br s), 2.537–2.672(2H,m), 3.361–3.438(2H,m), 3.574(1.2H,br s), 3.999(0.8H,br s), 4.447(0.8H,br s), 4.772(1.2H,br s), 6.092 (1H,s), 6.631(1H,dd,J=1.5&3.7 Hz), 7.273(1H,dd,J= 0.7&3.3 Hz), 7.564(2H,d,J=8.4 Hz), 7.742(1H,dd,J= 0.8&1.8 Hz), 8.034(2H,d,J=8.0 Hz)

IR (neat): 2939, 2856, 2775, 1645, 1461, 1433, 1292, 1238, 1043, 1020, 872, 773 cm$^{-1}$ c) Synthesis of N,N-dimethyl-[6-[4-(2-furoyl)benzoyl]-4,5,6,7-tetrahydrofuro[2,3-c]pyridin-2-ylmethyl]amine hydrochloride N,N-Dimethyl-[6-[4-(2-furoyl)benzoyl]-4,5,6,7-tetrahydrofuro[2,3-c]pyridin-2-ylmethyl]amine 0.310 g was dissolved in 2 ml of methanol; hydrogen chloride in methanol was added in excess, followed by stirring. This mixture was then concentrated to yield the desired product.

Pale yellow foam Yield 0.290 g $^1$H-NMR (CD$_3$OD, 200 MHz) δ: 2.619(2H,br s), 2.907 (6H,br s), 3.636(1.4H,br s), 4.002(0.6H,br s), 4.365(0.6H,br s), 4.436(1.4H,br s), 4.554(0.6H,br s), 4.784(1.4H,br s), 6.697(1H,s), 6.744(1H,dd,J=1.8&3.6 Hz), 7.402(1H,d,J=3.6 Hz), 7.633(2H,d,J=8.0 Hz), 7.944(1H,d,J=1.8 Hz), 8.050 (2H,d,J=8.0 Hz)

IR (neat): 2954, 2671, 1641, 1462, 1302, 961, 872, 777 cm$^{-1}$

Anal. Calcd for C$_{22}$H$_{23}$ClN$_2$O$_4$·1.3H$_2$O: C, 60.29; H, 5.89; N, 6.39. Found: C, 60.38; H, 5.96; N, 6.30.

EXAMPLE 91

Synthesis of N,N-dimethyl-[5-[4-(2-furoyl)benzoyl]-4,5,6,7-tetrahydrofuro[3,2-c]pyridin-2-ylmethyl]amine hydrochloride a) Synthesis of N,N-dimethyl-[5-[4-(2-furoyl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.237 g (1.1 mmol) of 4-(2-furoyl)benzoic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.148 g (39%)

$^1$H-NMR (CDCl$_3$, 200 MHz) δ: 2.278(6H,s), 2.712–2.875 (2H,m), 3.439(2H,s), 3.615–6.695(1.2H,m), 4.050–4.142 (0.8H,m), 4.298(0.8H,br s), 4.652(1.2H,br s), 5.928(0.4H,br s), 6.136(0.6H,br s), 6.631(1H,dd,J=1.6&3.7 Hz), 7.277(1H,d,J=2.8 Hz), 7.566(2H,d,J=8.6 Hz), 7.736–7.744(1H,m), 8.039(2H,d,J=8.0 Hz)

IR (neat): 2936, 2854, 2771, 1733, 1682, 1460, 1282, 1113, 874, 775 cm$^{-1}$ b) Synthesis of N,N-dimethyl-[5-[4-(2-furoyl)benzoyl]-4,5,6,7-tetrahydrofuro[3,2-c]pyridin-2-ylmethyl]amine hydrochloride N,N-Dimethyl-[5-[4-(2-furoyl)benzoyl]-4,5,6,7-tetrahydrofuro[3,2-c]pyridin-2-ylmethyl]amine 0.148 g was dissolved in 2 ml of methanol; hydrogen chloride in ethyl acetate was added in excess, followed by stirring. This mixture was then concentrated and washed with diethyl ether to yield the desired product.

Pale brown solid Yield 0.149 g $^1$H-NMR (CD$_3$OD, 200 MHz) δ: 2.874(8H,br S), 3.689–3.777(1.2H,m), 4.071–4.100(0.8H,m), 4.334–4.479 (2.8H,m), 4.641–4.865(1.2H,m), 6.500–6.513(0.4H,m), 6.697–6.754(1.6H,m), 7.410(1H,d,J=3.6 Hz), 7.623(2H,d,J= 8.2 Hz), 7.925–7.934(1H,m), 8.066(2H,d,J=7.8 Hz)

IR (nujol): 2673, 1626, 1302, 1117, 953, 723 cm$^{-1}$

Anal. Calcd for C$_{22}$H$_{23}$ClN$_2$O$_4$·1.0H$_2$O: C, 61.04; H, 5.82; N, 6.47. Found: C, 61.06; H, 5.74; N, 6.37.

EXAMPLE 92

Synthesis of (Z)-N,N-dimethyl-[6-(4-chlorostilbene-4'-carbonyl)-4,5,6,7-tetrahydrofuro[2,3-c]pyridin-2-ylmethyl]amine hydrochloride a) Synthesis of (Z)-N,N-dimethyl-6-(4-chlorostilbene-4'-carbonyl)-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.569 g (2.2 mmol) of (Z)-4-chlorostilbene-4'-carboxylic acid and 1.1 ml (8.0 mmol) of triethylamine in 30 ml of dichloromethane, 0.489 g (3.0 mmol) of diethyl cyanophosphonate was added dropwise at room temperature, followed by overnight stirring at room temperature. After the solvent was distilled off, water was added, followed by 2 extractions with ethyl acetate. The combined organic layer was dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.348 g (41%)

$^1$H-NMR (CDCl$_3$, 200 MHz) δ: 2.294(6H,s), 2.580(2H,br s), 3.485(2H,br s), 3.500–3.950(2H,m), 4.400–4.700(2H,m), 6.102(1H,s), 6.608(2H,s), 7.147–7.356(8H,m)

IR (neat): 2939, 2858, 2777, 1632, 1429, 1236, 1092, 1043, 1016, 885, 737 cm$^{-1}$ b) Synthesis of (Z)-N,N-dimethyl-[6-(4-chlorostilbene-4'-carbonyl)-4,5,6,7-tetrahydrofuro[2,3-c]pyridin-2-ylmethyl]amine hydrochloride (Z)-N,N-dimethyl-[6-(4-chlorostilbene-4'-carbonyl)-4,5,6,7-tetrahydrofuro[2,3-c]pyridin-2-ylmethyl]amine 0.348 g was dissolved in 2 ml of methanol; hydrogen chloride in ethyl acetate was added in excess, followed by stirring. This mixture was then concentrated and washed with diethyl ether to yield the desired product.

White solid Yield 0.334 g $^1$H-NMR (CD$_3$OD, 200 MHz) δ: 2.588–2.661(2H,m), 2.863(6H,s), 3.634–4.000(2H,m), 4.374(2H,s), 4.550–4.746 (2H,m), 6.654(1H,s), 6.700(2H,s), 7.162–7.341(8H,m)

IR (nujol): 2661, 2474, 1647, 1234, 1090, 949, 829, 739 cm$^{-1}$

Anal. Calcd for C$_{25}$H$_{26}$Cl$_2$N$_2$O$_2$·0.5H$_2$O: C, 64,38; H, 5.83; N, 6.01. Found: C, 64.68; H, 5.73; N, 5.92.

EXAMPLE 93

Synthesis of (Z)-6-(4-chlorostilbene-4'-carbonyl)-2-(1-pyrrolidinylmethyl)-4,5,6,7-tetrahydrofuro[2,3-c]pyridine hydrochloride a) Synthesis of (Z)-6-(4-chlorostilbene-4'-carbonyl)-4,5,6,7-tetrahydrofuro[2,3-c]pyridine To a solution of 1.173 g (7.349 mmol) of 4,5,6,7-tetrahydrofuro[2,3-c]pyridine hydrochloride, 1.90 g (7.35 mmol) of (Z)-4-chloro-4'-stilbenecarboxylic acid and 4.10 ml (29.4 mmol) of triethylamine in 30 ml of N,N-dimethylformamide, 1.34 ml (8.82 mmol) of diethyl cyanophosphonate was added dropwise, followed by overnight stirring at room temperature. This mixture was poured into water and extracted with diethyl ether 3 times. The combined organic layer was dried over anhydrous sodium sulfate; the solvent was distilled off under reduced pressure. The resulting crude product was purified by silica gel column chromatography (hexane/ethyl acetate=6/1 to 3/1) to yield the desired product.

Yellow oil Yield 2.528 g (95%)

$^1$H-NMR (CDCl$_3$, 200 MHz) δ: 2.597(2H,br s), 3.612 (1.2H,br s), 3.930(0.8H,br s), 4.497(0.8H,br s), 4.725(1.2H, br s), 6.278(1H,d,J=1.8 Hz), 6.609(2H,s), 7.176(2H,d,J=8.8 Hz), 7.209(2H,d,J=7.8 Hz), 7.279(2H,d,J=8.8 Hz), 7.342 (2H,d,J=8.4 Hz)

IR (neat): 2927, 2852, 1630, 1423, 1265, 1232, 1092, 1039, 887, 827, 735 cm$^{-1}$ b) Synthesis of (Z)-6-(4-chlorostilbene-4'-carbonyl)-2-(1-(pyrrolidinylmethyl)-4,5,6,7-tetrahydrofuro[2,3-c]pyridine To a solution of 0.867 g (2.383 mmol) of (Z)-6-(4-chlorostilbene-4'-carbonyl)-4,5,6,7-tetrahydrofuro[2,3-c]pyridine in 10 ml of acetic acid, 0.30 ml (3.57 mmol) of pyrrolidine and 0.29 g (3.57 mmol) of 37% aqueous formaldehyde were added, followed by stirring at 100° C. for 1 hour. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.768 g (72%)

$^1$H-NMR (CDCl$_3$, 200 MHz) δ: 1.797(4H,br s), 2.544 (4H,br s), 3.581(3.2H,br s), 3.916(0.8H,br s), 4.469(0.8H,br s), 4.704(1.2H,br s), 6.065(1H,s), 6.601(2H,s), 7.178(2H,d, J=7.8 Hz), 7.209(2H,d,J=7.8 Hz), 7.266(2H,d,J=8.8 Hz), 7.328(2H,d,J=8.4 Hz)

IR (neat): 2964, 2789, 1632, 1423, 1281, 1236, 1111, 1092, 1043, 883, 824 cm$^{-1}$ c) Synthesis of (Z)-6-(4-chlorostilbene-4'-carbonyl)-2-(1-pyrrolidinylmethyl)-4,5,6,7-tetrahydrofuro[2,3-c]pyridine hydrochloride (Z)-6-(4-Chlorostilbene-4'-carbonyl)-2-(1-pyrrolidinylmethyl)-4,5,6,7-tetrahydrofuro[2,3-c]pyridine 0.768 g was dissolved in 2 ml of methanol; hydrogen chloride in methanol was added in excess, followed by stirring. This mixture was concentrated to yield the desired product.

Pale yellow foam Yield 0.822 g $^1$H-NMR (CD$_3$OD, 200 MHz) δ: 1.975–2.143(4H,m), 2.605(2H,br s), 3.209(2H,br s), 3.513–3.727(3.2H,m), 3.958 (0.8H,br s), 4.440(2H,br s), 4.568(0.8H,br s), 4.722(1.2H,br s), 6.633(1H,s), 6.695(2H,s), 7.194(2H,d,J=7.6 Hz), 7.225 (2H,d,J=7.6 Hz), 7.336(4H,s)

IR (neat): 2953, 2588, 1626, 1427, 1230, 1090, 1045, 1014, 885, 827 cm$^{-1}$

Anal. Calcd for C$_{27}$H$_{28}$Cl$_2$N$_2$O$_2$·1.2H$_2$O: C, 64.21; H, 6.07; N, 5.55. Found: C, 64.35; H, 6.15; N, 5.81

EXAMPLE 94

Synthesis of (Z)-N,N-dimethyl-[5-(4-chlorostilbene-4'-carbonyl)-4,5,6,7-tetrahydrofuro[3,2-c]pyridin-2-ylmethyl]amine hydrochloride a) Synthesis of (Z)-N,N-dimethyl-[5-(4-chlorostilbene-4'-carbonyl)-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.285 g (1.1 mmol) of (Z)-4-chlorostilbene-4'-carboxylic acid and 0.5 ml (4.0 mmol) of triethylamine in 30 ml of dichloromethane, 0.245 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.134 g (32%)

$^1$H-NMR (CDCl$_3$, 200 MHz) δ: 2.289(6H,s), 2.730–2.794 (2H,m), 3.465(2H,s), 3.600–4.050(2H,m), 4.300–4.600(2H, m), 5.900–6.150(1H,m), 6.602(2H,s), 7.138–7.352(8H,m)

IR (neat): 2939, 2856, 2775, 1736, 1633, 1427, 1240, 1113, 1043, 1016, 885, 824 cm$^{-1}$ b) Synthesis of (Z)-N,N-dimethyl-[5-(4-chlorostilbene-4'-carbonyl)-4,5,6,7-tetrahydrofuro[3,2-c]pyridin-2-ylmethyl]amine hydrochloride (Z)-N,N-Dimethyl-[5-(4-chlorostilbene-4'-carbonyl)-4,5,6,7-tetrahydrofuro[3,2-c]pyridin-2-ylmethyl]amine 0.134 g was dissolved in 2 ml of methanol; hydrogen chloride in ethyl acetate was added in excess, followed by stirring. This mixture was concentrated and washed with diethyl ether to yield the desired product.

Brown solid Yield 0.133 g $^1$H-NMR (CD$_3$OD, 200 MHz) δ: 2.857(8H,br s), 3.702–3.766(0.9H,m), 4.022–4.063(1.1H,m), 4.361(2H,br s), 4.401–4.651(2H,m), 6.500–6.600(1H,m), 6.698(2H,s), 7.160–7.382(8H,m)

IR (nujol): 2582, 2476, 1633, 1267, 1111, 951, 829, 737 cm$^{-1}$

Anal. Calcd for C$_{25}$H$_{26}$Cl$_2$N$_2$O$_2$·0.3H$_2$O: C, 64.88; H, 5.79; N, 6.05. Found: C, 64.84; H, 5.66; N, 6.13.

EXAMPLE 95

Synthesis of (Z)-N,N-dimethyl-[6-(3-chlorostilbene-4'-carbonyl)-4,5,6,7-tetrahydrofuro[2,3-c]pyridin-2-ylmethyl]amine hydrochloride a) Synthesis of (Z)-N,N-dimethyl-[6-(3-chlorostilbene-4'-carbonyl)-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.569 g (2.2 mmol) of (Z)-3-chlorostilbene-4'-carboxylic acid and 1.1 ml (8.0 mmol) of triethylamine in 30 ml of dichloromethane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.538 g (64%)

$^1$H-NMR (CDCl$_3$, 200 MHz) δ: 2.262(6H,s), 2.529–2.565 (2H,m), 3.410(2H,br s), 3.560–3.595(1.2H,m), 3.900–4.000 (0.8H,m), 4.450–4.550(0.8H,m), 4.692–4.716(1.2H,m), 6.075(1H,s), 6.555–6.694(2H,m), 7.100–7.357(8H,m)

IR (neat): 2937, 2854, 2775, 1738, 1633, 1427, 1238, 1043, 851, 683 cm$^{-1}$ b) Synthesis of (Z)-N,N-dimethyl-[6-(3-chlorostilbene-4'-carbonyl)-4,5,6,7-tetrahydrofuro[2,3-c]pyridin-2-ylmethyl]amine hydrochloride (Z)-N,N-Dimethyl-[6-(3-chlorostilbene-4'-carbonyl)-4,5,6,7-tetrahydrofuro[2,3-c]pyridin-2-ylmethyl]amine 0.538 g was dissolved in 2 ml of methanol; hydrogen chloride in ethyl acetate was added in excess, followed by stirring. This mixture was concentrated to yield the desired product.

Brown foam Yield 0.569 g $^1$H-NMR (CD$_3$OD, 200 MHz) δ: 2.613(2H,br s), 2.868 (6H,s), 3.647(1.3H,br s), 3.900–4.000(0.7H,m), 4.387(2H, s), 4.500–4.600(0.7H,m), 4.743(1.3H,s), 6.665(1H,s), 6.731 (2H,d,J=3.2 Hz), 7.145–7.247(4H,m), 7.301–7.402(4H,m)

IR (nujol): 2665, 1622, 1161, 972, 851, 723 cm$^{-1}$

Anal. Calcd for C$_{25}$H$_{26}$Cl$_2$N$_2$O$_2$·0.7H$_2$O: C, 63.89; H, 5.88; N, 5.96. Found: C, 64.02; H, 6.14; N, 5.81

EXAMPLE 96

Synthesis of (Z)-N,N-dimethyl-(5-(3-chlorostilbene-4'-carbonyl)-4,5,6,7-tetrahydrofuro[3,2-c]pyridin-2-ylmethyl]amine hydrochloride a) Synthesis of (Z)-N,N-dimethyl-[5-(3-chlorostilbene-4'-carbonyl)-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.285 g (1.1 mmol) of (Z)-3-chlorostilbene-4'-carboxylic acid and 0.55 ml (4.0 mmol) of triethylamine in 30 ml of dichloromethane, 0.245 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 90 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.275 g (65%)

$^1$H-NMR (CDCl$_3$, 200 MHz) δ: 2.263(6H,s), 2.740(2H,br s), 3.404(2H,s), 3.600–3.700(1.1H,m), 4.000–4.100(0.9H, m), 4.600–4.700(0.9H,m), 4.597(1.1H,br s), 5.919(0.5H,br s), 6.101(0.5H,br s), 6.550–6.700(2H,m), 7.105–7.357(8H, m)

IR (neat): 2939, 2858, 2775, 1738, 1633, 1427, 1240, 1113, 851, 793, 683 cm$^{-1}$ b) Synthesis of (Z)-N,N-dimethyl-[5-(3-chlorostilbene-4'-carbonyl)-4,5,6,7-tetrahydrofuro[3,2-c]pyridin-2-ylmethyl)amine hydrochloride (Z)-N,N-dimethyl-[5-(3-chlorostilbene-4'-carbonyl)-4,5,6,7-tetrahydrofuro[3,2-c]pyridin-2-ylmethyl]amine 0.275 g was dissolved in 2 ml of methanol; hydrogen chloride in ethyl acetate was added in excess, followed by stirring. This mixture was concentrated to yield the desired product.

Pale brown foam Yield 0.281 g $^1$H-NMR (CD$_3$OD, 200 MHz) δ: 2.860(8H,br s), 3.729 (1.1H,br s), 4.000–4.100(0.9H,br s), 4.369–4.400(2.9H,m), 4.626(1.1H,br s), 6.450–6.500(0.5H,m), 6.661–6.800(2.5H, m), 7.126–7.254(4H,m), 7.285–7.398(4H,m)

IR (nujol): 2666, 1622, 1113, 851, 723 cm$^{-1}$

Anal. Calcd for C$_{25}$H26Cl$_2$N$_2$O$_2$·0.6H$_2$O: C, 64.13; H, 5.86; N, 5.98. Found: C, 64.05; H, 6.06; N, 5.87.

EXAMPLE 97

Synthesis of (Z)-N,N-dimethyl-[6-(2-chlorostilbene-4'-carbonyl)-4,5,6,7-tetrahydrofuro[2,3-c]pyridin-2-ylmethyl]amine hydrochloride a) Synthesis of (Z)-N,N-dimethyl-[6-(2-chlorostilbene-4'-carbonyl)-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.569 g (2.2 mmol) of (Z)-2-chlorostilbene-4'-carboxylic acid and 1.1 ml (8.0 mmol) of triethylamine in 30 ml of dichloromethane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.602 g (72%)

$^1$H-NMR (CDCl$_3$, 200 MHz) δ: 2.260(6H,s), 2.467–2.612 (2H,m), 3.406(2H,br s), 3.521–3.567(1.1H,m), 3.905–3.952 (0.9H,m), 4.423–4.455(0.9H,m), 4.652–4.692(1.1H,m), 6.070(1H,s), 6.667–6.802(2H,m), 7.023–7.306(7H,m), 7.415(1H,dd,J=3.9&6.6 Hz)

IR (neat): 2937, 2854, 2773, 1738, 1633, 1427, 1238, 1045, 845, 743 cm$^{-1}$ b) Synthesis of (Z)-N,N-dimethyl-[6-(2-chlorostilbene-4'-carbonyl)-4,5,6,7-tetrahydrofuro[2,3-c]pyridin-2-ylmethyl]amine hydrochloride (Z)-N,N-Dimethyl-[6-(2-chlorostilbene-4'-carbonyl)-4,5,6,7-tetrahydrofuro[2,3-c]pyridin-2-ylmethyl]amine 0.602 g was dissolved in 2 ml of methanol; hydrogen chloride in ethyl acetate was added in excess, followed by stirring. This mixture was concentrated to yield the desired product.

Yellow foam Yield 0.597 g $^1$H-NMR (CD$_3$OD, 200 MHz) δ: 2.597(2H,br s), 2.860 (6H,s), 3.623(1.2H,br s), 3.933(0.8H,br s), 4.377(2H,s), 4.526(0.8H,br s), 4.710(1.2H,br s), 6.652(1H,s), 6.795(2H, s), 7.107–7.333(7H,m), 7.454(1H,d,J=8.2 Hz)

IR (nujol): 2467, 1622, 1163, 1045, 941, 741 cm$^{-1}$

Anal. Calcd for C$_{25}$H$_{26}$Cl$_2$N$_2$O$_2$.1.0H$_2$O: C, 63.16; H, 5.94; N, 5.89. Found: C, 63.30; H, 5.95; N, 5.94

EXAMPLE 98

Synthesis of (Z)-N,N-dimethyl-[5-(2-chlorostilbene-4'-carbonyl)-4,5,6,7-tetrahydrofuro[3,2-c]pyridin-2-ylmethyl]amine hydrochloride a) Synthesis of (Z)-N,N-dimethyl-[5-(2-chlorostilbene-4'-carbonyl)-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.285 g (1.1 mmol) of (Z)-2-chlorostilbene-4'-carboxylic acid and 0.55 ml (4.0 mmol) of triethylamine in 30 ml of dichloromethane, 0.245 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

White crystal Yield 0.304 g (72%)

$^1$H-NMR (CDCl$_3$, 200 MHz) δ: 2.282(6H,s), 2.740(2H,br s), 3.450(2H,s), 3.648(1.2H,br s), 3.850(0.8H,br s), 4.279–4.334(0.8H,m), 4.547–4.574(1.2H,m), 5.927–6.108 (1H,m), 6.665–6.801(2H,m), 7.012–7.439(1H,m)

IR (KBr): 2968, 2935, 2816, 2771, 1616, 1433, 1223, 1047, 843, 758 cm$^{-1}$ b) Synthesis of (Z)-N,N-dimethyl-[5-(2-chlorostilbene-4'-carbonyl)-4,5,6,7-tetrahydrofuro[3,2-c]pyridin-2-ylmethyl]amine hydrochloride (Z)-N,N-Dimethyl-[5-(2-chlorostilbene-4'-carbonyl)-4,5,6,7-tetrahydrofuro[3,2-c]pyridin-2-ylmethyl]amine 0.304 g was dissolved in 2 ml of methanol; solution of in hydrogen chloride in ethyl acetate was added in excess, followed by stirring. This mixture was concentrated to yield the desired product.

Pale yellow powder Yield 0.302 g $^1$H-NMR (CD$_3$OD, 200 MHz) δ: 2.767–2.856(8H,m), 3.681–3.700(1.1H,m), 4.024–4.045(0.9H,m), 4.367–4.607 (4H,m), 6.516–6.688(1H,m), 6.791(2H,s), 7.070–7.298(7H, m), 7.430–7.474(1H,m)

IR (nujol): 2663, 1620, 1113, 1045, 939, 721 cm$^{-1}$

Anal. Calcd for C$_{25}$H$_{26}$Cl$_2$N$_2$O$_2$.0.5H$_2$O: C, 64.38; H, 5.83; N, 6.01. Found: C, 64.18; H, 6.00; N, 6.01.

EXAMPLE 99

Synthesis of (Z)-N,N-dimethyl-[6-[3,5-bis (trifluoromethyl)stilbene-4'-carbonyl]-4,5,6,7-tetrahydrofuro[2,3-c]pyridin-2-ylmethyl]amine hydrochloride a) Synthesis of (Z)-N,N-dimethyl-[6-[3,5-bis (trifluoromethyl)stilbene-4'-carbonyl]-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.793 g (2.2 mmol) of (Z)-3,5-bis(trifluoromethyl)stilbene-4'-carboxylic acid and 1.1 ml (8.0 mmol) of triethylamine in 30 ml of dichloromethane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.694 g (66%)

$^1$H-NMR (CDCl$_3$, 200 MHz) δ: 2.274(6H,s), 2.483–2.509 (2H,m), 3.430(2H,s), 3.531–3.548(1.3H,m), 3.900–3.970

(0.7H,m), 4.350–4.450(0.7H,m), 4.712–4.722(1.3H,m), 6.084(1H,s), 6.682(1H,d,J=12.2 Hz), 6.871(1H,d,J=12.0 Hz), 7.225–7.385(4H,m), 7.649(2H,s), 7.702(1H,s)

IR (neat): 2943, 2860, 2774, 1740, 1633, 1429, 1363, 1281, 1180, 1136, 897, 683 cm$^{-1}$ b) Synthesis of (Z)-N,N-dimethyl-[6-[3,5-bis(trifluoromethyl)stilbene-4'-carbonyl]-4,5,6,7-tetrahydrofuro[2,3-c]pyridin-2-ylmethyl]amine hydrochloride (Z)-N,N-Dimethyl-[6-[3,5-bis(trifluoromethyl)stilbene-4'-carbonyl]-4,5,6,7-tetrahydrofuro[2,3-c]pyridin-2-ylmethyl]amine 0.694 g was dissolved in 2 ml of methanol; hydrogen chloride in ethyl acetate was added in excess, followed by stirring. This mixture was concentrated and washed with hexane to yield the desired product.

Pale brown solid Yield 0.688 g $^1$H-NMR (CD$_3$OD, 200 MHz) δ: 2.556–2.684(2H,m), 2.875(6H,br s), 3.614–3.637(1.4H,m), 3.900–4.000(0.6H,m), 4.392(2H,br s), 4.500–4.600(0.6H,m), 4.723–4.759 (1.4H,m), 6.671(1H,s), 6.857(1H,d,J=12.2 Hz), 6.995(1H,d,J=12.2 Hz), 7.389(4H,q,J=8.5 Hz), 7.762(2H,s), 7.802(1H,s)

IR (nujol): 2669, 1628, 1279, 1130, 897 cm$^{-1}$

Anal. Calcd for C$_{27}$H$_{25}$ClF$_6$N$_2$O$_2$.0.5H$_2$O: C, 57.10; H, 4.61; N, 4.93. Found: C, 57.26; H, 4.76; N, 4.85.

EXAMPLE 100

Synthesis of (Z)-N,N-dimethyl-[5-[3,5-bis(trifluoromethyl)stilbene-4'-carbonyl]-4,5,6,7-tetrahydrofuro[3,2-c]pyridin-2-ylmethyl]amine hydrochloride a) Synthesis of (Z)-N,N-dimethyl-[5-[3,5-bis(trifluoromethyl)stilbene-4'-carbonyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.396 g (1.1 mmol) of (Z)-3,5-bis(trifluoromethyl)stilbene-4'-carboxylic acid and 0.55 ml (4.0 mmol) of triethylamine in 30 ml of dichloromethane, 0.245 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.300 g (57%)

$^1$H-NMR (CDCl$_3$, 200 MHz) δ: 2.281(6H,s), 2.738–2.805 (2H,m), 3.442(2H,s), 3.614–3.650(1.1H,m), 4.032–4.072 (0.9H,m), 4.255–4.264(0.9H,m), 4.550–4.607(1.1H,m), 5.928–5.935(0.5H,m), 6.123–6.128(0.5H,m), 6.685(1H,d,J=12.0 Hz), 6.881(1H,d,J=12.0 Hz), 7.250(2H,d,J=9.4 Hz), 7.365(2H,d,J=8.2 Hz), 7.639(2H,s), 7.703(1H,s)

IR (neat): 2943, 2860, 2779, 1740, 1647, 1429, 1363, 1281, 1180, 1136, 1043, 897, 704 cm$^{-1}$ b) Synthesis of (Z)-N,N-dimethyl-[5-[3,5-bis(trifluoromethyl)stilbene-4'-carbonyl]-4,5,6,7-tetrahydrofuro[3,2-c]pyridin-2-ylmethyl]amine hydrochloride (Z)-N,N-Dimethyl-[5-[3,5-bis(trifluoromethyl)stilbene-4'-carbonyl]-4,5,6,7-tetrahydrofuro[3,2-c]pyridin-2-ylmethyl]amine 0.300 g was dissolved in 2 ml of methanol; hydrogen chloride in ethyl acetate was added in excess, followed by stirring. This mixture was concentrated and washed with hexane to yield the desired product.

Pale yellow solid Yield 0.266 g $^1$H-NMR (CD$_3$OD, 200 MHz) δ: 2.778–2.867(8H,m), 3.635–3.750(1.2H,m), 4.048–4.068(0.8H,m), 4.381(2.8H,br s), 4.642(1.2H,br s), 6.470–6.491(0.5H,m), 6.702(0.5H,br s), 6.854(1H,d,J=12.2 Hz), 6.995(1H,d,J=12.2 Hz), 7.304–7.491(4H,m), 7.758(2H,s), 7.799(1H,s)

IR (nujol): 2671, 1633, 1130, 897, 721 cm$^{-1}$

Anal. Calcd for C$_{27}$H$_{25}$ClF$_6$N$_2$O$_2$.0.5H$_2$O: C, 57.10; H, 4.61; N, 4.93. Found: C, 57.07; H, 4.89; N, 4.80.

EXAMPLE 101

Synthesis of (Z)-N,N-dimethyl-[6-[5-(2-phenylethenyl)thiophene-2-carbonyl]-4,5,6,7-tetrahydrofuro[2,3-c]pyridin-2-ylmethyl]amine hydrochloride a) Synthesis of (Z)-N,N-dimethyl-[6-[5-(2-phenylethenyl)thiophene-2-carbonyl]-4,5,6,7-tetrahydrofuro[2,3-c]pyridin-2-ylmethyl]amine To a solution of 0.160 g (1.000 mmol) of 4,5,6,7-tetrahydrofuro[2,3-c]pyridine hydrochloride, 0.230 g (1.0 mmol) of (Z)-5-(2-phenylethenyl)thiophene-2-carboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow-brown oil Yield 0.157 g (40%)

$^1$H-NMR (CDCl$_3$, 200 MHz) δ: 2.260(6H,s), 2.506–2.570 (2H,m), 3.412(2H,s), 3.817(2H,t,J=5.7 Hz), 4.647(2H,s), 6.067(1H,s), 6.673(2H,d,J=1.6 Hz), 6.887(1H,d,J=3.6 Hz), 7.130(1H,d,J=4.0 Hz), 7.319–7.362(5H,m)

IR (neat): 2935, 2854, 2773, 1734, 1618, 1444, 1415, 1225, 1028, 814, 700 cm$^{-1}$ b) Synthesis of (Z)-N,N-dimethyl-[6-[5-(2-phenylethenyl)thiophene-2-carbonyl]-4,5,6,7-tetrahydrofuro[2,3-c]pyridin-2-ylmethyl]amine hydrochloride (Z)-N,N-Dimethyl-[6-[5-(2-phenylethenyl)thiophene-2-carbonyl]-4,5,6,7-tetrahydrofuro[2,3-c]pyridin-2-ylmethyl]amine 0.157 g was dissolved in methanol; hydrogen chloride in ethyl acetate was added in excess, followed by stirring. This mixture was concentrated, and recrystallized from methanol-diethyl ether to yield the desired product.

Brown solid Yield 0.146 g $^1$H-NMR (CD$_3$OD, 200 MHz) δ: 2.607(2H,t,J=5.3 Hz), 2.852(6H,s), 3.861(2H,t,J=5.7 Hz), 4.361(2H,s), 4.687(2H,s), 6.645(1H,s), 6.761(2H,s), 7.007(1H,d,J=4.0 Hz), 7.276 (1H,d,J=4.0 Hz), 7.332–7.362(5H,m)

IR (nujol): 2578, 1616, 1225, 1045, 947, 822, 702 cm$^{-1}$

Anal. Calcd for $C_{23}H_{25}ClN_2O_2S \cdot 0.5H_2O$: C, 63.07; H, 5.98; N, 6.40. Found: C, 63.21; H, 5.88; N, 6.25.

EXAMPLE 102

Synthesis of (Z)-N,N-dimethyl-[5-[5-(2-phenylethenyl)thiophene-2-carbonyl]-4,5,6,7-tetrahydrofuro[3,2-c]pyridin-2-ylmethyl]amine hydrochloride a) Synthesis of (Z)-N,N-dimethyl-[5-[5-(2-phenylethenyl)thiophene-2-carbonyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.230 g (1.0 mmol) of (Z)-5-(2-phenylethenyl)thiophene-2-carboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid and 10 ml of dichloromethane; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=4/1) to yield the desired product.

Yellow oil Yield 0.095 g (24%)

$^1$H-NMR (CDCl$_3$, 200 MHz) δ: 2.277(6H,s), 2.743(2H,t,J=5.6 Hz), 3.443(2H,s), 3.888(2H,t,J=5.6 Hz), 4.514(2H,s), 6.037(1H,s), 6.670(2H,d,J=1.0 Hz), 6.894(1H,d,J=3.8 Hz), 7.142(1H,d,J=4.0 Hz), 7.343(5H,s)

IR (neat): 2933, 2858, 2777, 1614, 1454, 1417, 1236, 1101, 1026, 814, 698 cm$^{-1}$ b) Synthesis of (Z)-N,N-dimethyl-[5-[5-(2-phenylethenyl)thiophene-2-carbonyl]-4,5,6,7-tetrahydrofuro[3,2-c]pyridin-2-ylmethyl]amine hydrochloride (Z)-N,N-Dimethyl-[5-[5-(2-phenylethenyl)thiophene-2-carbonyl]-4,5,6,7-tetrahydrofuro[3,2-c]pyridin-2-ylmethyl]amine 0.095 g was dissolved in 2 ml of methanol; hydrogen chloride in ethyl acetate was added in excess, followed by stirring. This mixture was concentrated, and recrystallized from methanol-diethyl ether to yield the desired product.

Brown solid Yield 0.069 g $^1$H-NMR (CD$_3$OD, 200 MHz) δ: 2.771–2.852(8H,m), 3.947(2H,t,J=5.9 Hz), 4.352(2H,s), 4.583(2H,s), 6.603(1H,s), 6.761(2H,s), 7.003(1H,d,J=4.2 Hz), 7.273(1H,d,J=4.0 Hz), 7.319–7.360(5H,m)

IR (nujol): 2474, 1606, 1236, 1103, 818, 698 cm$^{-1}$

Anal. Calcd for $C_{23}H_{25}ClN_2O_2S \cdot 1.0H_2O$: C, 61.80; H, 6.09; N, 6.27. Found: C, 61.82; H, 6.38; N, 6.00

EXAMPLE 103

Synthesis of (E)-N,N-dimethyl-[6-[5-(2-phenylethenyl)thiophene-2-carbonyl]-4,5,6,7-tetrahydrofuro[2,3-c]pyridin-2-ylmethyl]amine hydrochloride a) Synthesis of (E)-N,N-dimethyl-[6-[5-(2-phenylethenyl)thiophene-2-carbonyl]-4,5,6,7-tetrahydrofuro[2,3-c]pyridin-2-ylmethyl]amine To a solution of 0.160 g (1.000 mmol) of 4,5,6,7-tetrahydrofuro[2,3-c]pyridine hydrochloride, 0.253 g (1.1 mmol) of (E)-5-(2-phenylethenyl)thiophene-2-carboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.165 g (42%)

$^1$H-NMR (CDCl$_3$, 200 MHz) δ: 2.272(6H,s), 2.646(2H,t,J=5.6 Hz), 3.431(2H,s), 3.924(2H,t,J=5.6 Hz), 4.754(2H,s), 6.100(1H,s), 6.956–7.148(3H,m), 7.258–7.507(6H,m)

IR (neat): 2926, 2845, 2756, 1612, 1449, 1417, 1024, 951, 748 cm$^{-1}$ b) Synthesis of (E)-N,N-dimethyl-[6-[5-(2-phenylethenyl)thiophene-2-carbonyl]-4,5,6,7-tetrahydrofuro[2,3-c]pyridin-2-ylmethyl]amine hydrochloride (E)-N,N-Dimethyl-[6-[5-(2-phenylethenyl)thiophene-2-carbonyl]-4,5,6,7-tetrahydrofuro[2,3-c]pyridin-2-ylmethyl]amine 0.165 g was dissolved in 2 ml of methanol; hydrogen chloride in ethyl acetate was added in excess, followed by stirring. This mixture was concentrated and washed with diethyl ether to yield the desired product.

Brown solid Yield 0.137 g $^1$H-NMR (CD$_3$OD, 200 MHz) δ: 2.680–2.741(2H,m), 2.866(6H,s), 3.977(2H,t,J=5.6 Hz), 4.375(2H,s), 4.793(2H,s), 6.674(1H,s), 7.033–7.183(2H,m), 7.295–7.425(5H,m), 7.521–7.562(2H,m)

IR (nujol): 2663, 1603, 1230, 964, 818, 758 cm$^{-1}$

Anal. Calcd for $C_{23}H_{25}ClN_2O_2S \cdot 0.5H_2O$: C, 63.07; H, 5.98; N, 6.40. Found: C, 63.21; H, 6.23; N, 6.32

EXAMPLE 104

Synthesis of (E)-N,N-dimethyl-[5-[5-(2-phenylethenyl)thiophene-2-carbonyl]-4,5,6,7-tetrahydrofuro[3,2-c]pyridin-2-ylmethyl]amine hydrochloride a) Synthesis of (E)-N,N-dimethyl-[5-[5-(2-phenylethenyl)thiophene-2-carbonyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.253 g (1.1 mmol) of (E)-5-(2-phenylethenyl)thiophene-2-carboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid and 10 ml of dichloromethane; 0.135 ml (1.50 mmol) of 50% aqueous dimethylamine and 0.122 ml (1.50 mmol) of 37% aqueous formaldehyde were added, followed by stirring at 100° C. for 100 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow solid Yield 0.124 g (32%)

$^1$H-NMR (CDCl$_3$, 200 MHz) δ: 2.277(6H,s), 2.826–2.881 (2H,m), 3.433(2H,s), 3.999(2H,t,J=5.7 Hz), 4.621(2H,s), 6.061(1H,s), 6.957–7.153(3H,m), 7.233–7.501(6H,m)

IR (neat): 2937, 2859, 2773, 1612, 1454, 1419, 1279, 1101, 1026, 951, 804, 733 cm$^{-1}$ b) Synthesis of (E)-N,N-dimethyl-[5-[5-(2-phenylethenyl) thiophene-2-carbonyl]-4,5,6,7-tetrahydrofuro[3,2-c] pyridin-2-ylmethyl]amine hydrochloride (E)-N,N-Dimethyl-[5-[5-(2-phenylethenyl)thiophene-2-carbonyl]-4,5,6,7-tetrahydrofuro[3,2-c]pyridin-2-ylmethyl] amine 0.124 g was dissolved in 2 ml of methanol; hydrogen chloride in ethyl acetate was added in excess, followed by stirring. This mixture was concentrated and washed with diethyl ether to yield the desired product.

Brown solid Yield 0.122 g $^1$H-NMR (CD$_3$OD, 200 MHz) δ: 2.864(6H,s), 2.850–2.900(2H,m), 4.050(2H,t,J=5.6 Hz), 4.371(2H,s), 4.692(2H,s), 6.646(1H,s), 7.028–7.181(2H,m), 7.266–7.423 (5H,m), 7.536(2H,d,J=6.8 Hz)

IR (nujol): 2459, 1597, 1234, 949, 813, 743 cm$^{-1}$

Anal. Calcd for C$_{23}$H$_{25}$ClN$_2$O$_2$S.0.3H$_2$O: C, 63.60; H, 5.94; N, 6.45. Found: C, 63.57; H, 5.74; N, 6.37

EXAMPLE 105

Synthesis of N,N-dimethyl-[6-(9-fluorenone-2-carbonyl)-4,5,6,7-tetrahydrofuro[2,3-c]pyridin-2-ylmethyl]amine hydrochloride a) Synthesis of N,N-dimethyl-[6-(9-fluorenone-2-carbonyl)-4,5,6,7-tetrahydrofuro[2,3-c]pyridin-2-ylmethyl]amine To a solution of 0.160 g (1.000 mmol) of 4,5,6,7-tetrahydrofuro[2,3-c]pyridine hydrochloride, 0.246 g (1.1 mmol) of 9-fluorenone-2-carboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. This mixture was poured into water, followed by 2 extractions with dichloromethane. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with dichloromethane 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.188 g (49%)

$^1$H-NMR (CDCl$_3$, 200 MHz) δ: 2.319(6H,s), 2.651(2H,br s), 3.480(2H,s), 3.650–4.000(2H,m), 4.611–4.781(2H,m), 6.146(1H,s), 7.398(1H,td,J=1.8&7.0 Hz), 7.538–7.766(6H, m)

IR (neat): 2937, 2856, 2775, 1716, 1618, 1433, 1246, 1190, 1043, 742 cm$^{-1}$ b) Synthesis of N,N-dimethyl-(6-(9-fluorenone-2-carbonyl)-4,5,6,7-tetrahydrofuro[2,3-c]pyridin-2-ylmethyl] amine hydrochloride N,N-Dimethyl-[6-(9-fluorenone-2-carbonyl)-4,5,6,7-tetrahydrofuro[2,3-c]pyridin-2-ylmethyl]amine 0.188 g was dissolved in 2 ml of methanol; hydrogen chloride in ethyl acetate was added in excess, followed by stirring. This mixture was concentrated; the resulting solid was washed with diethyl ether to yield the desired product.

Yellow solid Yield 0.162 g $^1$H-NMR (CD$_3$OD, 200 MHz) δ: 2.635–2.661(2H,m), 2.871(6H,s), 3.630–4.000(2H,m), 4.381(2H,s), 4.648–4.900 (2H,m), 6.672(1H,s), 7.407(1H,dt,J=1.0&7.4 Hz), 7.591 (1H,dd,J=1.2 Hz,J=7.4 Hz), 7.643–7.824(5H,m)

IR (nujol): 2669, 1714, 1616, 1250, 1190, 941, 741 cm$^{-1}$

Anal. Calcd for C$_{24}$H$_{23}$ClN$_2$O$_3$.1.5H$_2$O: C, 64.07; H, 5.82; N, 6.23. Found: C, 64.23; H, 5.95; N, 6.02.

EXAMPLE 106

Synthesis of N,N-dimethyl-[5-(9-fluorenone-2-carbonyl)-4,5,6,7-tetrahydrofuro[3,2-c]pyridin-2-ylmethyl]amine hydrochloride a) Synthesis of N,N-dimethyl-[5-(9-fluorenone-2-carbonyl)-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.246 g (1.1 mmol) of 9-fluorenone-2-carboxylic acid and 0.55 ml (4.0 mmol) of triethylamine in 30 ml of dichloromethane, 0.24 g (1.5 mmol) of diethyl cyanophosphonate was added dropwise under ice-cooling, followed by overnight stirring at room temperature. After the solvent was distilled off under reduced pressure, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.186 g (48%)

$^1$H-NMR (CDCl$_3$, 200 MHz) δ: 2.284(6H,s), 2.808(2H,br s), 3.444(2H,s), 3.656–4.100(2H,m), 4.363–4.621(2H,m), 5.900–6.100(1H,m), 7.353(1H,dt,J=1.8 & 7.0 Hz), 7.497–7.721(6H,m)

IR (neat): 2937, 2858, 2773, 1716, 1616, 1433, 1221, 1115, 750 cm$^{-1}$ b) Synthesis of N,N-dimethyl-[5-(9-fluorenone-2-carbonyl)-4,5,6,7-tetrahydrofuro[3,2-c]pyridin-2-ylmethyl amine hydrochloride N,N-Dimethyl-[5-(9-fluorenone-2-carbonyl)-4,5,6,7-tetrahydrofuro[3,2-c]pyridin-2-ylmethyl]amine 0.186 g was dissolved in 2 ml of methanol; hydrogen chloride in ethyl acetate was added in excess, followed by stirring. This mixture was concentrated; the resulting solid was washed with diethyl ether to yield the desired product.

Yellow solid Yield 0.193 g $^1$H-NMR (CD$_3$OD, 200 MHz) δ: 2.868(6H,s), 3.700–4.100(2H,m), 4.370(2H,s), 4.500–4.900(2H,m), 6.500–6.800(1H,m), 7.409(1H,t,J=7.3 Hz), 7.574–7.820 (6H,m)

IR (nujol): 2669, 1714, 1614, 1248, 1117, 939, 737 cm$^{-1}$

Anal. Calcd for $C_{24}H_{23}ClN_2O_3 \cdot 1.8H_2O$: C, 63.31; H, 5.89; N, 6.15. Found: C, 63.58; H, 5.94; N, 5.89.

EXAMPLE 107

Synthesis of N,N-dimethyl-[6-(2-fluorenecarbonyl)-4,5,6,7-tetrahydrofuro[2,3-c]pyridin-2-ylmethyl]amine hydrochloride a) Synthesis of N,N-dimethyl-[6-(2-fluorenecarbonyl)-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.462 g (2.2 mmol) of 2-fluorenecarboxylic acid and 1.1 ml (8.0 mmol) of triethylamine in 30 ml of dichloromethonane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.432 g (58%)

$^1$H-NMR (CDCl$_3$, 200 MHz) δ: 2.250(6H,s), 2.543–2.643 (2H,m), 3.407(2H,s), 3.640–3.901(2H,m), 3.934(2H,s), 4.581–4.768(2H,m), 6.084(1H,s), 7.336–7.473(3H,m), 7.546–7.640(2H,m), 7.808(2H,d,J=7.4 Hz)

IR (neat): 2935, 2854, 2773, 1632, 1429, 1261, 1223, 1043, 748 cm$^{-1}$ b) Synthesis of N,N-dimethyl-[6-(2-fluorenecarbonyl)-4,5,6,7-tetrahydrofuro[2,3-c]pyridin-2-ylmethyl]amine hydrochloride N,N-Dimethyl-[6-(2-fluorenecarbonyl)-4,5,6,7-tetrahydrofuro[2,3-c]pyridin-2-ylmethyl]amine 0.432 g was dissolved in 2 ml of methanol; hydrogen chloride in ethyl acetate was added in excess, followed by stirring. This mixture was concentrated, and recrystallized from methanol-diethyl ether to yield the desired product.

Pale brown solid Yield 0.442 g $^1$H-NMR (CD$_3$OD, 200 MHz) δ: 2.619–2.828(2H,m), 2.866(6H,br s), 3.709–3.762(2H,m), 3.972(2H,s), 4.338–4.381(2H,m), 4.670–4.793(2H,m), 6.665(1H,s), 7.315–7.668(5H,m), 7.865–7.949(2H,m)

IR (nujol): 2565, 1622, 1263, 951, 750 cm$^{-1}$

Anal. Calcd for $C_{24}H_{25}ClN_2O_2 \cdot 0.5H_2O$: C, 68.97; H, 6.27; N, 6.70. Found: C, 68.84; H, 6.15; N, 6.65

EXAMPLE 108

Synthesis of (E)-N,N-dimethyl-[6-(2,3-diphenylpropenoyl)-4,5,6,7-tetrahydrofuro[2,3-c]pyridin-2-ylmethyl]amine hydrochloride a) Synthesis of (E)-N,N-dimethyl-[6-(2,3-diphenylpropenoyl)-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.493 g (2.2 mmol) of (E)-2,3-diphenylpropenoic acid and 1.1 ml (8.0 mmol) of triethylamine in 30 ml of dichloromethane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.509 g (66%)

$^1$H-NMR (CDCl$_3$, 200 MHz) δ: 2.043–2.598(2H,m), 2.252(6H,s), 3.391(2H,s), 3.677–3.870(2H,m), 4.389–4.694 (2H,m), 6.013(1H,br s), 6.793(1H,s), 7.088–7.286(10H,m)

IR (neat): 2937, 2854, 2775, 1632, 1427, 1225, 1174, 1020, 752, 696 cm$^{-1}$ b) Synthesis of (E)-N,N-dimethyl-[6-(2,3-diphenylpropenoyl)-4,5,6,7-tetrahydrofuro[2,3-c]pyridin-2-ylmethyl]amine hydrochloride (E)-N,N-Dimethyl-[6-(2,3-diphenylpropenoyl)-4,5,6,7-tetrahydrofuro[2,3-c]pyridin-2-ylmethyl]amine 0.509 g was dissolved in 2 ml of methanol; hydrogen chloride in ethyl acetate was added in excess, followed by stirring. This mixture was concentrated and washed with diethyl ether to yield the desired product.

Brown solid Yield 0.548 g $^1$H-NMR (CD$_3$OD, 200 MHz) δ: 2.188–2.700(2H,m), 2.847(6H,s), 3.790–3.825(2H,m), 4.350(2H,s), 4.647–4.675 (2H,m), 6.576(1H,s), 6.845(1H,s), 7.137–7.308(10H,m)

IR (nujol): 2472, 1614, 1227, 1171, 976, 937, 723, 696 cm$^{-1}$

Anal. Calcd for $C_{25}H_{27}ClN_2O_2 \cdot 0.5H_2O$: C, 69.51; H, 6.53; N, 6.49. Found: C, 69.42; H, 6.79; N, 6.30

EXAMPLE 109

Synthesis of (E)-N,N-dimethyl-[5-(2,3-diphenylpropenoyl)-4,5,6,7-tetrahydrofuro[3,2-c]pyridin-2-ylmethyl]amine hydrochloride a) Synthesis of (E)-N,N-dimethyl-[5-(2,3-diphenylpropenoyl)-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.247 g (1.1 mmol) of (E)-2,3-diphenylpropenoic acid and 0.5 ml (4.0 mmol) of triethylamine in 30 ml of dichloromethane, 0.245 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.241 g (62%)

$^1$H-NMR (CDCl$_3$, 200 MHz) δ: 2.255(6H,s), 2.308–2.800 (2H,m), 3.384(2H,s), 3.744–4.000(2H,m), 4.350–4.556(2H,m), 5.900–6.075(1H,m), 6.786(1H,br s), 7.113–7.203(5H,m), 7.253–7.393(5H,m)

IR (neat): 2939, 2856, 2775, 1632, 1429, 1221, 1126, 1016, 785, 698 cm$^{-1}$ b) Synthesis of (E)-N,N-dimethyl-[5-(2,3-diphenylpropenoyl)-4,5,6,7-tetrahydrofuro[3,2-c]pyridin-2-ylmethyl]amine hydrochloride (E)-N,N-Dimethyl-[5-(2,3-diphenylpropenoyl)-4,5,6,7-tetrahydrofuro[3,2-c]pyridin-2-ylmethyl]amine 0.241 g was dissolved in 2 ml of methanol; hydrogen chloride in ethyl acetate was added in excess, followed by stirring. This mixture was concentrated and washed with diethyl ether to yield the desired product.

White solid Yield 0.251 g $^1$H-NMR (CD$_3$OD, 200 MHz) δ: 2.351–2.383(1H,m), 2.700–2.800(1H,m), 2.838(6H,s), 2.870–3.969(2H,m), 4.337(2H,s), 4.553(2H,s), 6.500–6.652(1H,m), 6.841(1H,s), 7.133–7.303(10H,m)

IR (nujol): 2441, 1610, 1245, 1138, 976, 696 cm$^{-1}$

Anal. Calcd for C$_{25}$H$_{27}$ClN$_2$O$_2$.0.6H$_2$O: C, 69.23; H, 6.55; N, 6.46. Found: C, 69.16; H, 6.42; N, 6.44

EXAMPLE 110

Synthesis of N,N-dimethyl-[6-(1-benzoylpiperidine-4-carbonyl)-4,5,6,7-tetrahydrofuro[2,3-c]pyridin-2-ylmethyl]amine hydrochloride a) Synthesis of N,N-dimethyl-[6-(l-benzoylpiperidine-4-carbonyl)-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.513 g (2.2 mmol) of 1-benzoyl-4-piperidinecarboxylic acid and 1.1 ml (8.0 mmol) of triethylamine in 30 ml of N,N-dimethylformamide, 0.489 g (3.0 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=4/1) to yield the desired product.

Brown oil Yield 0.330 g (42%)

$^1$H-NMR (CDCl$_3$, 200 MHz) δ: 1.791–1.896(4H,m), 2.262(6H,s), 2.504–2.581(2H,m), 2.700–3.100(3H,m), 3.407(2H,s), 3.698(1H,t,J=5.5 Hz), 3.825(1H,t,J=5.7 Hz), 3.650–4.000(1H,m), 4.352(1H,s), 4.608(1H,s), 4.500–4.800(1H,m), 6.065(1H,s), 7.404(5H,s)

IR (neat): 2937, 2856, 2775, 1630, 1433, 1209, 1028, 912, 743 cm$^{-1}$ b) Synthesis of N,N-dimethyl-[6-(1-benzoylpiperidine-4-carbonyl)-4,5,6,7-tetrahydrofuro[2,3-c]pyridin-2-ylmethyl]amine hydrochloride N,N-Dimethyl-[6-(1-benzoylpiperidine-4-carbonyl)-4,5,6,7-tetrahydrofuro[2,3-c]pyridin-2-ylmethyl]amine 0.330 g was dissolved in 2 ml of methanol; hydrogen chloride in ethyl acetate was added in excess, followed by stirring. This mixture was concentrated and washed with diethyl ether to yield the desired product.

Brown solid Yield 0.324 g $^1$H-NMR (CD$_3$OD, 200 MHz) δ: 1.689–2.000(4H,m), 2.533–2.658(2H,m), 2.857(6H,s), 3.000–3.400(3H,m), 3.750–3.881(3H,m), 4.374(2H,s), 4.610–4.744(3H,m), 6.651(1H,s), 7.391–7.493(5H,m), IR (nujol): 2679, 1616, 1296, 1209, 937, 712 cm$^{-1}$ Anal. Calcd for C$_{23}$H$_{30}$ClN$_3$O$_3$.1.5H$_2$O: C, 60.19; H, 7.25; N, 9.16. Found: C, 60.43; H, 7.55; N, 9.39.

EXAMPLE 111

Synthesis of N,N-dimethyl-[5-(1-benzoylpiperidine-4-carbonyl)-4,5,6,7-tetrahydrofuro[3,2-c]pyridin-2-ylmethyl]amine hydrochloride a) Synthesis of N,N-dimethyl-[5-(1-benzoylpiperidine-4-carbonyl)-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.348 g (1.1 mmol) of 1-benzoyl-4-piperidinecarboxylic acid and 0.55 ml (4.0 mmol) of triethylamine in 30 ml of N,N-dimethylformamide, 0.245 g (1.5 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in acetic acid; 0.135 ml (1.50 mmol) of 50% aqueous dimethylamine and 0.122 ml (1.50 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=4/1 to 7/3) to yield the desired product.

Brown oil Yield 0.242 g (61%)

$^1$H-NMR (CDCl$_3$, 200 MHz) δ: 1.825–1.860(4H,m), 2.274(6H,d,J=2.0 Hz), 2.712–2.998(5H,m), 3.421(2H,s), 3.780(2H,t,J=5.6 Hz), 3.886–3.899(1H,m), 4.410–4.491 (2H,m), 4.650–4.700(1H,m), 6.075(1H,s), 7.411(5H,s)

IR (neat): 2939, 2858, 2775, 1630, 1433, 1292, 1222, 1126, 1012, 912, 733 cm$^{-1}$ b) Synthesis of N,N-dimethyl-[5-(1-benzoylpiperidine-4-carbonyl)-4,5,6,7-tetrahydrofuro[3,2-c]pyridin-2-ylmethyl]amine hydrochloride N,N-Dimethyl-[5-(1-benzoylpiperidine-4-carbonyl)-4,5,6,7-tetrahydrofuro[3,2-c]pyridin-2-ylmethyl]amine 0.242 g was dissolved in 2 ml of methanol; hydrogen chloride in ethyl acetate was added in excess, followed by stirring. This mixture was concentrated and washed with diethyl ether to yield the desired product.

White solid Yield 0.238 g $^1$H-NMR (CD$_3$OD, 200 MHz) δ: 1.686(4H,br s), 2.650–2.800(2H,m), 2.859(6H,s), 2.950–3.300(3H,m), 3.700–3.850(1H,m), 3.919–3.941(2H,m), 4.373(2H,s), 4.498(1H,s), 4.600(1H,s), 4.650–4.750(1H,m), 6.648(0.5H, s), 6.685(0.5H,s), 7.408–7.500(5H,m)

IR (nujol): 2679, 1614, 1294, 1211, 1134, 939, 712 cm$^{-1}$

Anal. Calcd for C$_{23}$H$_{30}$ClN$_3$O$_3$·1.7H$_2$O: C, 59.72; H, 7.28; N, 9.08. Found: C, 59.68; H, 7.40; N, 8.96.

EXAMPLE 112

Synthesis of N,N-dimethyl-[6-(4-phenethylbenzoyl)-4,5,6,7-tetrahydrofuro[2,3-c]pyridin-2-ylmethyl]amine hydrochloride a) Synthesis of N,N-dimethyl-[6-(4-phenethylbenzoyl)-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.498 g (2.2 mmol) of 4-phenethylbenzoic acid and 1.1 ml (8.0 mmol) of triethylamine in 30 ml of dichloromethane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.498 g (64%)

$^1$H-NMR (CDCl$_3$, 200 MHz) δ: 2.260(6H,s), 2.555(2H,br s), 2.890–2.965(4H,m), 3.403(2H,br s), 3.586(1.1H,br s), 3.920(0.9H,br s), 4.400–4.701(2H,m), 6.072(1H,s), 7.145–7.376(9H,m)

IR (neat): 2937, 2856, 2776, 1633, 1427, 1286, 1259, 1230, 1043, 1022, 831, 748 cm$^{-1}$ b) Synthesis of N,N-dimethyl-[6-(4-phenethylbenzoyl)-4,5,6,7-tetrahydrofuro[2,3-c]pyridin-2-ylmethyl]amine hydrochloride N,N-Dimethyl-[6-(4-phenethylbenzoyl)-4,5,6,7-tetrahydrofuro[2,3-c]pyridin-2-ylmethyl]amine 0.498 g was dissolved in 2 ml of methanol; hydrogen chloride in ethyl acetate was added in excess, followed by stirring. This mixture was concentrated and washed with diethyl ether to yield the desired product.

Brown solid Yield 0.486 g $^1$H-NMR (CD$_3$OD, 200 MHz) δ: 2.617(2H,br s), 2.861 (6H,s), 2.956(4H,s), 3.636(1.1H,br s), 3.800(0.9H,br s), 4.372(2H,s), 4.550–4.740(2H,m), 6.656(1H,s), 7.136–7.378 (9H,m)

IR (nujol): 2463, 1624, 1248, 974, 828, 698 cm$^{-1}$

Anal. Calcd for C$_{25}$H$_{29}$ClN$_2$O$_2$·0.3H$_2$O: C, 69.77; H, 6.93; N, 6.51. Found: C, 69.67; H, 6.79; N, 6.46

EXAMPLE 113

Synthesis of 6-(4-phenethylbenzoyl)-2-(1-pyrrolidinylmethyl)-4,5,6,7-tetrahydrofuro[2,3-c]pyridine hydrochloride a) Synthesis of 6-(4-phenethylbenzoyl)-2-(1-pyrrolidinylmethyl)-4,5,6,7-tetrahydrofuro[2,3-c]pyridine To a solution of 0.552 g (3.458 mmol) of 4,5,6,7-tetrahydrofuro[2,3-c]pyridine hydrochloride, 0.78 g (3.46 mmol) of 4-phenethylbenzoic acid and 1.93 ml (13.8 mmol) of triethylamine in 15 ml of N,N-dimethylformamide, 0.63 ml (4.15 mmol) of diethyl cyanophosphonate was added dropwise, followed by overnight stirring at room temperature. This mixture was poured into water and extracted with diethyl ether 3 times. The combined organic layer was dried over anhydrous sodium sulfate; the solvent was distilled off under reduced pressure. The resulting crude product was purified by silica gel column chromatography (hexane/ethyl acetate=6/1 to 3/1) to yield 6-(4-phenethylbenzoyl)-4,5,6,7-tetrahydrofuro[2,3-c]pyridine.

Yellow oil Yield 1.078 g (94%)

To a solution of 1.078 g (3.253 mmol) of the above 6-(4-phenethylbenzoyl)-4,5,6,7-tetrahydrofuro[2,3-c]pyridine in 10 ml of acetic acid, 0.41 ml (4.88 mmol) of pyrrolidine and 0.40 g (4.88 mmol) of 37% aqueous formaldehyde were added, followed by stirring at 100° C. for 1 hour. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl-acetate to ethyl acetate/methanol=4/1) to yield the desired product.

Yellow oil Yield 1.004 g (75%)

$^1$H-NMR (CDCl$_3$, 200 MHz) δ: 1.793(4H,br s), 2.540 (4H,br s), 2.940(4H,s), 3.579(3.2H,br s), 3.918(0.8H,br s), 4.478(0.8H,br s), 4.707(1.2H,br s), 6.065(1H,s), 7.154–7.376(9H,m)

IR (neat): 2927, 2791, 1637, 1425, 1281, 1234, 1113, 1043, 906, 829, 756, 702 cm$^{-1}$ b) Synthesis of 6-(4-phenethylbenzoyl)-2-(1-pyrrolidinylmethyl)-4,5,6,7-tetrahydrofuro[2,3-c]pyridine hydrochloride 6-(4-Phenethylbenzoyl)-2-(1-pyrrolidinylmethyl)-4,5,6,7-tetrahydrofuro[2,3-c]pyridine 1.004 g was dissolved in 2 ml of methanol; hydrogen chloride in methanol was added in excess, followed by stirring. This mixture was concentrated; the resulting solid was washed with diethyl ether to yield the desired product.

Pale brown solid Yield 0.962 g $^1$H-NMR (CD$_3$OD, 200 MHz) δ: 2.031(4H,br s), 2.584 (2H,br s), 2.934(4H,s), 3.198(2H,br s), 3.500–3.621(3.2H, m), 3.938(0.8H,br s), 4.436(2H,br s), 4.544(0.8H,br s), 4.724(1.2H,br s), 6.643(1H,s), 7.133–7.376(9H,m)

IR (nujol): 2603, 2492, 1614, 1421, 1228, 1155, 1047, 966, 912, 833, 768, 702 cm$^{-1}$ Anal. Calcd for C$_{27}$H$_{31}$ClN$_2$O$_2$·0.5H$_2$O: C, 70.50; H, 7.01; N, 6.09. Found: C, 70.41; H, 6.80; N, 6.28

EXAMPLE 114

Synthesis of N,N-dimethyl-[6-(4-benzyloxybenzoyl)-4,5,6,7-tetrahydrofuro[2,3-c]pyridin-2-ylmethyl]amine hydrochloride a) Synthesis of N,N-dimethyl-[6-(4-benzyloxybenzoyl)-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.502 g (2.2 mmol) of 4-benzyloxybenzoic acid and 1.1 ml (8.0 mmol) of triethylamine in 30 ml of dichloromethane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.470 g (60%)

$^1$H-NMR (CDCl$_3$, 200 MHz) δ: 2.269(6H,s), 2.575(2H,br s), 3.415(2H,s), 3.664–3.796(2H,m), 4.577–4.621(2H,m), 5.108(2H,s), 6.086(1H,s), 6.996(2H,d,J=8.4 Hz), 7.310–7.444(7H,m)

IR (neat): 2939, 2856, 2773, 1630, 1425, 1244, 1174, 1020, 841, 721 cm$^{-1}$ b) Synthesis of N,N-dimethyl-[6-(4-benzyloxybenzoyl)-4,5,6,7-tetrahydrofuro[2,3-c]pyridin-2-ylmethyl]amine hydrochloride N,N-Dimethyl-[6-(4-benzyloxybenzoyl)-4,5,6,7-tetrahydrofuro[2,3-c]pyridin-2-ylmethyl]amine 0.470 g was dissolved in 2 ml of methanol; hydrogen chloride in ethyl acetate was added in excess, followed by stirring. This mixture was concentrated, and recrystallized from ethanol-diethyl ether to yield the desired product.

Pale brown crystal Yield 0.433 g $^1$H-NMR (CD$_3$OD, 200 MHz) δ: 2.607–2.661(2H,m), 2.856(6H,s), 3.698–3.778(2H,m), 4.370(2H,s), 4.679(2H,s), 5.154(2H,s), 6.661(1H,s), 7.098(2H,d,J=8.8 Hz), 7.311–7.470(7H,m)

IR (nujol): 2463, 1620, 1248, 887, 740 cm$^{-1}$

Anal. Calcd for C$_{24}$H$_{27}$ClN$_2$O$_3$.0.2H$_2$O: C, 66.95; H, 6.41; N, 6.51. Found: C, 66.98; H, 6.38; N, 6.39.

EXAMPLE 115

Synthesis of N,N-dimethyl-[5-(4-benzyloxybenzoyl)-4,5,6,7-tetrahydrofuro[3,2-c]pyridin-2-ylmethyl]amine hydrochloride a) Synthesis of N,N-dimethyl-[5-(4-benzyloxybenzoyl)-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.251 g (1.1 mmol) of 4-benzyloxybenzoic acid and 0.55 ml (4.0 mmol) of triethylamine in 30 ml of dichloromethane, 0.245 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

White crystal Yield 0.252 g (65%)

$^1$H-NMR (CDCl$_3$, 200 MHz) δ: 2.267(6H,s), 2.778(2H,br s), 3.410(2H,s), 3.727–3.907(2H,m), 4.408–4.546(2H,m), 5.105(2H,s), 6.007–6.033(1H,m), 7.000(2H,d,J=8.0 Hz), 7.309–7.422(7H,m)

IR (KBr): 2930, 2860, 2779, 1622, 1429, 1246, 1016, 841, 743 cm$^{-1}$ b) Synthesis of N,N-dimethyl-[5-(4-benzyloxybenzoyl)-4,5,6,7-tetrahydrofuro[3,2-c]pyridin-2-ylmethyl]amine hydrochloride N,N-Dimethyl-[5-(4-benzyloxybenzoyl)-4,5,6,7-tetrahydrofuro[3,2-c]pyridin-2-ylmethyl]amine 0.252 g was dissolved in 2 ml of methanol; hydrogen chloride in ethyl acetate was added in excess, followed by stirring. This mixture was concentrated, and recrystallized from ethanol-diethyl ether to yield the desired product.

White crystal Yield 0.233 g $^1$H-NMR (CD$_3$OD, 200 MHz) δ: 2.854(8H,s), 3.750–4.000(2H,m), 4.359(2H,s), 4.541(2H,br s), 5.152(2H,s), 6.500–6.700(1H,m), 7.092(2H,d,J=8.0 Hz), 7.309–7.478 (7H,m)

IR (nujol): 2461, 1618, 1269, 839, 735 cm$^{-1}$

Anal. Calcd for C$_{24}$H$_{27}$ClN$_2$O$_3$.0.5H$_2$O: C, 66.12; H, 6.47; N, 6.43. Found: C, 66.14; H, 6.44; N, 6.36.

EXAMPLE 116

Synthesis of N,N-dimethyl-[6-[4-(phenoxymethyl)benzoyl)-4,5,6,7-tetrahydrofuro[2,3-c]pyridin-2-ylmethyl]amine hydrochloride a) Synthesis of N,N-dimethyl-[6-[4-(phenoxymethyl)benzoyl]-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.502 g (2.2 mmol) of 4-(phenoxymethyl)benzoic acid and 1.1 ml (8.0 mmol) of triethylamine in 30 ml of N,N-dimethylformamide, 0.489 g (3.0 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.400 g (51%)

$^1$H-NMR (CDCl$_3$, 200 MHz) δ: 2.123(6H,s), 2.543(2H,br s), 3.427(2H,br s), 3.547–3.586(1H,m), 3.945–3.959(1H,m), 4.441–4.462(1H,m), 4.688–4.765(1H,m), 5.112(2H,s), 6.086(1H,s), 6.958–7.016(3H,m), 7.296–7.350(2H,m), 7.440–7.528(4H,m),

IR (neat): 2931, 2852, 2767, 1734, 1632, 1493, 1427, 1238, 1043, 831, 754, 692 cm$^{-1}$ b) Synthesis of N,N-dimethyl-[6-[4-(phenoxymethyl)benzoyl]-4,5,6,7-tetrahydrofuro[2,3-c]pyridin-2-ylmethyl]amine hydrochloride N,N-Dimethyl-[6-[4-(phenoxymethyl)benzoyl]-4,5,6,7-tetrahydrofuro[2,3-c]pyridin-2-ylmethyl]amine 0.400 g was dissolved in 2 ml of methanol; hydrogen chloride in ethyl acetate was added in excess, followed by stirring. This mixture was concentrated, and recrystallized from ethanol-diethyl ether to yield the desired product.

Brown solid Yield 0.366 g $^1$H-NMR (CD$_3$OD, 200 MHz) δ: 2.621(2H,br s), 2.870 (6H,s), 3.638–3.672(1.4H,m), 3.950–4.000(0.6H,m), 4.389 (2H,br s), 4.500–4.600(0.6H,m), 4.759(1.4H,br s), 5.158 (2H,s), 6.667(1H,s), 6.903–7.015(3H,m), 7.239–7.319(2H,m), 7.466–7.612(4H,m)

IR (nujol): 2360, 1626, 1246, 1043, 949, 756 cm$^{-1}$

Anal. Calcd for C$_{24}$H$_{27}$ClN$_2$O$_3$.0.2H$_2$O: C, 66.95; H, 6.41; N, 6.51. Found: C, 66.81; H, 6.29; N, 6.68.

EXAMPLE 117

Synthesis of N,N-dimethyl-[5-[4-(phenoxymethyl)benzoyl]-4,5,6,7-tetrahydrofuro[3,2-c]pyridin-2-ylmethyl]amine hydrochloride a) Synthesis of N,N-dimethyl-[5-[4-(phenoxymethyl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.251 g (1.1 mmol) of 4-(phenoxymethyl)benzoic acid and 0.55 ml (4.0 mmol) of triethylamine in 30 ml of N,N-dimethylformamide, 0.245 g (1.5 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 90 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Colorless oil Yield 0.275 g (71%)

$^1$H-NMR (CDCl$_3$, 200 MHz) δ: 2.266(6H,s), 2.718–2.841 (2H,m), 3.405(2H,s), 3.638–3.695(1.2H,m), 4.028–4.044 (0.8H,m), 4.325–4.347(0.8H,m), 4.579–4.614(1.2H,m), 5.105(2H,s), 5.906–5.912(0.4H,m), 6.105–6.111(0.6H,m), 6.942–7.014(3H,m), 7.292–7.347(2H,m), 7.435–7.530(4H,m)

IR (neat): 2931, 2860, 2773, 1637, 1456, 1367, 1244, 1043, 829, 756 cm$^{-1}$ b) Synthesis of N,N-dimethyl-[5-[4-(phenoxymethyl)benzoyl]-4,5,6,7-tetrahydrofuro[3,2-c]pyridin-2-ylmethyl]amine hydrochloride N,N-Dimethyl-[5-[4-(phenoxymethyl)benzoyl]-4,5,6,7-tetrahydrofuro[3,2-c]pyridin-2-ylmethyl]amine 0.275 g was dissolved in 2 ml of methanol; hydrogen chloride in ethyl acetate was added in excess, followed by stirring. This mixture was concentrated, and recrystallized from ethanol-diethyl ether to yield the desired product.

Pale brown solid Yield 0.278 g $^1$H-NMR (CD$_3$OD, 200 MHz) δ: 2.854(8H,br s), 3.685–3.746(1.1H,m), 4.043–4.090(0.9H,m), 4.305–4.469 (2.9H,m), 4.599–4.642(1.1H,m), 5.147(2H,s), 6.495(0.4H, br s), 6.686–6.706(0.6H,m), 6.896–7.006(3H,m), 7.232–7.312(2H,m), 7.453–7.596(4H,m)

IR (nujol): 2565, 1628, 1240, 1115, 1041, 943, 758 cm$^{-1}$

Anal. Calcd for C$_{24}$H$_{27}$ClN$_2$O$_3$.0.5H$_2$O: C, 66.12; H, 6.47; N, 6.43. Found: C, 66.01; H, 6.43; N, 6.45.

EXAMPLE 118

Synthesis of N,N-dimethyl-[6-[4-(2-phenylcyclopropyl)benzoyl]-4,5,6,7-tetrahydrofuro[2,3-c]pyridin-2-ylmethyl]amine hydrochloride a) Synthesis of N,N-dimethyl-[6-[4-(2-phenylcyclopropyl)benzoyl]-4,5,6,7-tetrahydrofuro[2,3-c]pyridin-2-ylmethyl]amine To a solution of 0.160 g (1.000 mmol) of 4,5,6,7-tetrahydrofuro[2,3-c]pyridine hydrochloride, 0.237 g (1.0 mmol) of 4-(2-phenylcyclopropyl)benzoic acid and 0.55 ml (4.0 mmol) of triethylamine in 30 ml of N,N-dimethylformamide, 0.245 g (1.5 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 90 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.203 g (51%)

$^1$H-NMR (CDCl$_3$, 200 MHz) δ: 1.359–1.570(1H,m), 2.258(6H,s), 2.469–2.575(4H,m), 3.402(3H,br s), 3.750–4.000(0.6H,m), 4.250–4.700(2H,m), 6.057(1H,s), 6.949(4H,d,J=7.6 Hz), 7.043–7.548(5H,m)

IR (neat): 2933, 2852, 2767, 1734, 1627, 1421, 1236, 906, 843, 698 cm$^{-1}$ b) Synthesis of N,N-dimethyl-[6-[4-(2-phenylcyclopropyl)benzoyl]-4,5,6,7-tetrahydrofuro[2,3-c]pyridin-2-ylmethyl]amine hydrochloride N,N-Dimethyl-[6-[4-(2-phenylcyclopropyl)benzoyl]-4,5,6,7-tetrahydrofuro[2,3-c]pyridin-2-ylmethyl]amine 0.203 g was dissolved in 2 ml of methanol; hydrogen chloride in ethyl acetate was added in excess, followed by stirring. This mixture was concentrated and washed with diethyl ether to yield the desired product.

Pale brown solid Yield 0.195 g $^1$H-NMR (CD$_3$OD, 200 MHz) δ: 1.467–1.608(2H,m), 2.548–2.621(4H,m), 2.852(6H,s), 3.400–4.000(2H,m), 4.363(3H,br s), 4.679(1H,br s), 6.640(1H,s), 6.975–7.700 (9H,m), IR (nujol): 2671, 1616, 1232, 972, 939, 841, 723 cm$^{-1}$ Anal. Calcd for C$_{26}$H$_{29}$ClN$_2$O$_2$.1.0H$_2$O: C, 68.63; H, 6.87; N, 6.16. Found: C, 68.70; H, 6.88; N, 6.30

EXAMPLE 119

Synthesis of N,N-dimethyl-[5-[4-(2-phenylcyclopropyl)benzoyl]-4,5,6,7-tetrahydrofuro[3,2-c]pyridin-2-ylmethyl]amine hydrochloride a) Synthesis of N,N-dimethyl-[5-[4-(2-phenylcyclopropyl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.210 g (0.88 mmol) of 4-(2-phenylcyclopropyl)benzoic acid and 0.55 ml (4.0 mmol) of triethylamine in 30 ml of N,N-dimethylformamide, 0.245 g (1.5 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 90 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.180 g (51%)

$^1$H-NMR (CDCl$_3$, 200 MHz) δ: 1.377–1.564(2H,m), 2.258(6H,s), 2.471–2.720(4H,m), 3.394(2H,s), 3.450–3.500 (1.2H,m), 3.900–4.100(0.8H,m), 4.100–4.200(0.8H,m), 4.524–4.530(1.2H,m), 5.850–6.100(1H,m), 6.933–7.600 (9H,m)

IR (neat): 2939, 2856, 2773, 1632, 1423, 1281, 1221, 1113, 1018, 773cm$^{-1}$ b) Synthesis of N,N-dimethyl-[5-[4-(2-phenylcyclopropyl) benzoyl]-4,5,6,7-tetrahydrofuro[3,2-c]pyridin-2-ylmethyl] amine hydrochloride N,N-Dimethyl-[5-[4-(2-phenylcyclopropyl)benzoyl]-4,5, 6,7-tetrahydrofuro[3,2-c]pyridin-2-ylmethyl]amine 0.180 g was dissolved in 2 ml of methanol; hydrogen chloride in ethyl acetate was added in excess, followed by stirring. This mixture was concentrated and washed with diethyl ether to yield the desired product.

Brown solid Yield 0.175 g $^1$H-NMR (CD$_3$OD, 200 MHz) δ: 1.463–1.575(2H,m), 2.577(2H,t,7.3 Hz), 2.705–2.804(2H,m), 2.848(6H,s), 3.500–3.700(1H,m), 3.900–4.100(1H,m), 4.200–4.300(1H, m), 4.350(2H,s), 4.536–4.560(1H,m), 6.400–6.700(1H,m), 6.969–7.665(9H,m)

IR (nujol): 2671, 1614, 1234, 1115, 972, 939, 841, 723 cm$^{-1}$

Anal. Calcd for C$_{26}$H$_{29}$ClN$_2$O$_2$·1.0H$_2$O: C, 68.63; H, 6.87; N, 6.16. Found: C, 68.51; H, 6.80; N, 6.25

EXAMPLE 120

Synthesis of 4-(2-dimethylaminomethyl-5,7-dihydro-4H-furo[2,3-c]pyridin-6-ylcarbonyl) phenylphenylmethanol To a solution of 0.196 g (0.461 mmol) of N,N-dimethyl-[6-(4-benzoylbenzoyl)-4,5,6,7-tetrahydrofuro[2,3-c] pyridin-2-ylmethyl]amine hydrochloride in 10 ml of methanol, 70 mg (1.9 mmol) of sodium borohydride was added under ice-cooling, followed by overnight stirring at room temperature. Aqueous sodium hydroxide was added, followed by 3 extractions with dichloromethane. The combined organic layer was dried over anhydrous magnesium sulfate; the solvent was distilled off under reduced pressure to yield the desired product.

Pale yellow foam Yield 0.178 g (99%)

$^1$H-NMR (CDCl$_3$, 200 MHz) δ: 2.192(6H,br s), 2.534 (2H,br s), 3.361(2H,br s), 3.531(1.2H,br s), 3.890(1.8H,br s), 4.417(0.8H,br s), 4.669(1.2H,br s), 5.764(1H,s), 6.052 (1H,s), 7.196–7.418(9H,m)

IR (neat): 3373, 2939, 2856, 1626, 1430, 1263, 1232, 1045, 1020, 756, 735, 702 cm$^{-1}$ HRMS m/z Calcd for C$_{24}$H$_{26}$N$_2$O$_3$ 390.1945, Found: 390.1960.

EXAMPLE 121

Synthesis of N,N-dimethyl-[6-[4-(1-phenylethenyl) benzoyl]-4,5,6,7-tetrahydrofuro[2,3-c]pyridin-2-ylmethyl]amine hydrochloride a) Synthesis of N,N-dimethyl-[6-[4-(1-phenylethenyl) benzoyl]-4,5,6,7-tetrahydrofuro[2,3-c]pyridin-2-ylmethyl] amine To a solution of 0.319 g (2.000 mmol) of 4,5,6,7-tetrahydrofuro[2,3-c]pyridine hydrochloride, 0.493 g (2.2 mmol) of 4-(1-phenylethenyl)benzoic acid and 1.1 ml (8.0 mmol) of triethylamine in 30 ml of dichloromethane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1). The resulting purified product was recrystallized from ethyl acetate-hexane to yield the desired product.

Brown crystal Yield 0.503 g (65%)

$^1$H-NMR (CDCl$_3$, 200 MHz) δ: 2.268(6H,s), 2.555–2.585 (2H,m), 3.416(2H,br s), 3.597–3.964(2H,m), 4.485–4.736 (2H,m), 5.513(2H,d,J=3.2 Hz), 6.088(1H,s), 7.347(5H,s), 7.408(4H,s)

IR (KBr): 2937, 2816, 2764, 1630, 1435, 1284, 1109, 903, 856, 777, 704 cm$^{-1}$ b) Synthesis of N,N-dimethyl-[6-[4-(1-phenylethenyl) benzoyl]-4,5,6,7-tetrahydrofuro[2,3-c]pyridin-2-ylmethyl] amine hydrochloride N,N-Dimethyl-[6-[4-(1-phenylethenyl)benzoyl]-4,5,6,7-tetrahydrofuro[2,3-c]pyridin-2-ylmethyliamine 0.503 g was dissolved in 2 ml of methanol; hydrogen chloride in ethyl acetate was added in excess, followed by stirring. This mixture was concentrated, dissolved in 2 ml of methanol and recrystallized from diethyl ether to yield the desired product.

Brown crystal Yield 0.455 g $^1$H-NMR (CD$_3$OD, 200 MHz) δ: 2.643(2H,br s), 2.867 (6H,s), 3.667–4.000(2H,m), 4.381(2H,br s), 4.550–4.777 (2H,m), 5.542(2H,d,J=2.2 Hz), 6.666(1H,s), 7.285–7.378 (5H,m), 7.450(4H,s)

IR (nujol): 2470, 1626, 1234, 906, 773, 702 cm$^{-1}$

Anal. Calcd for C$_{25}$H$_{27}$ClN$_2$O$_2$·0.6H$_2$O: C, 69.23; H, 6.55; N, 6.46. Found: C, 69.19; H, 6.39; N, 6.40

EXAMPLE 122

Synthesis of 6-[4-(1-phenylethenyl)benzoyl]-2-(1-pyrrolidinylmethyl)-4,5,6,7-tetrahydrofuro[2,3-c] pyridine hydrochloride a) Synthesis of 6-[4-(1-phenylethenyl)benzoyl]-2-(1-pyrrolidinylmethyl)-4,5,6,7-tetrahydrofuro[2,3-c]pyridine To a solution of 0.527 g (3.302 mmol) of 4,5,6,7-tetrahydrofuro[2,3-c]pyridine hydrochloride, 0.74 g (3.30 mmol) of 4-(1-phenylethenyl)benzoic acid and 1.84 ml (13.2 mmol) of triethylamine in 15 ml of N,N-dimethylformamide, 0.60 ml (3.96 mmol) of diethyl cyanophosphonate was added dropwise, followed by overnight stirring at room temperature. This mixture was poured into water and extracted with diethyl ether 3 times. The combined organic layer was dried over anhydrous sodium sulfate; the solvent was distilled off under reduced pressure. The resulting crude product was purified by silica gel column chromatography (hexane/ethyl acetate=6/1 to 3/1) to yield 6-[4-(1-phenylethenyl)benzoyl]-4,5,6,7-tetrahydrofuro[2,3-c]pyridine.

Yellow oil Yield 0.724 g (67%)

To a solution of 0.724 g (2.198 mmol) of the above 6-[4-(1-phenylethenyl)benzoyl]-4,5,6,7-tetrahydrofuro[2,3-c]pyridine in 10 ml of acetic acid, 0.28 ml (3.30 mmol) of pyrrolidine and 0.27 g (3.30 mmol) of 37% aqueous formaldehyde were added, followed by stirring at 100° C. for 1 hour. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.688 g (76%)

$^1$H-NMR (CDCl$_3$, 200 MHz) δ: 1.797(4H,br s), 2.546 (4H,br s), 3.592(3.2H,br s), 3.956(0.8H,br s), 4.502(0.8H,br s), 4.735(1.2H,br s), 5.502(1H,s), 5.517(1H,s), 6.072(1H,s), 7.343(5H,s), 7.402(4H,s)

IR (neat): 2964, 2791, 1643, 1425, 1281, 1238, 1159, 1113, 1043, 906, 856, 779, 704 cm$^{-1}$ b) Synthesis of 6-[4-(1-phenylethenyl)benzoyl]-2-(1-pyrrolidinylmethyl)-4,5,6,7-tetrahydrofuro[2,3-c]pyridine hydrochloride 6-[4-(1-Phenylethenyl)benzoyl]-2-(1-pyrrolidinylmethyl)-4,5,6,7-tetrahydrofuro[2,3-c]pyridine 0.688 g was dissolved in 2 ml of methanol and hydrogen chloride in methanol was added in excess, followed by stirring. This mixture was concentrated to yield the desired product.

Orange form Yield 0.732 g $^1$H-NMR (CD$_3$OD, 200 MHz) δ: 2.048–2.134(4H,m), 2.612(2H,br s), 3.218(2H,br s), 3.517–3.724(3.2H,m), 3.969 (0.8H,br s), 4.455(2H,br s), 4.601(0.8H,br s), 4.751(1.2H,br s), 5.522(1H,s), 5.537(1H,s), 6.653(1H,s), 7.220–7.481(9H, m)

IR (neat): 2947, 2681, 2590, 1624, 1429, 1232, 1161, 1045, 905, 856, 777, 704 cm$^{-1}$ Anal. Calcd for C$_{27}$H$_{29}$ClN$_2$O$_2$.3.0H$_2$O: C, 64.47; H, 7.01; N, 5.57. Found: C, 64.65; H, 6.90; N, 5.67

EXAMPLE 123

Synthesis of N,N-dimethyl-[5-[4-(1-phenylethenyl) benzoyl]-4,5,6,7-tetrahydrofuro[3,2-c]pyridin-2-ylmethyl]amine hydrochloride a) Synthesis of N,N-dimethyl-[5-[4-(1-phenylethenyl) benzoyl]-4,5,6,7-tetrahydrofuro[3,2-c]pyridin-2-ylmethyl] amine To a solution of 0.160 g (1.000 mmol) of 4,5,6,7-tetrahydrofuro[3,2-c]pyridine hydrochloride, 0.247 g (1.1 mmol) of 4-(1-phenylethenyl)benzoic acid and 0.55 ml (4.0 mmol) of triethylamine in 30 ml of dichloromethane, 0.245 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Yellow oil Yield 0.325 g (84%)

$^1$H-NMR (CDCl$_3$, 200 MHz) δ: 2.267(6H,s), 2.783(2H,br s), 3.408(2H,s), 3.694–4.105(2H,m), 4.350–4.619(2H,m), 5.511(2H,s), 5.900–6.103(1H,m), 7.342(5H,s), 7.410(4H,s)

IR (neat): 2937, 2818, 2773, 1633, 1425, 1282, 1113, 1020, 854, 777, 704 cm$^{-1}$ b) Synthesis of N,N-dimethyl-[5-[4-(1-phenylethenyl) benzoyl]-4,5,6,7-tetrahydrofuro[3,2-c]pyridin-2-ylmethyl] amine hydrochloride N,N-Dimethyl-[5-[4-(1-phenylethenyl)benzoyl]-4,5,6,7-tetrahydrofuro[3,2-c]pyridin-2-ylmethyl]amine 0.325 g was dissolved in 2 ml of methanol; hydrogen chloride in ethyl acetate was added in excess, followed by stirring. This mixture was concentrated and washed with diethyl ether to yield the desired product.

Pale brown solid Yield 0.349 g $^1$H-NMR (CD$_3$OD, 200 MHz) δ: 2.864(6H,s), 3.763–3.777(1.1H,m), 4.050–4.100(0.9H,m), 4.373(2H,br s), 4.467–4.476(0.9H,m), 4.632–4.653(1.1H,m), 5.535–5.549(2H,m), 5.518–6.705(1H,m), 7.286–7.414(5H, m), 7.453(4H,s)

IR (nujol): 2472, 1633, 1115, 906, 773, 706 cm$^{-1}$

Anal. Calcd for C$_{25}$H$_{27}$ClN$_2$O$_2$.1.0H$_2$O: C, 68.09; H, 6.63; N, 6.35. Found: C, 68.24; H, 6.64; N, 6.44.

EXAMPLE 124

Synthesis of N,N-dimethyl-[6-[4-(1-phenylethyl) benzoyl]-4,5,6,7-tetrahydrofuro[2,3-c]pyridin-2-ylmethyl]amine hydrochloride a) Synthesis of N,N-dimethyl-[6-[4-(1-phenylethyl) benzoyl]-4,5,6,7-tetrahydrofuro[2,3-c]pyridin-2-ylmethyl] amine To a solution of 0.319 g (2.000 mmol) of 4,5,6,7-tetrahydrofuro[2,3-c]pyridine hydrochloride, 0.498 g (2.2 mmol) of 4-(1-phenylethyl)benzoic acid and 1.1 ml (8.0 mmol) of triethylamine in 30 ml of dichloromethane, 0.489 g (3.0 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 90 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.404 g (52%)

$^1$H-NMR (CDCl$_3$, 200 MHz) δ: 1.649(3H,d,7.2 Hz), 2.258(6H,s), 2.546(2H,br s), 3.407(2H,br s), 3.551–3.587 (1.2H,m), 3.920–3.948(0.8H,m), 4.185(1H,q,J=7.2 Hz), 4.447–4.495(0.8H,m), 4.659–4.709(1.2H,m), 6.073(1H,s), 7.160–7.385(9H,m)

IR (neat): 2937, 2858, 2779, 1738, 1633, 1464, 1240, 1045, 849, 702 cm$^{-1}$ b) Synthesis of N,N-dimethyl-[6-[4-(1-phenylethyl) benzoyl]-4,5,6,7-tetrahydrofuro[2,3-c]pyridin-2-ylmethyl] amine hydrochloride N,N-Dimethyl-[6-[4-(1-phenylethyl)benzoyl]-4,5,6,7-tetrahydrofuro[2,3-c]pyridin-2-ylmethyl]amine 0.404 g was dissolved in 2 ml of methanol; hydrogen chloride in ethyl acetate was added in excess, followed by stirring. This mixture was concentrated and washed with diethyl ether to yield the desired product.

Pale yellow powder Yield 0.414 g $^1$H-NMR (CD$_3$OD, 200 MHz) δ: 1.648(3H,d,J=7.4 Hz), 2.608(2H,br s), 2.857(6H,s), 3.623–3.661(1.1H,m), 3.900–4.000(0.9H,m), 4.220(1H,q,J=7.2 Hz), 4,376(2H,br s), 4.500–4.600(0.9H,m), 4.728(1.1H,br s), 6.651(1H,s), 7.162–7.281(5H,m), 7.380(4H,s)

IR (nujol): 2669, 1624, 1260, 974, 723 cm$^{-1}$

Anal. Calcd for C$_{25}$H$_{29}$ClN$_2$O$_2$.0.7H$_2$O: C, 68.62; H, 7.00; N, 6.40. Found: C, 68.65; H, 7.09; N, 6.28.

EXAMPLE 125

Synthesis of N,N-dimethyl-[5-[4-(1-phenylethyl) benzoyl]-4,5,6,7-tetrahydrofuro[3,2-c]pyridin-2-ylmethyl]amine hydrochloride a) Synthesis of N,N-dimethyl-[5-[4-(1-phenylethyl) benzoyl]-4,5,6,7-tetrahydrofuro[3,2-c]pyridin-2-ylmethyl] amine To a solution of 0.160 g (1.000 mmol) of 4,5,6,7-tetrahydrofuro[3,2-c]pyridine hydrochloride, 0.249 g (1.1 mmol) of 4-(1-phenylethyl)benzoic acid and 0.55 ml (4.0 mmol) of triethylamine in 30 ml of dichloromethane, 0.245 g (1.5 mmol) of diethyl cyanophosphonate was added dropwise under ice-cooling, followed by overnight stirring at room temperature. After the solvent was distilled off, water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.282 g (73%)

$^1$H-NMR (CDCl$_3$, 200 MHz) δ: 1.648(3H,d,J=7.4 Hz), 2.260(6H,s), 2.731–2.804(2H,m), 3.398(2H,s), 3.634–3.682 (1.2H,m), 3.950–4.050(0.8H,m), 4.180(1H,q,J=7.2 Hz), 4.300–4.350(0.8H,m), 4.546–4.588(1.2H,m), 5.950–6.000 (0.4H,m), 6.000–6.100(0.6H,m), 7.164–7.384(9H,m)

IR (neat): 2970, 2818, 2775, 1633, 1425, 1282, 1113, 847, 702 cm$^{-1}$ b) Synthesis of N,N-dimethyl-[5-[4-(1-phenylethyl) benzoyl]-4,5,6,7-tetrahydrofuro[3,2-c]pyridin-2-ylmethyl] amine hydrochloride N,N-Dimethyl-[5-[4-(1-phenylethyl)benzoyl]-4,5,6,7-tetrahydrofuro[3,2-c]pyridin-2-ylmethyl]amine 0.282 g was dissolved in 2 ml of methanol; hydrogen chloride in ethyl acetate was added in excess, followed by stirring. This mixture was concentrated and washed with diethyl ether to yield the desired product.

Pale yellow powder Yield 0.305 g $^1$H-NMR (CD$_3$OD, 200 MHz) δ: 1.645(3H,d,J=7.2 Hz), 2.846(8H,br s), 3.680–3.753(1.2H,m), 4.013–4.059(0.8H, m), 4.214(1H,q,J=7.2 Hz), 4.352–4.457(2.8H,m), 4.563–4.634(1.2H,m), 6.490(0.4H,br s), 6.682(0.6H,br s), 7.134–7.277(5H,m), 7.318–7.373(4H,m)

IR (nujol): 2669, 1626, 1302, 1115, 974, 723 cm$^{-1}$

Anal. Calcd for C$_{25}$H$_{29}$ClN$_2$O$_2$.1.0H$_2$O: C, 67.78; H, 7.05; N, 6.32. Found: C, 67.62; H, 6.89; N, 6.26.

EXAMPLE 126

Synthesis of N,N-dimethyl-[6-[4-(1-phenylcyclopropyl)benzoyl]-4,5,6,7-tetrahydrofuro [2,3-c]pyridin-2-ylmethyl]amine hydrochloride a) Synthesis of N,N-dimethyl-[6-[4-(1-phenylcyclopropyl) benzoyl]-4,5,6,7-tetrahydrofuro[2,3-c]pyridin-2-ylmethyl] amine To a solution of 0.160 g (1.000 mmol) of 4,5,6,7-tetrahydrofuro[2,3-c]pyridine hydrochloride, 0.238 g (1.0 mmol) of 4-(1-phenylcyclopropyl)benzoic acid and 0.55 ml (4.0 mmol) of triethylamine in 30 ml of N,N-dimethylformamide, 0.245 g (1.5 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 90 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.183 g (46%)

$^1$H-NMR (CDCl$_3$, 200 MHz) δ: 1.329(4H,d,J=4.8 Hz), 2.258(6H,s), 2.504–2.612(2H,m), 3.409(2H,br s), 3.566–3.610(1.3H,m), 3.900–4.000(0.7H,m), 4.400–4.500 (0.7H,m), 4.669–4.726(1.3H,m), 6.070(1H,s), 7.167–7.358 (9H,m)

IR (neat): 2937, 2854, 2773, 1738, 1633, 1425, 1238, 1043, 847, 702 cm$^{-1}$ b) Synthesis of N,N-dimethyl-[6-[4-(1-phenylcyclopropyl) benzoyl]-4,5,6,7-tetrahydrofuro[2,3-c]pyridin-2-ylmethyl] amine hydrochloride N,N-Dimethyl-[6-[4-(1-phenylcyclopropyl)benzoyl]-4,5, 6,7-tetrahydrofuro[2,3-c]pyridin-2-ylmethyl]amine 0.183 g was dissolved in 2 ml of methanol; hydrogen chloride in ethyl acetate was added in excess, followed by stirring. This mixture was concentrated and washed with diethyl ether to yield the desired product.

Brown solid Yield 0.177 g $^1$H-NMR (CD$_3$OD, 200 MHz) δ: 1.333(4H,s), 2.572–2.627(2H,m), 2.856(6H,s), 3.619–3.652(1.4H,m), 3.900–4.000(0.6H,m), 4.372(2H,br s), 4.500–4.600(0.6H,m), 4.711–4.729(1.4H,m), 6.647(1H,s), 7.186–7.385(9H,m)

IR (nujol): 2465, 1620, 1259, 951, 754 cm$^{-1}$

Anal. Calcd for C$_{26}$H$_{29}$ClN$_2$O$_2$·0.5H$_2$O: C, 70.02; H, 6.78; N, 6.28. Found: C, 69.97; H, 6.71; N, 6.15.

EXAMPLE 127

Synthesis of 6-[4-(1-phenylcyclopropyl)benzoyl]-2-(1-pyrrolidinylmethyl)-4,5,6,7-tetrahydrofuro[2,3-c]pyridine hydrochloride a) Synthesis of 6-[4-(1-phenylcyclopropyl)benzoyl]-4,5,6,7-tetrahydrofuro[2,3-c]pyridine To a solution of 1.209 g (7.575 mmol) of 4,5,6,7-tetrahydrofuro[2,3-c]pyridine hydrochloride, 1.80 g (7.58 mmol) of 4-(1-phenylcyclopropyl)benzoic acid and 4.22 ml (30.3 mmol) of triethylamine in 50 ml of N,N-dimethylformamide, 1.38 ml (9.09 mmol) of diethyl cyanophosphonate was added dropwise, followed by overnight stirring at room temperature. This mixture was poured into water and extracted with diethyl ether 3 times. The combined organic layer was dried over anhydrous sodium sulfate; the solvent was distilled off under reduced pressure. The resulting crude product was purified by silica gel column chromatography (hexane/ethyl acetate=6/1 to 3/1) to yield the desired product.

Yellow oil Yield 2.037 g (78%)

$^1$H-NMR (CDCl$_3$, 200 MHz) δ: 1.321–1.344(4H,m), 2.584(2H,br s), 3.612(1.2H,br s), 3.949(0.8H,br s), 4.504(0.8H,br s), 4.718(1.2H,br s), 6.273(1H,d,J=1.8 Hz), 7.208–7.373(10H,m)

IR (neat): 2926, 2852, 1630, 1423, 1282, 1265, 1232, 1092, 1024, 897, 843, 762, 702 cm$^{-1}$ b) Synthesis of 6-[4-(1-phenylcyclopropyl)benzoyl]-2-(1-pyrrolidinylmethyl)-4,5,6,7-tetrahydrofuro[2,3-c]pyridine To a solution of 0.454 g (1.322 mmol) of 6-[4-(1-phenylcyclopropyl)benzoyl]-4,5,6,7-tetrahydrofuro[2,3-c]pyridine in 10 ml of acetic acid, 0.17 ml (1.98 mmol) of pyrrolidine and 0.16 g (1.98 mmol) of 37% aqueous formaldehyde were added, followed by stirring at 100° C. for 1 hour. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.481 g (85%)

$^1$H-NMR (CDCl$_3$, 200 MHz) δ: 1.317–1.339(4H,m), 1.793(4H,br s), 2.540(4H,br s), 3.577(3.2H,br s), 3.900(0.8H,br s), 4.469(0.8H,br s), 4.687(1.2H,br s), 6.059(1H,s), 7.155–7.356(9H,m)

IR (neat): 2964, 2791, 1633, 1425, 1281, 1238, 1113, 1045, 935, 906, 762, 702 cm$^{-1}$ c) Synthesis of 6-[4-(1-phenylcyclopropyl)benzoyl]-2-(1-pyrrolidinylmethyl)-4,5,6,7-tetrahydrofuro[2,3-c]pyridine hydrochloride 6-[4-(1-Phenylcyclopropyl)benzoyl]-2-(1-pyrrolidinylmethyl)-4,5,6,7-tetrahydrofuro[2,3-c]pyridine 0.481 g was dissolved in 2 ml of methanol; hydrogen chloride in methanol was added in excess, followed by stirring. This mixture was concentrated to yield the desired product.

Pale brown foam Yield 0.503 g $^1$H-NMR (CD$_3$OD, 200 MHz) δ: 1.330(4H,s), 1.956–2.182(4H,m), 2.594(2H,br s), 3.191(2H,br s), 3.502–3.704(3.2H,m), 3.925(0.8H,br s), 4.429(2H,br s), 4.539(0.8H,br s), 4.717(1.2H,br s), 6.614(1H,s), 7.164–7.384(9H,m)

IR (neat): 2949, 2586, 1626, 1427, 1232, 1045, 1018, 905, 841, 762, 702 cm$^{-1}$ Anal. Calcd for C$_{28}$H$_{31}$ClN$_2$O$_2$·1.5H$_2$O: C, 68.63; H, 6.99; N, 5.72. Found: C, 68.80; H, 6.88; N, 5.99.

EXAMPLE 128

Synthesis of N,N-dimethyl-[5-[4-(1-phenylcyclopropyl)benzoyl]-4,5,6,7-tetrahydrofuro[3,2-c]pyridin-2-ylmethyl]amine hydrochloride a) Synthesis of N,N-dimethyl-[5-[4-(1-phenylcyclopropyl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.215 g (0.9 mmol) of 4-(1-phenylcyclopropyl)benzoic acid and 0.55 ml (4.0 mmol) of triethylamine in 30 ml of N,N-dimethylformamide, 0.245 g (1.5 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Pale yellow oil Yield 0.270 g (67%)

$^1$H-NMR (CDCl$_3$, 200 MHz) δ: 1.327(4H,d,J=4.8 Hz), 2.262(6H,s), 2.700–2.815(2H,m), 3.400(2H,s), 3.641–3.694(1.3H,m), 3.950–4.050(0.7H,m), 4.250–4.400(0.7H,m), 4.546–4.607(1.3H,m), 5.850–6.000(0.4H,m), 6.068–6.100(0.6H,m), 7.173–7.409(9H,m)

IR (neat): 2939, 2858, 2775, 1738, 1633, 1427, 1240, 1043, 847, 702 cm$^{-1}$ b) Synthesis of N,N-dimethyl-[5-[4-(1-phenylcyclopropyl)benzoyl]-4,5,6,7-tetrahydrofuro[3,2-c]pyridin-2-ylmethyl]amine hydrochloride N,N-Dimethyl-[5-[4-(1-phenylcyclopropyl)benzoyl]-4,5,6,7-tetrahydrofuro[3,2-c]pyridin-2-ylmethyl]amine 0.270 g was dissolved in 2 ml of methanol; hydrogen chloride in ethyl acetate was added in excess, followed by stirring. This mixture was concentrated and washed with diethyl ether to yield the desired product.

Pale brown powder Yield 0.276 g $^1$H-NMR (CD$_3$OD, 200 MHz) δ: 1.328(4H,s), 2.850(8H, br s), 3.684–3.744(1H,m), 4.013–4.055(1H,m), 4.308–4.460(3H,m), 4.566–4.618(1H,m), 6.450–6.600(0.5H,m), 6.684(0.5H,br s), 7.158–7.382(9H,m)

IR (nujol): 2638, 1624, 1113, 933, 760 cm$^{-1}$

Anal. Calcd for C$_{26}$H$_{29}$ClN$_2$O$_2$·1.3H$_2$O: C, 67.83; H, 6.92; N, 6.08. Found: C, 67.42; A, 6.86; N, 6.66.

EXAMPLE 129

Synthesis of N,N-dimethyl-[6-[4-(2-phenyl-1,3-dithiolan-2-yl)benzoyl]-4,5,6,7-tetrahydrofuro[2,3-c]pyridin-2-ylmethyl]amine hydrochloride a) Synthesis of N,N-dimethyl-[6-[4-(2-phenyl-1,3-dithiolan-2-yl)benzoyl]-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.665 g (2.2 mmol) of 4-(2-phenyl-1,3-dithiolan-2-yl)benzoic acid and 1.1 ml (8.0 mmol) of triethylamine in 30 ml of N,N-dimethylformamide, 0.489 g (3.0 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 60 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.384 g (41%)

$^1$H-NMR (CDCl$_3$, 200 MHz) δ: 2.260(6H,s), 2.489–2.536 (2H,m), 3.347–3.472(6H,m), 3.571–3.596(1.2H,m), 3.949 (0.8H,br s), 4.471(0.8H,br s), 4.721(1.2H,br s), 6.079(1H,s), 7.240–7.332(3H,m), 7.364(2H,d,J=8.4 Hz), 7.589(2H,d,J= 6.4 Hz), 7.680(2H,d,J=8.4 Hz)

IR (neat): 2924, 2852, 2773, 1632, 1427, 1238, 1163, 1043, 906, 731 cm$^{-1}$ b) Synthesis of N,N-dimethyl-[6-[4-(2-phenyl-1,3-dithiolan-2-yl)benzoyl]-4,5,6,7-tetrahydrofuro[2,3-c]pyridin-2-ylmethyl]amine hydrochloride N,N-Dimethyl-[6-[4-(2-phenyl-1,3-dithiolan-2-yl)benzoyl]-4,5,6,7-tetrahydrofuro[2,3-c]pyridin-2-ylmethyl]amine 0.384 g was dissolved in 2 ml of methanol; hydrogen chloride in ethyl acetate was added in excess, followed by stirring. This mixture was concentrated and washed with diethyl ether to yield the desired product.

Brown solid Yield 0.398 g $^1$H-NMR (CD$_3$OD, 200 MHz) δ: 2.611–2.631(2H,m), 2.862(6H,s), 3.430(4H,s), 3.640(1.4H,br s), 3.963(0.6H,br s), 4.380(2H,br s), 4.549(0.6H,br s), 4.741(1.4H,br s), 6.657 (1H,s), 7.254–7.293(3H,m), 7.387(2H,d,J=8.4 Hz), 7.575 (2H,dd,J=1.5&8.0 Hz), 7.695(2H,d,J=8.4 Hz)

IR (nujol): 2667, 1624, 1232, 1163, 972, 723 cm$^{-1}$

Anal. Calcd for C$_{26}$H$_{29}$ClN$_2$O$_2$S$_2$.1.0H$_2$O: C, 60.16; H, 6.02; N, 5.40. Found: C, 60.19; H, 6.07; N, 5.37

EXAMPLE 130

Synthesis of 6-[4-(2-phenyl-1,3-dithiolan-2-yl)benzoyl]-2-(1-pyrrolidinylmethyl)-4,5,6,7-tetrahydrofuro[2,3-c]pyridine hydrochloride a) Synthesis of 6-[4-(2-phenyl-1,3-dithiolan-2-yl)benzoyl]-4,5,6,7-tetrahydrofuro[2,3-c]pyridine To a solution of 1.582 g (9.912 mmol) of 4,5,6,7-tetrahydrofuro[2,3-c]pyridine hydrochloride, 3.00 g (9.91 mmol) of 4-(2-phenyl-1,3-dithiolan-2-yl)benzoic acid and 5.53 ml (39.6 mmol) of triethylamine in 50 ml of N,N-dimethylformamide, 1.80 ml (11.9 mmol) of diethyl cyanophosphonate was added dropwise, followed by overnight stirring at room temperature. This mixture was poured into water and extracted with diethyl ether 3 times. The combined organic layer was dried over anhydrous sodium sulfate; the solvent was distilled off under reduced pressure. The resulting crude product was purified by silica gel column chromatography (hexane/ethyl acetate=6/1 to 2/1) to yield the desired product.

Yellow oil Yield 2.709 g (67%)

$^1$H-NMR (CDCl$_3$, 200 MHz) δ: 2.584(2H,br s), 3.439 (4H,s), 3.635(1.2H,br s), 3.955(0.8H,br s), 4.510(0.8H,br s), 4.738(1.2H,br s), 6.280(1H,d,J=1.8 Hz), 7.240–7.339(3H, m), 7.375(2H,d,J=8.6 Hz), 7.572–7.620(2H,m), 7.680(2H, d,J=8.4 Hz)

IR (neat): 2924, 1628, 1423, 1238, 1092, 1039, 893, 735, 700 cm$^{-1}$ b) Synthesis of 6-[4-(2-phenyl-1,3-dithiolan-2-yl)benzoyl]-2-(1-pyrrolidinylmethyl)-4,5,6,7-tetrahydrofuro[2,3-c]pyridine To a solution of 0.719 g (1.764 mmol) of 6-[4-(2-phenyl-1,3-dithiolan-2-yl)benzoyl]-4,5,6,7-tetrahydrofuro[2,3-c]pyridine in 10 ml of acetic acid, 0.22 ml (2.65 mmol) of pyrrolidine and 0.21 g (2.65 mmol) of 37% aqueous formaldehyde were added, followed by stirring at 100° C. for 1 hour. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.624 g (72%)

$^1$H-NMR (CDCl$_3$, 200 MHz) δ: 1.773–1.791(4H,m), 2.541(4H,br s), 3.376–3.480(4H,m), 3.585(3.2H,br s), 3.935 (0.8H,br s), 4.466(0.8H,br s), 4.708(1.2H,br s), 6.063(1H,s), 7.239–7.303(3H,m), 7.354(2H,d,J=8.0 Hz), 7.567–7.607 (2H,m), 7.672(2H,d,J=8.4 Hz)

IR (neat): 2926, 2791, 1632, 1423, 1279, 1238, 1113, 1043, 906, 743, 700 cm$^{-1}$ c) Synthesis of 6-[4-(2-phenyl-1,3-dithiolan-2-yl)benzoyl]-2-(1-pyrrolidinylmethyl)-4,5,6,7-tetrahydrofuro[2,3-c]pyridine hydrochloride 6-[4-(2-Phenyl-1,3-dithiolan-2-yl)benzoyl]-2-(1-pyrrolidinylmethyl)-4,5,6,7-tetrahydrofuro[2,3-c]pyridine 0.624 g was dissolved in 2 ml of methanol; hydrogen chloride in methanol was added in excess, followed by stirring. This mixture was concentrated to yield the desired product.

Pale yellow foam Yield 0.665 g $^1$H-NMR (CD$_3$OD, 200 MHz) δ: 1.938–2.146(4H,m), 2.611(2H,br s), 3.204(2H,br s), 3.436(4H,s), 3.494–3.655 (3.2H,m), 3.960(0.8H,br s), 4.435(2H,br s), 4.538(0.8H,br s), 4.732(1.2H,br s), 6.621(1H,s), 7.228–7.341(3H,m), 7.390(2H,d,J=8.2 Hz), 7.543–7.607(2H,m), 7.701(2H,d,J= 8.2 Hz)

IR (neat): 2926, 2584, 1626, 1427, 1230, 1161, 1045, 1016, 980, 905, 743, 698 cm$^{-1}$ Anal. Calcd for C$_{28}$H$_{31}$ClN$_2$O$_2$S$_2$.1.2H$_2$O: C, 61.28; H, 6.13; N, 5.10. Found: C, 61.12; H, 6.12; N, 5.24.

EXAMPLE 131

Synthesis of N,N-dimethyl-[5-[4-(2-phenyl-1,3-dithiolan-2-yl)benzoyl]-4,5,6,7-tetrahydrofuro[3,2-c]pyridin-2-ylmethyl]amine hydrochloride a) Synthesis of N,N-dimethyl-[5-[4-(2-phenyl-1,3-dithiolan-2-yl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.332 g (1.1 mmol) of 4-(2-phenyl-1,3-dithiolan-2-yl)benzoic acid and 0.55 ml (4.0 mmol) of triethylamine in 30 ml of N,N-dimethylformamide, 0.245 g (1.5 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 120 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.271 g (58%)

$^1$H-NMR (CDCl$_3$, 200 MHz) δ: 2.264(6H,s), 2.700–2.848 (2H,m), 3.405(2H,s), 3.434(4H,s), 3.656–3.720(1.2H,m), 3.991–4.061(0.8H,m), 4.328–4.369(0.8H,m), 4.550–4.631 (1.2H,m), 5.933(0.4H,br s), 6.076–6.107(0.6H,m), 7.239–7.305(3H,m), 7.361(2H,d,J=8.4 Hz), 7.590(2H,dd,J= 1.8&8.0 Hz), 7.666(2H,d,J=8.0 Hz)

IR (neat): 2931, 2818, 2775, 1633, 1427, 1238, 1113, 1041, 802, 735 cm$^{-1}$ b) Synthesis of N,N-dimethyl-[5-[4-(2-phenyl-1,3-dithiolan-2-yl)benzoyl]-4,5,6,7-tetrahydrofuro[3,2-c]pyridin-2-ylmethyl]amine hydrochloride N,N-Dimethyl-[5-[4-(2-phenyl-1,3-dithiolan-2-yl)benzoyl]-4,5,6,7-tetrahydrofuro[3,2-c]pyridin-2-ylmethyl]amine 0.271 g was dissolved in 2 ml of methanol; hydrogen chloride in ethyl acetate was added in excess, followed by stirring. This mixture was concentrated and washed with diethyl ether to yield the desired product.

Pale brown solid Yield 0.239 g $^1$H-NMR (CD$_3$OD, 200 MHz) δ: 2.854(8H,br s), 3.434 (4H,s), 3.705–3.759(1.1H,m), 4.035–4.066(0.9H,m), 4.367–4.460(0.9H,m), 4.592–4.627(1.1H,m), 6.513(0.5H,br s), 6.682–6.693(0.5H,br s), 7.230–7.338(3H,m), 7.386(2H, d,J=8.4 Hz), 7.579(2H,dd,J=1.6&7.8 Hz), 7.691(2H,d,J=8.0 Hz)

IR (nujol): 2667, 1622, 1238, 1115, 937, 737 cm$^{-1}$

Anal. Calcd for C$_{26}$H$_{29}$ClN$_2$O$_2$S$_2$.1.0H$_2$O: C, 60.16; H, 6.02; N, 5.40. Found: C, 60.32; H, 6.14; N, 5.35.

EXAMPLE 132

Synthesis of N,N-dimethyl-[6-[4-(2-phenyl-1,3-dithian-2-yl)benzoyl]-4,5,6,7-tetrahydrofuro[2,3-c]pyridin-2-ylmethyl]amine hydrochloride a) Synthesis of N,N-dimethyl-[6-[4-(2-phenyl-1,3-dithian-2-yl)benzoyl]-4,5,6,7-tetrahydrofuro[2,3-c]pyridin-2-ylmethyl]amine To a solution of 0.319 g (2.000 mmol) of 4,5,6,7-tetrahydrofuro[2,3-c]pyridine hydrochloride, 0.696 g (2.2 mmol) of 4-(2-phenyl-1,3-dithian-2-yl)benzoic acid and 1.1 ml (8.0 mmol) of triethylamine in 30 ml of N,N-dimethylformamide, 0.489 g (3.0 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.270 ml (3.00 mmol) of 50% aqueous dimethylamine and 0.245 ml (3.00 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Brown oil Yield 0.533 g (56%)

$^1$H-NMR (CDCl$_3$, 200 MHz) δ: 1.987–2.022(2H,m), 2.258(6H,s), 2.531–2.597(2H,m), 2.767–2.822(4H,m), 3.357–3.425(2H,m), 3.601–3.637(1.1H,m), 3.967(0.9H,br s), 4.489(0.9H,br s), 4.720–4.736(1.1H,m), 6.075(1H,s), 7.264–7.447(5H,m), 7.654–7.814(4H,m)

IR (neat): 2939, 2906, 2773, 1632, 1423, 1277, 1020, 752 cm$^{-1}$ b) Synthesis of N,N-dimethyl-[6-[4-(2-phenyl-1,3-dithian-2-yl)benzoyl]-4,5,6,7-tetrahydrofuro[2,3-c]pyridin-2-ylmethyl]amine hydrochloride N,N-Dimethyl-[6-[4-(2-phenyl-1,3-dithian-2-yl)benzoyl]-4,5,6,7-tetrahydrofuro[2,3-c]pyridin-2-ylmethyl]amine 0.533 g was dissolved in 2 ml of methanol; hydrogen chloride in ethyl acetate was added in excess, followed by stirring. This mixture was concentrated and washed with diethyl ether to yield the desired product.

White solid Yield 0.542 g $^1$H-NMR (CD$_3$OD, 200 MHz) δ: 1.985–2.018(2H,m), 2.630(2H,br s), 2.768–2.868(10H,m), 3.660(1.4H,br s), 3.962(0.6H,br s), 4.385(2H,br s), 4.545(0.6H,br s), 4.754 (1.4H,br s), 6.659(1H,s), 7.295–7.474(5H,m), 7.699–7.800 (4H,m)

IR (nujol): 2467, 1628, 1232, 1257, 974, 743 cm$^{-1}$

Anal. Calcd for C$_{27}$H$_{31}$ClN$_2$O$_2$S$_2$.0.5H$_2$O: C, 61.87; H, 6.15; N, 5.34. Found: C, 61.59; H, 6.19; N, 5.24

EXAMPLE 133

Synthesis of N,N-dimethyl-[5-[4-(2-phenyl-1,3-dithian-2-yl)benzoyl]-4,5,6,7-tetrahydrofuro(3,2-c]pyridin-2-ylmethyl]amine hydrochloride a) Synthesis of N,N-dimethyl-[5-[4-(2-phenyl-1,3-dithian-2-yl)benzoyl]-4,5,6,7-tetrahydrofuro[3,2-c]pyridin-2-ylmethyl]amine To a solution of 0.160 g (1.000 mmol) of 4,5,6,7-tetrahydrofuro[3,2-c]pyridine hydrochloride, 0.348 g (1.1 mmol) of 4-(2-phenyl-1,3-dithian-2-yl)benzoic acid and 0.55 ml (4.0 mmol) of triethylamine in 30 ml of N,N-dimethylformamide, 0.245 g (1.5 mmol) of diethyl cyanophosphonate was added dropwise under ice-cooling, followed by overnight stirring at room temperature. Water was added, followed by 2 extractions with ethyl acetate. The combined organic layer was washed with water and dried over anhydrous sodium sulfate; the solvent was distilled off under reduced pressure. The resulting crude product was dissolved in 10 ml of acetic acid; 0.135 ml (1.50 mmol) of 50% aqueous dimethylamine and 0.122 ml (1.50 mmol) of 37% aqueous formaldehyde were added, followed by stirring at 100° C. for 30 minutes. After the solvent was distilled off under reduced pressure, the residual solution was alkalified with 5% aqueous sodium hydrogen carbonate, and extracted with ethyl acetate 2 times. The combined organic layer was washed with water and dried over anhydrous sodium sulfate; the solvent was distilled off under reduced pressure. The resulting crude product was purified by silica gel column chromatography (ethyl acetate/methanol=5/1) to yield the desired product.

Pale brown oil Yield 0.368 g (77%)

$^1$H-NMR (CDCl$_3$, 200 MHz) δ: 1.963–2.020(2H,m), 2.267(6H,s), 2.769–2.825(6H,m), 3.406(2H,s), 3.679(1.2H, br s), 4.070(0.8H,br s), 4.332(0.8H,br s), 4.613(1.2H,br s), 5.910(0.4H,br s), 6.108(0.6H,br s), 7.271–7.444(5H,m), 7.694–7.786(4H,m)

IR (neat): 2904, 2818, 2773, 1630, 1423, 1279, 1113, 908, 731 cm$^{-1}$ b) Synthesis of N,N-dimethyl-[5-[4-(2-phenyl-1,3-dithian-2-yl)benzoyl]-4,5,6,7-tetrahydrofuro[3,2-c]pyridin-2-ylmethyl]amine hydrochloride N,N-Dimethyl-[5-[4-(2-phenyl-1,3-dithian-2-yl)benzoyl]-4,5,6,7-tetrahydrofuro[3,2-c]pyridin-2-ylmethyl] amine 0.368 g was dissolved in 2 ml of methanol; hydrogen chloride in ethyl acetate was added in excess, followed by stirring. This mixture was concentrated and washed with diethyl ether to yield the desired product.

Pale yellow solid Yield 0.394 g $^1$H-NMR (CD$_3$OD, 200 MHz) δ: 1.980–2.048(2H,m), 2.764–2.856(12H,m), 3.713–3.755(1.1H,m), 4.054–4.076 (0.9H,m), 4.372–4.449(2.9H,m), 4.634–4.914(1.1H,m), 6.526(0.5H,br s), 6.697(0.5H,br s), 7.292–7.466(5H,m), 7.699–7.785(4H,m)

IR (nujol): 2677, 1622, 1238, 1115, 939, 733 cm$^{-1}$

Anal. Calcd for C$_{27}$H$_{31}$ClN$_2$O$_2$S$_2$.1.5H$_2$O: C, 59.82; H, 6.32; N, 5.17. Found: C, 59.95; H, 6.08; N, 5.12

EXAMPLE 134

Synthesis of N,N-dimethyl-[6-(4-benzoylphenylsulfonyl)-4,5,6,7-tetrahydrofuro[2,3-c]pyridin-2-ylmethyl]amine hydrochloride a) Synthesis of 4-(5,7-dihydro-4H-furo[2,3-c]pyridin-6-ylsulfonyl)benzoic acid To a solution of 0.970 g (6.077 mmol) of 4,5,6,7-tetrahydrofuro[2,3-c]pyridine hydrochloride and 3.39 ml (24.3 mmol) of triethylamine in 50 ml of dichloromethane, 1.61 g (7.29 mmol) of 4-chlorosulfonylbenzoic aced was added under ice-cooling, followed by stirring at room temperature for 4 hours. After the solvent was distilled off under reduced pressure, 1 N hydrochloric acid was added; the resulting precipitate was filtered, washed with 1 N hydrochloric acid and dried to yield the desired product.

Pale brown solid Yield 1.852 g (99%)

$^1$H-NMR (CDCl$_3$-DMSO-d$_6$, 200 MHz) δ: 2.560(2H,t,J= 4.9 Hz), 3.409(2H,t,J=5.5 Hz), 4.231(2H,s), 6.184(1H,s), 7.270(1H,s), 7.865(2H,d,J=8.0 Hz), 8.184(2H,d,J=8.0 Hz)

IR (nujol): 2675, 2555, 1695, 1433, 1350, 1315, 1290, 1169, 943, 740 cm$^{-1}$ b) Synthesis of 4-(5,7-dihydro-4H-furo[2,3-c]pyridin-6-ylsulfonyl)benzaldehyde To a suspension of 1.745 g (5.678 mmol) of 4-(5,7-dihydro-4H-furo[2,3-c]pyridin-6-ylsulfonyl)benzoic acid in 50 ml of tetrahydrofuran, 8.5 ml (8.5 mmol) of 1.0 M borane in tetrahydrofuran was added dropwise under ice-cooling, followed by overnight stirring at room temperature. Dilute hydrochloric acid was added, followed by stirring at room temperature for 0.5 hours and 3 extractions with ethyl acetate. The combined organic layer was dried over anhydrous magnesium sulfate; the solvent was distilled off under reduced pressure. The resulting crude 4-(5,7-dihydro-4H-furo[2,3-c]pyridin-6-ylsulfonyl)benzyl alcohol was used for the next reaction without purification.

Pale brown oil Yield 1.650 g

To a solution of 1.07 g (8.44 mmol) of oxalyl chloride in 50 ml of dichloromethane, 1.20 ml (16.9 mmol) of dimethyl sulfoxide was added dropwise at −78° C., followed by stirring for 5 minutes. To this solution, a solution of 1.650 g of the above crude 4-(5,7-dihydro-4H-furo[2,3-c]pyridin-6-ylsulfonyl)benzyl alcohol in 10 ml of dichloromethane was added at −78° C., followed by stirring for 15 minutes. To this mixture, 4.70 ml (33.7 mmol) of triethylamine was added; the mixture was allowed to warm to room temperature. The reaction mixture was diluted with diethyl ether, washed with water and dried over anhydrous magnesium sulfate; the solvent was distilled off under reduced pressure. The resulting crude product was purified by silica gel column chromatography (dichloromethane) and crystallized from diethyl ether-hexane to yield the desired product.

White solid Yield 0.579 g (35%)

$^1$H-NMR (CDCl$_3$, 200 MHz) δ: 2.550(2H,tt,J=1.7&5.7 Hz), 3.448(2H,t,J=5.7 Hz), 4.275(2H,s), 6.170(1H,d,J=1.8 Hz), 7.257(1H,d,J=2.0 Hz), 7.973(2H,d,J=8.8 Hz), 8.032 (2H,d,J=8.8 Hz), 10.095(1H,s)

IR (nujol): 1707, 1350, 1298, 1200, 1169, 945, 897, 750, 704 cm$^{-1}$ c) Synthesis of 4-(5,7-dihydro-4H-furo[2,3-c]pyridin-6-ylsulfonyl)phenylphenylmethanol To a solution of 0.142 g (0.487 mmol) of 4-(5,7-dihydro-4H-furo[2,3-c]pyridin-6-ylsulfonyl)benzaldehyde in 30 ml of tetrahydrofuran, phenylmagnesium bromide in tetrahydrofuran (prepared from 2.0 g of bromobenzene and 0.31 g of magnesium in 30 ml of tetrahydrofuran) was added at room temperature until the starting material disappeared on thin-layer chromatography (TLC). To the reaction mixture, aqueous ammonium chloride was added, followed by stirring and 3 extractions with ethyl acetate. The combined organic layer was dried over anhydrous magnesium sulfate; the solvent was distilled off under reduced pressure. The resulting crude product was purified by silica gel column chromatography (hexane/ethyl acetate=3/1 to 2/1) to yield the desired product.

White solid Yield 0.153 g (85%)

$^1$H-NMR (CDCl$_3$, 200 MHz) δ: 2.526(2H,t,J=5.7 Hz), 2.731(1H,br d,J=2.8 Hz), 3.332(2H,t,J=5.7 Hz), 4.158(2H, s), 5.843(1H,br s), 6.148(1H,d,J=2.0 Hz), 7.231(1H,d,J=1.8 Hz), 7.261–7.356(5H,m), 7.521(2H,d,J=8.0 Hz), 7.725(2H, d,J=8.4 Hz)

IR (nujol): 3527, 1319, 1161, 1032, 945, 743, 698 cm$^{-1}$ d) Synthesis of 6-(4-benzoylphenylsulfonyl)-4,5,6,7-tetrahydrofuro[2,3-c]pyridine To a solution of 0.04 ml (0.5 mmol) of oxalyl chloride in 30 ml of dichloromethane, 0.07 ml (1.0 mmol) of dimethyl sulfoxide was added dropwise at −78° C., followed by stirring for 5 minutes. To this solution, a solution of 0.122 g (0.330 mmol) of 4-(5,7-dihydro-4H-furo[2,3-c]pyridin-6-ylsulfonyl)phenylphenylmethanol in 10 ml of dichloromethane and 1 ml of dimethyl sulfoxide was added at −78° C., followed by stirring for 15 minutes. To this mixture, 0.28 ml (2.0 mmol) of triethylamine was added; the mixture was allowed to warm to room temperature. After the reaction mixture was washed with water, the water layer was re-extracted with diethyl ether. The combined organic layer was dried over anhydrous magnesium sulfate; the solvent was distilled off under reduced pressure. The resulting crude product was purified by silica gel column chromatography (hexane/ethyl acetate=3/1) to yield the desired product.

Pale yellow solid Yield 0.121 g (100%)

$^1$H-NMR (CDCl$_3$, 200 MHz) δ: 2.574(2H,t,J=5.7 Hz), 3.458(2H,t,J=5.7 Hz), 4.282(2H,s), 6.191(1H,d,J=1.8 Hz), 7.269(1H,d,J=2.0 Hz), 7.468–7.547(2H,m), 7.602–7.688 (1H,m), 7.759–7.803(2H,m), 7.889(2H,d,J=8.8 Hz), 7.943 (2H,d,J=9.2 Hz)

IR (nujol): 1662, 1342, 1317, 1275, 1163, 1113, 909, 743, 704 cm$^{-1}$ e) Synthesis of N,N-dimethyl-[6-(4-benzoylphenylsulfonyl)-4,5,6,7-tetrahydrofuro[2,3-c]pyridin-2-ylmethyl]amine To a solution of 0.111 g (0.302 mmol) of 6-(4-benzoylphenylsulfonyl)-4,5,6,7-tetrahydrofuro[2,3-c]pyridine in 10 ml of acetic acid, 41 mg (0.45 mmol) of 50% aqueous dimethylamine and 37 mg (0.45 mmol) of 37% aqueous formaldehyde were added, followed by stirring at 100° C. for 0.5 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.079 g (62%)

$^1$H-NMR (CDCl$_3$, 200 MHz) δ: 2.231(6H,s), 2.544(2H,t,J=5.7 Hz), 3.381(2H,s), 3.451(2H,t,J=5.7 Hz), 4.271(2H,s), 6.002(1H,s), 7.283–7.554(2H,m), 7.598–7.686(1H,m), 7.755–7.805(2H,m), 7.881(2H,d,J=9.2 Hz), 7.935(2H,d,J=8.8 Hz)

IR (neat): 2937, 2773, 1662, 1450, 1352, 1313, 1275, 1171, 935, 702 cm$^{-1}$ f) Synthesis of N,N-dimethyl-[6-(4-benzoylphenylsulfonyl)-4,5,6,7-tetrahydrofuro[2,3-c]pyridin-2-ylmethyl]amine hydrochloride N,N-Dimethyl-[6-(4-benzoylphenylsulfonyl)-4,5,6,7-tetrahydrofuro[2,3-c]pyridin-2-ylmethyl]amine 79 mg was dissolved in 2 ml of methanol; hydrogen chloride in methanol was added in excess, followed by stirring. This mixture was concentrated to yield the desired product.

Pale yellow foam Yield 85 mg $^1$H-NMR (CD$_3$OD, 200 MHz) δ: 2,553(2H,br t,J=5.1 Hz), 2.839(6H,s), 3.476(2H,t,J=5.7 Hz), 4.330(2H,s), 4.352(2H,s), 6.570(1H,s), 7.499–7.572(2H,m), 7.636–7.781(3H,m), 7.899(2H,d,J=8.4 Hz), 7.994(2H,d,J=8.4 Hz)

IR (nujol): 2956, 1660, 1348, 1315, 1277, 1169, 931, 764, 702 cm$^{-1}$

Anal. Calcd for C$_{23}$H$_{25}$ClN$_2$O$_4$S.1.0H$_2$O: C, 57.67; H, 5.68; N, 5.85. Found: C, 57.40; H, 5.74; N, 5.60

EXAMPLE 135

Synthesis of N,N-dimethyl-[5-(4-benzoylphenylsulfonyl)-4,5,6,7-tetrahydrofuro[3,2-c]pyridin-2-ylmethyl]amine hydrochloride a) Synthesis of 4-(6,7-dihydro-4H-furo[3,2-c]pyridin-5-ylsulfonyl)benzoic acid To a solution of 2.900 g (18.169 mmol) of 4,5,6,7-tetrahydrofuro[3,2-c]pyridine hydrochloride and 12.7 ml (90.8 mmol) of triethylamine in 100 ml of dichloromethane, 4.81 g (21.8 mmol) of 4-chlorosulfonylbenzoic acid was added under ice-cooling, followed by overnight stirring at room temperature. After the solvent was distilled off under reduced pressure, 1 N hydrochloric acid was added; the resulting precipitate was filtered, washed with 1 N hydrochloric acid and dried to yield the desired product.

Pale brown solid Yield 6.137 g (100%)

$^1$H-NMR (CDCl$_3$-DMSO-d$_6$, 200 MHz) δ: 2.731(2H,t,J=5.6 Hz), 3.499(2H,t,J=5.8 Hz), 4.137(2H,t,H=1.7 Hz), 6.203 (1H,d,J=2.0 Hz), 7.262(1H,d,J=2.0 Hz), 7.862(2H,d,J=8.6 Hz), 8.179(2H,d,J=8.4 Hz)

IR (nujol): 2673, 2549, 1680, 1348, 1290, 1169, 1122, 945, 756 cm$^{-1}$ b) Synthesis of 4-(6,7-dihydro-4H-furo[3,2-c]pyridin-5-ylsulfonyl)benzyl alcohol To a suspension of 19.040 g (61.953 mmol) of 4-(6,7-dihydro-4H-furo[3,2-c]pyridin-5-ylsulfonyl)benzoic acid in 100 ml of tetrahydrofuran, 74.3 ml (74.3 mmol) of 1.0 M borane in tetrahydrofuran was added dropwise under ice-cooling, followed by overnight stirring at room temperature. Dilute hydrochloric acid was added, followed by stirring at room temperature for 0.5 hours and 3 extractions with ethyl acetate. The combined organic layer was dried over anhydrous magnesium sulfate; the solvent was distilled off under reduced pressure. The residue was dissolved in 50 ml of methanol; 15 ml of concentrated hydrochloric acid was added, followed by stirring at 70° C. for 1 hour. The reaction mixture was poured into water and extracted with ethyl acetate 3 times. The combined organic layer was dried over anhydrous magnesium sulfate; the solvent was distilled off under reduced pressure. The resulting crude product was purified by silica gel column chromatography (hexane/ethyl acetate=3/1 to 1/1) to yield the desired product.

Yellow oil Yield 9.453 g (52%)

$^1$H-NMR (CDCl$_3$, 200 MHz) δ: 2.612(1H,br s), 2.731 (2H,t,J=5.8 Hz), 3.464(2H,t,J=5.7 Hz), 4.109(2H,s), 4.805 (2H,s), 6.182(1H,d,J=2.2 Hz), 7.252(1H,d,J=2.2 Hz), 7.497 (2H,d,J=8.0 Hz), 7.789(2H,d,J=8.4 Hz)

IR (neat): 3456, 2926, 2856, 1404, 1342, 1242, 1163, 1090, 1057, 1001, 947, 752, 690 cm$^{-1}$ c) Synthesis of 4-(6,7-dihydro-4H-furo[3,2-c]pyridin-5-ylsulfonyl)benzaldehyde To a solution of 4.27 g (33.6 mmol) of oxalyl chloride in 100 ml of dichloromethane, 4.78 ml (67.3 mmol) of dimethyl sulfoxide was added dropwise at –78° C., followed by stirring for 5 minutes. To this solution, a solution of 6.580 g (22.431 mmol) of 4-(6,7-dihydro-4H-furo[3,2-c]pyridin-5-ylsulfonyl)benzyl alcohol in 50 ml of dichloromethane was added at –78° C., followed by stirring for 15 minutes. To this mixture, 18.8 ml (135 mmol) of triethylamine was added; the mixture was allowed to warm to room temperature. After the reaction mixture was washed with water, the water layer was re-extracted with diethyl ether. The combined organic layer was dried over anhydrous magnesium sulfate; the solvent was distilled off under reduced pressure. The resulting crude product was purified by silica gel column chromatography (hexane/ethyl acetate=6/1 to 3/1 to 2/1) to yield the desired product.

Pale yellow solid Yield 5.586 g (86%)

$^1$H-NMR (CDCl$_3$, 200 MHz) δ: 2.731(2H,t,J=5.8 Hz), 3.547(2H,t,J=5.8 Hz), 4.194(2H,t,J=1.7 Hz), 6.197(1H,d,J= 1.8 Hz), 7.263(1H,d,J=1.8 Hz), 7.981(2H,d,J=8.8 Hz), 8.035 (2H,d,J=8.8 Hz), 10.104(1H,s)

IR (nujol): 1707, 1344, 1319, 1298, 1168, 1119, 1086, 999, 945, 889, 825, 739, 702 cm$^{-1}$ d) Synthesis of 4-(6,7-dihydro-4H-furo[3,2-c]pyridin-5-ylsulfonyl)phenylphenylmethanol To a solution of 0.252 g (0.865 mmol) of 4-(6,7-dihydro-4H-furo[3,2-c]pyridin-5-ylsulfonyl)benzaldehyde in 30 ml of tetrahydrofuran, phenylmagnesium bromide in tetrahydrofuran (prepared from 2.0 g of bromobenzene and 0.31 g of magnesium in 30 ml of tetrahydrofuran) was added at room temperature until the starting material disappeared on TLC. To the reaction mixture, aqueous ammonium chloride was added, followed by stirring and 3 extractions with ethyl acetate. The combined organic layer was dried over anhydrous magnesium sulfate; the solvent was distilled off under reduced pressure. The resulting crude product was purified by silica gel column chromatography (hexane/ethyl acetate= 3/1 to 2/1) to yield the desired product.

Colorless oil Yield 0.303 g (95%)

$^1$H-NMR (CDCl$_3$, 200 MHz) δ: 2.685(2H,br t, J=5.9 Hz), 2.911(1H,br d,J=3.0 Hz), 3.403(2H,t,J=5.9 Hz), 4.054(2H,t,J=1.7 Hz), 5.830(1H,br d,J=1.8 Hz), 6.148(1H,d,J=2.2 Hz), 7.216(1H,d,J=2.0 Hz), 7.252–7.338(5H,m), 7.503(2H,d,J=8.2 Hz), 7.705(2H,d,J=8.4 Hz)

IR (neat): 3500, 2852, 1456, 1402, 1344, 1319, 1244, 1163, 1041, 1001, 947, 752, 702 cm$^{-1}$ e) Synthesis of 5-(4-benzoylphenylsulfonyl)-4,5,6,7-tetrahydrofuro[3,2-c]pyridine To a solution of 0.16 ml (1.2 mmol) of oxalyl chloride in 30 ml of dichloromethane, 0.17 ml (2.5 mmol) of dimethyl sulfoxide was added dropwise at −78° C., followed by stirring for 5 minutes. To the solution, a solution of 0.303 g (0.820 mmol) of 4-(6,7-dihydro-4H-furo[3,2-c]pyridin-5-ylsulfonyl)phenylphenylmethanol in 10 ml of dichloromethane was added at −78° C., followed by stirring for 15 minutes. To this mixture, 0.69 ml (4.9 mmol) of triethylamine was added; the mixture was allowed to warm to room temperature. After the reaction mixture was washed with water, the water layer was re-extracted with diethyl ether. The combined organic layer was dried over anhydrous magnesium sulfate; the solvent was distilled off under reduced pressure. The resulting crude product was purified by silica gel column chromatography (hexane/ethyl acetate=3/1) and washed with diethyl ether-hexane to yield the desired product.

White solid Yield 0.269 g (89%)

$^{1}$H-NMR (CDCl$_3$, 200 MHz) δ: 2.758(2H,t,J=5.7 Hz), 3.553(2H,t,J=5.7 Hz), 4.198(2H,t,J=1.6 Hz), 6.204(1H,d,J=2.2 Hz), 7.269(1H,d,J=2.2 Hz), 7.470–7.691(3H,m), 7.763–7.812(2H,m), 7.867–7.951(4H,m)

IR (nujol): 1664, 1346, 1317, 1281, 1171, 1144, 945, 770, 727, 700 cm$^{-1}$ f) Synthesis of N,N-dimethyl-[5-(4-benzoylphenylsulfonyl)-4,5,6,7-tetrahydrofuro[3,2-c]pyridin-2-ylmethyl]amine To a solution of 0.210 g (0.572 mmol) of 5-(4-benzoylphenylsulfonyl)-4,5,6,7-tetrahydrofuro[3,2-c]pyridine in 10 ml of acetic acid, 77 mg (0.86 mmol) of 50% aqueous dimethylamine and 70 mg (0.86 mmol) of 37% aqueous formaldehyde were added, followed by stirring at 100° C. for 0.5 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was crystallized from diethyl ether-hexane to yield the desired product.

Pale yellow solid Yield 0.213 g (88%)

$^{1}$H-NMR (CDCl$_3$, 200 MHz) δ: 2.225(6H,s), 2.753(2H,t,J=5.6 Hz), 3.368(2H,s), 3.539(2H,t,J=5.7 Hz), 4.160(2H,s), 6.004(1H,s), 7.475–7.554(2H,m), 7.607–7.688(1H,m), 7.768–7.812(2H,m), 7.895(2H,d,J=8.8 Hz), 7.947(2H,d,J=9.2 Hz)

IR (nujol): 1657, 1342, 1309, 1281, 1169, 694 cm$^{-1}$ g) Synthesis of N,N-dimethyl-[5-(4-benzoylphenylsulfonyl)-4,5,6,7-tetrahydrofuro[3,2-c]pyridin-2-ylmethyl]amine hydrochloride N,N-Dimethyl-[5-(4-benzoylphenylsulfonyl)-4,5,6,7-tetrahydrofuro[3,2-c]pyridin-2-ylmethyl]amine 0.182 g was dissolved in 2 ml of methanol; hydrogen chloride in methanol was added in excess, followed by stirring. This mixture was concentrated and washed with diethyl ether to yield the desired product.

Pale yellow solid Yield 0.178 g $^{1}$H-NMR (CD$_3$OD, 200 MHz) δ: 2.754(2H,t,J=5.9 Hz), 2.818(6H,s), 3.601(2H,t,J=5.8 Hz), 4.224(2H,t,J=1.8 Hz), 4.320(2H,s), 6.595(1H,s), 7.504–7.583(2H,m), 7.640–7.721(1H,m), 7.763–7.806(2H,m), 7.912(2H,d,J=8.8 Hz), 8.009(2H,d,J=8.8 Hz)

IR (nujol): 2470, 1657, 1342, 1315, 1284, 1169, 1146, 928, 704 cm$^{-1}$

Anal. Calcd for $C_{23}H_{25}ClN_2O_4S \cdot 0.5H_2O$: C, 58.78; H, 5.58; N, 5.96. Found: C, 58.51; H, 5.42; N, 5.81

EXAMPLE 136

Synthesis of (Z)-N,N-dimethyl-[6-(4-stilbenesulfonyl)-4,5,6,7-tetrahydrofuro[2,3-c]pyridin-2-ylmethyl]amine hydrochloride a) Synthesis of (Z)-[6-(4-stilbenesulfonyl)-4,5,6,7-tetrahydrofuro[2,3-c]pyridine To a solution of 0.410 g (1.407 mmol) of 4-(5,7-dihydro-4H-furo[2,3-c]pyridin-6-ylsulfonyl)benzaldehyde and 0.66 g (1.7 mmol) of benzyltriphenylphosphonium chloride in 30 ml of methanol, 0.33 g (1.7 mmol) of 28% sodium methoxide in methanol was added dropwise at room temperature, followed by overnight stirring at room temperature. The reaction mixture was poured into water and extracted with ethyl acetate 3 times. The combined organic layer was dried over anhydrous magnesium sulfate; the solvent was distilled off under reduced pressure. The resulting crude product was subjected to silica gel column chromatography (hexane/ethyl acetate=3/1) to remove triphenylphosphine oxide, followed by crystallization from diethyl ether-hexane to yield the (E)-isomer.

White crystal Yield 0.157 g (31%)

$^{1}$H-NMR (CDCl$_3$, 200 MHz) δ: 2.577(2H,t,J=5.7 Hz), 3.401(2H,t,J=5.7 Hz), 4.233(2H,s), 6.185(1H,d,J=1.8 Hz), 7.096(1H,d,J=16.0 Hz), 7.191–7.437(5H,m), 7.517–7.565 (2H,m), 7.623(2H,d,J=8.6 Hz), 7.797(2H,d,J=8.6 Hz)

IR (nujol): 1352, 1323, 1163, 1092, 970, 947, 899, 820, 754, 737 cm$^{-1}$

The mother liquor was concentrated under reduced pressure, and purified by silica gel flush column chromatography (hexane/ethyl acetate=6/1) to yield the (Z)-isomer (desired product).

Colorless oil Yield 0.155 g (30%)

$^{1}$H-NMR (CDCl$_3$, 200 MHz) δ: 2.541(2H,t,J=5.7 Hz), 3.368(2H,t,J=5.7 Hz), 4.200(2H,s), 6.181(1H,d,J=2.0 Hz), 6.560(1H,d,J=12.0 Hz), 6.746(1H,d,J=12.4 Hz), 7.131–7.297(6H,m), 7.348(2H,d,J=8.4 Hz), 7.641(2H,d,J=8.4 Hz)

IR (neat): 2922, 2852, 1592, 1452, 1348, 1319, 1165, 1090, 945, 903, 785, 735, 700 cm$^{-1}$ b) Synthesis of (Z)-N,N-dimethyl-[6-(4-stilbenesulfonyl)-4,5,6,7-tetrahydrofuro[2,3-c]pyridin-2-ylmethyl]amine To a solution of 0.155 g (0.424 mmol) of (Z)-6-(4-stilbenesulfonyl)-4,5,6,7-tetrahydrofuro[2,3-c]pyridin in 10 ml of acetic acid, 57 mg (0.64 mmol) of 50% aqueous dimethylamine and 52 mg (0.64 mmol) of 37% aqueous formaldehyde were added, followed by stirring at 100° C. for 0.5 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.138 g (77%)

$^{1}$H-NMR (CDCl$_3$, 200 MHz) δ: 2.233(6H,s), 2.509(2H,t,J=5.7 Hz), 3.358(2H,t,J=5.6 Hz), 3.385(2H,s), 4.185(2H,s), 5.997(1H,s), 6.555(1H,d,J=12.2 Hz), 6,744(1H,d,J=12.4 Hz), 7.140–7.266(5H,m), 7.341(2H,d,J=8.6 Hz), 7.632(2H,d,J=8.4 Hz)

IR (neat): 2935, 2773, 1452, 1348, 1242, 1185, 1092, 1012, 941, 787, 700 cm$^{-1}$ c) Synthesis of (Z)-N,N-dimethyl-[6-(4-stilbenesulfonyl)-4,5,6,7-tetrahydrofuro[2,3-c]pyridin-2-ylmethyl]amine hydrochloride (Z)-N,N-Dimethyl-[6-(4-stilbenesulfonyl)-4,5,6,7-tetrahydrofuro[2,3-c]pyridin-2-ylmethyl]amine 0.138 g was dissolved in 2 ml of methanol; hydrogen chloride in methanol was added in excess, followed by stirring. This mixture was concentrated to yield the desired product.

Pale yellow foam Yield 0.151 g $^1$H-NMR (CD$_3$OD, 200 MHz) δ: 2.499(2H,t,J=5.5 Hz), 2.828(6H,s), 3.362(2H,t,J=5.7 Hz), 4.227(2H,s), 4.345(2H,s), 6.569(1H,s), 6.622(1H,d,J=12.2 Hz), 6.780(1H,d,J=12.2 Hz), 7.120–7.253(5H,m), 7.376(2H,d,J=8.2 Hz), 7.647(2H,d,J=8.6 Hz)

IR (neat): 2958, 2667–2472, 1470, 1346, 1165, 1092, 943, 787, 702 cm$^{-1}$

Anal. Calcd for C$_{24}$H$_{27}$ClN$_2$O$_3$S.1.0H$_2$O: C, 60.43; H, 6.13; N, 5.87. Found: C, 60.62; H, 6.16; N, 6.01

EXAMPLE 137

Synthesis of (Z)-N,N-dimethyl-[5-(4-stilbenesulfonyl)-4,5,6,7-tetrahydrofuro[3,2-c]pyridin-2-ylmethyl]amine hydrochloride a) Synthesis of (Z)-5-(4-stilbenesulfonyl)-4,5,6,7-tetrahydrofuro[3,2-c]pyridine To a solution of 0.503 g (1.727 mmol) of 4-(6,7-dihydro-4H-furo[3,2-c]pyridin-5-ylsulfonyl)benzaldehyde and 0.81 g (2.1 mmol) of benzyltriphenylphosphonium chloride in 30 ml of methanol, 0.40 g (2.1 mmol) of 28% sodium methoxide in methanol was added dropwise at room temperature, followed by overnight stirring at room temperature. The reaction mixture was poured into water and extracted with ethyl acetate 3 times. The combined organic layer was dried over anhydrous magnesium sulfate; the solvent was distilled off under reduced pressure. The resulting crude product was subjected to silica gel column chromatography (hexane/ethyl acetate=3/1) to remove triphenylphosphine oxide, followed by crystallization from diethyl ether-hexane to yield the (E)-isomer.

White crystal Yield 0.167 g (27%)

$^1$H-NMR (CDCl$_3$, 200 MHz) δ: 2.747(2H,t,J=5.7 Hz), 3.495(2H,t,J=5.9 Hz), 4.141(2H,t,J=1.9 Hz), 6.191(1H,d,J=1.8 Hz), 7.093(1H,d,J=16.4 Hz), 7.186–7.431(5H,m), 7.514–7.559(2H,m), 7.617(2H,d,J=8.4 Hz), 7.792(2H,d,J=8.8 Hz)

IR (nujol): 1342, 1319, 1161, 945, 756, 731, 694 cm$^{-1}$

The mother liquor was concentrated under reduced pressure, and purified by silica gel flush column chromatography (hexane/ethyl acetate=6/1) to yield the (Z)-isomer (desired product).

Colorless oil Yield 0.153 g (24%)

$^1$H-NMR (CDCl$_3$, 200 MHz) δ: 2.676(2H,t,J=5.8 Hz), 3.451(2H,t,J=5.8 Hz), 4.110(2H,t,J=1.6 Hz), 6.164(1H,d,J=2.2 Hz), 6.548(1H,d,J=12.2 Hz), 6.729(1H,d,J=12.2 Hz), 7.125–7.255(6H,m), 7.330(2H,d,J=8.6 Hz), 7.632(2H,d,J=8.4 Hz)

IR (neat): 2918, 2852, 1593, 1498, 1346, 1317, 1165, 1090, 999, 947, 920, 785, 735, 692 cm$^{-1}$ b) Synthesis of (Z)-N,N-dimethyl-[5-(4-stilbenesulfonyl)-4,5,6,7-tetrahydrofuro[3,2-c]pyridin-2-ylmethyl]amine To a solution of 0.153 g (0.419 mmol) of (Z)-5-(4-stilbenesulfonyl)-4,5,6,7-tetrahydrofuro[3,2-c]pyridine in 10 ml of acetic acid, 57 mg (0.63 mmol) of 50% aqueous dimethylamine and 51 mg (0.63 mmol) of 37% aqueous formaldehyde were added, followed by stirring at 100° C. for 0.5 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale orange oil Yield 0.148 g (84%)

$^1$H-NMR (CDCl$_3$, 200 MHz) δ: 2.227(6H,s), 2.703(2H,t,J=5.7 Hz), 3.367(2H,s), 3.453(2H,t,J=5.9 Hz), 4.083(2H,t,J=1.8 Hz), 5.988(1H,s), 6.558(1H,d,J=12.0 Hz), 6.746(1H,d,J=12.4 Hz), 7.123–7.266(5H,m), 7.340(2H,d,J=8.2 Hz), 7.639(2H,d,J=8.4 Hz)

IR (neat): 2937, 2773, 1454, 1346, 1307, 1167, 1092, 1003, 930, 787, 694 cm$^{-1}$ c) Synthesis of (Z)-N,N-dimethyl-[5-(4-stilbenesulfonyl)-4,5,6,7-tetrahydrofuro[3,2-c]pyridin-2-ylmethyl]amine hydrochloride (Z)-N,N-Dimethyl-[5-(4-stilbenesulfonyl)-4,5,6,7-tetrahydrofuro[3,2-c]pyridin-2-ylmethyl]amine 0.148 g was dissolved in 2 ml of methanol; hydrogen chloride in methanol was added in excess, followed by stirring. This mixture was concentrated to yield the desired product.

Pale yellow solid Yield 0.165 g $^1$H-NMR (CD$_3$OD, 200 MHz) δ: 2.687(2H,br t,J=5.6 Hz), 2.819(6H,s), 3.462(2H,t,J=5.7 Hz), 4.103(2H,s), 4.334(2H,s), 6.614(1H,s), 6.626(1H,d,J=12.0 Hz), 6.782(1H,d,J=12.0 Hz), 7.123–7.257(5H,m), 7.373(2H,d,J=8.4 Hz), 7.648(2H,d,J=8.4 Hz)

IR (nujol): 2472, 1340, 1317, 1165, 1146, 1090, 1005, 930, 690 cm$^{-1}$

Anal. Calcd for C$_{24}$H$_{27}$ClN$_2$O$_3$S.0.5H$_2$O: C, 61.59; H, 6.03; N, 5.99. Found: C, 61.68; H, 5.92; N, 6.05

EXAMPLE 138

Synthesis of N,N-dimethyl-[5-(4-phenethylbenzenesulfonyl)-4,5,6,7-tetrahydrofuro[3,2-c]pyridin-2-ylmethyl]amine hydrochloride a) Synthesis of 5-(4-phenethylbenzenesulfonyl)-4,5,6,7-tetrahydrofuro[3,2-c]pyridine To a solution of 0.377 g (1.294 mmol) of 4-(6,7-dihydro-4H-furo[3,2-c]pyridin-5-ylsulfonyl)benzaldehyde and 0.60 g (1.55 mmol) of benzyltriphenylphosphonium chloride in 30 ml of methanol, 0.30 g (1.55 mmol) of 28% sodium methoxide in methanol was added dropwise at room temperature, followed by overnight stirring at room temperature. The reaction mixture was poured into water and extracted with ethyl acetate 3 times. The combined organic layer was dried over anhydrous magnesium sulfate; the solvent was distilled off under reduced pressure. The resulting crude product was subjected to silica gel column chromatography (hexane/ethyl acetate=3/1) to yield 5-(stilbene-4-sulfonyl)-4,5,6,7-tetrahydrofuro[3,2-c]pyridine as a mixture of the (E) and (Z)-isomers.

White oily solid Yield 0.391 g (83%)

A solution of the above 5-(stilbene-4-sulfonyl)-4,5,6,7-tetrahydrofuro[3,2-c]pyridine in 20 ml of toluene-ethanol (5:1) was hydrogenated at room temperature at atmospheric pressure over 49 mg (0.053 mmol) of chlorotris(triphenylphosphine)rhodium (I) until the starting material disappeared on TLC. After the reaction mixture was concentrated under reduced pressure, the resulting crude product was purified by silica gel column chromatography (hexane/ethyl acetate=6/1) and crystallized from diethyl ether-hexane to yield the desired product.

White solid Yield 0.271 g (69%)

$^1$H-NMR (CDCl$_3$, 200MHz) δ: 2.722(2H,t,J=5.5 Hz), 2.861–3.041(4H,m), 3.456(2H,t,J=5.9 Hz), 4.105(2H,s), 6.189(1H,d,J=1.8 Hz), 7.098–7.292(8H,m), 7.705(2H,d,J=8.4 Hz)

IR (nujol): 1344, 1315, 1167, 1126, 1090, 1001, 941, 756, 729, 696 cm$^{-1}$ b) Synthesis of N,N-dimethyl-[5-(4-phenethylbenzenesulfonyl)-4,5,6,7-tetrahydrofuro[3,2-c]pyridin-2-ylmethyl]amine To a solution of 0.240 g (0.653 mmol) of 5-(4-phenethylbenzenesulfonyl)-4,5,6,7-tetrahydrofuro[3,2-c]pyridine in 10 ml of acetic acid, 0.09 g (1.0 mmol) of 50% aqueous dimethylamine and 0.08 g (1.0 mmol) of 37% aqueous formaldehyde were added, followed by stirring at 100° C. for 1 hour. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale yellow solid Yield 0.204 g (74%)

$^1$H-NMR (CDCl$_3$, 200 MHz) δ: 2.229(6H,s), 2.715(2H,t,J=5.9 Hz), 2.859–3.037(4H,m), 3.370(2H,s), 3.440(2H,t,J=5.7 Hz), 4.070(2H,t,J=1.6 Hz), 5.993(1H,s), 7.094–7.318 (7H,m), 7.704(2H,d,J=8.0 Hz)

IR (nujol): 1342, 1308, 1163, 1095, 1003, 958, 895, 814, 762, 721, 698 cm$^{-1}$ c) Synthesis of N,N-dimethyl-[5-(4-phenethylbenzenesulfonyl)-4,5,6,7-tetrahydrofuro(3,2-c]pyridin-2-ylmethyl]amine hydrochloride N,N-Dimethyl-[5-(4-phenethylbenzenesulfonyl)-4,5,6,7-tetrahydrofuro[3,2-c]pyridin-2-ylmethyl]amine 0.171 g was dissolved in 2 ml of methanol; hydrogen chloride in methanol was added in excess, followed by stirring. This mixture was concentrated; the resulting solid was washed with diethyl ether to yield the desired product.

White solid Yield 0.166 g $^1$H-NMR (CD$_3$OD, 200 MHz) δ: 2.735(2H,t,J=5.9 Hz), 2.824(6H,s), 2.870–3.055(4H,m), 3.464(2H,t,J=5.9 Hz), 4.088(2H,s), 4.321(2H,s), 6.587(1H,s), 7.101–7.266(5H,m), 7.365(2H,d,J=8.0 Hz), 7.713(2H,d,J=8.0 Hz)

IR (nujol): 2561, 2470, 1342, 1315, 1165, 1095, 1007, 953, 931, 897, 818, 762, 704 cm$^{-1}$ Anal. Calcd for C$_{24}$H$_{29}$ClN$_2$O$_3$S.0.5H$_2$O: C, 61.33; H, 6.43; N, 5.96. Found: C, 61.54; H, 6.22; N, 6.15

EXAMPLE 139

Synthesis of (Z)-N,N-dimethyl-[5-(2-chlorostilbene-4'-sulfonyl)-4,5,6,7-tetrahydrofuro[3,2-c]pyridin-2-ylmethyl]amine hydrochloride a) Synthesis of 5-(2-chlorostilbene-4'-sulfonyl)-4,5,6,7-tetrahydrofuro[3,2-c]pyridine To a solution of 0.836 g (2.870 mmol) of 4-(6,7-dihydro-4H-furo[3,2-c]pyridin-5-ylsulfonyl)benzaldehyde and 1.21 g (2.87 mmol) of 2-chlorobenzyltriphenylphosphonium chloride in 30 ml of methanol, 0.55 g (2.87 mmol) of 28% sodium methoxide in methanol was added dropwise at room temperature, followed by overnight stirring at room temperature. The reaction mixture was poured into water and extracted with ethyl acetate 3 times. The combined organic layer was dried over anhydrous magnesium sulfate; the solvent was distilled off under reduced pressure. The resulting crude product was subjected to silica gel column chromatography (hexane/ethyl acetate=3/1) and silica gel flush column chromatography (hexane/ethyl acetate=6/1) to yield the (Z)-isomer.

Colorless oil Yield 0.588 g (51%)

$^1$H-NMR (CDCl$_3$, 200 MHz) δ: 2.693(2H,t,J=5.7 Hz), 3.460(2H,t,J=5.7 Hz), 4.110(2H,s), 6.179(1H,d,J=1.6 Hz), 6.703(1H,d,J=12.2 Hz), 6.841(1H,d,J=12.2 Hz), 7.054–7.076(2H,m), 7.120–7.283(4H,m), 7.425(1H,d,J=8.6 Hz), 7.623(2H,d,J=8.2 Hz)

IR (neat): 2918, 2850, 1593, 1465, 1437, 1348, 1317, 1242, 1165, 1070, 1053, 999, 945, 889, 760, 687 cm$^{-1}$ At the same time, the fraction mainly containing the (E)-isomer was concentrated and recrystallized from diethyl ether to yield the (E)-isomer.

White solid Yield 0.144 g (13%)

$^1$H-NMR (CDCl$_3$, 200 MHz) δ: 2.755(2H,t,J=5.9 Hz), 3.499(2H,t,J=5.8 Hz), 4.146(2H,s), 6.198(1H,d,J=1.6 Hz), 7.084(1H,d,J=16.4 Hz), 7.243–7.337(3H,m), 7.399–7.445 (1H,m), 7.589–7.719(4H,m), 7.818(2H,d,J=8.4 Hz)

IR (nujol): 1348, 1321, 1165, 941, 746 cm$^{-1}$ b) Synthesis of (Z)-N,N-dimethyl-[5-(2-chlorostilbene-4'-sulfonyl)-4,5,6,7-tetrahydrofuro[3,2-c]pyridin-2-ylmethyl]amine To a solution of 0.582 g (1.458 mmol) of (Z)-5-(2-chlorostilbene-4'-sulfonyl)-4,5,6,7-tetrahydrofuro[3,2-c]pyridine in 10 ml of acetic acid, 0.20 g (2.19 mmol) of 50% aqueous dimethylamine and 0.18 g (2.19 mmol) of 37% aqueous formaldehyde were added, followed by stirring at 100° C. for 0.5 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Orange oil Yield 0.573 g (86%)

$^1$H-NMR (CDCl$_3$, 200 MHz) δ: 2.220(6H,s), 2.689(2H,br t,J=5.8 Hz), 3.356(2H,s), 3.436(2H,t,J=5.7 Hz), 4.066(2H,s), 5.973(1H,s), 6.692(1H,d,J=12.0 Hz), 6.833(1H,d,J=12.0 Hz), 7.030–7.111(2H,m), 7.167–7.275(3H,m), 7.419(1H,d,J=7.6 Hz), 7.615(2H,d,J=8.4 Hz)

IR (neat): 2974–2773, 1593, 1464, 1348, 1309, 1167, 1092, 1003, 762, 690 cm$^{-1}$ c) Synthesis of (Z)-N,N-dimethyl-[5-(2-chlorostilbene-4'-sulfonyl)-4,5,6,7-tetrahydrofuro[3,2-c]pyridin-2-ylmethyl]amine hydrochloride (Z)-N,N-Dimethyl-[5-(2-chlorostilbene-4'-sulfonyl)-4,5,6,7-tetrahydrofuro[3,2-c]pyridin-2-ylmethyl]amine 0.573 g was dissolved in 2 ml of methanol; hydrogen chloride in methanol was added in excess, followed by stirring. This mixture was concentrated to yield the desired product.

Pale yellow foam Yield 0.620 g $^1$H-NMR (CD$_3$OD, 200 MHz) δ: 2.698(2H,br t,J=5.7 Hz), 2.821(6H,s), 3.471(2H,t,J=5.6 Hz), 4.101(2H,s), 4.325(2H, s), 6.585(1H,s), 6.786(1H,d,J=12.2 Hz), 6.863(1H,d,J=12.2 Hz), 7.069–7.166(2H,m), 7.222–7.319(3H,m), 7.451(1H,d, J=7.8 Hz), 7.648(2H,d,J=8.4 Hz)

IR (neat): 2958, 2667–2472, 1468, 1435, 1344, 1165, 1092, 1005, 949, 760, 689 cm$^{-1}$ Anal. Calcd for C$_{24}$H$_{26}$Cl$_2$N$_2$O$_3$S.1.0H$_2$O: C, 56.36; H, 5.52; N, 5.48. Found: C, 56.56; H, 5.54; N, 5.26

EXAMPLE 140

Synthesis of (Z)-N,N-dimethyl-[5-(3-chlorostilbene-4'-sulfonyl)-4,5,6,7-tetrahydrofuro[3,2-c]pyridin-2-ylmethyl]amine hydrochloride a) Synthesis of 5-(3-chlorostilbene-4'-sulfonyl)-4,5,6,7-tetrahydrofuro[3,2-c]pyridine To a solution of 0.882 g (3.027 mmol) of 4-(6,7-dihydro-4H-furo[3,2-c]pyridin-5-ylsulfonyl)benzaldehyde and 1.54 g (3.63 mmol) of 3-chlorobenzyltriphenylphosphonium chloride in 30 ml of methanol, 0.70 g (3.63 mmol) of 28% sodium methoxide in methanol was added dropwise at room temperature, followed by overnight stirring at room temperature. The reaction mixture was poured into water and extracted with ethyl acetate 3 times. The combined organic layer was dried over anhydrous magnesium sulfate; the solvent was distilled off under reduced pressure. The resulting crude product was subjected to silica gel column chromatography (hexane/ethyl acetate=3/1) to remove triphenylphosphine oxide, followed by crystallization from diethyl ether-hexane to yield the (E)-isomer.

White solid Yield 0.375 g (31%)

$^1$H-NMR (CDCl$_3$, 200 MHz) δ: 2.749(2H,t,J=5.9 Hz), 3.498(2H,t,J=5.7 Hz), 4.145(2H,t,J=1.8 Hz), 6.194(1H,d,J= 1.8 Hz), 7.125(2H,s), 7.263–7.424(4H,m), 7.525(1H,s), 7.615(2H,d,J=8.4 Hz), 7.806(2H,d,J=8.4 Hz)

IR (nujol): 1338, 1319, 1163, 1128, 1090, 987, 943, 758, 733, 685 cm$^{-1}$

The mother liquor concentrated under reduced pressure to yield the (Z)-isomer.

Pale yellow oil Yield 0.702 g (58%)

$^1$H-NMR (CDCl$_3$, 200 MHz) δ: 2.722(2H,t,J=5.8 Hz), 3.471(2H,t,J=5.6 Hz), 4.121(2H,t,J=1.7 Hz), 6.187(1H,d,J= 1.8 Hz), 6.628(1H,d,J=12.0 Hz), 6.697(1H,d,J=12.6 Hz), 7.003–7.074(1H,m), 7.125–7.263(4H,m), 7.331(2H,d,J=8.4 Hz), 7.676(2H,d,J=8.4 Hz)

IR (neat): 2918, 2852, 1593, 1468, 1427, 1348, 1315, 1242, 1165, 1090, 999, 947, 906, 847, 795, 758, 683 cm$^{-1}$ b) Synthesis of (Z)-N,N-dimethyl-[5-(3-chlorostilbene-4'-sulfonyl)-4,5,6,7-tetrahydrofuro[3,2-c]pyridin-2-ylmethyl]amine To a solution of 0.693 g (1.733 mmol) of (Z)-5-(3-chlorostilbene-4'-sulfonyl)-4,5,6,7-tetrahydrofuro[3,2-c]pyridine in 10 ml of acetic acid, 0.23 g (2.60 mmol) of 50% aqueous dimethylamine and 0.21 g (2.60 mmol) of 37% aqueous formaldehyde were added, followed by stirring at 100° C. for 0.5 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1); the resulting solid was washed with diethyl ether to yield the desired product.

White solid Yield 0.458 g (58%)

$^1$H-NMR (CDCl$_3$, 200 MHz) δ: 2.226(6H,s), 2.722(2H,br t,J=5.8 Hz), 3.365(2H,s), 3.447(2H,t,J=5.9 Hz), 4.076(2H, t,J=1.9 Hz), 5.990(1H,s), 6.627(1H,d,J=12.4 Hz), 6.698(1H, d,J=12.2 Hz), 7.012–7.065(1H,m), 7.123–7.129(1H,m), 7.166–7.230(2H,m), 7.333(2H,d,J=8.4 Hz), 7.679(2H,d,J= 8.4 Hz)

IR (nujol): 1348, 1304, 1165, 1090, 1024, 966, 949, 806, 756, 723, 687 cm$^{-1}$ c) Synthesis of (Z)-N,N-dimethyl-[5-(3-chlorostilbene-4'-sulfonyl)-4,5,6,7-tetrahydrofuro[3,2-c]pyridin-2-ylmethyl]amine hydrochloride (Z)-N,N-Dimethyl-[5-(3-chlorostilbene-4'-sulfonyl)-4,5, 6,7-tetrahydrofuro[3,2-c]pyridin-2-ylmethyl]amine 0.390 g was dissolved in 2 ml of methanol; hydrogen chloride in methanol was added in excess, followed by stirring. This mixture was concentrated; the resulting solid was washed with diethyl ether to yield the desired product.

White solid Yield 0.381 g $^1$H-NMR (CD$_3$OD, 200 MHz) δ: 2.749(2H,br t,J=5.9 Hz), 2.826(6H,s), 3.482(2H,t,J=5.8 Hz), 4.105(2H,t,J=1.6 Hz), 4.325(2H,s), 6.585(1H,s), 6.766(2H,s), 7.074–7.136(2H,m), 7.182–7.246(2H,m), 7.401(2H,d,J=8.4 Hz), 7.729(2H,d,J= 8.4 Hz)

IR (nujol): 2565–2447, 1346, 1302, 1167, 1149, 1088, 958, 931, 800, 756, 719, 685 cm$^{-1}$ Anal. Calcd for C$_{24}$H$_{26}$Cl$_2$N$_2$O$_3$S: C, 58.42; H, 5.31; N, 5.68. Found: C, 58.13; H, 5.33; N, 5.46

EXAMPLE 141

Synthesis of (Z)-5-(3-chlorostilbene-4'-sulfonyl)-2-(1-pyrrolidinylmethyl)-4,5,6,7-tetrahydrofuro[3,2-c]pyridine hydrochloride a) Synthesis of (Z)-5-(3-chlorostilbene-4'-sulfonyl)-2-(1-pyrrolidinylmethyl)-4,5,6,7-tetrahydrofuro[3,2-c]pyridine To a solution of 0.666 g (1.665 mmol) of (Z)-5-(3-chlorostilbene-4'-sulfonyl)-4,5,6,7-tetrahydrofuro[3,2-c] pyridin in 10 ml of acetic acid, 0.21 ml (2.5 mmol) of pyrrolidine and 0.20 g (2.5 mmol) of 37% aqueous formaldehyde were added, followed by stirring at 100° C. for 1 hour. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Yellow oil Yield 0.613 g (76%)

$^1$H-NMR (CDCl$_3$, 200 MHz) δ: 1.747–1.811(4H,m), 2.473–2.551(4H,m), 2.709(2H,t,J=5.6 Hz), 3.445(2H,t,J= 5.7 Hz), 3.542(2H,s), 4.072(2H,s), 5.979(1H,s), 6.622(1H, d,J=12.6 Hz), 6.691(1H,d,J=12.4 Hz), 7.008–7.057(1H,m), 7.120–7.189(2H,m), 7.325(2H,d,J=8.0 Hz), 7.670(2H,d,J= 8.4 Hz)

IR (neat): 2964, 2792, 1639, 1592, 1462, 1425, 1348, 1240, 1167, 1092, 1003, 939, 905, 847, 795, 760, 687 cm$^{-1}$ b) Synthesis of (Z)-5-(3-chlorostilbene-4'-sulfonyl)-2-(1-pyrrolidinylmethyl)-4,5,6,7-tetrahydrofuro[3,2-c]pyridine hydrochloride (Z)-5-(3-Chlorostilbene-4'-sulfonyl)-2-(1-pyrrolidinylmethyl)-4,5,6,7-tetrahydrofuro[3,2-c]pyridine 0.613 g was dissolved in 2 ml of methanol; hydrogen chloride in methanol was added in excess, followed by stirring. This mixture was concentrated; the resulting solid was washed with diethyl ether to yield the desired product.

White solid Yield 0.460 g $^1$H-NMR (CD$_3$OD, 200 MHz) δ: 1.929–2.171(4H,m), 2.737(2H,t,J=5.9 Hz), 3.132–3.238(2H,m), 3.453–3.537 (4H,m), 4.101(2H,s), 4.381(2H,s), 6.550(1H,s), 6.764(2H, s), 7.074–7.134(2H,m), 7.193–7.286(2H,m), 7.398(2H,d,J= 8.8 Hz), 7.725(2H,d,J=8.4 Hz)

IR (nujol): 2565, 2492, 1346, 1304, 1165, 1146, 1086, 999, 903, 800, 756, 685 cm$^{-1}$ Anal. Calcd for C$_{26}$H$_{28}$Cl$_2$N$_2$O$_3$S.0.5H$_2$O: C, 59.09; H, 5.53; N, 5.30. Found: C, 59.10; H, 5.57; N, 5.34

EXAMPLE 142

Synthesis of (Z)-N,N-dimethyl-[5-(4-chlorostilbene-4'-sulfonyl)-4,5,6,7-tetrahydrofuro[3,2-c]pyridin-2-ylmethyl]amine hydrochloride a) Synthesis of 5-(4-chlorostilbene-4'-sulfonyl)-4,5,6,7-tetrahydrofuro[3,2-c]pyridine To a solution of 0.800 g (2.746 mmol) of 4-(6,7-dihydro-4H-furo[3,2-c]pyridine-5-ylsulfonyl)benzaldehyde and 1.16 g (2.75 mmol) of 4-chlorobenzyltriphenylphosphonium chloride in 30 ml of methanol, 0.53 g (2.75 mmol) of 28% sodium methoxide in methanol was added dropwise at room temperature, followed by overnight stirring at room temperature. The reaction mixture was poured into water and extracted with ethyl acetate 3 times. The combined organic layer was dried over anhydrous magnesium sulfate; the solvent was distilled off under reduced pressure. The resulting crude product was subjected to silica gel column chromatography (hexane/ethyl acetate=3/1) to remove triphenylphosphine oxide, followed by crystallization from diethyl ether-hexane to yield the (E)-isomer.

White solid Yield 0.303 g (28%)

$^1$H-NMR (CDCl$_3$, 200 MHz) δ: 2.746(2H,br t,J=5.7 Hz), 3.499(2H,t,J=5.7 Hz), 4.145(1H,s), 6.193(1H,d,J=2.2 Hz), 7.060(1H,d,J=16.4 Hz), 7.176(1H,d,J=16.6 Hz), 7.352(2H, d,J=8.8 Hz), 7.466(2H,d,J=8.8 Hz), 7.609(2H,d,J=8.8 Hz), 7.798(2H,d,J=8.6 Hz)

IR (nujol): 1344, 1321, 1165, 1140, 1088, 1005, 966, 945, 833, 756, 733 cm$^{-1}$ The mother liquor was concentrated under reduced pressure to yield the (Z)-isomer.

Colorless oil Yield 0.668 g (61%)

$^1$H-NMR (CDCl$_3$, 200 MHz) δ: 2.705(2H,t,J=5.7 Hz), 3.498(2H,t,J=5.9 Hz), 4.149(2H,s), 6.194(1H,d,J=1.8 Hz), 6.589(1H,d,J=12.6 Hz), 6.689(1H,d,J=12.2 Hz), 7.091(2H, d,J=8.4 Hz), 7.217(2H,d,J=8.8 Hz), 7.323(2H,d,J=8.0 Hz), 7.663(2H,d,J=8.4 Hz)

IR (neat): 2918, 2852, 1591, 1491, 1346, 1317, 1242, 1165, 1090, 1001, 945, 887, 827, 754, 731, 685 cm$^{-1}$ b) Synthesis of (Z)-N,N-dimethyl-[5-(4-chlorostilbene-4'-sulfonyl)-4,5,6,7-tetrahydrofuro[3,2-c]pyridin-2-ylmethyl]amine To a solution of 0.664 g (1.660 mmol) of (Z)-5-(4-chlorostilbene-4'-sulfonyl)-4,5,6,7-tetrahydrofuro[3,2-c]pyridine in 10 ml of acetic acid, 0.22 g (2.49 mmol) of 50% aqueous dimethylamine and 0.20 g (2.49 mmol) of 37% aqueous formaldehyde were added, followed by stirring at 100° C. for 0.5 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale orange oil Yield 0.652 g (86%)

$^1$H-NMR (CDCl$_3$, 200 MHz) δ: 2.224(6H,s), 2.707(2H,br t,J=5.7 Hz), 3.363(2H,s), 3.467(2H,t,J=5.7 Hz), 4.097(2H, t,J=1.7 Hz), 5.990(1H,s), 6.582(1H,d,J=12.0 Hz), 6.687(1H, d,J=12.2 Hz), 7.100(2H,d,J=8.8 Hz), 7.205(2H,d,J=8.4 Hz), 7.326(2H,d,J=8.4 Hz), 7.663(2H,d,J=8.4 Hz)

IR (neat): 2971–2773, 1591, 1489, 1346, 1308, 1168, 1092, 1009, 825, 756, 690 cm$^{-1}$ c) Synthesis of (Z)-N,N-dimethyl-[5-(4-chlorostilbene-4'-sulfonyl)-4,5,6,7-tetrahydrofuro[3,2-c]pyridin-2-ylmethyl]amine hydrochloride (Z)-N,N-Dimethyl-[5-(4-chlorostilbene-4'-sulfonyl)-4,5, 6,7-tetrahydrofuro[3,2-c]pyridin-2-ylmethyl]amine 0.652 g was dissolved in 2 ml of methanol; hydrogen chloride in methanol was added in excess, followed by stirring. This mixture was concentrated to yield the desired product.

Pale yellow foam Yield 0.707 g $^1$H-NMR (CD$_3$OD, 200 MHz) δ: 2.716(2H,br t,J=5.7 Hz), 2.828(6H,s), 3.497(2H,t,J=5.9 Hz), 4.129(2H,s), 4.337(2H, s), 6.612(1H,s), 6.692(1H,d,J=12.0 Hz), 6.777(1H,d,J=12.2 Hz), 7.154(2H,d,J=8.4 Hz), 7.249(2H,d,J=8.4 Hz), 7.398 (2H,d,J=8.0 Hz), 7.709(2H,d,J=8.4 Hz)

IR (neat): 2958, 2669–2470, 1485, 1344, 1313, 1165, 1090, 1007, 949, 825, 756, 689 cm$^{-1}$ Anal. Calcd for C$_{24}$H$_{26}$Cl$_2$N$_2$O$_3$S.0.8H$_2$O: C, 56.76; H, 5.48; N, 5.52. Found: C, 56.85; H, 5.44; N. 5.43

EXAMPLE 143

Synthesis of 5-benzyl-2-dimethylaminomethyl-6,7-dihydro-5H-furo[3,2-c]pyridin-4-one hydrochloride a) Synthesis of methyl 2-(2-hydroxyethyl)furan-3-carboxylate To a solution of 1.287 g (6.494 mmol) of methyl 3-methoxycarbonylfuran-2-ylacetate in 50 ml of methanol, 1.23 g (32.5 mmol) of sodium borohydride was added at room temperature, followed by stirring at room temperature for 1 hour. The reaction mixture was poured into water and extracted with diethyl ether 3 times. The combined organic layer was dried over anhydrous magnesium sulfate; the solvent was distilled off under reduced pressure. The resulting crude product was purified by silica gel column chromatography (hexane/ethyl acetate=3/1 to 1/1) to yield the desired product.

Colorless oil Yield 0.899 g (81%)

$^1$H-NMR (CDCl$_3$, 200 MHz) δ: 2.211(1H,br s), 3.269 (2H,t,J=6.2 Hz), 3.832(3H,s), 3.932(2H,t,J=6.1 Hz), 6.658 (1H,d,J=2.2 Hz), 7.292(1H,d,J=2.2 Hz)

IR (neat): 3417, 2953, 2889, 1718, 1601, 1520, 1444, 1313, 1201, 1159, 1134, 1088, 1049, 995, 744 cm$^{-1}$ b) Synthesis of 5-benzyl-6,7-dihydro-5H-furo[3,2-c]pyridin-4-one To a solution of 1.035 g (6.083 mmol) of methyl 2-(2-hydroxyethyl)furan-3-carboxylate and 1.27 ml (9.12 mmol) of triethylamine in 30 ml of diethyl ether, 0.56 ml (7.3 mmol) of methanesulfonyl chloride was added dropwise under ice-cooling, followed by stirring for 0.5 hours. The reaction mixture was poured into water and extracted with diethyl ether 3 times. The combined organic layer was dried over anhydrous magnesium sulfate; the solvent was distilled off under reduced pressure. The resulting crude methyl 2-(2-mesyloxyethyl)furan-3-carboxylate was used for the next reaction without purification.

A solution of the above crude methyl 2-(2-mesyloxyethyl)furan-3-carboxylate, 0.65 g (6.1 mmol) of benzylamine and 2.33 ml (13.4 mmol) of N,N-diisopropylethylamine in 50 ml of acetonitrile was refluxed for 1 week. The reaction mixture was poured into water and extracted with ethyl acetate 3 times. The combined organic layer was dried over anhydrous magnesium sulfate; the solvent was distilled off under reduced pressure. The resulting residue was purified by silica gel column chromatography (hexane/ethyl acetate=3/1) to yield the desired product.

Yellow oil Yield 0.239 g (17%)

$^1$H-NMR (CDCl$_3$, 200 MHz) δ: 2.866(2H,t,J=7.2 Hz), 3.495(2H,t,J=7.2 Hz), 4.667(2H,s), 6.737(1H,d,J=2.0 Hz), 7.185–7.280(6H,m)

IR (neat): 1660, 1603, 1487, 1450, 1306, 1205, 1124, 737, 702 cm$^{-1}$ c) Synthesis of 5-benzyl-2-dimethylaminomethyl-6,7-dihydro-5H-furo[3,2-c]pyridin-4-one To a solution of 0.181 g (0.796 mmol) of 5-benzyl-6,7-dihydro-5H-furo[3,2-c]pyridin-4-one in 10 ml of acetic acid, 0.36 g (4.0 mmol) of 50% aqueous dimethylamine and 0.32 g (4.0 mmol) of 37% aqueous formaldehyde were added, followed by refluxing for 6 hours. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/methanol=4/1) to yield the desired product.

Pale yellow oil Yield 0.110 g (49%)

$^1$H-NMR (CDCl$_3$, 200 MHz) δ: 2.274(6H,s), 2.899(2H, t,J=7.3 Hz), 3.439(2H,s), 3.520(2H,t,J=7.2 Hz), 4.689(2H, s), 6.562(1H,s), 7.310(5H,s)

IR (neat): 2943, 2775, 1660, 1489, 1452, 1362, 1294, 1257, 1099, 1024, 768, 741, 702 cm$^{-1}$ d) Synthesis of 5-benzyl-2-dimethylaminomethyl-6,7-dihydro-5H-furo[3,2-c]pyridin-4-one hydrochloride 5-Benzyl-2-dimethylaminomethyl-6,7-dihydro-5H-furo [3,2-c]pyridin-4-one 0.110 g was dissolved in 2 ml of methanol; hydrogen chloride in methanol was added in excess, followed by stirring. This mixture was concentrated; the resulting solid was washed with diethyl ether to yield the desired product.

White solid Yield 0.108 g $^1$H-NMR (CD$_3$OD, 200 MHz) δ: 2.892(6H,s), 3.022(2H, t,J=7.3 Hz), 3.652(2H,t,J=7.3 Hz), 4.444(2H,s), 4.698(2H, s), 7.003(1H,s), 7.264–7.356(5H,m)

IR (nujol): 2467, 1651, 1606, 1263, 1211, 1103, 955, 733 cm$^{-1}$

Anal. Calcd for C$_{17}$H$_{21}$ClN$_2$O$_2$: C, 63.65; H, 6.60; N, 8.73. Found: C, 63.84; H, 6.36; N, 9.01

EXAMPLE 144

Synthesis of 2-dimethylaminomethyl-5-(6-phenylhexyl)-6,7-dihydro-5H-furo[3,2-c]pyridin-4-one hydrochloride a) Synthesis of 5-(6-phenylhexyl)-6,7-dihydro-5H-furo[3,2-c]pyridin-4-one To a solution of 0.899 g (5.283 mmol) of methyl 2-(2-hydroxyethyl)furan-3-carboxylate and 1.10 ml (7.92 mmol) of triethylamine in 20 ml of diethyl ether, 0.49 ml (6.3 mmol) of methanesulfonyl chloride was added dropwise under ice-cooling, followed by stirring for 0.5 hours. The reaction mixture was poured into water and extracted with diethyl ether 3 times. The combined organic layer was dried over anhydrous magnesium sulfate; the solvent was distilled off under reduced pressure. The resulting crude methyl 2-(2-mesyloxyethyl)furan-3-carboxylate was used for the next reaction without purification.

A solution of the above crude methyl 2-(2-mesyloxyethyl) furan-3-carboxylate, crude 6-phenylhexylamine [prepared by refluxing a solution of 1.79 g (5.81 mmol) of N-(6-phenylhexyl)phthalimide and 0.28 ml (5.8 mmol) of hydrazine monohydrate in 20 ml of ethanol for 1 hour, cooling the reaction mixture to room temperature, then pouring it into aqueous sodium hydroxide, extracting with ethyl acetate 3 times, drying the combined organic layer over anhydrous magnesium sulfate, and distilling off the solvent] and 2.02 ml (11.6 mmol) of N,N-diisopropylethylamine in 50 ml of acetonitrile was refluxed for 3 days. The reaction mixture was poured into water and extracted with ethyl acetate 3 times. The combined organic layer was dried over anhydrous magnesium sulfate; the solvent was distilled off under reduced pressure. The resulting residue was purified by silica gel column chromatography (hexane/ethyl acetate=6/1 to 3/1) to yield the desired product.

Yellow oil Yield 0.242 g (15%)

$^1$H-NMR (CDCl$_3$, 200 MHz) δ: 1.295–1.398(4H,m), 1.500–1.676(4H,m), 2.601(2H,t,J=7.5 Hz), 2.940(2H,t,J= 7.2 Hz), 3.458(2H,t,J=7.3 Hz), 3.592(2H,t,J=7.2 Hz), 6.711 (1H,d,J=1.8 Hz), 7.125–7.261(5H,m), 7.301(1H,d,J=1.8 Hz)

IR (neat): 2929, 2856, 1664, 1605, 1489, 1452, 1304, 1203, 1126, 1070, 737, 702 cm$^{-1}$ b) Synthesis of 2-dimethylaminomethyl-5-(6-phenylhexyl)-6,7-dihydro-5H-furo[3,2-c]pyridin-4-one To a solution of 0.242 g (0.814 mmol) of 5-(6-phenylhexyl)-6,7-dihydro-5H-furo[3,2-c]pyridin-4-one in 10 ml of acetic acid, 0.37 g (4.1 mmol) of 50% aqueous dimethylamine and 0.33 g (4.1 mmol) of 37% aqueous formaldehyde were added, followed by overnight refluxing. After the solvent was distilled off under reduced pressure, the residual solution was alkalified with aqueous sodium hydroxide and extracted with ethyl acetate 3 times. The combined organic layer was dried over anhydrous magnesium sulfate; the solvent was distilled off under reduced pressure. The resulting crude product was purified by silica gel column chromatography (ethyl acetate to ethyl acetate/ methanol=4/1) to yield the desired product.

Pale yellow oil Yield 0.159 g (55%)

$^1$H-NMR (CDCl$_3$, 200 MHz) δ: 1.339–1.377(4H,m), 1.511–1.655(4H,m), 2.265(6H,s), 2.599(2H,t,J=7.6 Hz), 2.931(2H,t,J=7.2 Hz), 3.425(2H,s), 3.446(2H,t,J=7.2 Hz), 3.575(2H,t,J=7.2 Hz), 6.506(1H,s), 7.149–7.311(5H,m)

IR (neat): 2929, 2856, 1662, 1608, 1489, 1454, 1296, 1103, 1024, 768, 700 cm$^{-1}$ c) Synthesis of 2-dimethylaminomethyl-5-(6-phenylhexyl)-6,7-dihydro-5H-furo[3,2-c]pyridin-4-one hydrochloride 2-Dimethylaminomethyl-5-(6-phenylhexyl)-6,7-dihydro-5H-furo[3,2-c]pyridin-4-one 0.159 g was dissolved in 2 ml of methanol; hydrogen chloride in methanol was added in excess, followed by stirring. This mixture was concentrated; the resulting solid was washed with diethyl ether to yield the desired product.

Pale yellow solid Yield 0.161 g $^1$H-NMR (CD$_3$OD, 200 MHz) δ: 1.335–1.432(4H,m), 1.575–1.682(4H,m), 2.602(2H,t,J=7.6 Hz), 2.890(6H,s), 3.045(2H,t,J=7.2 Hz), 3.476(2H,t,J=7.2 Hz), 3.715(2H,t,J= 7.3 Hz), 4.436(2H,s), 6.950(1H,s), 7.106–7.274(5H,m)

IR (nujol): 2559, 1653, 1562, 1163, 1105, 947, 752, 702 cm$^{-1}$

Anal. Calcd for C$_{22}$H$_{31}$ClN$_2$O$_2$.1.5H$_2$O: C, 63.22; H, 8.20; N, 6.70. Found: C, 63.14; H, 7.85; N, 6.68

Test Example 1

Inhibition of 2,3-oxidosqualene Cyclase Activity

1) Preparation of Crude Rat Enzyme

After a male SD rat (6 weeks of age) was sacrificed by bleeding, the liver was excised. About 50 g of the liver was washed with ice-cold physiological saline and homogenized in 75 ml of ice-cold buffer [100 mM potassium phosphate buffer (pH 7.4), 15 mM nicotinamide, 2 mM MgCl$_2$] and centrifuged at 10,000×g for 20 minutes (4° C.). The resulting supernatant was further centrifuged at 105,00033 g for 90 minutes (4° C.) and the resulting sediment was suspended in ice-cold 100 mM potassium phosphate buffer (pH 7.4), and again centrifuged at 105,000×g for 90 minutes (4° C.). The resulting sediment (microsome fraction) was suspended in 8 ml of ice-cold 100 mM Tris-HCl buffer (pH 7.5) containing 1 mM EDTA-1 mM dithiothreitol (TED buffer) (protein concentration was about 30 mg/ml by BCA protein assay kit of PIAS Corporation), and then 2 ml of 10% n-dodecyl β-D-maltoside (Sigma Ltd.) was added, and incubated in ice water for 20 minutes. A 3-fold volume of ice-cold TED buffer was added and centrifuged at 105,000×g for 90 minutes (4° C.). The supernatant was thus obtained as a crude enzyme solution and was stored at −80° C. until use.

2) Determination of 2,3-oxidosqualene cyclase activity

To 200 μl of a reaction mixture containing 10 FM 2,3-oxidosqualene, 50 mM Tris-HCl (pH 7.5), 0.5 mM EDTA, 0.5 mM dithiothreitol, 0.1% Tween 80, 0.25% n-dodecyl β-D-maltoside and the test drug, the crude enzyme (protein content 40 μg) was added and incubated at 37° C. for 20 minutes. After the reaction was stopped by the addition of 200 μl of 6% potassium hydroxide/methanol, saponification was performed at 37° C. for 1 hour. After 5 μg of cholestane was added as an internal standard, the reaction product was extracted with 700 μl of n-hexane and the hexane layer was evaporated to dryness under reduced pressure. The residue was dissolved in 50 μl of ethyl acetate and a 5 μl of this solution was injected into a gas chromatograph/mass analyzer (GC/Mass). The resulting lanosterol was quantitated with the cholestane as internal standard (gas chromatograph: Yokogawa-Hewlett-Packard HP-5890J; column: Yokogawa-Hewlett-Packard ULTRA-1, 0.32 mm dia., 0.52μ, 10 m; mass analyzer: JEOL JMS-DX303/DA5000). Oxidosqualene cyclase inhibitory Activity was expressed as the concentration to inhibit 50% of lanosterol production ($IC_{50}$). For blank determination, the crude enzyme was added after potassium hydroxide/methanol was added. The results are shown in Table 1.

TABLE 1

Oxidosqualene Cyclase Inhibitory Activity

| Compound (Example Number) | Oxidosqualene Cyclase Inhibitory Activity $IC_{50}$ (μM) |
|---|---|
| 5 | 0.015 |
| 11 | 0.084 |

From Table 1, the compound of the present invention or a salt thereof inhibited 2,3-oxidosqualene cyclase. It is suggested that it serves excellently as an 2,3-oxidosqualene cyclase inhibitor.

Test Example 2

Inhibition of Cholesterogenesis in HepG2 Cells

Human hepatoma cell line HepG2 (ATCC HB8065) was seeded to 24-well multiplates ($10^5$ cells/well) and cultured for 6 days in Dulbecco's modified Eagle minimal medium (DMEM, Gibco) containing 10% inactivated fetal bovine serum (Gibco), followed by overnight preincubation in DMEM containing 10% lipoprotein-deficient human serum (Sigma Ltd.) (LPDS medium). After the medium was replaced with 250 μl of LPDS medium containing the test compound, followed by 1 hour of incubation, 10 μl of 25 mM [$^{14}$C] mevalonic acid (2 μCi/,mole, NEN Company) was added, followed by incubation for 2 more hours. After the cells were washed twice with Dulbecco's phosphate-buffered saline (Wako Pure Chemical Industries), 100 μl of 15% potassium hydroxide was added to lyse the cells at 37° C. After 400 μl of 15% potassium hydroxide/80% ethanol was added, followed by saponification at 75° C. for 1 hour, 300 μl of distilled water and 800 μl of n-hexane were added to extract the unsaponified lipid. After 400 μl of the hexane layer was evaporated to dryness under reduced pressure and dissolved in 200 μl of a 0.1% cholesterol solution in acetone:ethanol=1:1, 400 μl of a 0.5% digitonin solution in 50% ethanol was added and the mixture was kept standing at room temperature overnight. The resulting precipitate was collected onto a glass filter (Advantec Toyo, GC-50) and washed with 50% acetone. Cholesterogenesis inhibitory activity was calculated by comparing the radioactivity incorporated into the digitonin precipitate with the control radioactivity. The test compound was added as DMSO solution, the final DMSO concentration was at 0.4% or less. The results are shown in Table 2.

TABLE 2

Inhibition of Cholesterogenesis in HepG2 cells

| Compound (Example Number) | Inhibition of Cholesterogenesis at 0.1 μM (% of Control) |
|---|---|
| 5 | 14.3 |
| 6 | 33.7 |
| 9 | 33.3 |
| 11 | 34.1 |
| 21 | 20.4 |
| 27 | 7.0 |
| 28 | 7.4 |
| 31 | 12.2 |
| 32 | 13.5 |
| 33 | 10.2 |
| 34 | 17.5 |
| 37 | 55.5 |
| 38 | 47.1 |
| 39 | 43.6 |
| 43 | 21.7 |
| 44 | 30.4 |
| 47 | 44.8 |
| 48 | 37.9 |
| 53 | 21.3 |
| 57 | 33.1 |
| 59 | 51.2 |
| 62 | 49.1 |
| 63 | 10.6 |
| 66 | 42.3 |
| 67 | 36.5 |
| 74 | 17.6 |
| 75 | 15.9 |
| 76 | 20.8 |
| 77 | 15.7 |
| 78 | 17.2 |
| 79 | 25.8 |
| 80 | 8.3 |
| 81 | 9.1 |
| 82 | 12.7 |
| 83 | 23.9 |
| 86 | 11.0 |
| 87 | 16.2 |
| 88 | 30.4 |
| 92 | 18.3 |
| 93 | 19.7 |
| 94 | 18.1 |
| 95 | 27.3 |
| 97 | 43.9 |
| 101 | 35.4 |
| 103 | 31.5 |
| 112 | 36.0 |
| 114 | 20.0 |
| 115 | 35.9 |
| 116 | 16.7 |
| 119 | 48.3 |
| 120 | 49.7 |
| 121 | 24.0 |
| 122 | 21.5 |
| 124 | 13.4 |
| 125 | 37.2 |
| 126 | 7.2 |
| 127 | 24.5 |
| 128 | 47.2 |
| 129 | 23.2 |
| 140 | 33.3 |
| 141 | 19.4 |
| 144 | 16.1 |

From Table 2, it is evident that the compound of the present invention or a salt thereof inhibits cholesterogenesis potently.

Test Example 3

Inhibition of Cholesterogenesis in Rat Liver

An aqueous solution of the test drug was administered, by a stomach tube, to male Sprague-Dawley rats at 5 weeks of age; 1 hour later, [$^{14}$C] acetic acid was intravenously administered at a dose of 10 μCi per animal. One hour later, the animals were bled, livers were excised and a portion of liver was treated with a chloroform:methanol mixture to extract lipids. After the lipid fraction was saponified, sterol was extracted with petroleum ether, precipitated using digitonin and the radioactivity in the precipitate fraction was determined using a scintillation counter. The control group orally received 0.5% methyl cellulose solution alone.

The results are shown in Table 3 (lower percent control values indicate higher cholesterol synthesis inhibitory activity).

TABLE 3

| Compound (Example Number) | Dose (mg/kg) | % Control |
|---|---|---|
| \multicolumn{3}{c}{Inhibition of cholesterogenesis in Rat Liver} |
| 5 | 30 | 48.9 |
| 11 | 1.0 | 23.3 |
|  | 0.3 | 52.6 |
| 38 | 30 | 29.9 |
| 39 | 3.0 | 64.6 |
| 53 | 10 | 42.3 |

From Table 3, it is evident that the compound of the present invention or a salt thereof potently inhibits cholesterogenesis in rat liver.

Test Example 4
Determination of Antifungal Activity (Agar Plate Dilution Method)

RPMI 1640 (Gibco BRL) was dissolved in 0.3 M MOPS buffer, pH 7.0, to obtain a 2-fold dilution; this solution was filtered to remove germ cells (0.45 μm). Separately, 1.4% agar (Wako Pure Chemical Industries) was thermally sterilized (121° C., 15 minutes). This agar was mixed with an equal amount of the above 2-fold diluted RPMI 1640 (0.15 M MOPS, pH 7.0). To 9.9 ml of this RPMI 1640 (0.15 M MOPS, pH 7.0)–0.7% agar medium, 0.1 ml of a 100-fold diluted DMSO solution of the test drug was added; this mixture was prepared as an agar plate in a petri dish 9 cm in diameter. The drug (dissolved in DMSO to 100-fold dilution) was used in a series of 2-fold dilutions of a starting concentration of 64 μg/ml in the agar medium. For drug-free control, an agar medium containing 0.1 ml of DMSO or 1 ml of sterile water was prepared. An inoculum of frozen cells was diluted with physiological saline and spot inoculated onto the agar medium (0.005 ml; 700–15,000 cfu) using a microplanter (Sakuma Seisakusho), followed by cultivation at 35° C. for 20 hours. Antifungal activity was assessed macroscopically; the minimum concentration for complete growth inhibition was expressed as MIC (minimum growth inhibitory concentration). The results are shown in Table 4.

TABLE 4

| Compound (Example Number) | Antifungal Activity Test Organism MIC (μg/ml) | | | | | | | | |
|---|---|---|---|---|---|---|---|---|---|
|  | A | B | C | D | E | F | G | H | I |
| 5 | 16 | 16 | 64 | 32 | 8 | 8 | 2 | 8 | 8 |
| 6 | 16 | 2 | 16 | 32 | 4 | 16 | 2 | 16 | 8 |
| 21 | 2 | 2 | 2 | 4 | 1 | 2 | 1 | 1 | 1 |
| 27 | 16 | 32 | 64 | 16 | 4 | 8 | 2 | 2 | 2 |
| 28 | 8 | 2 | 32 | 16 | 4 | 8 | 2 | 4 | 4 |
| 31 | 8 | 2 | 16 | 64 | 16 | 32 | 4 | 0.5 | 0.5 |
| 32 | 16 | 8 | 32 | 32 | 32 | 32 | 8 | 2 | 2 |
| 33 | 32 | 16 | 64 | 16 | 8 | 16 | 4 | 0.5 | 0.25 |
| 43 | 8 | 2 | 8 | 16 | 16 | 16 | 2 | 8 | 4 |
| 44 | 16 | 8 | 8 | 32 | 8 | 16 | 4 | 8 | 8 |
| 48 | 16 | 8 | 64 | 32 | 8 | 16 | 2 | 32 | 16 |

Test organisms
A: *Candida albicans* IFO 0583
B: *Candida tropicalis* IFO 0587
C: *Candida tropicalis* IFO 10241
D: *Candida glabrata* IFO 0622
E: *Candida krusei* IFO 0584
F: *Candida krusei* IFO 1162
G: *Candida utilis* IFO 0619
H: *Aspergillus fumigatus* IFO 6344
I: *Aspergillus niger* IFO 4414

From Table 4, it is evident that the compound of the present invention or a salt thereof possesses antifungal activity, suggesting that it serves excellently as an antifungal agent.

Test Example 5

Determination of Low-density Lipoprotein (LDL) Receptor-increasing Activity

Human hepatoma cell line HepG2 was seeded to 96-multiwell plates ($10^4$ cells/well) and cultured for 5 days in Dulbecco's minimal essential medium (DMEM) medium supplemented with 10% inactivated fetal bovine serum, followed by 20 hours of pretreatment in 100 μl of DMEM medium containing 10% lipoprotein-deficient fetal bovine serum and the test compound. After being washed with Dulbecco's phosphate-buffered saline (PBS), the cells were fixed in 4% formalin at room temperature for 1 hour. Three hundreds μl of PBS containing 3% bovine serum albumin was added; the mixture was kept standing at 5° C. overnight, after which the PBS was replaced with 50 μl of PBS containing both 5 μg/ml anti-LDL receptor monoclonal antibody (Oncogene Science) and 0.5% bovine serum albumin, followed by incubation at room temperature for 2 hours. After the cells were washed with PBS containing both 0.05% Triton X-100 and 0.5% bovine serum albumin (Triton-containing PBS), 50 μl of 400-fold diluted peroxidase-labeled anti-mouse antibody (produced by BIO-RAD) was added, followed by incubation at room temperature for 1 hour. After the cells were washed with Triton-containing PBS, peroxidase activity was determined using a Peroxidase Assay Kit A (Sumitomo Bakelite Co., Ltd.). LDL receptor-inducing activity was calculated by comparing the peroxidase activity with control activity; data were analyzed for significant difference by Student's t-test. Blank determination was performed in the absence of the anti-LDL receptor monoclonal antibody. The results are shown in Table 5.

TABLE 5

LDL Receptor-increasing Activity

| Compound (Example Number) | Concentration ($\mu M$) | LDL Receptor Expression (% of Control) mean ± SD (n = 3) |
|---|---|---|
| Control | — | 100.0 ± 3.9 |
| 11 | 0.2 | 113.3 ± 10.6 |
|  | 2 | 143.1 ± 19.7* |
|  | 20 | 148.9 ± 20.5* |

*$p < 0.05$

From Table 5, it is evident that the compound of the present invention or a salt thereof increases low-density lipoprotein (LDL) receptors.

Test Example 6
Plasma HDL-cholesterol-elevating Effect in Wistar Fatty Rats
Method Female Wistar fatty rats (19 weeks of age, bred in Experimental Animals Unit, Takeda Chemical Industries, Ltd.) were given a 0.5% methyl-cellulose solution of compound 31 by a stomach tube for 1 week. Blood was collected via the orbital sinus under non-fasting conditions; plasma total cholesterol and HDL-cholesterol were enzymatically determined using a commercial kit (produced by Wako Pure Chemical Industries, Ltd.). Non-HDL-cholesterol levels were obtained by subtracting HDL-cholesterol from total cholesterol levels. Triglyceride and glucose were also enzymatically determined using commercial kits (both produced by Iatron Laboratories, Inc.). The results are shown in Table 6.

TABLE 6

HDL-cholesterol-elevating Effect in Wistar Fatty Rats

| Dose (mg/kg-day) | Control Group | Compound 31 (Example No.) | |
|---|---|---|---|
|  | 0 | 0.1 | 0.3 |
| Number of animals | 5 | 5 | 5 |
| Total cholesterol (mg/dl) | 154 ± 13$^a$ | 175 ± 21$^{ab}$ | 192 ± 24$^b$ |
| HDL-cholesterol (mg/dl) | 92.4 ± 9.2$^a$ | 113 ± 15.4$^b$ | 135 ± 16.2$^c$ |
| Non-HDL-cholesterol (mg/dl) | 62.0 ± 12.5$^a$ | 62.5 ± 7.9$^a$ | 57.1 ± 10.7$^a$ |
| Triglyceride (mg/dl) | 694 ± 192$^a$ | 599 ± 195$^a$ | 538 ± 155$^a$ |
| Glucose (mg/dl) | 285 ± 45$^a$ | 251 ± 72$^a$ | 242 ± 39$^a$ |

Data represents the mean ± standard deviation. Different superscript letters in the table indicate a statistically significant ($p<0.05$) difference between the respective values by Duncan's multiple range test.
Results The plasma HDL-cholesterol-elevating action of Compound 31 in Wistar fatty rats is shown in Table 6. Plasma HDL-cholesterol and total cholesterol levels increased significantly, depending on dose of compound 31. However, plasma non-HDL-cholesterol, triglyceride or glucose levels was not affected.
Industrial Applicability The present invention provides new condensed furan compounds which exhibit excellent 2,3-oxidosqualene cyclase inhibiting and high density lipoprotein-cholesterol elevating activities and the compounds are useful as lipid-modifying agent and in the prevention and the treatment of hyperlipidemia, hypercholesterolemia and atherosclerosis.

We claim:

1. A compound represented by the formula:

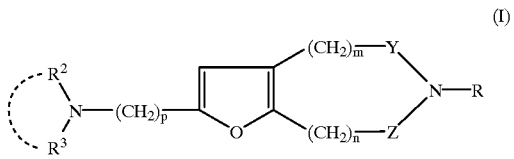

(I)

wherein R represents an acyl group or a hydrocarbon group that may be substituted; $R^2$ and $R^3$, independently, represent a hydrogen atom or a hydrocarbon group that may be substituted, or may form a ring with the adjacent nitrogen atom; Y and Z independently represent —CO— or a bond; p represents an integer of 1 to 5, m and n independently represent an integer of 0 to 5 with the proviso that both m and n are not identically 0, or a salt thereof.

2. A compound of claim 1, wherein Y and Z are a bond, m and n independently represent an integer of 1 to 5.

3. A compound of claim 1, wherein R is —A—$R^1$ in which $R^1$ represents a hydrocarbon group that may be substituted or a heterocyclic group that may be substituted; A represents a bond, —CO—, —SO$_2$—, —SO—, —COO— or —CON($R^4$)— ($R^4$ represents a hydrogen atom or a hydrocarbon group that may be substituted).

4. A compound of claim 1, wherein the hydrocarbon group represented by R is an alkyl group, a cycloalkyl group, an alkenyl group, an aryl group or an aralkyl group.

5. A compound of claim 1, wherein the substituent for said hydrocarbon group represented by R is (i) nitro group, (ii) hydroxyl group, (iii) cyano group, (iv) carbamoyl group, (v) a mono- or di-$C_{1-4}$ alkyl-carbamoyl group (vi) carboxyl group, (vii) a $C_{1-4}$ alkoxy-carbonyl group, (viii) sulfone group, (ix) a halogen atom, (x) a $C_{1-6}$ alkoxy group, (xi) phenoxy group, naphthoxy group or benzyloxy group, (xii) a halogenophenoxy group, (xiii) a $C_{1-4}$ alkylthio group, (xiv) mercapto group, (xv) phenylthio group, (xvi) pyridylthio group, (xvii) a $C_{1-4}$ alkylsulfinyl group or phenylsulfinyl group, (xviii) a $C_{1-4}$ alkylsulfonyl group or phenylsulfonyl group, (xix) amino group, (xx) a $C_{1-3}$ acylamino group, (xxi) a mono- or di-$C_{1-4}$ alkylamino group, (xxii) a 4- to 6-membered cyclic amino group, (xxiii) a $C_{1-6}$ acyl group, (xxiv) a benzoyl group that may be substituted by halogen atom(s), (xxv) a 5- to 10-membered heterocyclic group or (xxvi) a 5- to 10-membered heterocyclic ring-carbonyl group.

6. A compound of claim 3, wherein the hydrocarbon group represented by $R^1$ and $R^4$ is an alkyl group, a cycloalkyl group, an alkenyl group, an aryl group or an aralkyl group.

7. A compound of claim 3, wherein the substituent for said hydrocarbon group represented by $R^1$ and $R^4$ is (i) nitro group, (ii) hydroxyl group, (iii) cyano group, (iv) carbamoyl group, (v) a mono- or di-$C_{1-4}$ alkyl-carbamoyl group, (vi) carboxyl group, (vii) a $C_{1-4}$ alkoxy-carbonyl group, (viii) sulfone group, (ix) a halogen atom, (x) a $C_{1-6}$ alkoxy group, (xi) phenoxy group, naphthoxy group or benzyloxy group, (xii) a halogenophenoxy group, (xiii) a $C_{1-4}$ alkylthio group, (xiv) mercapto group, (xv) phenylthio group, (xvi) pyridylthio group, (xvii) a $C_{1-4}$ alkylsulfinyl group or phenylsulfinyl group, (xviii) a $C_{1-4}$ alkylsulfonyl group or phenylsulfonyl group, (xix) amino group, (xx) a $C_{1-3}$ acylamino group, (xxi) a mono- or di-$C_{1-4}$ alkylamino group, (xxii) a 4- to 6-membered cyclic amino group, (xxiii) a $C_{1-6}$ acyl groups, (xxiv) benzoyl group that may be substituted by halogen atoms, (xxv) a 5- to 10-membered heterocyclic group or (xxvi) a 5- to 10-membered heterocyclic ring-carbonyl group.

8. A compound of claim 3, wherein $R^1$ represents an aralkyl group or an aryl group.

9. A compound of claim 3, wherein said heterocyclic group represented by $R^1$ is a 5- to 8-membered ring or a condensed ring containing 1 to 4 hetero atoms selected from atoms of oxygen, sulfur and nitrogen.

10. A compound of claim 3, wherein $R^1$ represents a $C_{7-20}$ aralkyl group that may be substituted by one to four substituent(s) selected from the group consisting of (i) nitro group, (ii) hydroxyl group, (iii) cyano group, (iv) carbamoyl group, (v) mono- or di-$C_{1-4}$ alkyl-carbamoyl groups, (vi) carboxyl group, (vii) $C_{1-4}$ alkoxy-carbonyl groups, (viii) sulfone group, (ix) halogen atoms, (x) $C_{1-6}$ alkoxy groups, (xi) phenoxy group, naphthoxy group or benzyloxy group, (xii) halogenophenoxy groups, (xiii) $C_{1-4}$ alkylthio groups (xiv) mercapto group, (xv) phenylthio group, (xvi) pyridylthio group, (xvii) $C_{1-4}$ alkylsulfinyl groups or phenylsulfinyl group, (xviii) $C_{1-4}$ alkylsulfonyl groups or phenylsulfonyl group, (xix) amino group, (xx) $C_{1-3}$ acylamino groups, (xxi) mono- or di-$C_{1-4}$ alkyl amino groups, (xxiii) $C_{1-6}$ acyl groups, (xxiv) benzoyl groups that may be substituted by halogen atom(s), (xxv) 5- to 10-membered heterocyclic groups and (xxvi) 5- to 10-membered heterocyclic ring-carbonyl groups.

11. A compound of claim 3, wherein $R^1$ represents a $C_{6-14}$ aryl group that may be substituted by an acyl group.

12. A compound of claim 3, wherein A is —CO—, —$SO_2$— or —COO—.

13. A compound of claim 3, wherein A is —CO— or —$SO_2$—, $R^1$ is a halogeno-$C_{7-20}$ aralkyl group.

14. A compound of claim 1, wherein $R^2$ and $R^3$ are independently a lower alkyl group.

15. A compound of claim 1, wherein m or n is 1.

16. A compound of claim 1, wherein both m and n are independently an integer of 1 to 3.

17. A compound of claim 1, wherein p is an integer of 1 to 3.

18. A compound of claim 1, wherein Y is —CO—.

19. A compound of claim 18, wherein m is 0, n is an integer of 1 to 3 and Z is a bond.

20. A compound of claim 19, wherein R is a $C_{7-20}$ aralkyl group or a $C_{6-14}$ aryl group.

21. A compound of claim 1, which is 1-(2-dimethylaminomethyl-6,7-dihydro-4H-furo[3,2-c]pyridin-5-yl)-6-phenylhexan-1-one,
1-(2-dimethylaminomethyl-5,7-dihydro-4H-furo[2,3-c]pyridin-6-yl)-6-phenylhexan-1-one,
N,N-dimethyl-[6-(4-phenylbutoxycarbonyl)-4,5,6,7-tetrahydrofuro[2,3-c]pyridin-2-ylmethyl]amine,
N,N-dimethyl-[5-(5-phenylpentylsulfonyl)-4,5,6,7-tetrahydrofuro[3,2-c]pyridin-2-ylmethyl]amine,
N,N-dimethyl-[6-(4-benzoylbenzoyl)-4,5,6,7-tetrahydrofuro[2,3-c]pyridin-2-ylmethyl]amine,
N,N-diethyl-[6-(4-benzoylbenzoyl)-4,5,6,7-tetrahydrofuro[2,3-c]pyridin-2-ylmethyl]amine,
1-(2-methylaminomethyl-5,7-dihydro-4H-furo[2,3-c]pyridin-6-yl)-6-phenylhexan-1-one,
1-(2-dimethylaminomethyl-4,5,6,8-tetrahydrofuro[2,3-c]azepin-7-yl)-6-phenylhexan-1-one,
N,N-dimethyl-[6-(4-phenethylbenzoyl)-4,5,6,7-tetrahydrofuro[2,3-c]pyridin-2-ylmethyl]amine,
N,N-dimethyl-[6-(4-benzyloxybenzoyl)-4,5,6,7-tetrahydrofuro[2,3-c]pyridin-2-ylmethyl]amine,
6-[4-(1-phenylethenyl)benzoyl]-2-(1-pyrrolidinylmethyl)-4,5,6,7-tetrahydrofuro[2,3-c]pyridine,
N,N-dimethyl-[6-[4-(1-phenylcyclopropyl)benzoyl]-4,5,6,7-tetrahydrofuro[2,3-c]pyridin-2-ylmethyl]amine,
N,N-dimethyl-[6-[4-(2-phenyl-1,3-dithiolane-2-yl)benzoyl]-4,5,6,7-tetrahydrofuro[2,3-c]pyridin-2-ylmethyl]amine,
(Z)-5-(3-chlorostilbene-4'-sulfonyl)-2-(1-pyrrolidinylmethyl)-4,5,6,7-tetrahydrofuro[3,2-c]pyridine,
2-dimethylaminomethyl-5-(6-phenylhexyl)-6,7-dihydro-5H-furo[3,2-c]pyridin-4-one, or an acid addition salts thereof.

22. A method of producing the compound of claim 1, which comprises reacting a compound represented by the formula:

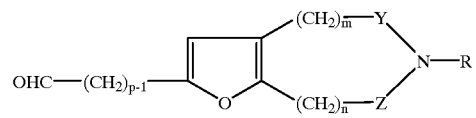

wherein the symbols have the same definitions as those given in claim 1, or a salt thereof, with a compound represented by the formula:

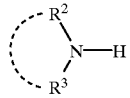

wherein the symbols have the same definitions as those given in claim 1, or a salt thereof, followed by reduction.

23. A method of producing the compound of claim 1, which comprises reacting a compound represented by the formula;

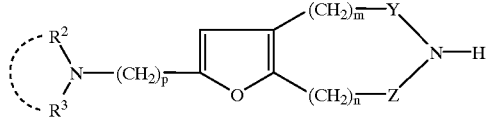

wherein the symbols have the same definitions as those given in claim 1, or a salt thereof, with a compound represented by the formula:

wherein $E^1$ represents a leaving group; R has the same definition as that given in claim 1, or a salt thereof.

24. A method for (i) inhibiting 2,3-oxidosqualene cyclase, (ii) inhibiting cholesterogenesis, (iii) increasing low-density lipoprotein receptor activity, (iv) elevating high-density lipoprotein-cholesterol, (v) modifying lipid or (vi) inhibiting fungus, which comprises steps of:

selecting a composition comprising a compound represented by the formula:

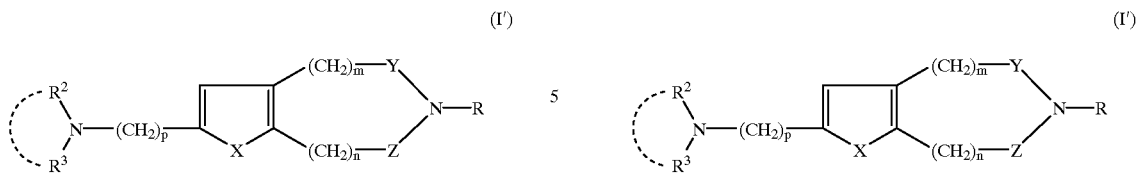

(I')

wherein X represents an oxygen atom or a sulfur atom; R represents an acyl group or a hydrocarbon group that may be substituted; $R^2$ and $R^3$ independently represent a hydrogen atom or a hydrocarbon group that may be substituted, or may form a ring with the adjacent nitrogen atom; Y and Z independently represent —CO— or a single bond; p represents an integer of 1 to 5; m and n independently represent an integer of 0 to 5 with the proviso that m and n are not both 0, or a salt thereof, and a pharmaceutically acceptable additive; and administering said composition to a patient in need thereof.

25. A method for preventing or treating hyperlipidemia, hypercholesteromia, atherosclerosis, hyperlipoproteinemia or hypertriglyceridemia in a mammal which comprises administering to said mammal a pharmaceutically effective amount of a compound represented by the formula:

wherein X represents an oxygen atom or a sulfur atom; R represents an acyl group or a hydrocarbon group that may be substituted; $R^2$ and $R^3$ independently represent a hydrogen atom or a hydrocarbon group that may be substituted, or may form a ring with the adjacent nitrogen atom; Y and Z independently represent —CO— or a single bond; p represents an interger of 1 to 5; m and n independently represent an integer of 0 to 5 with the priviso that m and n are not both 0, or a pharmaceutically acceptable salt thereof.

26. A method of claim 25, which is for inhibiting 2,3-oxidosqualene cyclase.
27. A method of claim 25, which is for inhibiting cholesterogenesis.
28. A method of claim 25, which is for increasing low-density lipoprotein receptor.
29. A method of claim 25, which is for elevating high-density lipoprotein-cholesterol.
30. A method of claim 25, which is for modifying lipid.
31. A method of claim 25, which is for inhibiting fungus.
32. A pharmaceutical composition comprising the compound of any of claims 1 to 21, and a pharmaceutically acceptable carrier.

* * * * *

UNITED STATES PATENT AND TRADEMARK OFFICE
CERTIFICATE OF CORRECTION

PATENT NO. : 5,998,433
DATED : December 7, 1999
INVENTOR(S) : MUNEO TAKATANI ET AL.     Page 1 of 3

It is certified that error appears in the above-identified patent and that said Letters Patent is hereby corrected as shown below:

COLUMN 2

Line 45, "a" should be deleted.

COLUMN 22

Line 18, "al" should read --α1--.

COLUMN 29

Line 58, "chromatog-raphy" should read --chromatography--.

COLUMN 72

Line 40, "(10H," should read --(10H,m);--.

COLUMN 83

Line 9, "-furo/m2,3-" should read --furo[2,3---.

COLUMN 119

Line 25, "The-resulting" should read --The resulting--.

UNITED STATES PATENT AND TRADEMARK OFFICE
CERTIFICATE OF CORRECTION

PATENT NO. : 5,998,433

DATED : December 7, 1999

INVENTOR(S) : MUNEO TAKATANI ET AL.

It is certified that error appears in the above-identified patent and that said Letters Patent is hereby corrected as shown below:

COLUMN 134

Line 56, "$C_{25}H26Cl_2N_2O_2.0.6H_2O$:" should read --$C_{25}H_{26}Cl_2N_2O_2.0.6H_2O$:--.

COLUMN 165

Line 37, "aced" should read --acid--.

COLUMN 180

Line 45, "105,00033 g" should read --105,000 x g--.

COLUMN 181

Line 11, "Activity" should read --activity--; and
Line 45, "(2 µCi/,mole," should read --2 µCi/µmole,--.

COLUMN 183

In Table 3, "cholesterogenesis" should read --Cholesterogenesis--.

UNITED STATES PATENT AND TRADEMARK OFFICE
CERTIFICATE OF CORRECTION

PATENT NO. : 5,998,433
DATED : December 7, 1999
INVENTOR(S) : MUNEO TAKATANI ET AL.

It is certified that error appears in the above-identified patent and that said Letters Patent is hereby corrected as shown below:

<u>COLUMN 184</u>

The blank line space at Line 24 should be deleted.

<u>COLUMN 188</u>

Line 43, "formula;" should read --formula:--.

Signed and Sealed this

Twenty-seventh Day of March, 2001

Attest:

NICHOLAS P. GODICI

Attesting Officer    Acting Director of the United States Patent and Trademark Office